(12) United States Patent
Tillack et al.

(10) Patent No.: US 11,541,179 B2
(45) Date of Patent: Jan. 3, 2023

(54) SYSTEM AND METHOD FOR SAFETY SYRINGE

(71) Applicant: CREDENCE MEDSYSTEMS, INC., Menlo Park, CA (US)

(72) Inventors: Jeff Tillack, Foster City, CA (US); Alan E. Shluzas, San Carlos, CA (US); Stephen H. Diaz, Palo Alto, CA (US); Gary Steese-Bradley, San Jose, CA (US); John Merhige, Menlo Park, CA (US); Conor Edward Shanley, Emerald Hills, CA (US); Mina M. Leung, Mountain View, CA (US)

(73) Assignee: CREDENCE MEDSYSTEMS, INC., Menlo Park, CA (US)

( * ) Notice: Subject to any disclaimer, the term of this patent is extended or adjusted under 35 U.S.C. 154(b) by 123 days.

(21) Appl. No.: 16/798,188

(22) Filed: Feb. 21, 2020

(65) Prior Publication Data

US 2020/0268973 A1 Aug. 27, 2020

Related U.S. Application Data

(60) Provisional application No. 62/864,509, filed on Jun. 21, 2019, provisional application No. 62/809,369, filed on Feb. 22, 2019.

(51) Int. Cl.
*A61M 5/24* (2006.01)
*A61M 5/20* (2006.01)
(Continued)

(52) U.S. Cl.
CPC ........ *A61M 5/2448* (2013.01); *A61M 5/2066* (2013.01); *A61M 5/284* (2013.01);
(Continued)

(58) Field of Classification Search
CPC .............. A61M 5/2448; A61M 5/2066; A61M 5/284; A61M 2005/1787;
(Continued)

(56) References Cited

U.S. PATENT DOCUMENTS

| | | | | |
|---|---|---|---|---|
| 3,150,661 A | * | 9/1964 | Maki | A61M 5/288 |
| | | | | D24/114 |
| 4,766,082 A | * | 8/1988 | Marteau | G01N 1/405 |
| | | | | 436/47 |
| 8,187,220 B2 | | 5/2012 | Griffiths et al. | |
| 2006/0168916 A1 | * | 8/2006 | Griebel | B65B 3/003 |
| | | | | 53/489 |

(Continued)

FOREIGN PATENT DOCUMENTS

| | | | |
|---|---|---|---|
| JP | 07213609 | * | 8/1955 |
| JP | 07213609 | * | 8/1995 |

(Continued)

OTHER PUBLICATIONS

PCT International Search Report and Written Opinion for International Patent Appln. No. PCT/US2020/019365, Applicant Credence Medsystems, Inc., dated Jul. 8, 2020 (20 pages).

*Primary Examiner* — Bhisma Mehta
*Assistant Examiner* — Rachel T. Smith
(74) *Attorney, Agent, or Firm* — Vista IP Law Group LLP

(57) ABSTRACT

A method for preparing a pre-filled multi-chamber injection system includes providing an injection system body, the injection system body defining an open proximal end, a body interior, and an open distal end. The method also includes introducing a first substance into a distal end of the body interior. The method further includes disposing a distal stopper member in the body interior, the distal stopper member and the injection system body defining proximal and distal chambers in the body interior. Moreover, the method includes introducing a second substance into the
(Continued)

body interior. In addition, the method includes disposing a proximal stopper member in the body interior. The method also includes inserting an elongate member at least partially into the body interior, the elongate member having a plurality of flow channels for fluidly coupling the proximal and distal chambers. The method further includes coupling a plunger member to the proximal stopper member.

20 Claims, 95 Drawing Sheets

(51) Int. Cl.
*A61M 5/28* (2006.01)
*A61M 5/178* (2006.01)
*A61M 5/31* (2006.01)

(52) U.S. Cl.
CPC ............... *A61M 2005/1787* (2013.01); *A61M 2005/3132* (2013.01)

(58) Field of Classification Search
CPC ........ A61M 2005/3132; A61M 5/3291; A61M 5/31596; A61M 5/008; A61M 5/3294; A61M 5/1782; A61M 2005/3114; A61J 1/2093

See application file for complete search history.

(56) References Cited

U.S. PATENT DOCUMENTS

| | | | |
|---|---|---|---|
| 2013/0035666 A1* | 2/2013 | Schulhof | A61M 5/2448 604/200 |
| 2014/0296791 A1* | 10/2014 | Wong | A61M 5/3134 604/191 |
| 2018/0105294 A1* | 4/2018 | Abboud | B65B 3/003 |
| 2018/0256818 A1* | 9/2018 | Lümkemann | A61M 5/3129 |
| 2019/0038829 A1* | 2/2019 | Nasker | A61B 50/22 |

FOREIGN PATENT DOCUMENTS

| | | | | |
|---|---|---|---|---|
| JP | 07265423 | * | 10/1995 | |
| WO | WO-2018085467 A2 | * | 5/2018 | ............ A61M 5/178 |

* cited by examiner

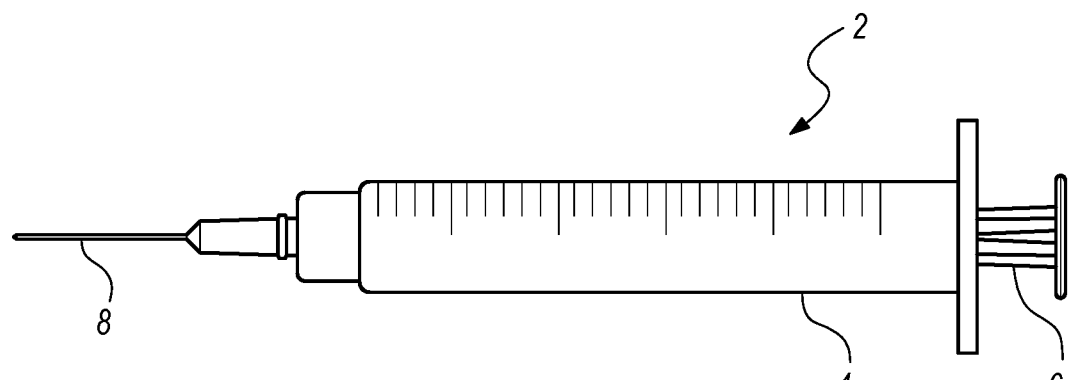
PRIOR ART  FIG. 1A
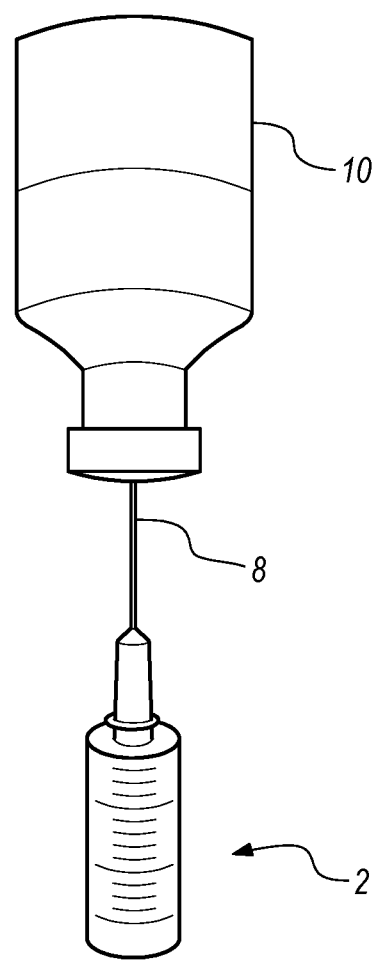
PRIOR ART  FIG. 1B

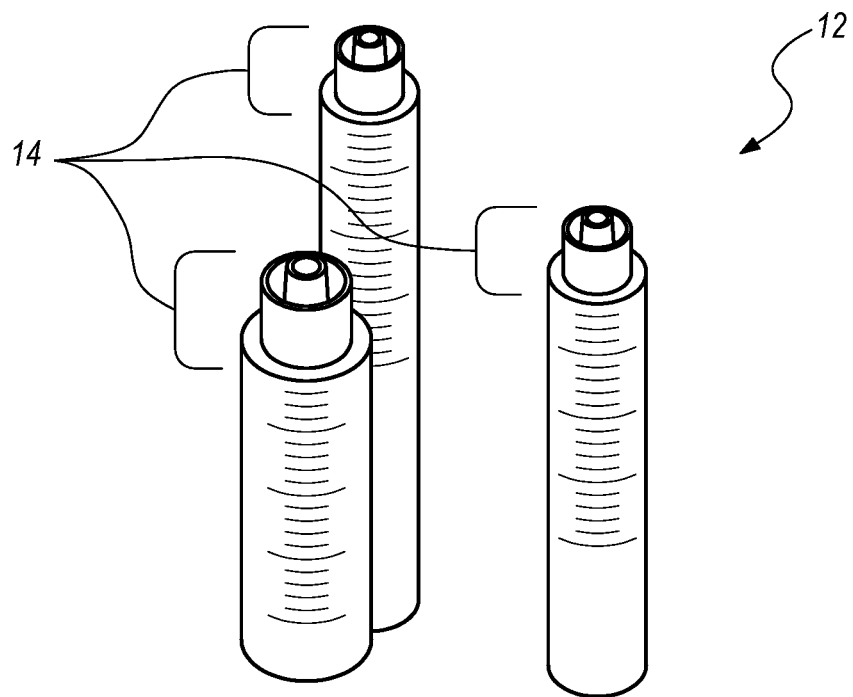
PRIOR ART  *FIG. 2A*
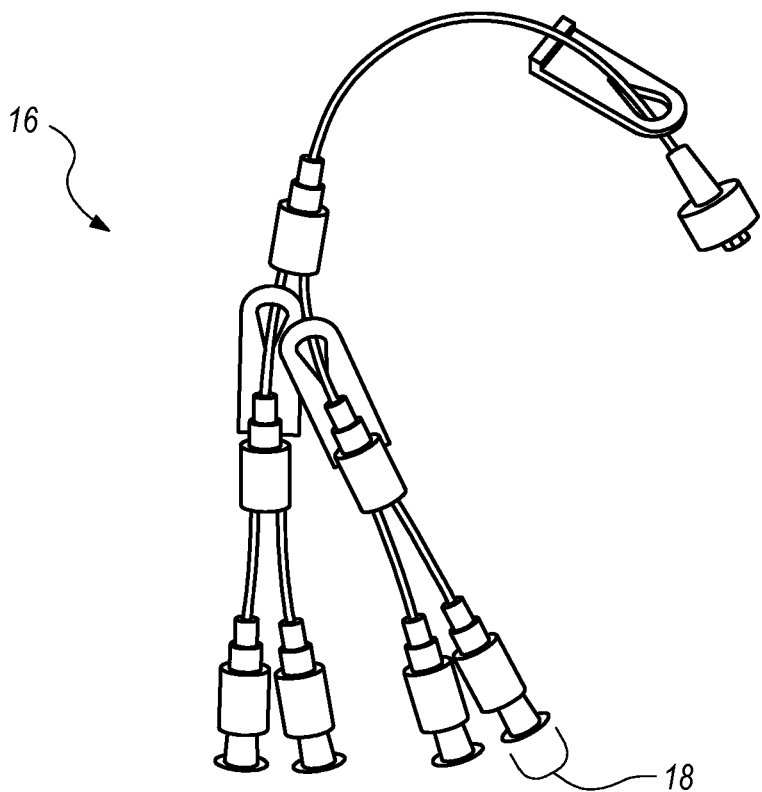
PRIOR ART  *FIG. 2B*

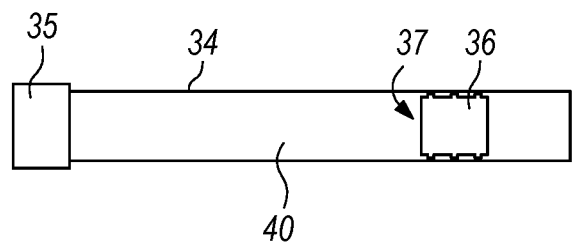
PRIOR ART   *FIG. 5A*
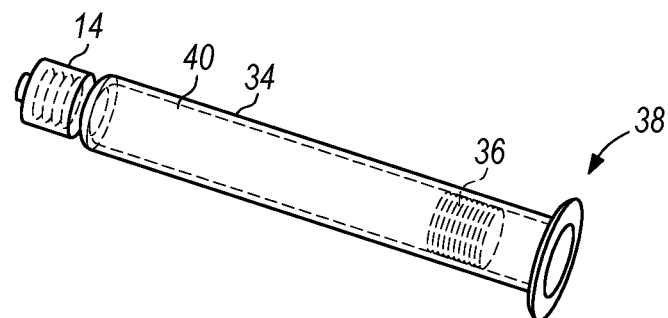
PRIOR ART   *FIG. 5B*
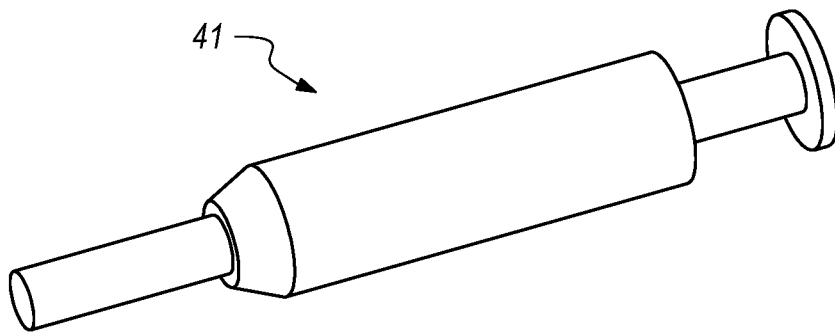
PRIOR ART   *FIG. 5C*

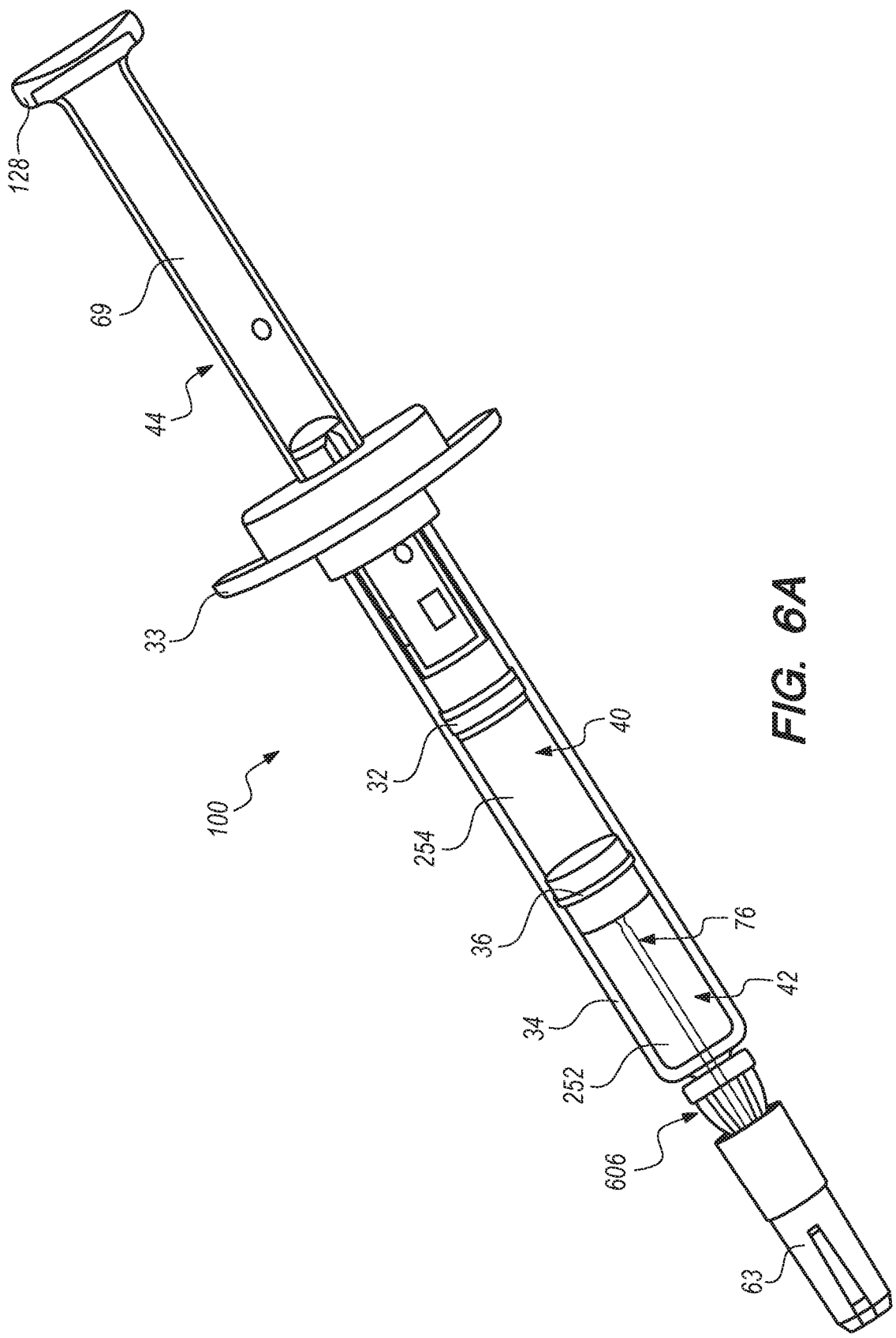

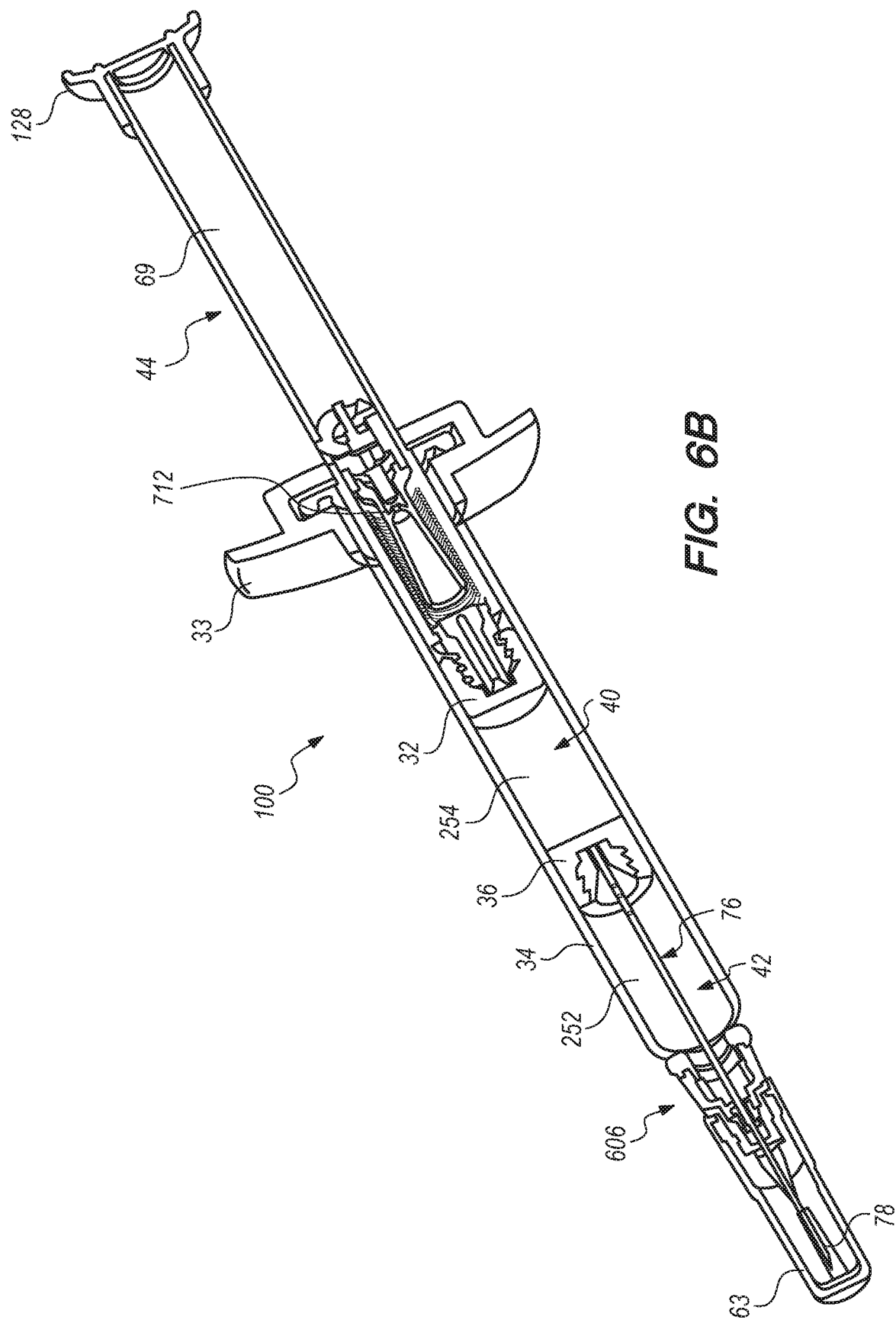

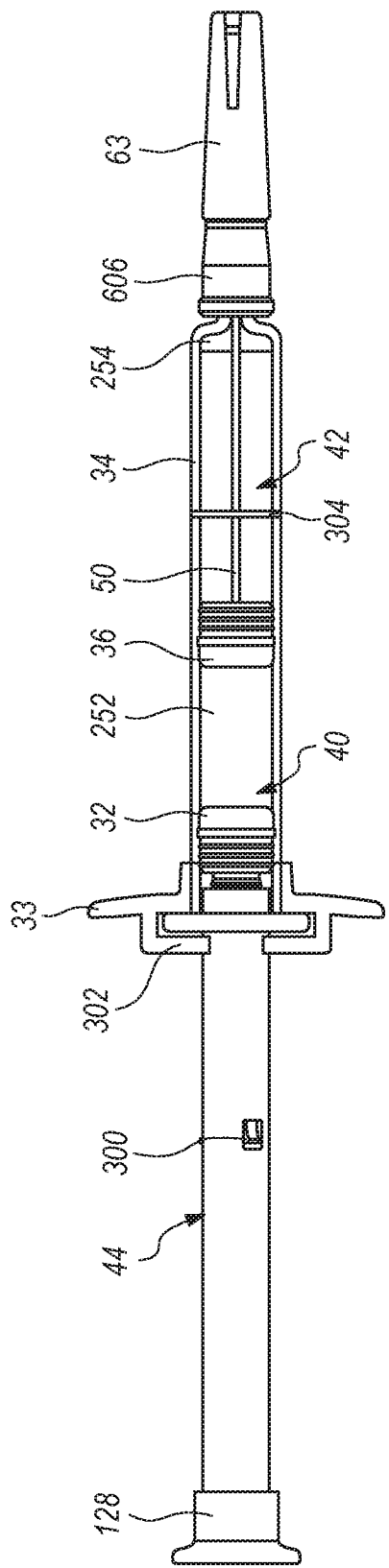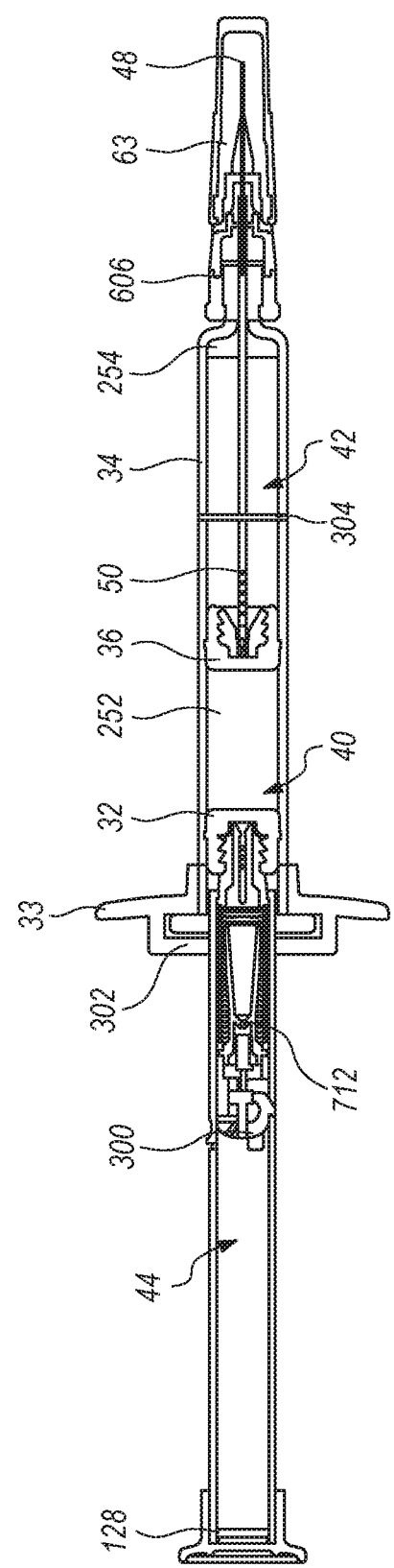
FIG. 7A
FIG. 7B

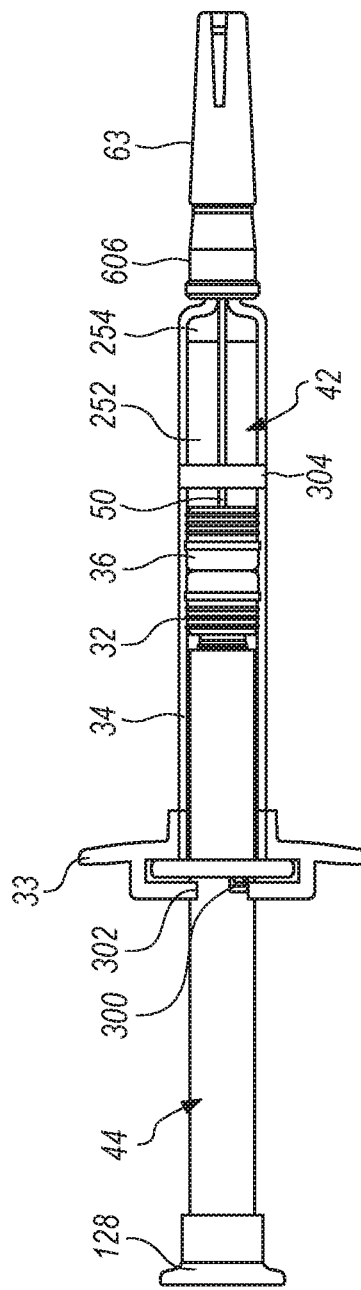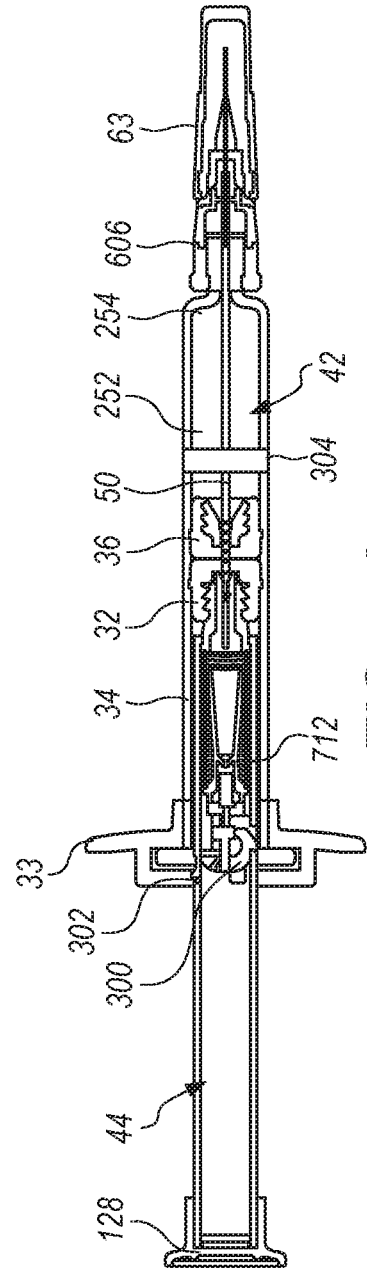

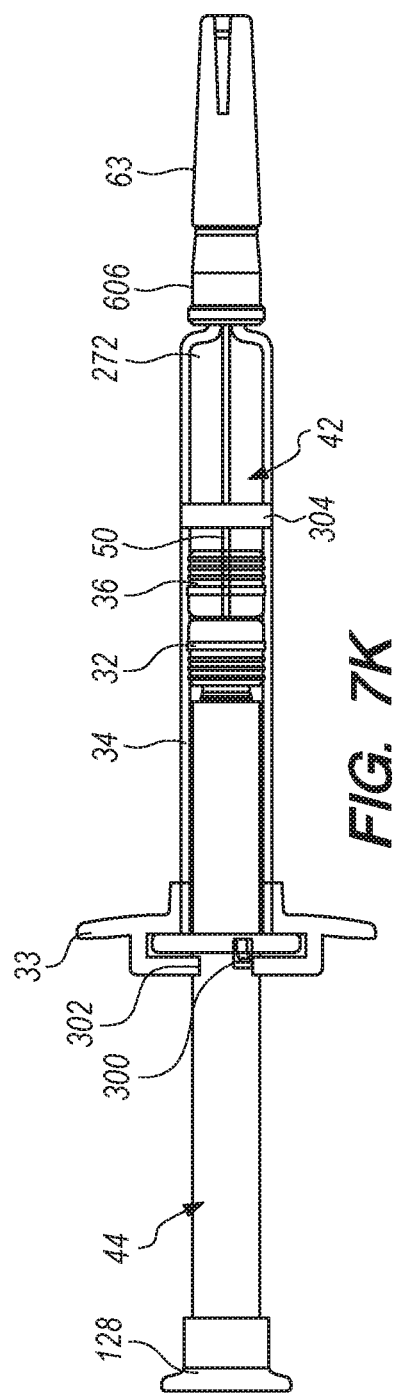
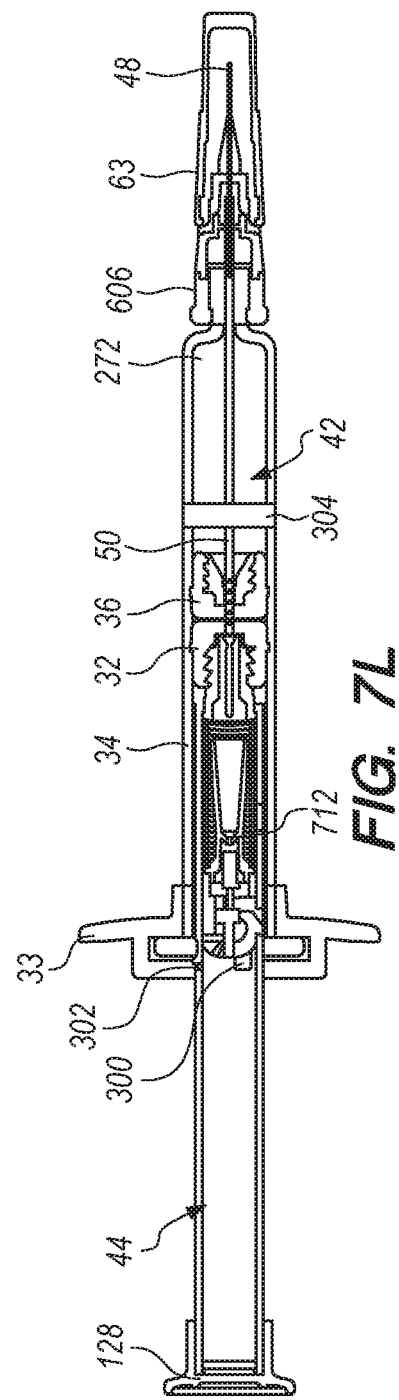
FIG. 7K
FIG. 7L

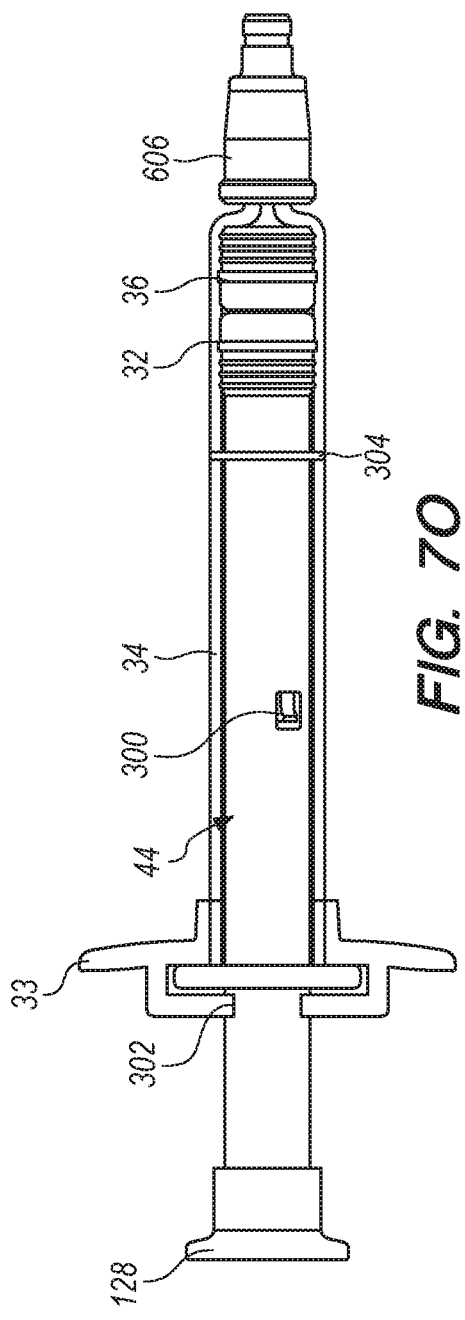
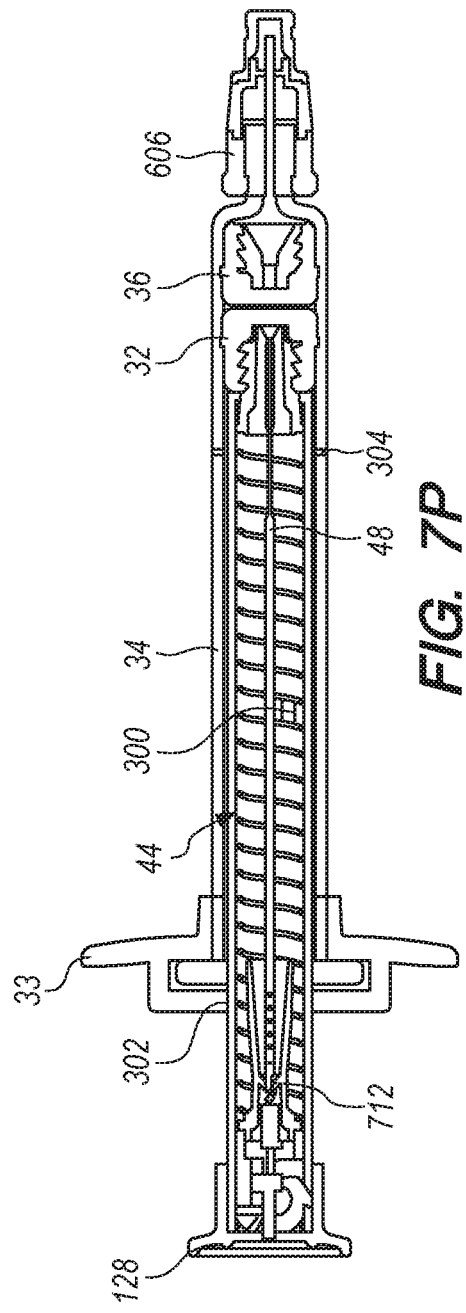
FIG. 7O
FIG. 7P

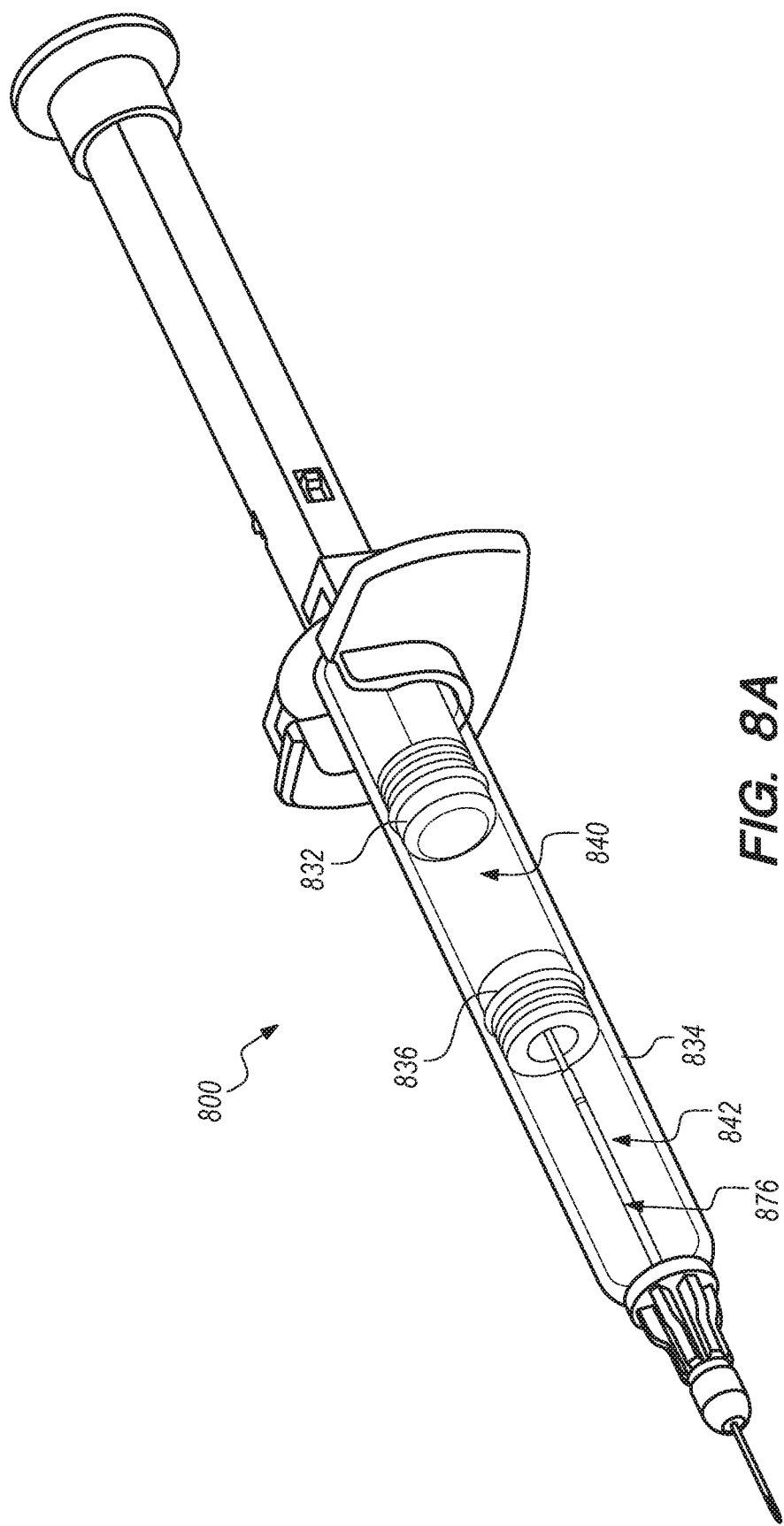

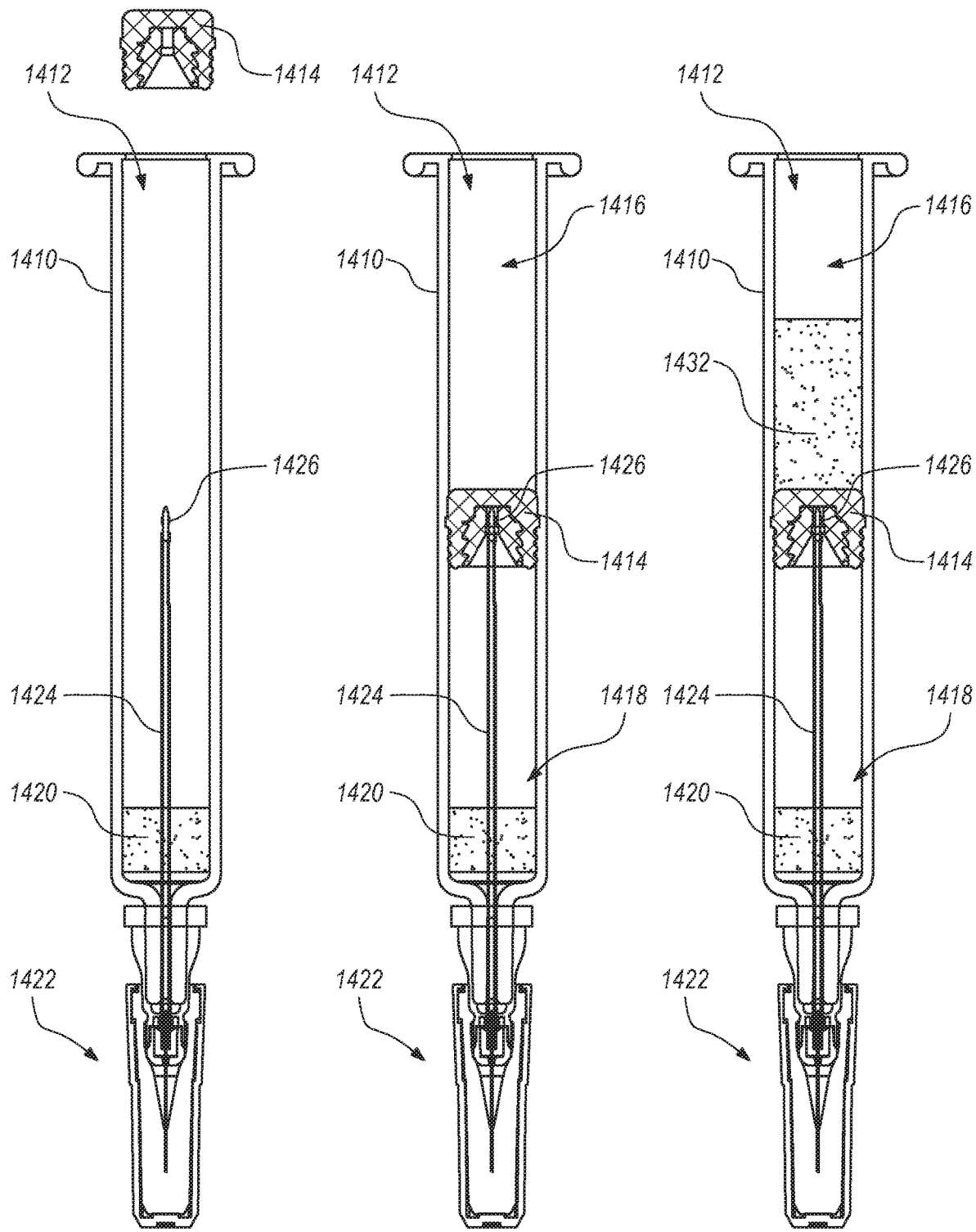

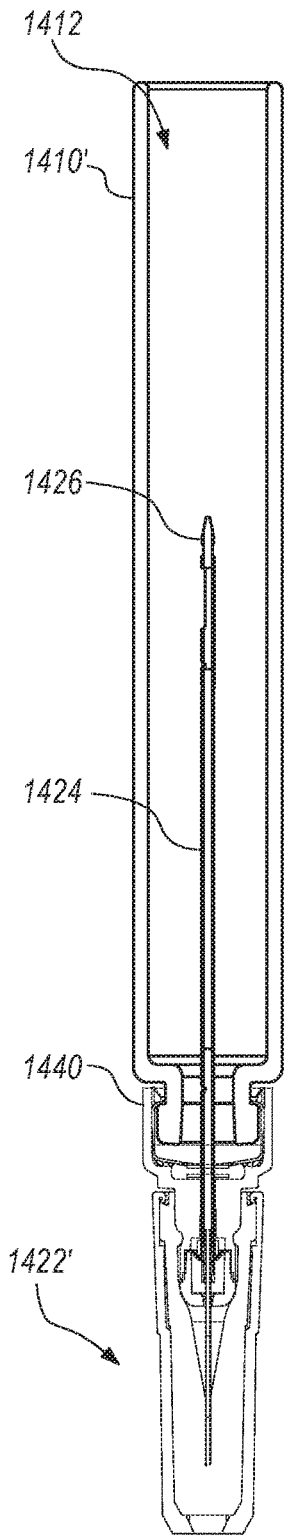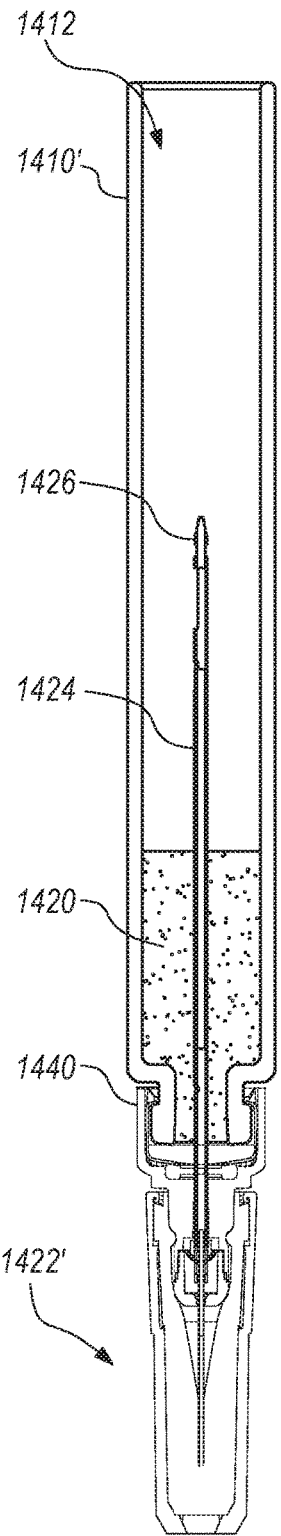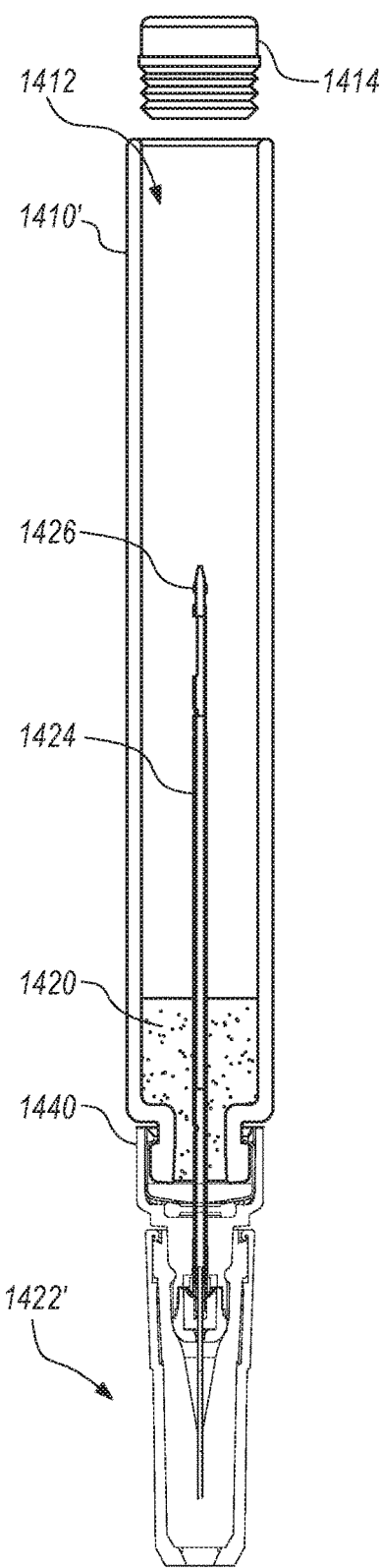
*FIG. 27A*     *FIG. 27B*     *FIG. 27C*

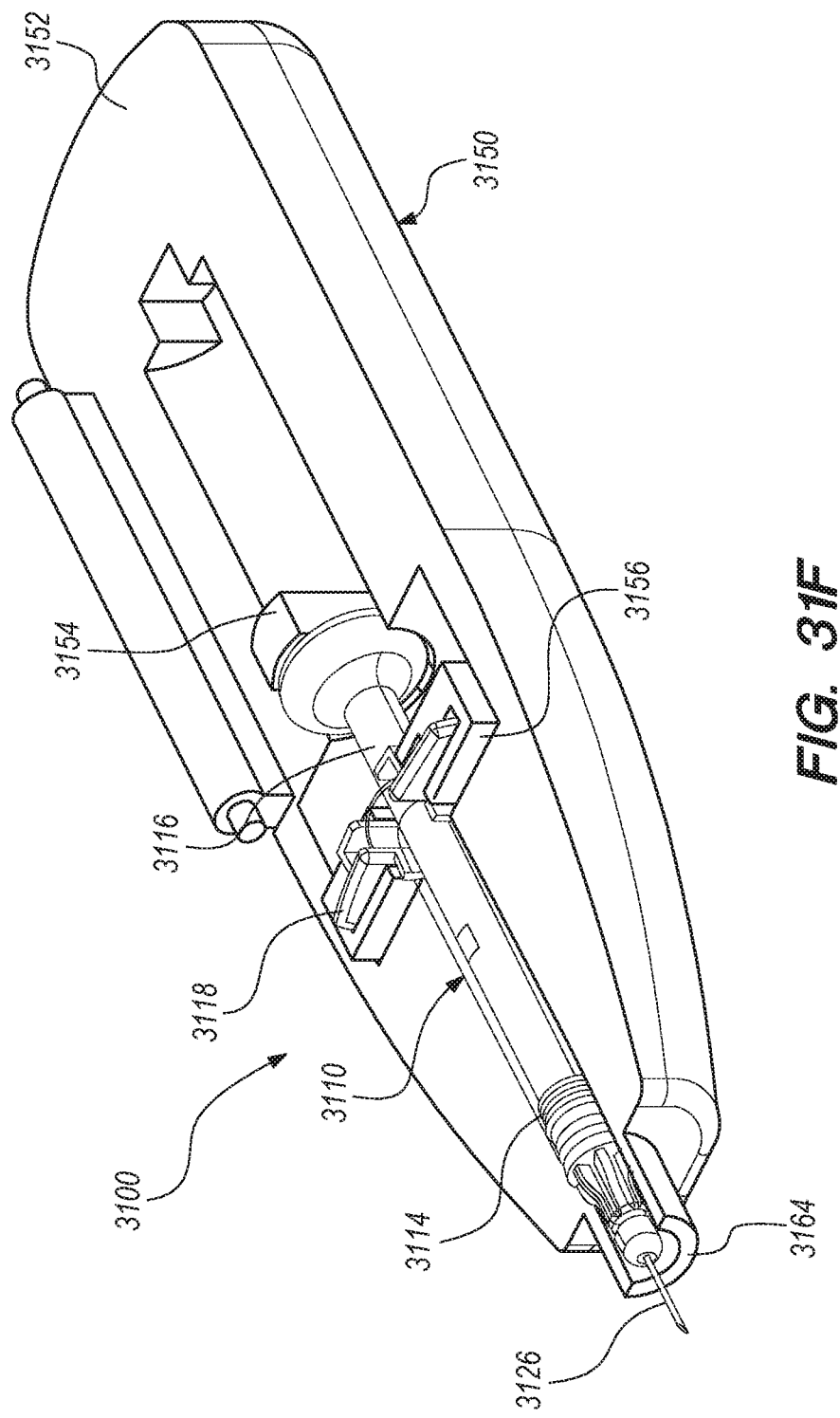

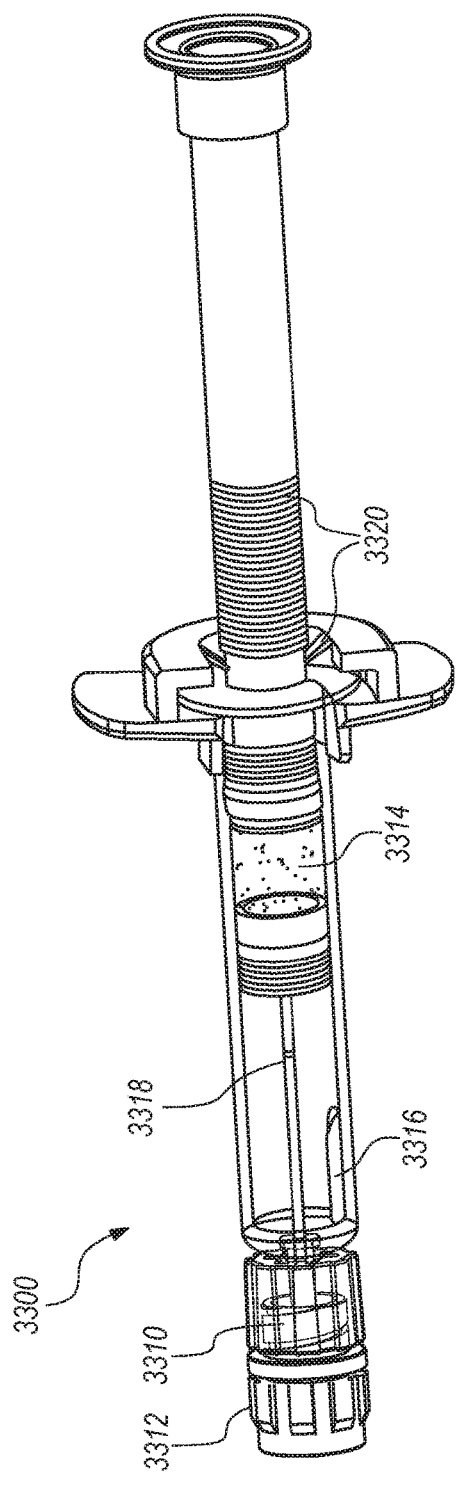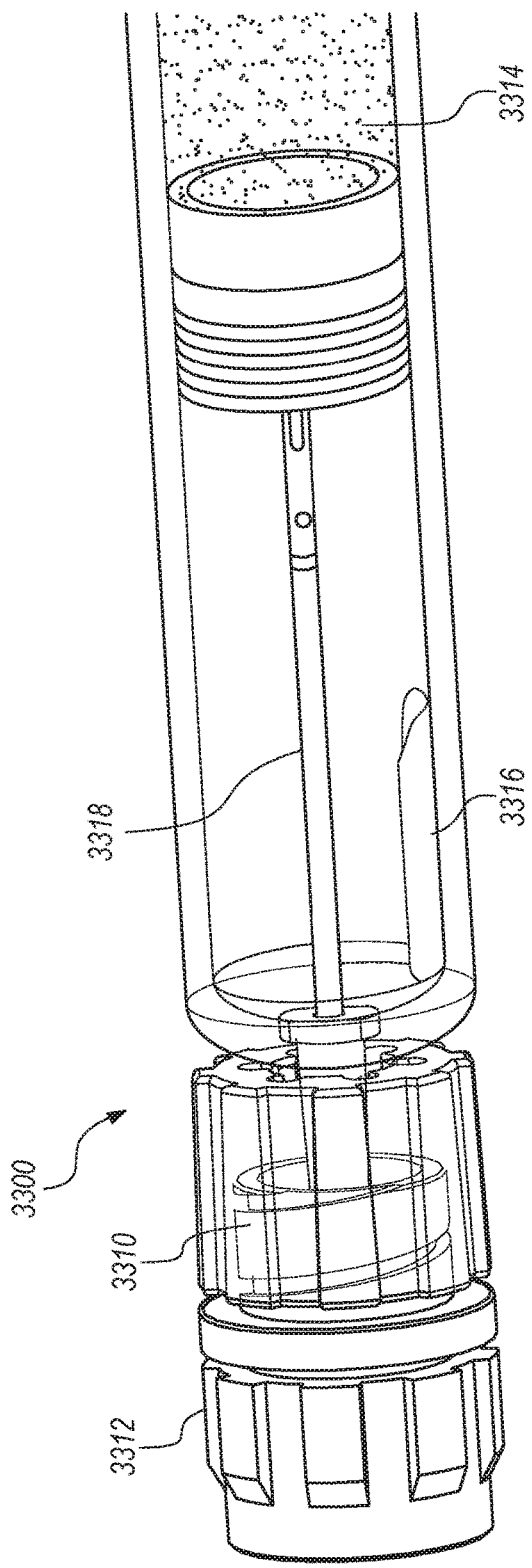
FIG. 33
FIG. 34

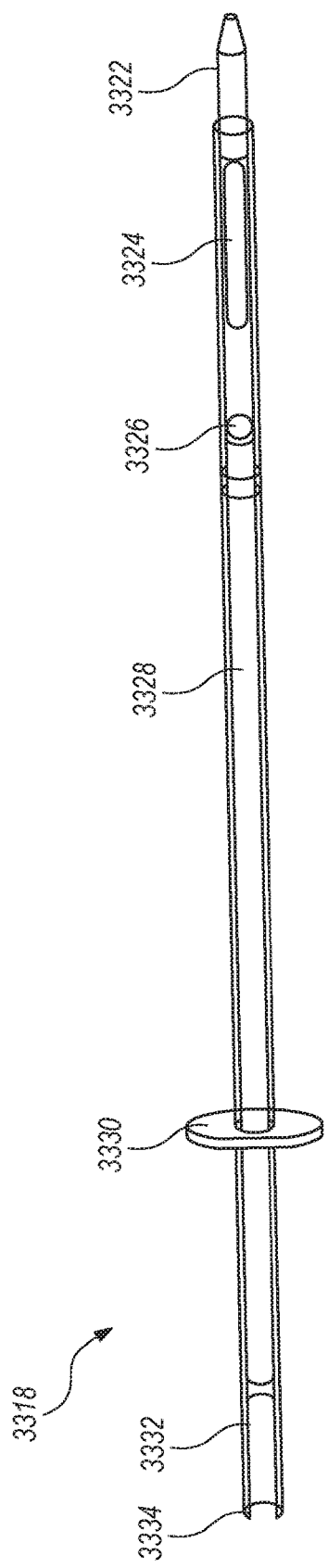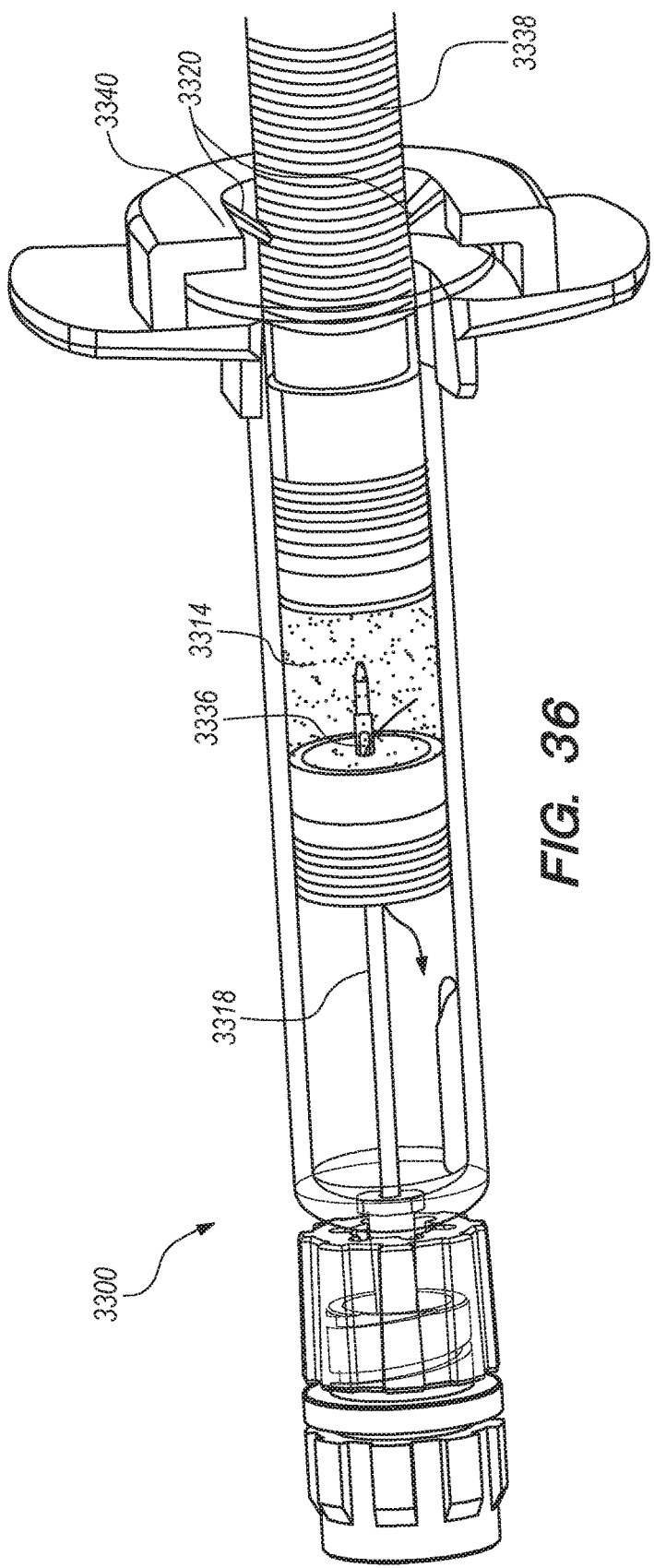

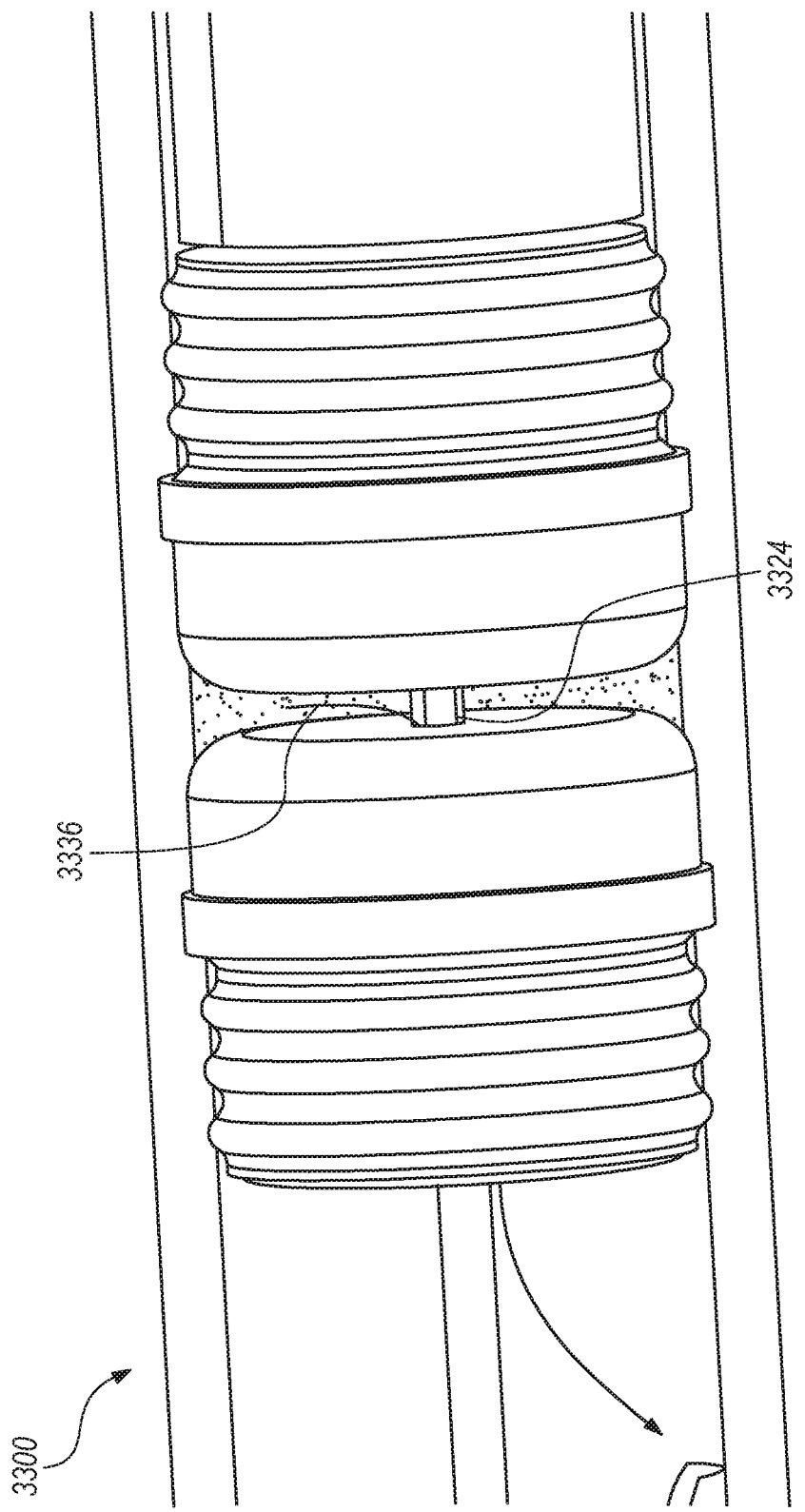

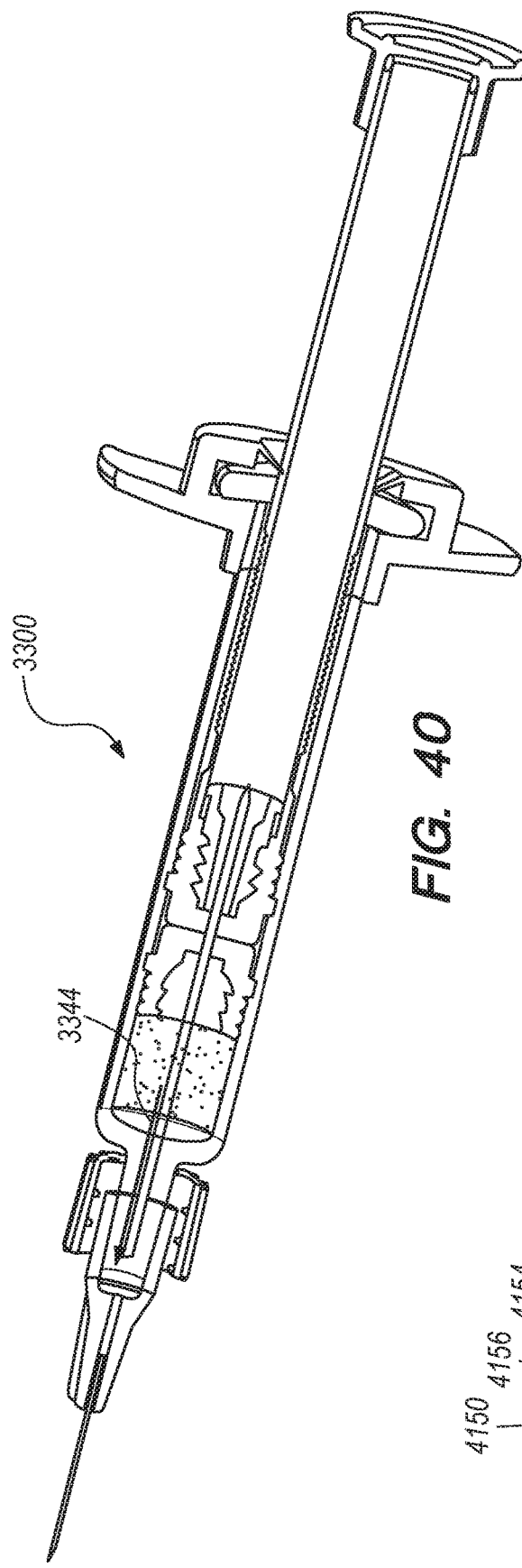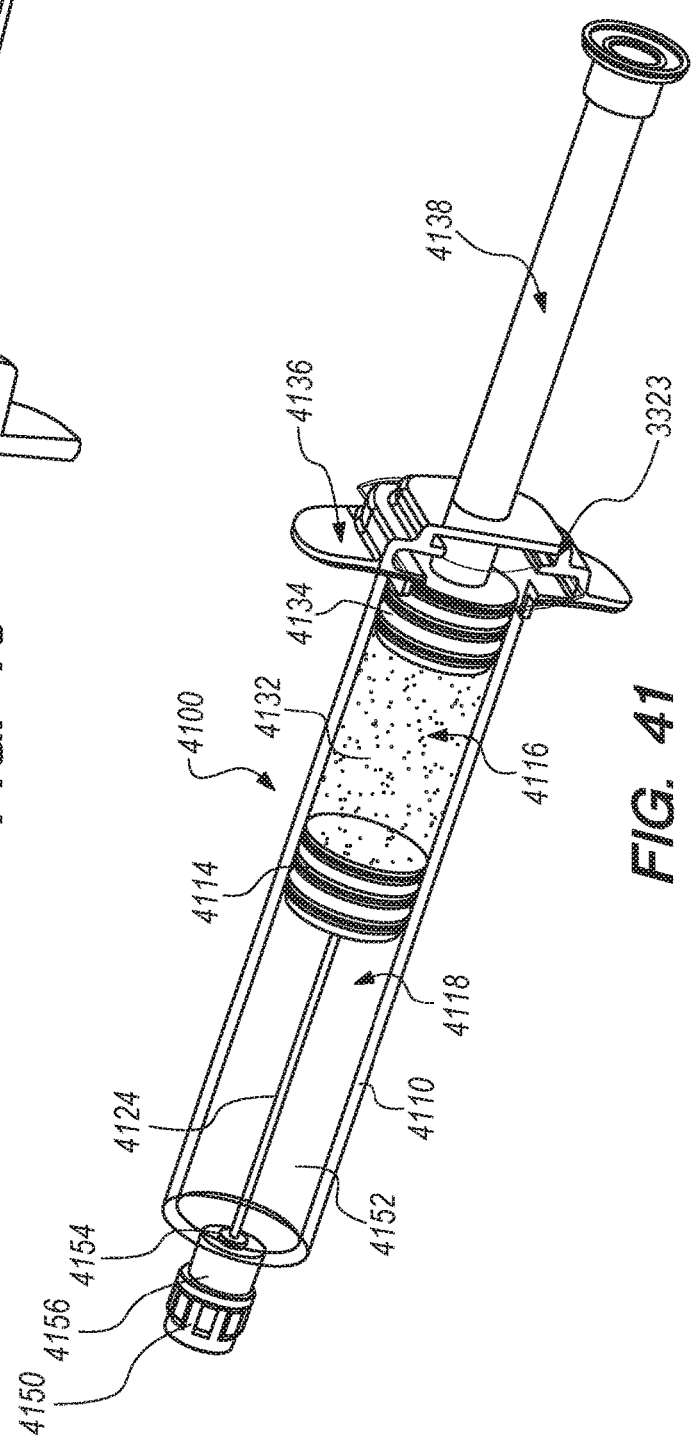
FIG. 40
FIG. 41

SYSTEM AND METHOD FOR SAFETY SYRINGE

The present application claims priority to (1) U.S. Provisional Patent Application Ser. No. 62/809,369, filed on Feb. 22, 2019, and entitled "SYSTEM AND METHOD FOR SAFETY SYRINGE" and (2) U.S. Provisional Patent Application Ser. No. 62/864,509, filed on Jun. 21, 2019, and entitled "SYSTEM AND METHOD FOR SAFETY SYRINGE." This application also includes subject matter similar to the subject matter described in the following co-owned U.S. patent applications: (3) U.S. Utility patent application Ser. No. 14/321,706, filed Jul. 1, 2014 and entitled "SAFETY SYRINGE"; (4) U.S. Utility patent application Ser. No. 14/543,787, filed Nov. 17, 2014 and entitled "SYSTEM AND METHOD FOR DRUG DELIVERY WITH A SAFETY SYRINGE"; (5) U.S. Utility patent application Ser. No. 14/696,342, filed Apr. 24, 2015 and entitled "SYSTEM AND METHOD FOR SAFETY SYRINGE"; (6) U.S. Utility patent application Ser. No. 15/801,239, filed on Nov. 1, 2017 and entitled "SYSTEM AND METHOD FOR SAFETY SYRINGE"; (7) U.S. Utility patent application Ser. No. 15/801,259, filed on Nov. 1, 2017 and entitled "SYSTEM AND METHOD FOR SAFETY SYRINGE"; (8) U.S. Utility patent application Ser. No. 15/801,281 filed on Nov. 1, 2017 and entitled "CARTRIDGE SAFETY INJECTION SYSTEM AND METHODS"; (9) U.S. Utility patent application Ser. No. 15/801,304 filed on Nov. 1, 2017 and entitled "SYSTEM AND METHOD FOR SAFETY SYRINGE"; (10) U.S. Provisional Patent Application Ser. No. 62/682,381 filed on Jun. 8, 2018 and entitled "SYSTEM AND METHOD FOR SAFETY SYRINGE"; and (11) U.S. Provisional Patent Application Ser. No. 62/729,880 filed on Sep. 11, 2018 and entitled "SYSTEM AND METHOD FOR SAFETY SYRINGE." The contents of the above-mentioned applications are fully incorporated herein by reference as though set forth in full.

FIELD OF THE INVENTION

The present invention relates generally to injection systems, devices, and processes for facilitating various levels of control over fluid infusion, and more particularly to systems and methods related to multiple chamber safety syringes in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling. The use of needle injection configurations, on the other hand, carries with it the risk of a sharp needle contacting or stabbing a person or structure that is not desired. For this reason, so called "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for prefilled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross-sectional shape may establish a seal against the syringe body (34)), or be configured to have other cross-sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

In some cases, multi-component injection systems may mix injectable components (e.g., liquids, solid, and/or powders) before injection. Several multiple chamber injection systems configured to mix and injection multiple components are disclosed in U.S. Utility patent application Ser. No. 14/696,342, which was previously incorporated by reference herein.

Moreover, an increasing number of injectable liquids (e.g., medicines) have an additional requirement that two or more components are preferably injected serially (e.g., into a patient) within a short time (e.g., seconds) of each other. Multiple components can be injected serially using separate injection devices (e.g., pre-loaded syringes) or using the same injection device to serially draw the multiple components from separate open containers and serially inject them. However, such serial injection using separate injection devices or serially drawing and injecting the multiple components necessarily results in multiple needle insertions into a patient, and can be inaccurate and lead to loss of components. Further, serial injection using separate injection devices or serially drawing the multiple components into a syringe can lead to unnecessary exposure of a user to one or more uncapped needles. Moreover, serial injection using separate injection devices or serially drawing and injecting the multiple components can cause an unacceptable lag between injections of the multiple components. Several multiple chamber injection systems that address these serial injection issues are disclosed in U.S. Provisional Patent Application Ser. No. 62/682,381, which was previously incorporated by reference herein.

In addition, an increasing number of injectable liquids (e.g., medicines) have yet another requirement that time of exposure of the injectable liquid to metals (e.g., stainless steel of a needle) be minimized. Still another requirement is the desirability of systems suitable for patient self-injection.

It is also desirable to incorporate needle stick prevention technology into the injection system. The ability to retract the sharp end of the needle at least partially inside of the syringe protects the person giving the injection and the patient from inadvertent needle stick injuries.

There is a need for injection systems which address the shortcomings of currently-available configurations. In particular, there is a need for multiple chamber safety injection solutions which may utilize the existing and relatively well-controlled supply chain of conventionally delivered prefilled syringe assemblies such as those described in reference to FIGS. 5A and 5B.

SUMMARY

Embodiments are directed to injection systems. In particular, the embodiments are directed to multiple chamber safe injection systems that move the needle into a protected configuration to minimize accidental user injury and contamination with used needles.

In one embodiment, a method for preparing a pre-filled multi-chamber injection system includes providing an injection system body, the injection system body defining an open proximal end, a body interior, and an open distal end. The method also includes introducing a first substance into a distal end of the body interior. The method further includes disposing a distal stopper member in the body interior through the open proximal end of the injection system body, the distal stopper member and the injection system body defining proximal and distal chambers in the body interior, wherein the first substance is disposed in the distal chamber. Moreover, the method includes introducing a second substance into the body interior. In addition, the method includes disposing a proximal stopper member in the body interior through the open proximal end of the injection system body, such that the proximal stopper member defines a proximal end of the proximal chamber, wherein the second substance is disposed in the proximal chamber. The method also includes inserting an elongate member at least partially into the body interior, the elongate member having a plurality of flow channels for fluidly coupling the proximal and distal chambers and a proximal end configured to penetrate the distal stopper member. The method further includes coupling a plunger member to the proximal stopper member.

In one or more embodiments, introducing the first substance into the distal end of the body interior includes introducing a liquid into the distal end of the body interior and lyophilizing the liquid. Introducing the first substance into the distal end of the body interior may include introducing a powder or solid into the distal end of the body interior. The method may include disposing the injection system body in a rack in a first configuration before disposing the distal stopper member in the body interior, where, when the injection system body is in the first configuration, the distal end of the injection system body is pointed in a downward direction. The method may also include turning the injection system body in the rack to a second configuration before introducing the first substance into the distal chamber through the open distal end, where, when the injection system body is in the first configuration, the proximal end of the injection system body is pointed in a downward direction. The method may include returning the injection system body in the rack to the first configuration before introducing a second substance into the body interior and disposing the proximal stopper member in the body.

In one or more embodiments, the rack includes a feature to hold the injection method body in the first and second configurations in the rack. The distal stopper member may include a funnel therein, the method further including the funnel guiding the needle proximal end to a center of the distal stopper member. The funnel may include a U-shaped retaining member/detent. The needle proximal end may include a 3D arrowhead shape, the method further including the 3D arrowhead interfering with the U-shaped retaining member/detent to temporarily prevent distal movement of the distal stopper member. The method may include lyophilizing the first substance in distal chamber before coupling the needle hub assembly to the distal end of the injection system body.

In one or more embodiments, the method includes utilizing a pressure differential on proximal and distal sides of the proximal stopper member to insert the proximal stopper member into the body interior through the open proximal end of the injection system body. The method may include maintaining a vacuum in the proximal chamber during insertion of the proximal stopper member into the body interior through the open proximal end of the injection system body. The method may include disposing the proximal stopper member above the open proximal end of the injection system body before inserting the proximal stopper member into the body interior. The method may include disposing a tube adjacent the proximal stopper member such that the proximal chamber is fluidly coupled to an atmosphere during insertion of the proximal stopper member into the body interior through the open proximal end of the injection system body. The method may include maintaining a vacuum in the distal chamber during the method. The method may include performing one or more steps of the method in a vacuum.

In one or more embodiments, the method includes coupling a flange to the injection system body such that the flange is preventing from moving along a longitudinal axis and the plunger is moveable on the longitudinal axis relative to the flange. The method may include coupling the plunger to the proximal stopper member to facilitate movement of the proximal stopper member along the longitudinal axis. The injection system body, the needle hub assembly, and the proximal and distal stopper members may be pre-sterilized. The method may include preparing a plurality of pre-filled multi-chamber injection systems. The method may include introducing a third substance into the body interior through the open proximal end, and disposing a second proximal stopper member in the body interior through the open proximal end of the injection system body, such that the second proximal stopper member defines a proximal end of a second proximal chamber, where the third substance is disposed in the second proximal chamber.

In one embodiment, a method for preparing a pre-filled multi-chamber injection system includes disposing an injection system body (syringe/cartridge) in a rack in a first configuration, the injection system body defining an open proximal end, a body interior, and an open distal end, where, when the injection system body is in the first configuration, the distal end of the injection system body is pointed in a downward direction. The method also includes disposing a distal stopper member in the body interior through the open proximal end of the injection system body, the distal stopper member and the injection system body defining proximal and distal chambers in the body interior. The method further includes turning the injection system body in the rack to a second configuration, in which the proximal end of the injection system body is pointed in the downward direction. Moreover, the method includes introducing a first substance into the distal chamber through the open distal end. In addition, the method includes coupling a needle hub assembly to the distal end of the injection system body, the needle hub assembly including a needle having a needle proximal end, such that the needle proximal end interferes with the distal stopper member to temporarily prevent distal movement of the distal stopper member. The method also includes returning the injection system body in the rack to the first configuration. The method further includes introducing a second substance into the body interior through the open proximal end. Moreover, the method includes disposing a proximal stopper member in the body interior through the open proximal end of the injection system body, such that the proximal stopper member defines a proximal end of the proximal chamber, where the second substance is disposed in the proximal chamber.

In another embodiment, a method for preparing a pre-filled multi-chamber injection system includes coupling a needle hub assembly to an injection system body (syringe/cartridge), the needle hub assembly including a needle having a needle proximal end, and the injection system body defining an open proximal end, a body interior, and a distal end closed by the needle hub assembly. The method also includes disposing the injection system body in a rack in a first configuration, where, when the injection system body is in the first configuration, the distal end of the injection system body is pointed in a downward direction. The method further includes introducing a first substance into the body interior through the open proximal end. Moreover, the method includes disposing a distal stopper member in the body interior through the open proximal end of the injection system body, the distal stopper member and the injection system body defining proximal and distal chambers in the body interior, such that the needle proximal end interferes with the distal stopper member to temporarily prevent distal movement of the distal stopper member, where the first substance is disposed in the distal chamber. In addition, the method includes introducing a second substance into the syringe interior through the open proximal end. The method also includes disposing a proximal stopper member in the body interior through the open proximal end of the injection system body, such that the proximal stopper member defines a proximal end of the proximal distal chamber, where the second substance is disposed in the proximal chamber.

In still another embodiment, a method for preparing a pre-filled multi-chamber cartridge includes disposing a cartridge body in a rack in a first configuration, the cartridge body defining an open proximal end, a body interior, and an open distal end. When the cartridge body is in the first configuration, the distal end of the cartridge body is pointed in a downward direction. The method also includes disposing a distal stopper member in the body interior through the open proximal end of the cartridge body, the distal stopper member and the cartridge body defining proximal and distal chambers in the body interior. The method further includes turning the cartridge body in the rack to a second configuration, in which the proximal end of the cartridge body is pointed in the downward direction. Moreover, the method includes introducing a first substance into the distal chamber through the open distal end. In addition, the method includes optionally coupling a cartridge cap to the distal end of the cartridge body. The method also includes coupling a needle hub assembly to the distal end of the cartridge body over the cartridge cap, the needle hub assembly including a needle having a needle proximal end, such that the needle proximal end interferes with the distal stopper member to temporarily prevent distal movement of the distal stopper member. The method further includes returning the cartridge body in the rack to the first configuration. Moreover, the method includes introducing a second substance into the body interior through the open proximal end. In addition, the method includes disposing a proximal stopper member in the body interior through the open proximal end of the cartridge body, such that the proximal stopper member defines a proximal end of the proximal chamber, where the second substance is disposed in the proximal chamber.

In yet another embodiment, a method for preparing a pre-filled multi-chamber cartridge includes optionally coupling a cartridge cap to a cartridge body, the cartridge body defining an open proximal end, a body interior, and a distal end closed by the cartridge cap. The method also includes coupling a needle hub assembly to the distal end of the cartridge body over the cartridge cap, the needle hub assembly including a needle having a needle proximal end. The method further includes disposing the cartridge body in a rack in a first configuration, where, when the cartridge body is in the first configuration, the distal end of the cartridge body is pointed in a downward direction. Moreover, the method includes introducing a first substance into the body interior through the open proximal end. In addition, the method includes disposing a distal stopper member in the body interior through the open proximal end of the cartridge body, the distal stopper member and the cartridge body defining proximal and distal chambers in the body interior, such that the needle proximal end interferes with the distal stopper member to temporarily prevent distal movement of the distal stopper member, where the first substance is disposed in the distal chamber. The method also includes introducing a second substance into the syringe interior through the open proximal end. The method further includes disposing a proximal stopper member in the body interior through the open proximal end of the cartridge body, such that the proximal stopper member defines a proximal end of the proximal chamber, where the second substance is disposed in the proximal chamber.

In another embodiment, a method for preparing a pre-filled multi-chamber cartridge includes optionally coupling a cartridge cap to a cartridge body, the cartridge body defining an open proximal end, a body interior, and a distal end closed by the cartridge cap. The method also includes disposing the cartridge body in a rack in a first configuration, where, when the cartridge body is in the first configuration, the distal end of the cartridge body is pointed in a downward direction. The method further includes introducing a first substance into the body interior through the open proximal end. Moreover, the method includes disposing a distal stopper member in the body interior through the open proximal end of the cartridge body, the distal stopper member and the cartridge body defining proximal and distal chambers in the body interior, such that the needle proximal end interferes with the distal stopper member to temporarily prevent distal movement of the distal stopper member, where the first substance is disposed in the distal chamber. In addition, the method includes coupling a needle hub assembly to the distal end of the cartridge body over the cartridge cap, the needle hub assembly including a needle having a needle proximal end, such that the needle proximal end pierces the cartridge cap. The method also includes introducing a second substance into the syringe interior through the open proximal end. The method further includes disposing a proximal stopper member in the body interior through the open proximal end of the cartridge body, such that the proximal stopper member defines a proximal end of the proximal chamber, where the second substance is disposed in the proximal chamber.

In still another embodiment, a method for preparing a pre-filled multi-chamber cartridge includes disposing a cartridge body in a rack in a first configuration, the cartridge body defining an open proximal end, a body interior, and an open distal end. When the cartridge body is in the first configuration, the distal end of the cartridge body is pointed in a downward direction. The method also includes disposing a distal stopper member in the body interior through the open proximal end of the cartridge body, the distal stopper member and the cartridge body defining proximal and distal chambers in the body interior. The method further includes turning the cartridge body in the rack to a second configuration, in which the proximal end of the cartridge body is pointed in the downward direction. Moreover, the method includes introducing a first substance into the distal chamber through the open distal end. In addition, the method includes coupling a cartridge cap to the distal end of the cartridge body, the cartridge cap including a transfer tube, such that the transfer tube interferes with the distal stopper member to temporarily prevent distal movement of the distal stopper member. The method also includes returning the cartridge body in the rack to the first configuration. The method further includes introducing a second substance into the body interior through the open proximal end. Moreover, the method includes disposing a proximal stopper member in the body interior through the open proximal end of the cartridge body, such that the proximal stopper member defines a proximal end of the proximal chamber, where the second substance is disposed in the proximal chamber.

In yet another embodiment, a method for preparing a pre-filled multi-chamber cartridge includes optionally coupling a cartridge cap to a cartridge body, the cartridge body defining an open proximal end, a body interior, and a distal end closed by the cartridge cap. The method also includes piercing the cartridge cap with a transfer tube. The method further includes disposing the cartridge body in a rack in a first configuration, where, when the cartridge body is in the first configuration, the distal end of the cartridge body is pointed in a downward direction. Moreover, the method includes introducing a first substance into the body interior through the open proximal end. In addition, the method includes disposing a distal stopper member in the body interior through the open proximal end of the cartridge body, the distal stopper member and the cartridge body defining proximal and distal chambers in the body interior, such that the transfer tube interferes with the distal stopper member to temporarily prevent distal movement of the distal stopper member, where the first substance is disposed in the distal chamber. The method also includes introducing a second substance into the syringe interior through the open proximal end. The method further includes disposing a proximal stopper member in the body interior through the open proximal end of the cartridge body, such that the proximal stopper member defines a proximal end of the proximal chamber, where the second substance is disposed in the proximal chamber.

In one or more embodiments, the method includes coupling a flange and a plunger member to the injection system body such that the flange is preventing from moving along a longitudinal axis and the plunger is moveable on the longitudinal axis.

In still another embodiment, an autoinjector system includes a disposable injection system (syringe/cartridge) and a reusable drive system. The disposable injection system includes an injection system body having proximal and distal ends, and an injection system body interior therebetween. The disposable injection system also includes a stopper member disposed in the injection system body interior. The disposable injection system further includes a plunger member coupled to the stopper member. Moreover, the disposable injection system includes a finger flange coupled to the injection system body at the proximal end thereof. In addition, the disposable injection system includes a needle hub assembly coupled to the injection system body at the distal end thereof. The disposable injection system also includes a rigid needle shield coupled to the needle hub assembly. The reusable drive system includes a drive system body having a drive system body interior. The disposable injection system also includes a plunger actuator/pusher to move the plunger member distally relative to the injection system body when the injection system is mounted in the drive system. The disposable injection system further includes a flange holder/carriage to move the injection system distally and/or proximally relative to the drive system body when the injection system is mounted in the drive system.

In one or more embodiments, the drive system includes a first motor to move the plunger actuator/pusher, a second motor to move the flange holder/carriage, a controller operatively coupled to the first and second motors, a display operatively coupled to the controller, and a sensor operative coupled to the controller. The sensor may be selected from the group consisting of an accelerometer, a contact sensor, a position sensor, a gyroscope, a thermometer, and a skin contact sensor. The drive system may include a plurality of sensors.

In yet another embodiment, an autoinjector system includes a disposable injection system (syringe/cartridge) and a reusable drive system. The disposable injection system includes an injection system body having proximal and distal ends, and an injection system body interior therebetween, The disposable injection system also includes first and second stopper members disposed in the injection system body interior, the first stopper member and the injection system body defining a first chamber, the first and second stopper members and the injection system body defining a second chamber. The disposable injection system further includes a plunger member coupled to the second stopper member. Moreover, the disposable injection system includes a finger flange coupled to the injection system body at the proximal end thereof. In addition, the disposable injection system includes a needle hub assembly coupled to the injection system body at the distal end thereof. The disposable injection system also includes a rigid needle shield coupled to the needle hub assembly. The reusable drive system includes a drive system body having a drive system body interior. The reusable drive system also includes a plunger actuator/pusher to move the plunger member distally relative to the injection system body when the injection system is mounted in the drive system. The reusable drive system further includes a flange holder/carriage to move the injection system distally and/or proximally relative to the drive system body when the injection system is mounted in the drive system.

In one or more embodiments, the drive system includes a first motor to move the plunger actuator/pusher, a second motor to move the flange holder/carriage, a controller operatively coupled to the first and second motors, a display operatively coupled to the controller, and a sensor operative coupled to the controller. The sensor may be selected from the group consisting of accelerometer, a contact sensor, a position sensor, a gyroscope, a thermometer, and a skin contact sensor. The drive system may include a plurality of sensors.

In another embodiment, a method for automatically mixing and injecting substances includes providing the autoinjector system described above with the injection system mounted in the drive system, and the plunger actuator/pusher and flange holder/carriage in a proximal first position. The method also includes the controller causing the first motor to move the plunger actuator and the plunger member and the second stopper member operatively coupled thereto distally relative to the injection system body to transfer a fluid from the second chamber to the first chamber to form an injectable medicine. The method further includes the controller causing the first motor to move the plunger actuator and the plunger member and the second stopper member operatively coupled thereto further distally relative to the injection system body to inject the injectable medicine through the needle hub assembly.

In one or more embodiments, the method includes the controller causing the display to render a message instructing a user to agitate the device to enhance mixing of the fluid with a powder in the first chamber to form the injectable medicine. The method may include the controller causing the display to render a message instructing the user to point the autoinjector system in an upward position and remove the rigid needle shield from the autoinjector system before the controller causes the first motor to move the plunger actuator and the plunger member and the second stopper member operatively coupled thereto further distally relative to the injection system body. The method may include the sensor detecting the upward position of the autoinjector system; and the controller causing the second motor to move the flange holder/carriage proximally relative to the drive system body to separate the rigid needle shield from the needle hub assembly only when the sensor detects the upward position of the autoinjector system.

In one or more embodiments, the method includes the controller causing the display to render a message instructing the user to position the autoinjector system in contact with a patient before the controller causes the first motor to move the plunger actuator and the plunger member and the second stopper member operatively coupled thereto further distally relative to the injection system body. The method may include the sensor detecting contact between the autoinjector system and the patient, and the controller causing the first motor to move the plunger actuator and the plunger member and the second stopper member operatively coupled thereto further distally relative to the injection system body only when the sensor detects the contact between the autoinjector system and the patient. The method may include the controller causing the display to render a message indicating an end of injection and instructing the user to remove the injection system after the controller causes the first motor to move the plunger actuator and the plunger member and the second stopper member operatively coupled thereto further distally relative to the injection system body.

In still another embodiment, a multiple chamber safe injection system includes a syringe body defining a syringe body interior and a distal coupling member at a distal end thereof. The system includes proximal and distal stopper members disposed in the syringe body interior, forming a proximal chamber between the proximal and distal stopper members and a distal chamber between the distal stopper member and the distal end of the syringe body. The system also includes a plunger member configured to be manually manipulated to insert the proximal stopper member relative to the syringe body. The system further includes a mix tube disposed in the syringe body interior. Moreover, the system includes a vent plug disposed at least partially in the distal coupling member and defining a plurality of channels configured to allow a gas to exit the syringe body interior while forming a liquid tight seal.

In yet another embodiment, an injection system includes a syringe body defining a proximal opening at a proximal end thereof and a distal needle interface at a distal end thereof. The system also includes proximal and distal stopper members disposed in the syringe body, forming a proximal drug chamber between the proximal and distal stopper members and a distal drug chamber between the distal stopper member and the distal end of the syringe body. The system further includes a plunger member configured to be manually manipulated to insert the proximal stopper member relative to the syringe body, where the plunger member has a smooth exterior surface. Moreover, the system includes a fluid conveying assembly. In addition, the system includes a finger flange including an anti-retraction mechanism. The anti-retraction mechanism has a brake tab configured to provide an opposing force to the plunger member to prevent proximal movement thereof relative to the brake tab, and a retention feature configured to maintain the anti-retraction mechanism in a recess in the finger flange.

In one or more embodiments, the finger flange also includes another recess configured to mount the finger flange on a flange of the syringe body. The anti-retraction mechanism may also include a plurality of fit tabs configured to reduce a tolerance between the recess and a dimension of the anti-retraction mechanism. The anti-retraction mechanism may be a metal clip.

In one or more embodiments, the brake tab is an elastic and self-energizing pawl. The brake tab may be disposed at an acute angle in a distal direction relative to a plane of the anti-retraction mechanism. The acute angle and an elasticity of the brake tab may increase a frictional force against the plunger member upon retraction in a proximal direction. The acute angle of the brake tab also creates a reaction force parallel to the plunger member, exerted by a sharp curved edge of the brake tab contacting the surface of the plunger member. This force also prevents the plunger member from moving in the proximal direction. The acute angle and an elasticity of the brake tab may cause the brake tab to exert an outward force through the anti-retraction mechanism to an inner wall of the finger flange when the plunger member is retracted in a proximal direction.

In one or more embodiments, the finger flange also includes an opening having an edge configured to interfere with and retain the anti-retraction mechanism in the recess. The anti-retraction mechanism may have a "C" or "O" shape. The anti-retraction mechanism may prevent removal of the plunger member from the syringe body after the plunger member has been inserted into the syringe body. The opposing force may include a frictional force and a reaction force. The brake tab may be configured to penetrate the smooth exterior surface of plunger member when the plunger member moves proximally relative to anti-retraction mechanism.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 1A to 5C illustrate various aspects of conventional injection syringe configurations.

FIGS. 6A and 6B illustrate various aspects of syringe based dual chamber safe injection systems wherein a distal needle end/tip may be withdrawn into a protected configuration after use according to some embodiments.

FIGS. 8A and 8B illustrate various aspects of syringe based dual chamber safe injection systems according to some embodiments.

FIGS. 19A to 19H illustrate various steps in a method for manufacturing/assembling a multiple chamber safe injection system according to some embodiments.

FIGS. 27A to 27G illustrate various steps in a method for manufacturing/assembling a multiple chamber safe injection system according to some embodiments.

FIGS. 31A to 31H illustrate various steps in a method for injecting a drug using an autoinjector according to some embodiments.

FIGS. 33 to 40 illustrate various steps in a method for mixing drug components and injecting the mixed drug using a syringe having a luer connector according to some embodiments.

FIGS. 41 and 42 to 47 illustrate various aspects of a multiple chamber safe injection system having a vent plug according to some embodiments.

Figure 3:
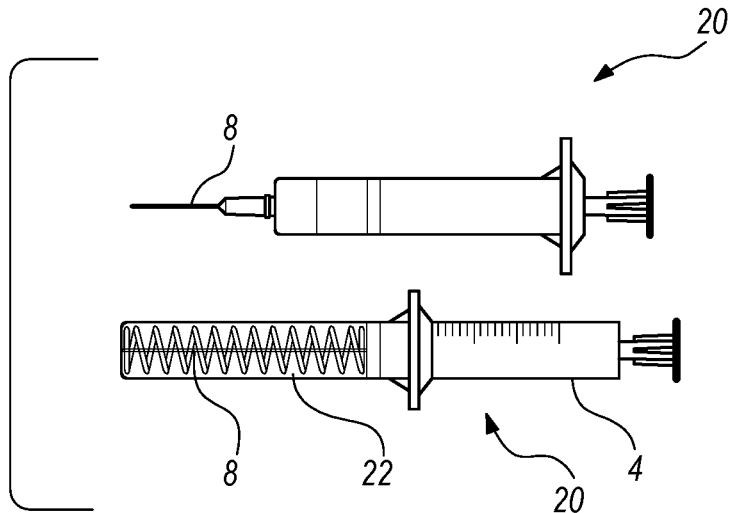
Figure 4A:
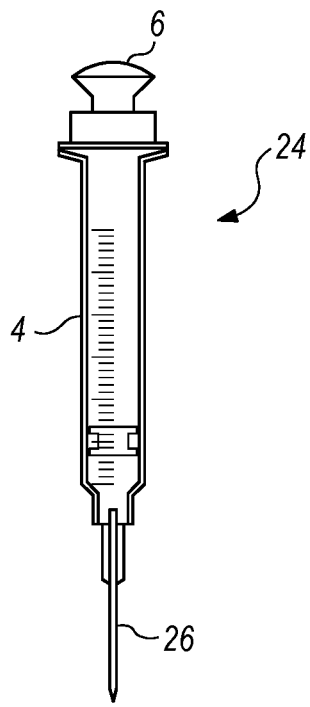
Figure 4B:
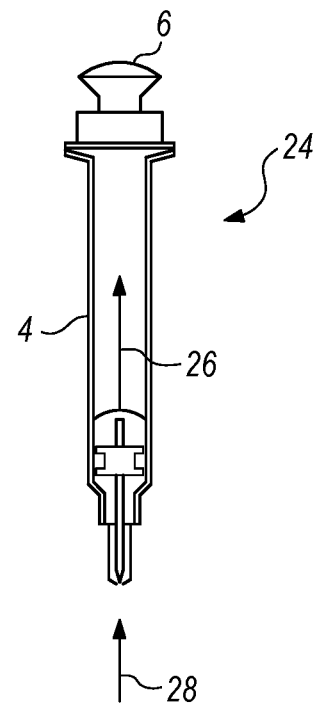

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Prefilled Dual Chamber Safe Injection Systems

Referring to FIGS. 6A and 6B, a perspective and a longitudinal cross-section view of a prefilled dual chamber safe injection system (100) are shown, with a conventional off-the-shelf prefilled syringe body (34) with conventional proximal and distal stopper members (32, 36) disposed therein. The proximal and distal stopper members (32, 36) together with the syringe body (34) define proximal and distal chambers (40, 42). The proximal and distal stopper members (32, 36) occlude the proximal and distal ends of the proximal chamber (40). The distal stopper member (36) occludes a proximal end of the distal chamber (42). In some embodiments, the distal end of the proximal stopper member (32) and the proximal end of the distal stopper member (36) may be coated with a lubricious polymer coating (e.g., PTFE), the first and second polymer coatings of the proximal and distal stopper members (32, 36), together with the syringe body (34) define the proximal chamber (40). The lubricious polymer coating also serves to isolate the rubber of the proximal and distal stopper members (32, 36) from the second liquid (254). The proximal and distal stopper members (32, 36) may be oriented as shown in FIGS. 6A and 6B or the distal stopper (36) may be flipped so the lubricious coating faces the distal chamber (42) such that the first liquid (252) in the distal chamber (42) contacts the lubricious coating for storage.

A needle coupling assembly (606) is disposed at the distal end of the distal chamber (42) with a needle cover member (63) installed for storage. The dual chamber safe injection system facilitates sequential injection of a first liquid (252) from the distal chamber (42) followed by injection of a second liquid (254) from the proximal chamber subject to sequential insertion of a plunger assembly (44) relative to the syringe body (34) to various degrees by a user. The plunger assembly (44) includes the proximal stopper member (32), a plunger housing member (69) and a plunger manipulation interface (128). The first and second liquids located in the distal and proximal chambers (42, 40) respectively may be any liquid or gel, such as aqueous or oil based medicine solutions.

The dual chamber safe injection system (100) has a staked needle configuration wherein upon presentation to the user, a needle assembly, including a needle spine assembly ("needle") (76) and a needle coupling assembly (606) are mounted in position ready for injection after removal of a needle cover member (63) which may comprise an elastomeric sealing material on its internal surface to interface with a needle distal end (78) and/or a distal housing portion during storage. Alternatively, the needle cover member (63) may comprise a vent (not shown) for allowing pressure resulting from the transfer of the liquids (252, 254) to escape from inside the syringe body (34) while preventing contamination from entering the syringe body (34). While, the staked needle is depicted as mounted in position, the staked needle may be removably coupled to the syringe body (34) using a Luer slip or a Luer lock interface (not shown), with the proximal end (50) of the needle member extending through the Luer interface and into the distal chamber (42). Alternatively, the needle may be fixedly or removably mounted to the flange on a cartridge body instead of a syringe. Such cartridge injection systems are disclosed in U.S. Utility patent application Ser. No. 15/801,281, which was previously incorporated by reference herein. In the embodiments depicted in FIGS. 6A and 6B, a significant portion of the safe needle retraction hardware resides within a plunger housing.

Referring to FIGS. 7A-7L, various aspects of configurations designed to facilitate injection of multi-part medications and retractions of a needle into a syringe body are illustrated, wherein two or more medication components are combined to form an injection combination or solution shortly before delivery into the patient. In one variation, a liquid first medicine component/diluent (252) may be combined with a substantially non-liquid second medicine component (254), such as a powdered and/or a solid (e.g., compressed powder) form, of a drug agent, such as a freeze-dried or lyophilized drug component, shortly before injection. The second medicine component (254) may be comprised of powdered medicine formed into a generally solid form. The solid form may be created by compressing powder and/or by using a binder material. This solid medicine component may be configured to be, cylindrical, tubular, spherical, a polygon, and/or or a toroidal shape. The solid medicine (254) may be placed inside the distal medicine chamber (42) during and/or in place of the lyophilization step. The solid form of the second medicine component (254) is configured to dissolve and/or disperse when contacted by liquid. The configurations described herein in reference to FIGS. 7A-7L relate to dual-chamber configurations, wherein two or more chambers within the same syringe body (34) are utilized to carry, mix, and inject an injection solution.

Referring to FIGS. 7A and 7B, proximal and distal medicine chambers (40, 42) are formed by a distal stopper member (36) in between two portions of the interior of a syringe body (34), such that the distal medicine chamber (42) contains an air or gas gap, as well as a non-liquid medication (254); a proximal medicine chamber (40), on the opposite side of the distal stopper member (36) contains a liquid diluent (252), which is proximally contained by a proximal stopper member (32). The liquid diluent (252) is a first component of a medicine and the non-liquid medication (254) is a second component of the medicine.

Figure 7C:
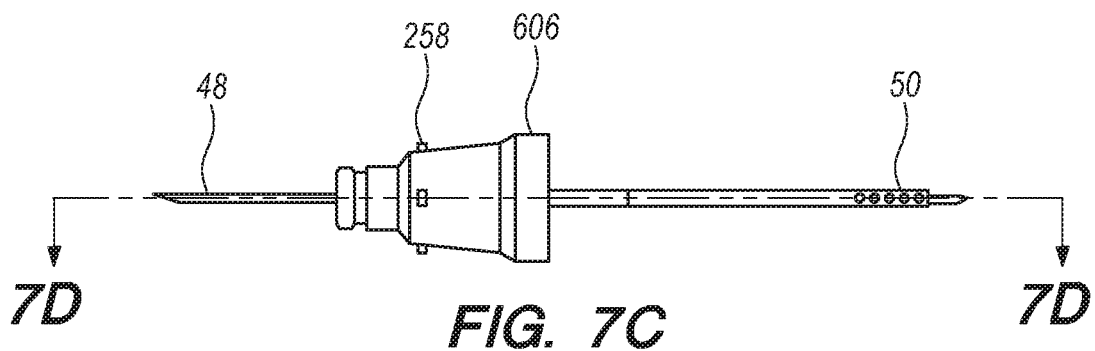
FIGS. 7A to 7P illustrate various aspects of syringe based dual chamber safe injection systems during steps in methods for mixing and injecting using same according to some embodiments.
Figure 7D:
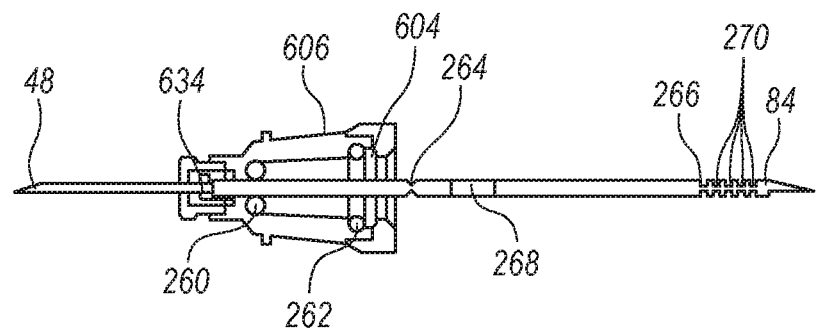

Referring to FIG. 7C, and the associated cross sectional view in FIG. 7D, various components of a needle coupling assembly (here a so-called "staked" needle coupling assembly (606) is illustrated, but other needle assemblies as described below, including Luer-coupled as well as staked configurations, may be utilized). Lug features (258) are configured to assist with coupling the needle coupling assembly (606) to a needle cover member (63), as shown in FIG. 7A, for example. A small O-ring may be utilized as a sealing member (260) around the needle shaft, while a larger O-ring may be utilized as a sealing member (262) at the syringe body (34)/needle coupling assembly (606) interface. Alternatively, the small O-ring (260) and the large O-ring (262) may be combined into a single seal that performs both of the O-ring sealing functions. Also, the small O-ring (260) may be used to seal both around the needle shaft and to the syringe body (34).

Figure 7E:
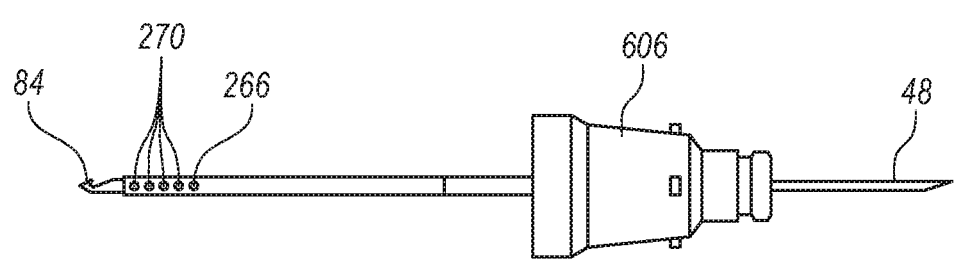
Figure 7F:
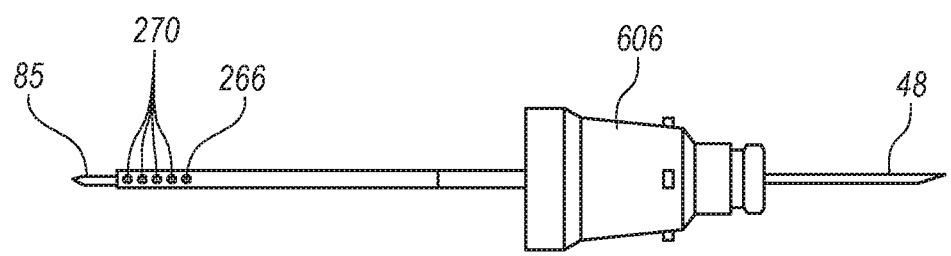
Figure 7G:
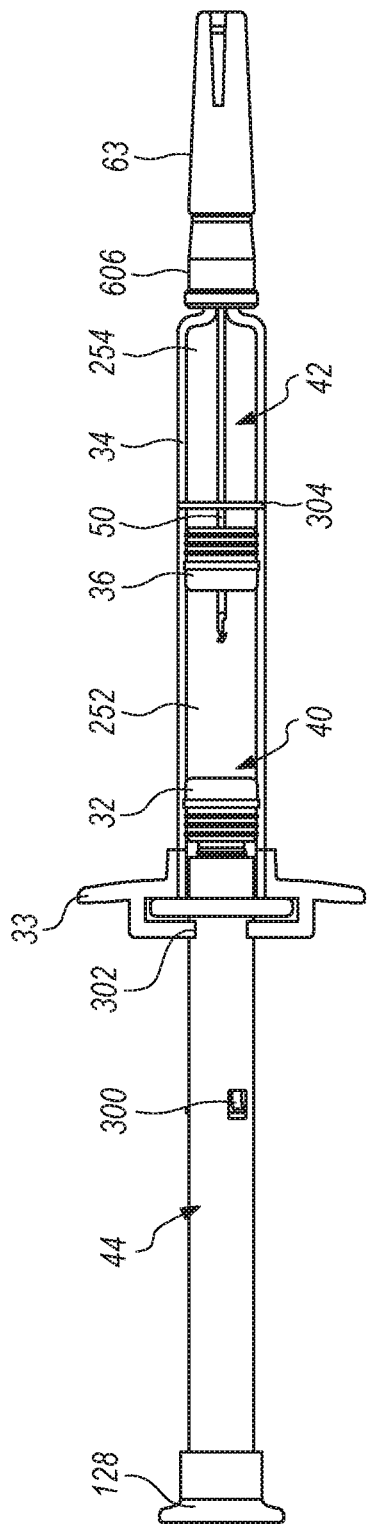
Figure 7H:
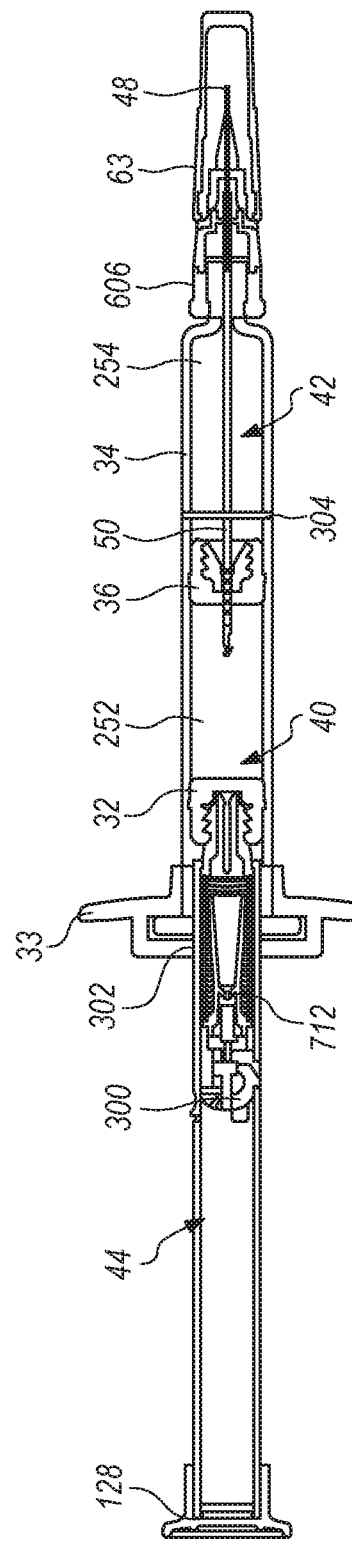

The needle includes a plurality (e.g., four) of proximal openings/ports (270) configured to allow for entry of a liquid diluent, to be expelled out of a more distally-located middle opening/aperture (266); a lumen plug (268) occludes the needle lumen to create the flow path from the proximal openings (270) to the middle opening (266) under conditions such as those described herein in reference to FIG. 7H. The needle also includes a distal opening (264) on the opposite side of the lumen plug (268) from the middle opening (266). The distal opening (264) is fluidly coupled to the needle distal end (48) through the needle to inject liquid into a patient.

Figure 7M:
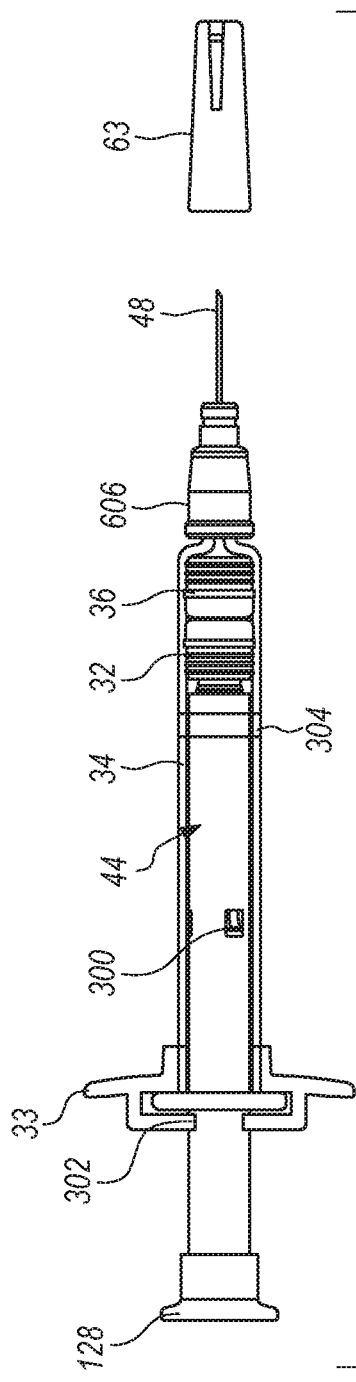
Figure 7N:
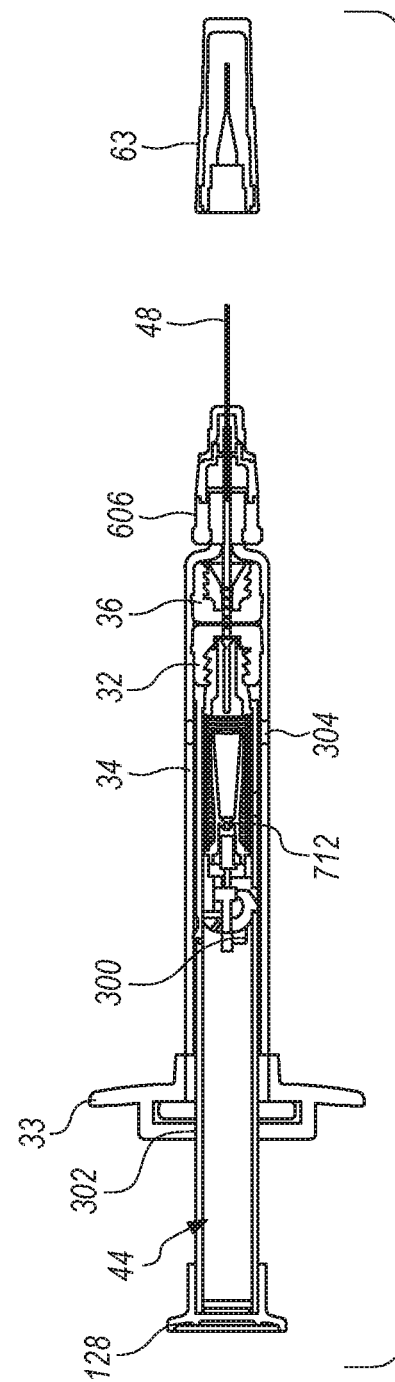

Referring to FIG. 7E, a proximal harpoon interface (84) is configured to serially penetrate proximal and distal stopper members (32, 36), and couple with a coupling feature (such as a needle retention feature are illustrated, for example, in FIGS. 7N and 7P, element 712) in the plunger rod. FIG. 7F illustrates a spike style harpoon coupling interface (85) that is configured to serially pierce both proximal and distal stopper members (32, 36) and couple with a coupling feature in the plunger rod to retract the needle member at least partially into the plunger rod after the injection has been given to the patient.

FIGS. 7A, 7B, and 7G-7P illustrate a sequence of actions for an injection procedure utilizing a dual chamber safe injection system such as that described above. Referring to FIGS. 7A and 7B, an injection assembly is in a stable configuration wherein it may be shipped or brought to an injection patient care scenario; a first drug component/liquid diluent (252) is isolated from a second non-liquid drug component (254), both within a syringe body on opposite sides of a distal stopper member (36).

FIGS. 7G and 7H illustrate initial insertion movement of the plunger assembly (44), advancing the distal (36) and proximal (32) stopper members together relative to the syringe body (34). Referring to FIG. 7H, with advancement sufficient to stab the proximal end (50) of the needle assembly across the distal stopper member (36), a fluid pathway is formed between the two previously isolated chambers (40, 42) of the syringe body (34), such that the liquid first drug component (252) in the proximal medicine chamber (40) may flow into at least one of the proximal openings (270), through the transfer pipe (46), and exit the more distal middle opening (266), to reach the non-liquid second drug component (254) in the distal medicine chamber (42).

FIGS. 7I and 7J illustrate that with further insertion until the stopper members (36, 32) are immediately adjacent each other, the liquid first drug component/diluent (252) has moved into the distal medicine chamber (42) to join the non-liquid second drug component (254). FIGS. 7K and 7L illustrate that with time and/or manual agitation, the liquid first drug component/diluent (252) and previously non-liquid second drug component (254) become mixed to form a mixed medication solution (272).

In some embodiment, especially with lyophilized non-liquid second drug components, the mixed medication solution (272) may be formed with minimal or no agitation or time passage. In another embodiment, especially with drugs which are held in suspension or emulsified drugs, vigorous shaking may be necessary to facilitate mixing. In the case of vigorous shaking it is useful to the user to be able to remove their thumb from the plunger manipulation interface (128). During transfer of liquid first medicine component (252) from the proximal to the distal medicine chambers (40, 42) pressure may build up in the distal medicine chamber (42). This pressure acts upon the proximal and distal stopper members (32, 36) to resist stopper motion. The pressure buildup may also move the stopper members (32, 36) and plunger manipulation interface (128) proximally if the user does not have their thumb restraining the plunger assembly (44). Mixed configuration latches or "mix clicks" in the plunger assembly (44) (depicted in FIGS. 9A and 9B and described below) may be utilized to provide resistance to plunger manipulation interface (128) motion due to pressure buildup and allow the user to release their thumb from the plunger manipulation interface (128) for shaking or mixing of the drug. The mix clicks may also provide an audible and/or tactile indication that the transfer of liquid first medicine component (252) has been completed. The distal medicine chamber (42) may also include an agitation device, which assists in mixing of the medicine components.

With the assembly ready for injection of the mixed solution (272), the needle cover member (63) may be removed and the patient may be injected with the exposed needle distal end (48) with depression/insertion of the plunger assembly (44) and associated stopper members (36, 32) as shown in FIGS. 7M and 7N. Referring to FIGS. 7O and 7P, with full depression/insertion of the plunger assembly (44) and associated stopper members (32, 36), the sharp needle distal end/point (48) may automatically retract at least partially through the distal and proximal stopper members (36, 32) to a safe position within either the syringe body (34), the needle coupling assembly (606), or at least partially within the plunger assembly (44). Automatic retraction of the needle at least partially within the plunger is described in U.S. utility patent application Ser. No. 14/696,342, which was previously incorporated by reference herein.

Further details regarding multiple chamber injection systems (components, methods using same, etc.) are disclosed in U.S. Utility patent application Ser. No. 15/801,259, and U.S. Provisional Patent Application Ser. Nos. 62/682,381 and 62/729,880, which were all previously incorporated by reference herein.

Exemplary Distal Bushings with Detents in Dual Chamber Safe Injection Systems

Figure 8B:
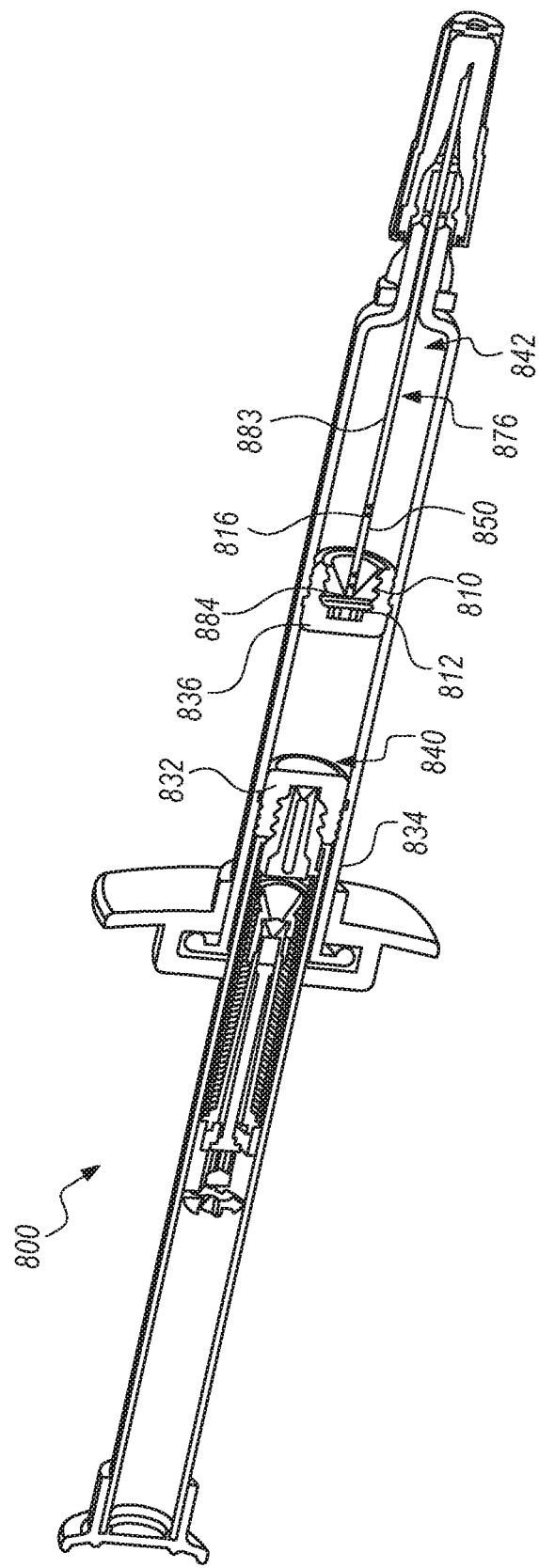

FIGS. 8A and 8B depict a prefilled dual chamber safe injection system (800) according to some embodiments. The system (800) includes a stopper bushing (810) having a detent (812) disposed therein (see FIG. 8B). The detent (812) is configured to interact with the sharpened proximal end (884) of the needle spine assembly (876) and a shoulder (816) at the junction between the needle proximal end (850) and the needle joining member (883) to provide resistance to distal movement of the distal stopper member (836) relative to the needle spine assembly (876) (see FIG. 8B).

The interaction between the detent (812) and the proximal end (884) maintains the distal stopper member (836) in a ready to use position during storage and transport, such as the configuration depicted in FIGS. 8A and 8B. This interaction will maintain the position of the distal stopper member (836) even with a vacuum or partial vacuum (e.g. for the lyophilized component) in the distal chamber (842). Without the detent (812) and with a vacuum in the distal chamber (842), the distal stopper member (836) will eventually move distally relative to the needle spine assembly (876) and be penetrated thereby. This would render the system unusable.

The interaction between the detent (812) and the shoulder (816) maintains the distal stopper member (836) in a transfer position during transfer of the liquid from the proximal chamber (840) to the distal chamber (842). This interaction allows the user to apply a wider range of force to the plunger member to transfer the liquid while minimizing the risk of premature movement of the distal stopper member (836).

Figure 9A:
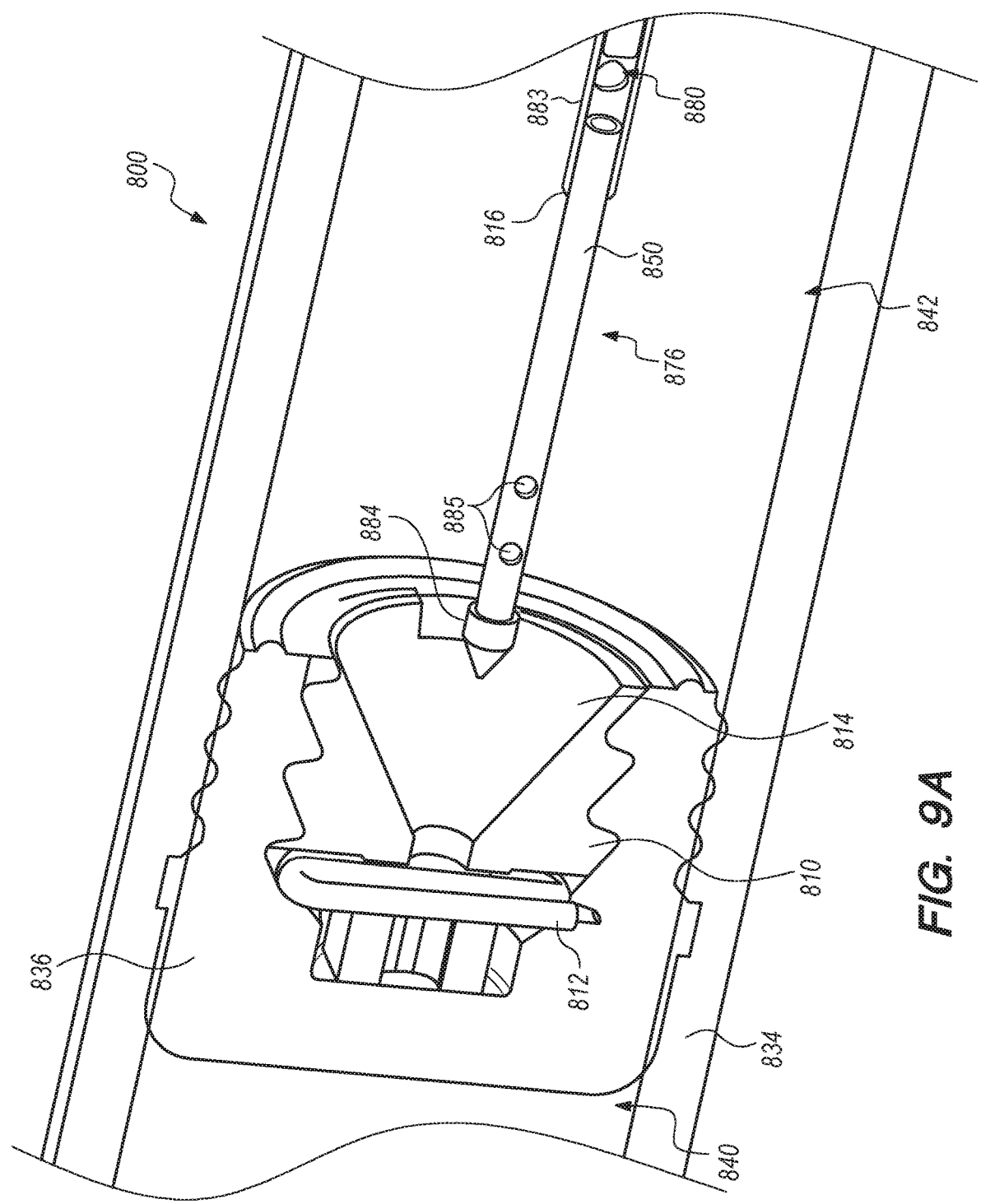
FIGS. 9A to 9C illustrate various aspects of a distal stopper member having a stopper bushing with a detent for use with syringe based dual chamber safe injection systems according to some embodiments.
Figure 9B:
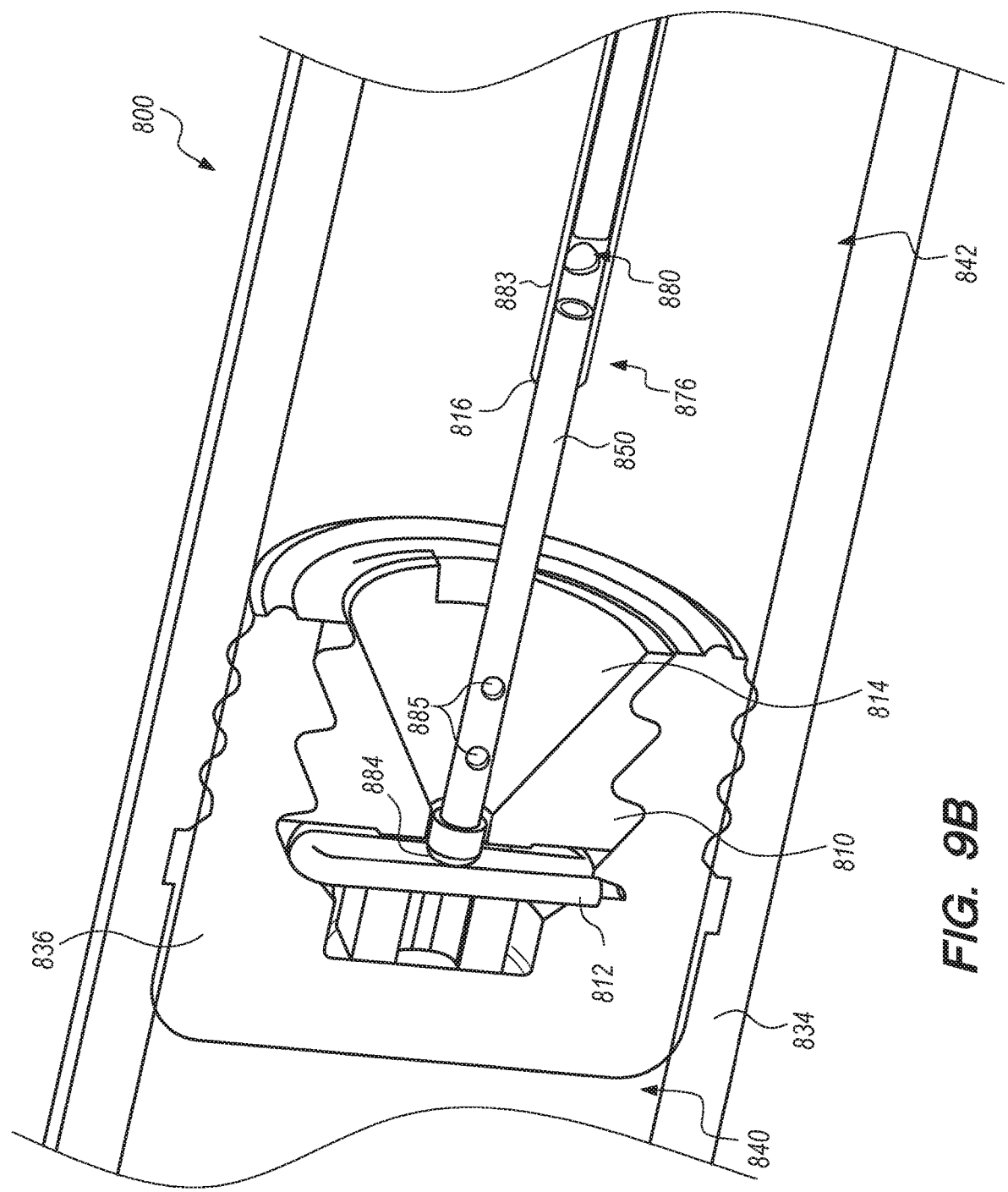
Figure 9C:
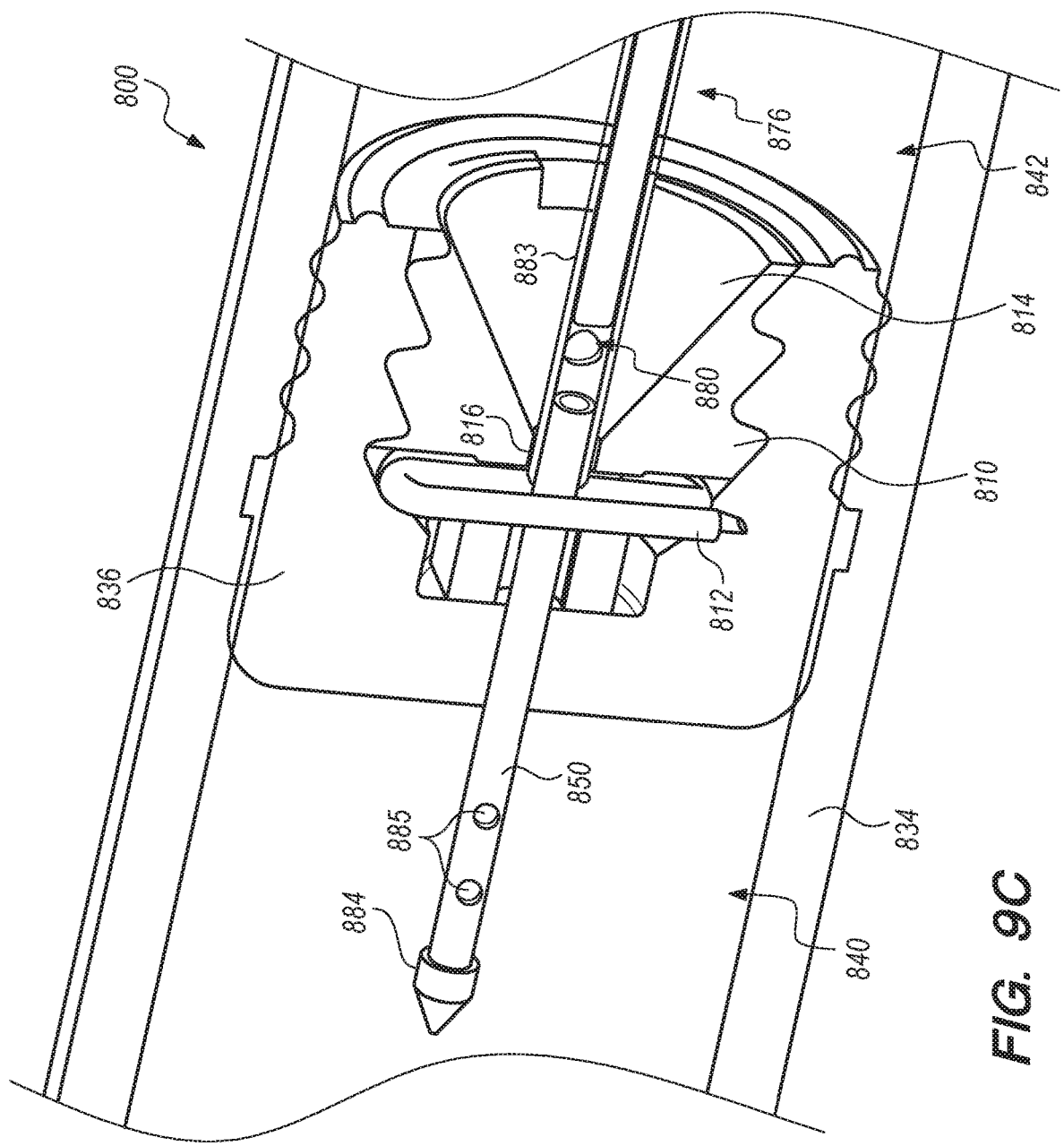

FIGS. 9A to 9C depict the interactions between the detent (812) and the sharpened proximal end (884) of the needle spine assembly (876) and a shoulder (816) on the needle spine assembly (876) in the prefilled dual chamber safe injection system (800) depicted in FIGS. 8A and 8B. FIG. 9A shows a distal stopper member (836) having a stopper bushing (810) with a detent (812) and defining an alignment funnel (814). In FIG. 9A the alignment funnel (814) guides a proximal end (884) of the needle spine assembly (876) into positioned adjacent the detent (812).

FIG. 9B shows the storage/transport configuration of the system (800). In this configuration, the sharpened proximal end (884) of the needle spine assembly (876) is disposed adjacent to and partially within the detent (812). Various properties of the proximal end (884) and the detent (812) (e.g., geometric, material, etc.) can be modified to modulate the force required to push the proximal end (884) past the detent (812). These properties are described in detail below. In one embodiment, the force required to push the proximal end (884) past the detent (812) is from about 2 pounds to about 5 pounds. As described above, even with a vacuum or partial vacuum in the distal chamber (842) urging the distal stopper member (836) in a distal direction, the interaction between the proximal end (884) and the detent (812) prevents premature movement of the distal stopper member (836) relative to the needle spine assembly (876). This allows the prefilled dual chamber system (800) to be stored while minimizing the risk of premature movement of the distal stopper member (836), which can render the system (800) unusable.

FIG. 9C shows the transfer configuration of the system (800). In this configuration, the distal stopper member (836) has been pushed distally past the sharpened proximal end (884) of the needle spine assembly (876) by user provided force on the plunger member. The proximal openings (885) are disposed in the proximal chamber (840) allowing liquid to transfer from the proximal chamber (840) to the distal chamber (842). While a vacuum in the distal chamber (842) withdraw the liquid out of the proximal chamber (840), user generated force applied to the proximal stopper member (832) via the plunger member will assist the liquid transfer. In this configuration, a shoulder (816) on the needle spine assembly (876) is disposed adjacent to the detent (812). Various properties of the shoulder (816) and the detent (812) (e.g., geometric, material, etc.) can be modified to modulate the force required to push the shoulder (816) past the detent (812). These properties are described in detail below. In one embodiment, the force required to push the shoulder (816) past the detent (812) is from about 2 pounds to about 5 pounds. The shoulder is formed at the joint between the needle proximal end (850) and the needle joining member (883). While the interaction between the shoulder (816) and the detent (812) holds the system (800) in the transfer configuration depicted in FIG. 9C, pressure applied to the plunger member will aid liquid transfer from the proximal chamber (840) to the distal chamber (842). The force required to overcome the interference between the shoulder (816) and the detent (812) provides more latitude for a user to press the plunger member to aid in the liquid transfer. This increases the chances of complete liquid transfer.

Figure 10A:
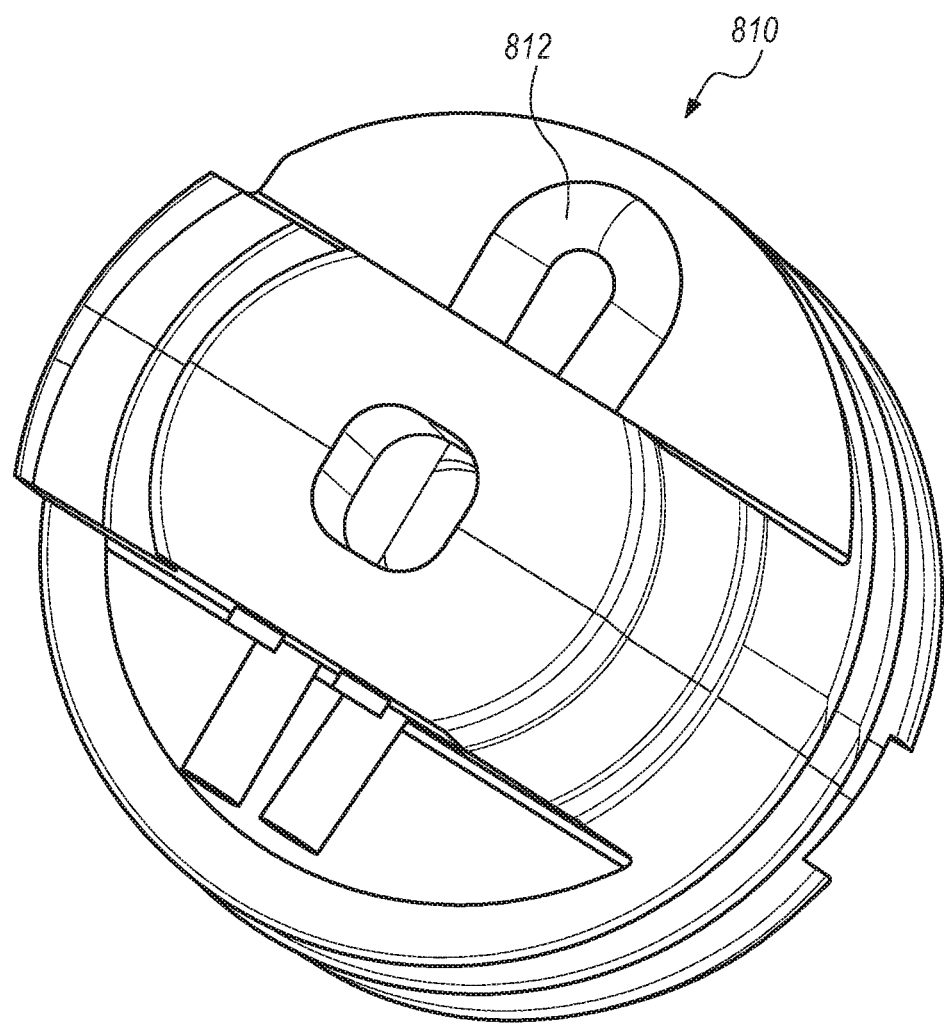
FIGS. 10A to 10C illustrate various aspects of a stopper member bushing with a detent for use with syringe based dual chamber safe injection systems according to some embodiments.
Figure 10B:
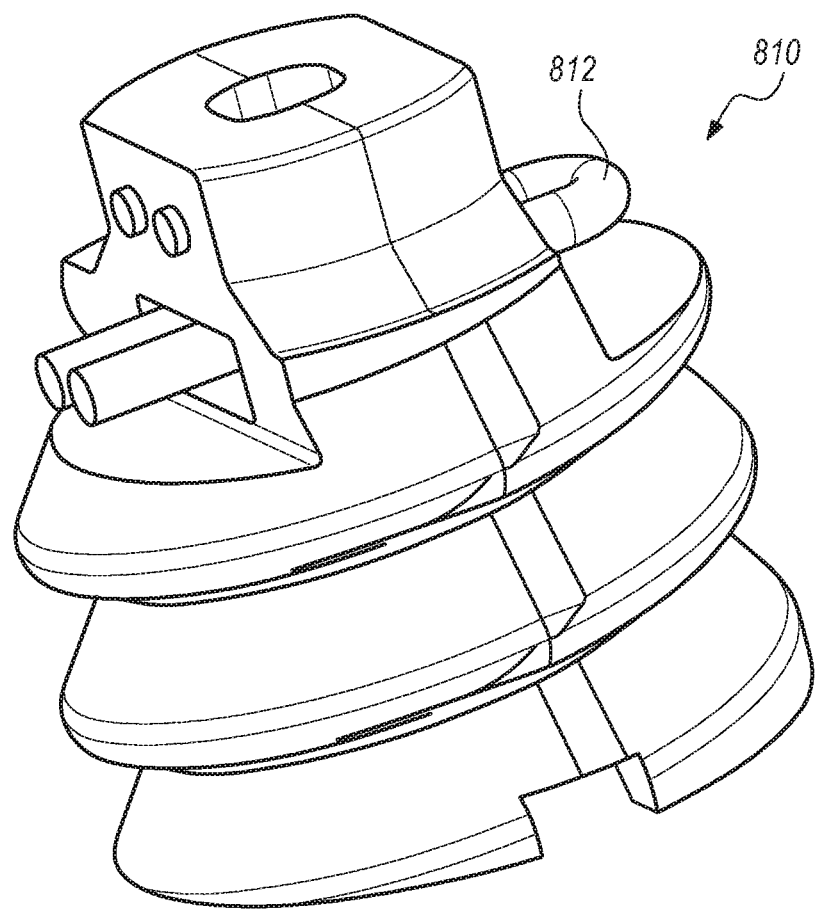
Figure 10C:
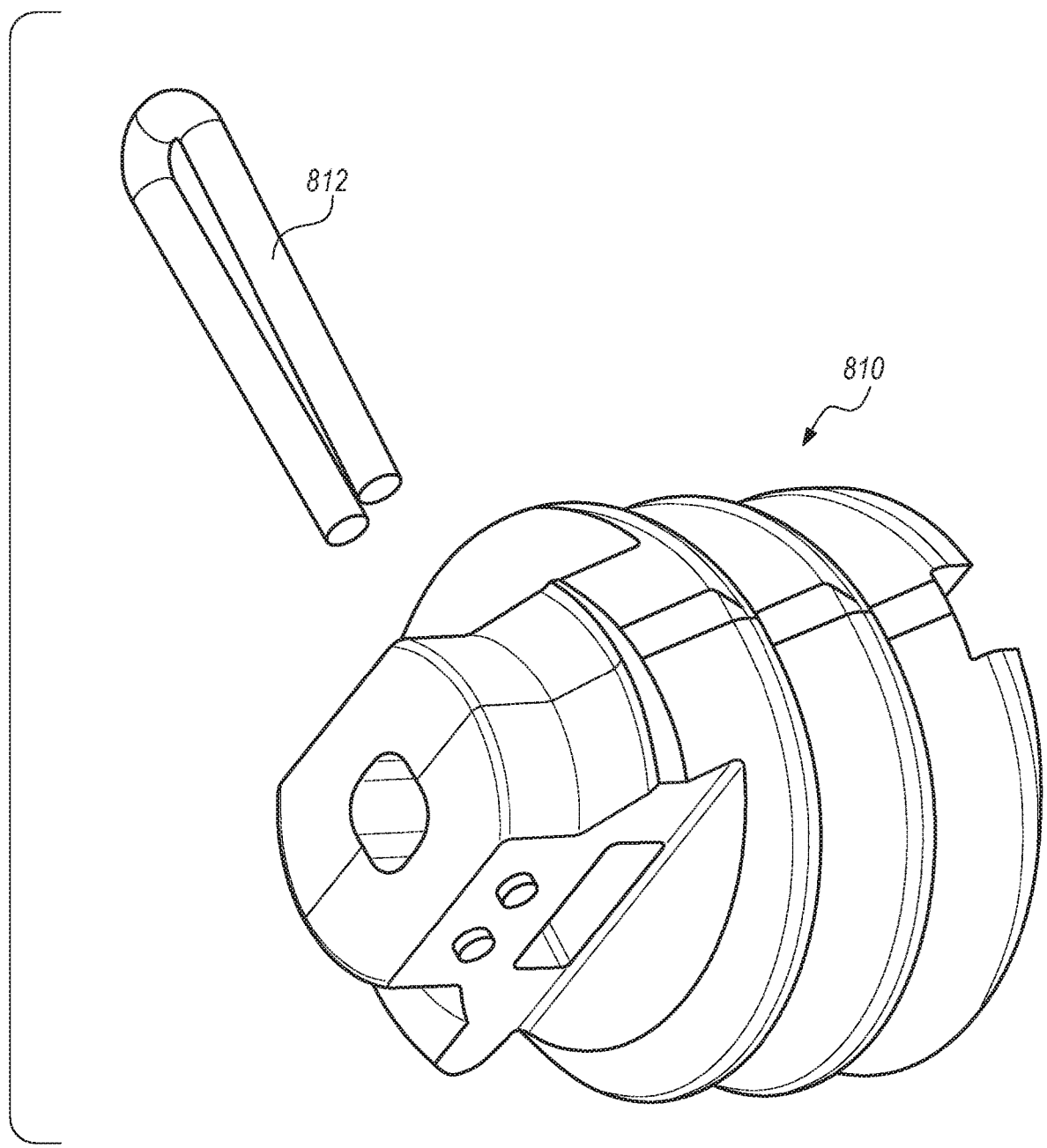

FIGS. 10A to 10C depict a stopper bushing (810) for use with the prefilled dual chamber safe injection system (800) depicted in FIGS. 8A and 8B. The stopper bushing (810) has a detent (812) inserted into a slot in the bushing (810) along an axis orthogonal to the longitudinal axis of the needle spine assembly. As shown in FIG. 10C, the detent may be made of a bent wire having a "U" shape.

Figure 11A:
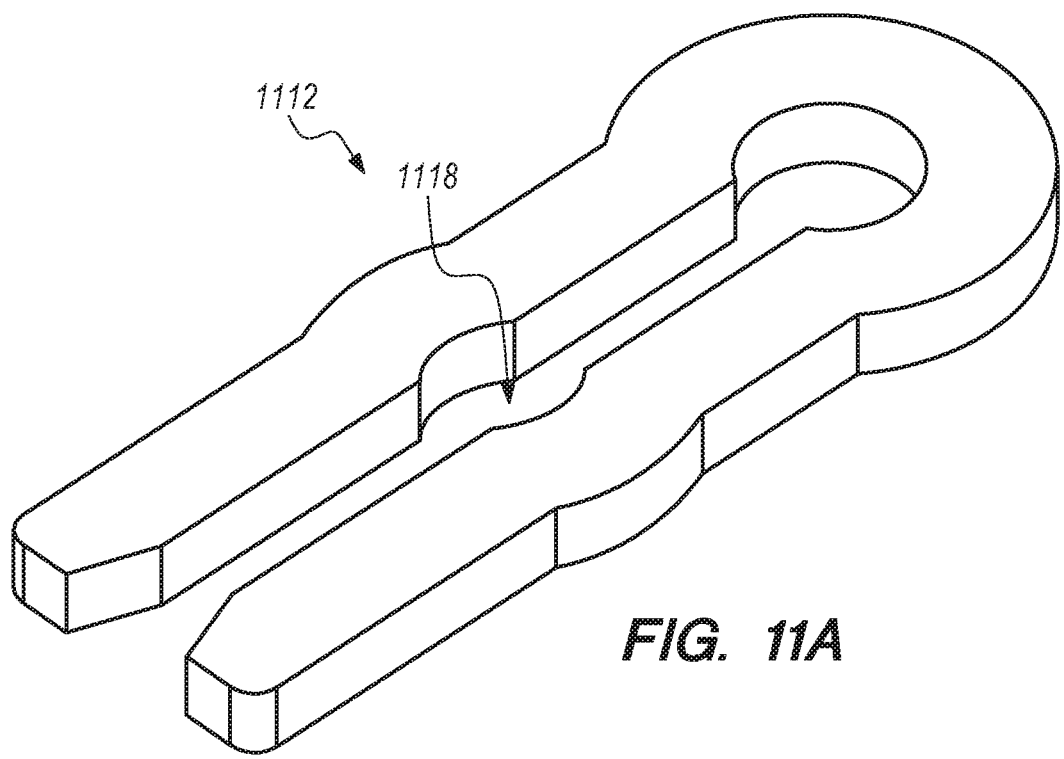
FIGS. 11A to 11C illustrate various aspects of a detent for use with a stopper member bushing for use with syringe based dual chamber safe injection systems according to some embodiments.
Figure 11B:
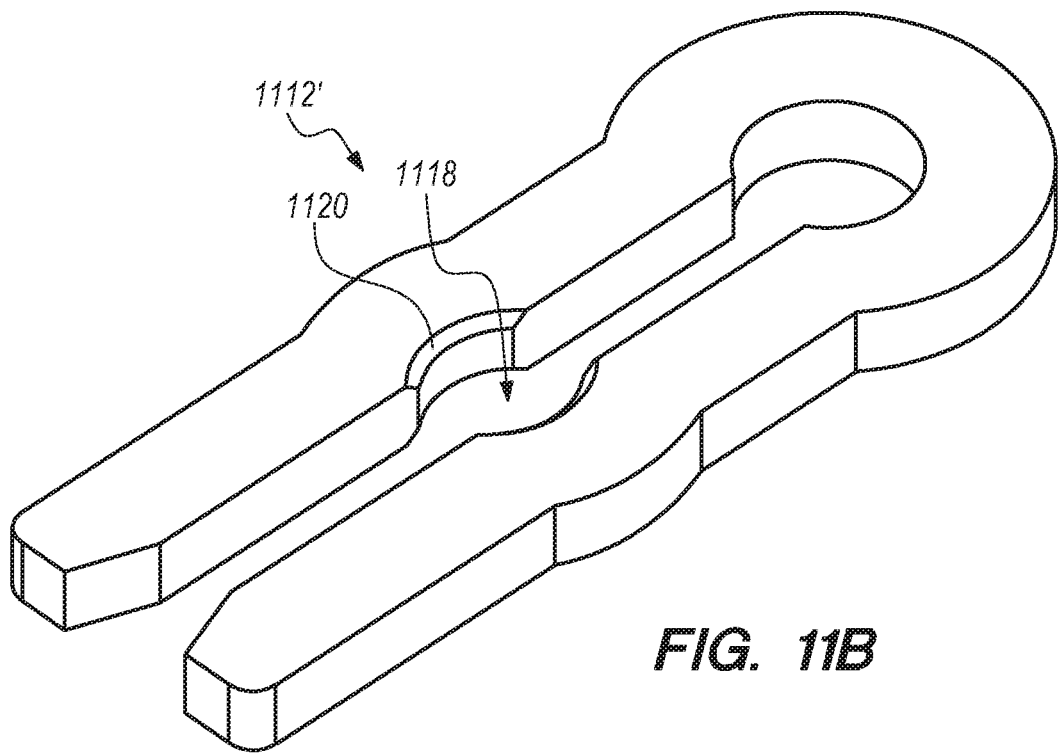
Figure 11C:
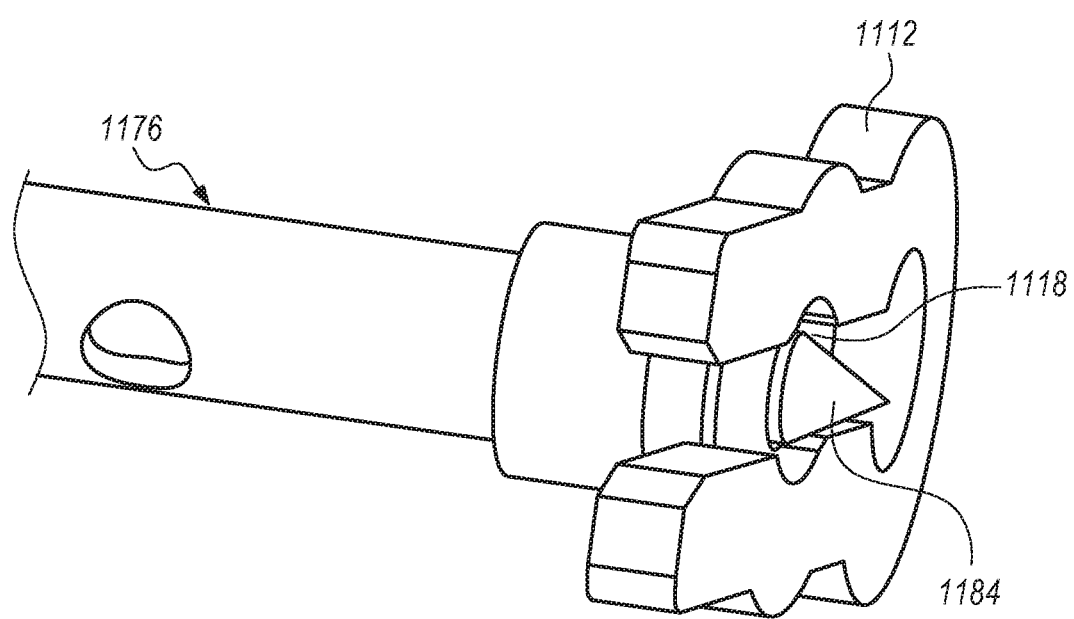

FIGS. 11A to 11C show detents (1112, 1112') for use with stopper bushings of prefilled dual chamber safe injection systems according to some embodiments. The detents (1112, 1112') are formed from a sheet of metallic material, and thus have a flat cross-section. The detents (1112, 1112') all have a "U" shape and include a notch (1118) configured to receive a round shape, such as those on sharpened proximal ends and shoulders of the needle spine assemblies. The detent (1112') depicted in FIG. 11B includes a chamfered/baffled penetration surface (1120) around a circumference of the notch (1118) on the side of the detent (1112') adjacent the sharpened proximal ends of the needle spine assemblies in the storage/transport configuration described above. The beveled penetration surface (1120) can be modified to modulate the amount of force required to penetrate the detent (1112').

FIG. 11C depicts the sharpened proximal end (1184) of a needle spine assembly (1176) disposed in the notch (1118) of a detent (1112), such as in a storage/transport configuration.

In one embodiment, the resistance force provided by the detent (1112) as it slides over a sharpened proximal end (1184) of a needle spine assembly (1176) is variable. The detent (1112) resist penetration by the proximal end (1184) during storage (e.g., for several years). With the application of a predetermined amount of force by the user, the proximal end (1184) slides through the detent (1112). Then, the resistance force to movement of the needle spine assembly (1176) through the detent (1112) is minimal until the detent (1112) reaches the shoulder (816, see FIG. 9C). When the detent (1112) abuts the shoulder, resistance force increases to reliably stop the progress of the detent (1112) (and distal stopper member) relative to the needle (1176). After liquid transfer described above, the user applies another predetermined amount of force to push the detent (1112) will over the shoulder. After the shoulder is cleared, the friction from the interaction of the detent (1112) and the needle (1176) is minimal to facilitate giving the injection and needle retraction.

The predetermined amount of force can be modulated to accommodate a combination of the system function requirements and the aesthetic impression on the user. If the activation force is too low, it may work, but be too difficult for the user to apply the force lightly enough, and the user may overshoot. If the force is too high, the user may find that it is "too hard" to activate the system. Fortunately, the predetermined amount of force can be "tune" a range by modifying various component characteristics.

While the embodiments described above include dual chamber safety injection systems, the scope of the claims also include other multiple chamber safety injection systems. For multiple chamber safety injection systems with more than two chambers, more than two stopper members are inserted into an injection system body (e.g., syringe body, cartridge body, etc.) to define a corresponding number of chambers.

Exemplary Multiple Chamber Safe Injection System Manufacturing Methods

Injection System/Syringe Fill Distal Chamber from Front

Figure 12A:
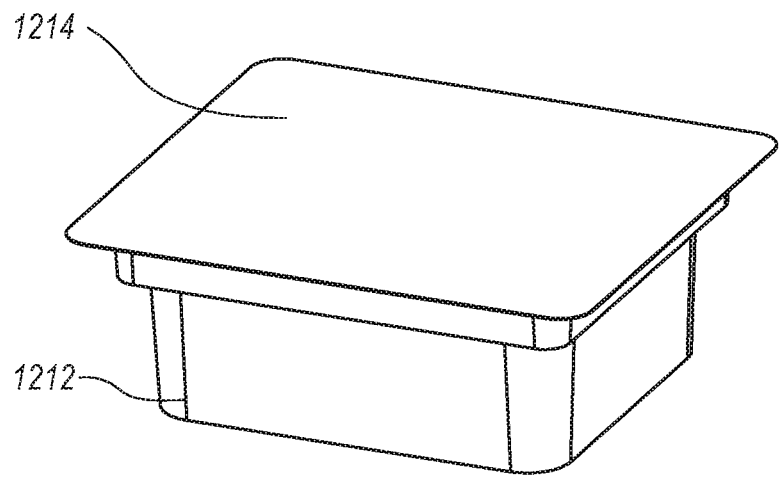
FIGS. 12A to 12C depict a rack containing a plurality of injection system/syringe bodies and stored in a container according to some embodiments.
Figure 12B:
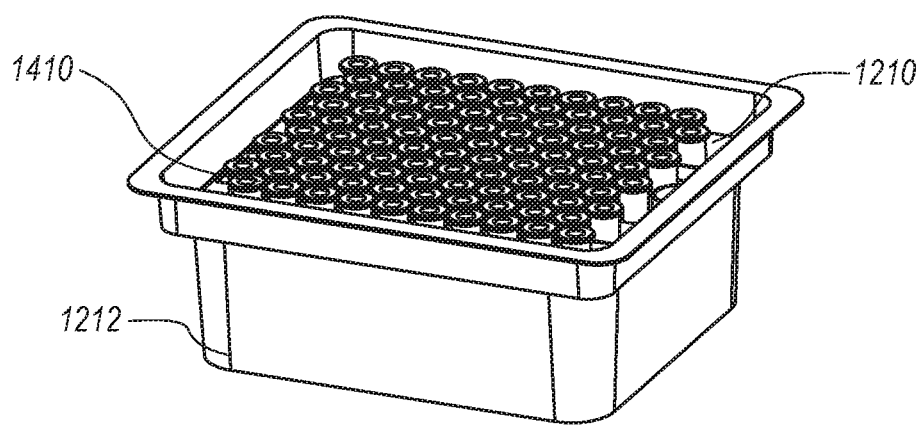

FIGS. 12A and 12B depict a rack 1210 containing a plurality of injection system/syringe bodies 1410 and stored in a container 1212. The rack 1210 and the container 1212 are made from materials that are sterilizable. The container 1212 is closable with a seal 1214 (FIG. 12A) to maintain the sterility of the rack 1210 and injection system/syringe bodies 1410 contained therein.

Figure 12C:
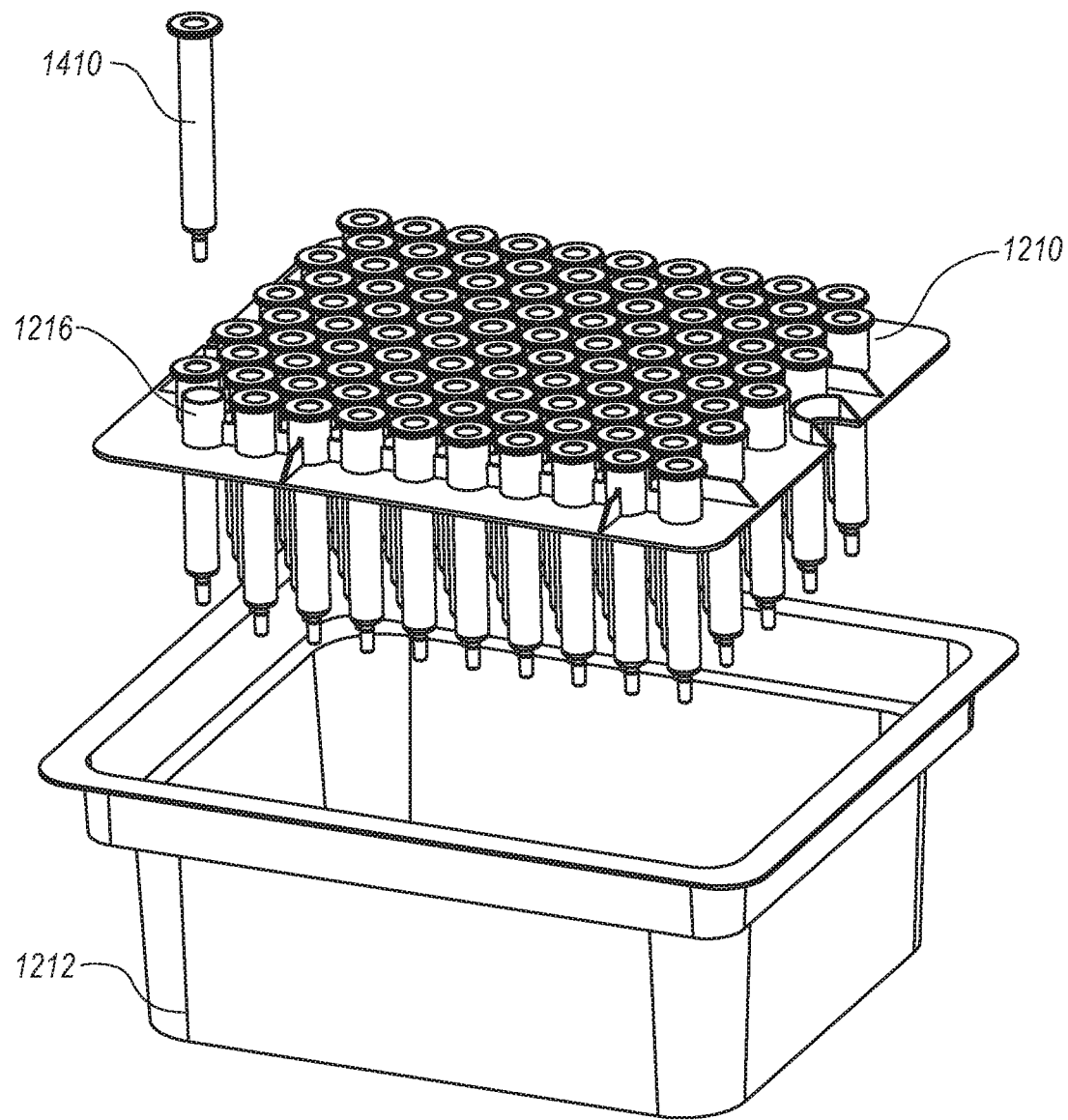

FIG. 12C depicts the rack 1210 removed from the container 1212 and one injection system/syringe body 1410 removed from the rack 1210. The rack 1210 has a plurality of features (e.g., sleeves and/or flanges) 1216 to hold the injection system/syringe bodies 1410 in a first configuration in which the distal end of the injection system/syringe body 1410 is pointed in a generally downward direction (see FIG. 14A). In some embodiments, the features 1216 are also configured to hold the injection system/syringe bodies 1410 in a second configuration in which the proximal end of the injection system/syringe body 1410 is pointed in a generally downward direction (see FIG. 14C).

Figure 13:
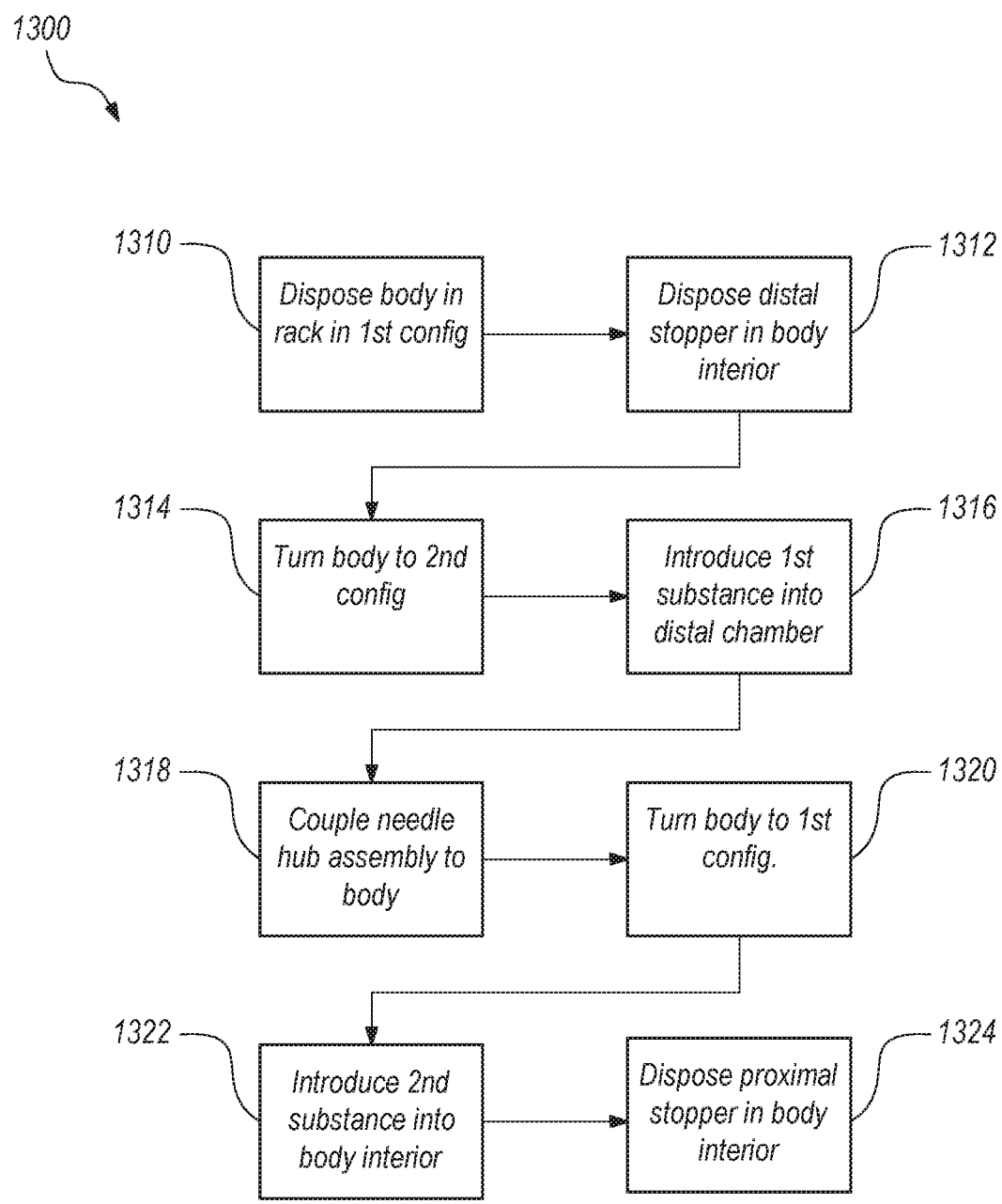
FIG. 13 is a flow chart illustrating a method for manufacturing/assembling a multiple chamber safe injection system according to some embodiments.

FIG. 13 depicts a method 1300 for manufacturing/assembling a multiple chamber safe injection system according to some embodiments. Corresponding partially assembled components are depicted in FIGS. 14A to 14J.

Figure 14A:
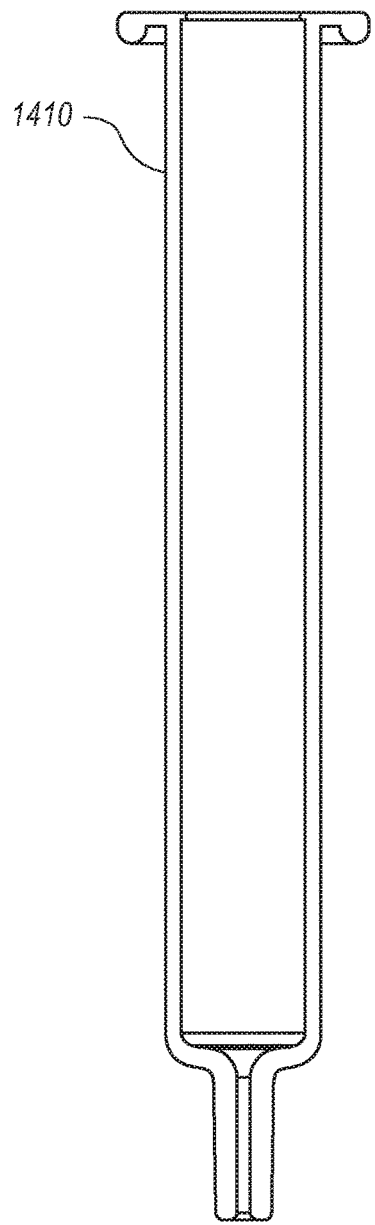
FIGS. 14A to 14J illustrate various steps in a method for manufacturing/assembling a multiple chamber safe injection system according to some embodiments.

At 1310, an injection system/syringe body 1410 is disposed in a rack in a first (downward) configuration as shown in FIG. 14A. The injection system/syringe body 1410 may be disposed in the rack by a user (e.g., using a tool) or by a mechanical device (e.g., robot).

Figure 14B:
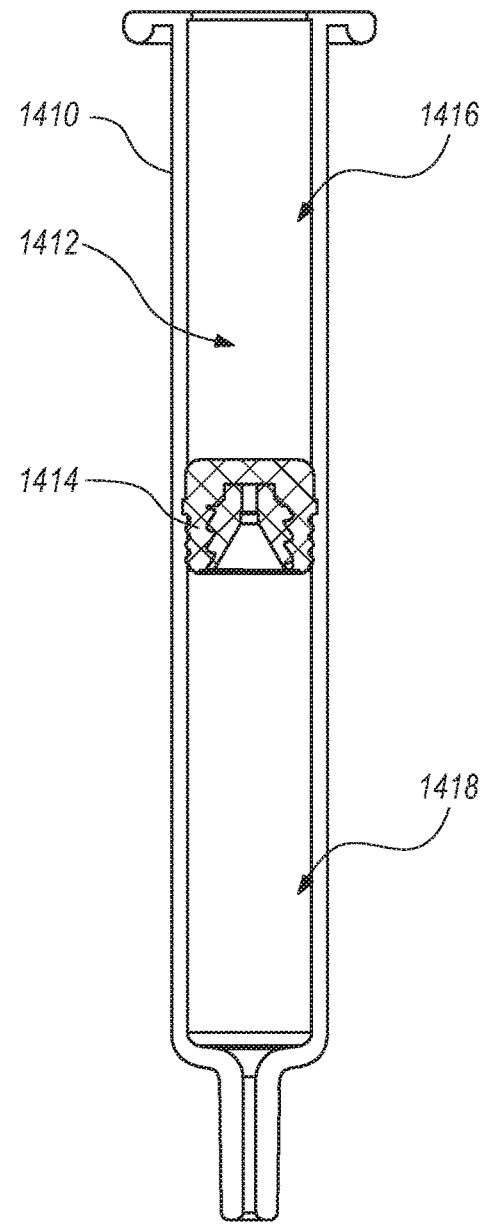

At 1312, a distal stopper member 1414 is disposed in an interior 1412 of the injection system/syringe body 1410 as shown in FIG. 14B. The distal stopper member 1414 may be inserted by a user (e.g., using a tool) or by a mechanical device (e.g., robot). The distal stopper member 1414 and the injection system/syringe body 1410 define proximal and distal chambers 1416, 1418 in the body interior 1412. The distal stopper member 1414 may be positioned over an open proximal end of the injection system/syringe body 1410 to facilitate insertion of the distal stopper member 1414 into the body interior 1412.

Figure 14C:
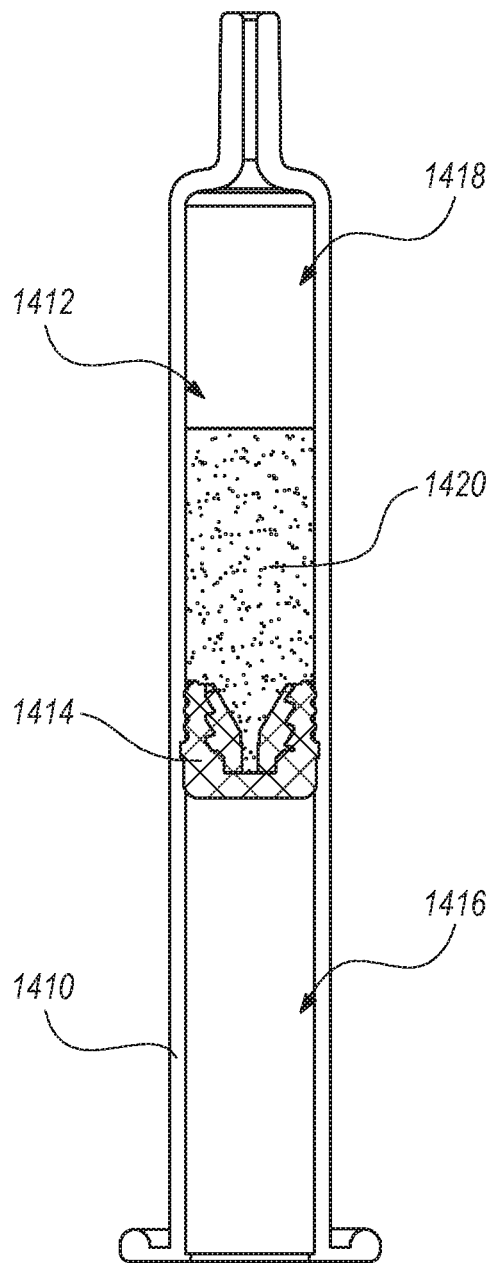

At 1314, the injection system/syringe body 1410 is turned to a second (upward) configuration as shown in FIG. 14C. The injection system/syringe body 1410 may be repositioned in the rack after being turned to the second configuration. Injection system/syringe body 1410 may be turned and/or repositioned by a user (e.g., using a tool) or by a mechanical device (e.g., robot).

Figure 14D:
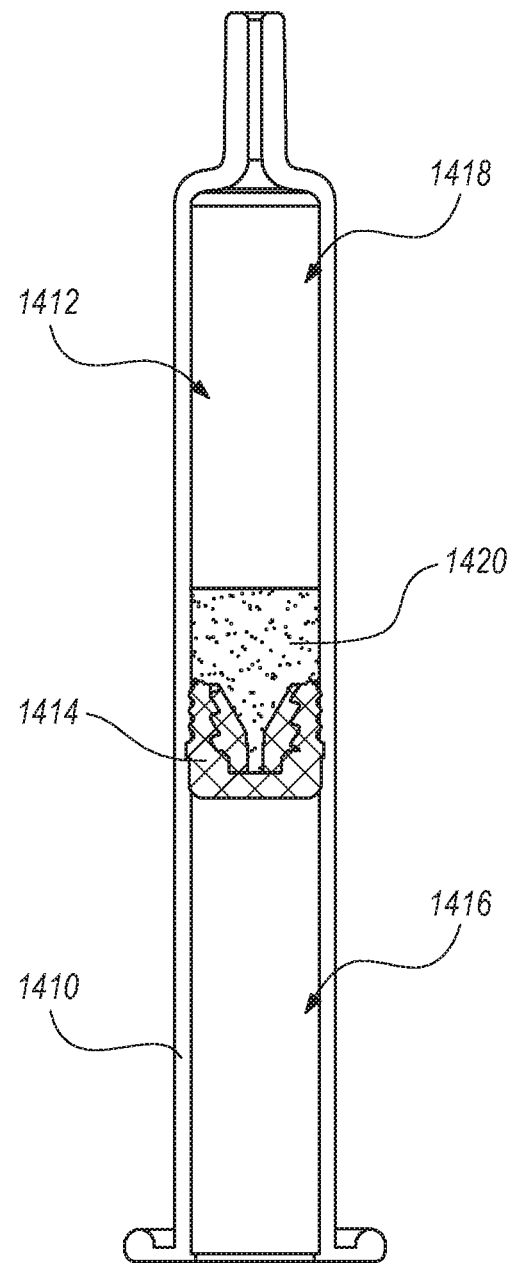

At 1316, a first substance 1420 is introduced into the distal chamber 1418 through the open distal end of the injection system/syringe body 1410 as shown in FIG. 14C. The first substance 1420 may be introduced directly through the opening at the distal end of the injection system/syringe body 1410. In some embodiments, a tube may be inserted through the opening at the distal end of the injection system/syringe body 1410, and the first substance 1420 may be introduced through the tube. The first substance 1420 may be a liquid, a solid (e.g., compressed powder), and/or a powder. In some embodiments where the first substance 1420 is a liquid, the first substance 1420 may be lyophilized in an optional step to form a powder as shown in FIG. 14D.

Figure 14E:
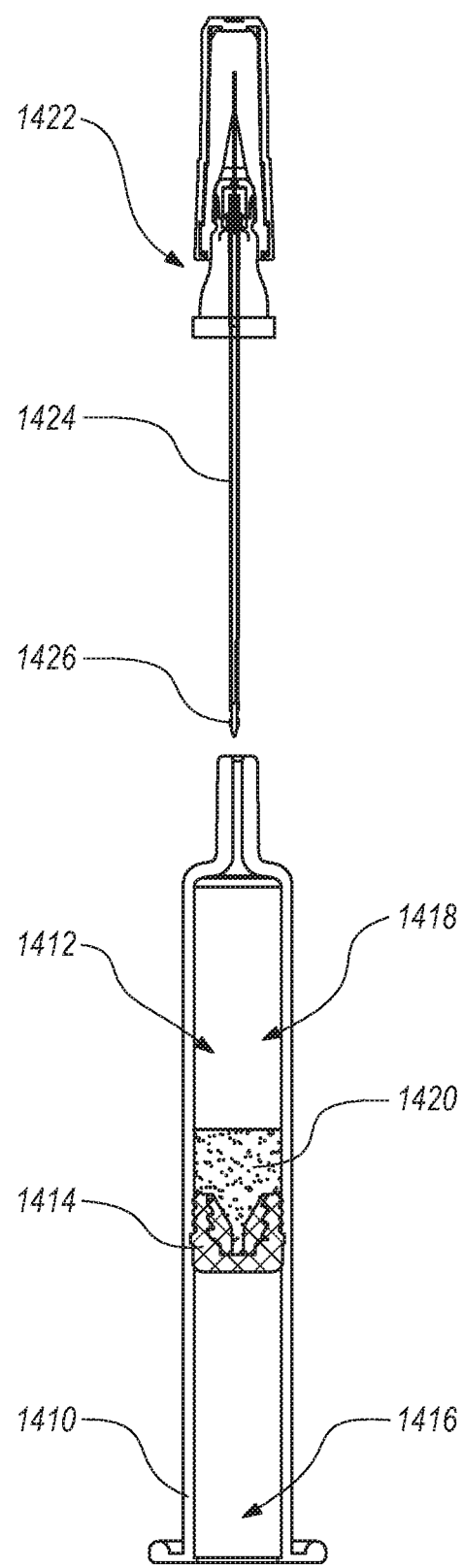
Figure 14F:
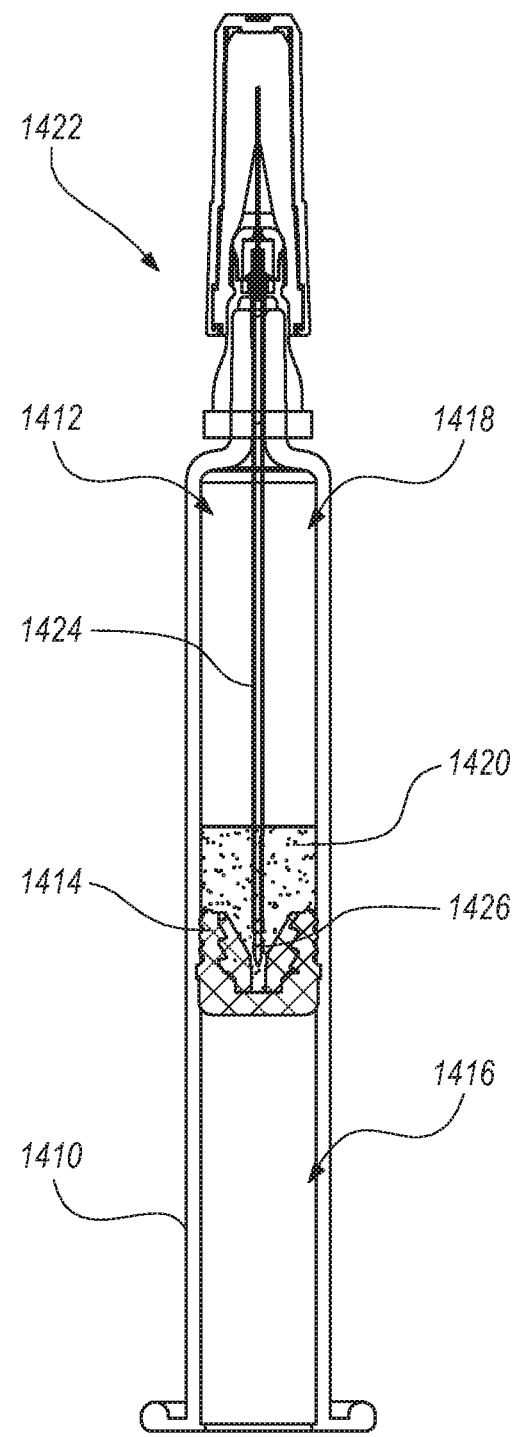

At 1318, a needle hub assembly 1422 is coupled to the distal end of the injection system/syringe body 1410 as shown in FIGS. 14E and 14F. The needle hub assembly 1422 includes a needle 1424 having a needle proximal end 1426. The needle proximal end 1426 interferes with the distal stopper member 1414 to temporarily prevent distal movement of the distal stopper member 1414 relative to the injection system/syringe body 1410. The needle hub assembly 1422 is coupled to the distal end of the injection system/syringe body 1410 by a user (e.g., using a tool) or by a mechanical device (e.g., robot). Alternatively, the injection system/syringe body 1410 may be closed with a luer cap as disclosed in FIGS. 33-40 and described below. In this case the dual chamber system would be provided without a pre-attached needle. The transfer tube component may be pre-inserted into the syringe body or installed at the time of placing the luer cap. The user may attach a needle at the time of use by using a luer slip or luer lock connection method.

In some alternative embodiments, the injection system/syringe body 1410 may be supplied with a needle hub assembly 1422 or luer cap coupled thereto. In some embodiments, the coupled the injection system/syringe body 1410, needle hub assembly 1422, and/or luer cap may be pre-sterilized. In other embodiments, pre-sterilized components may be supplied and assembled at the time of filling.

Figure 15A:
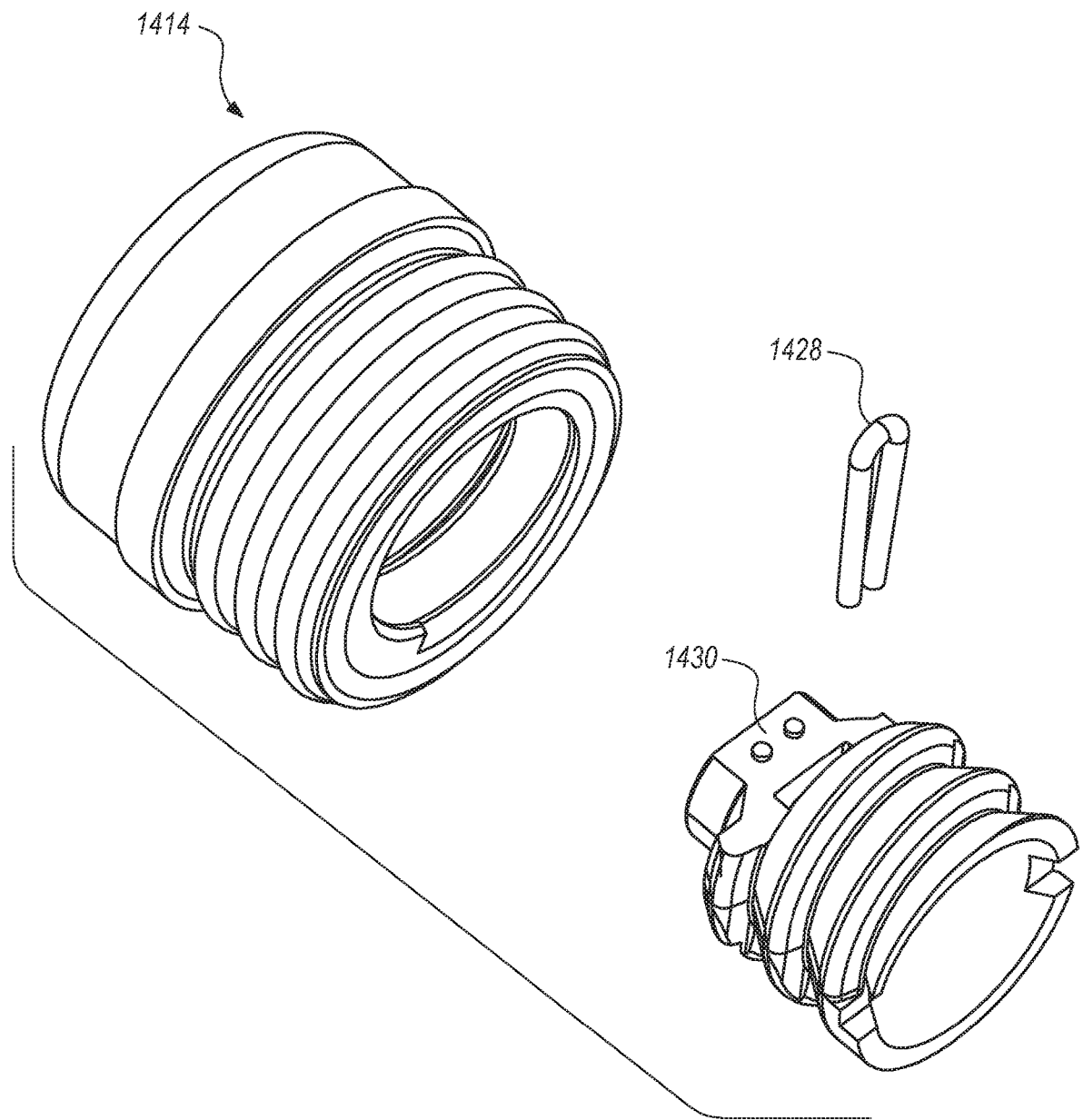
FIGS. 15A to 15D illustrate various aspects of a detent for use with a stopper member bushing for use with a multiple chamber safe injection system according to some embodiments.
Figure 15B:
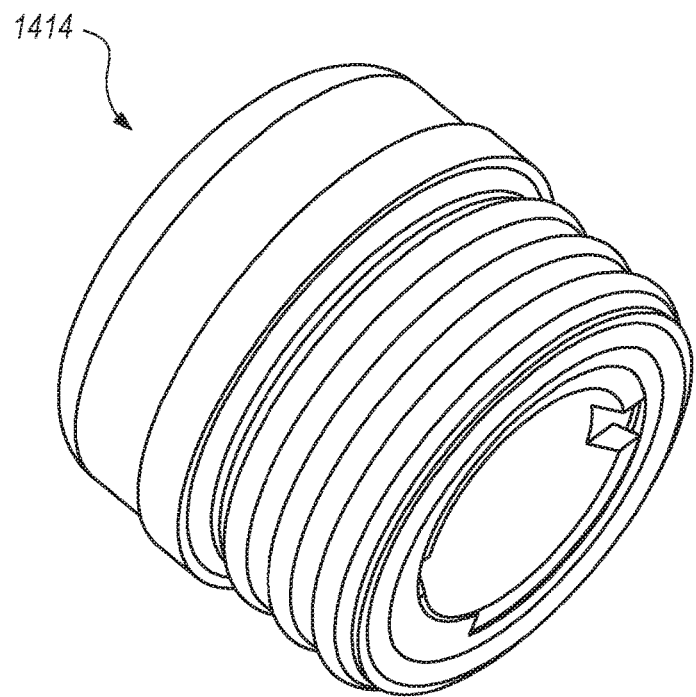
Figure 15C:
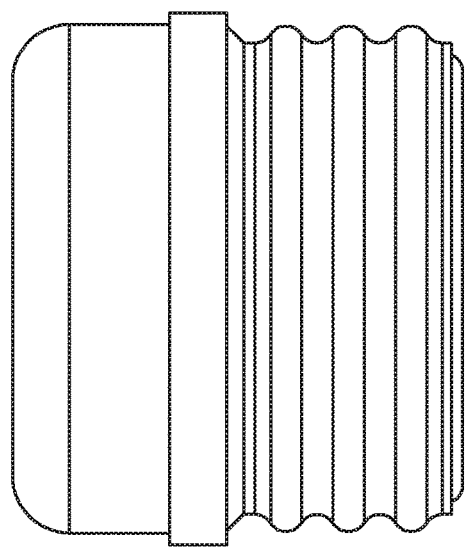
Figure 15D:
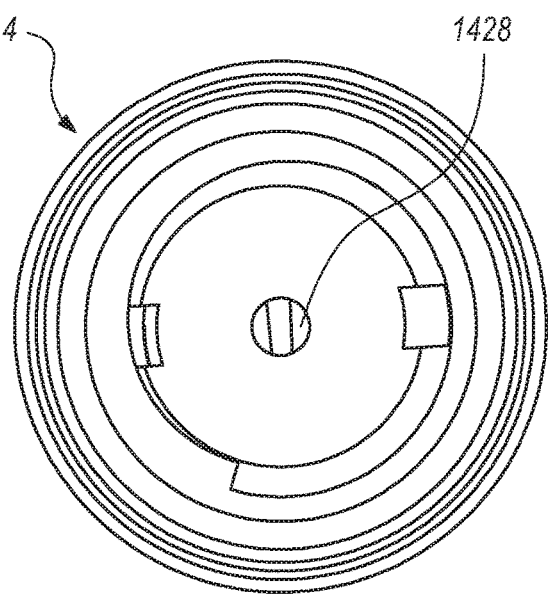
Figures 16, 16A:
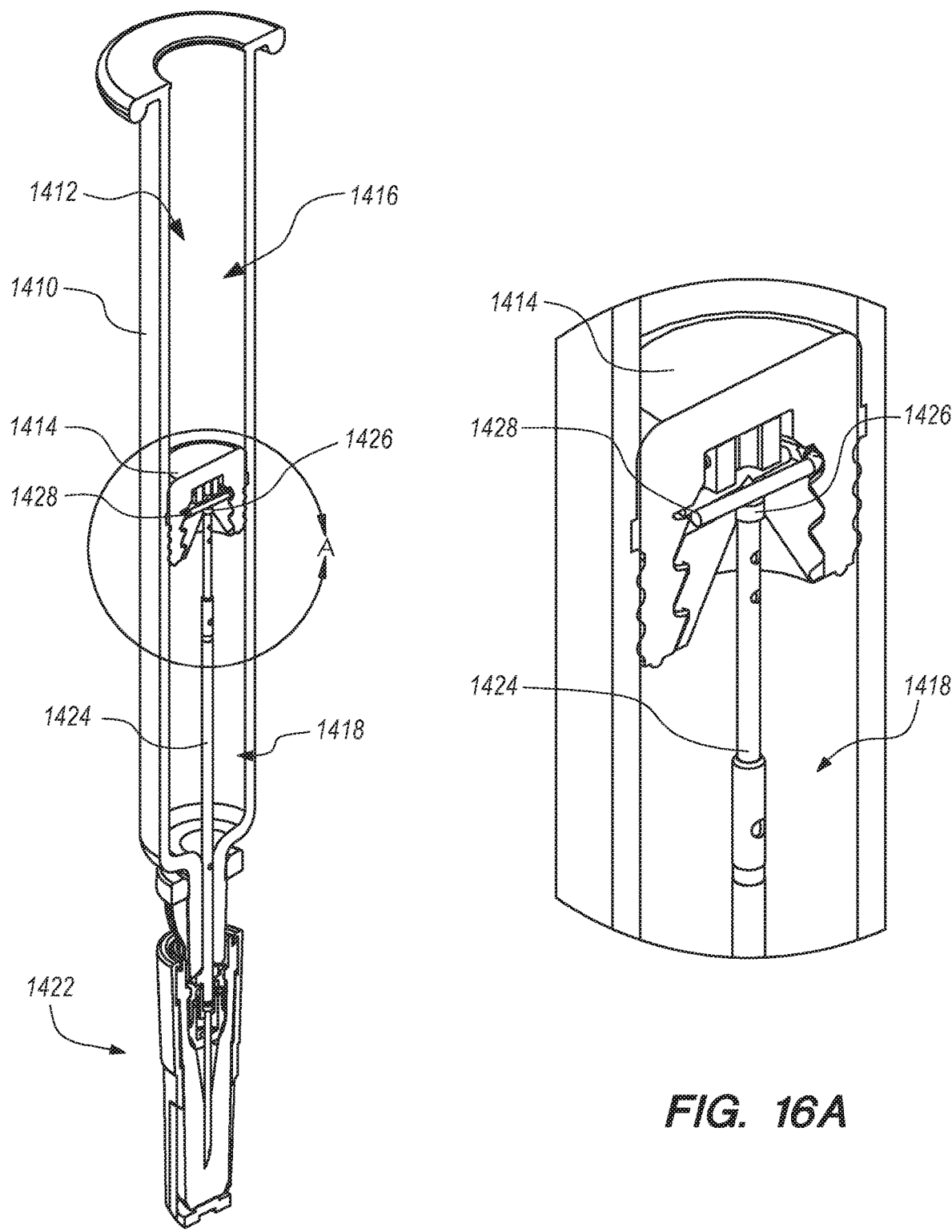
FIGS. 16 and 16A illustrate an interaction between a detent and a needle proximal end according to some embodiments.

Components of the distal stopper member 1414 that interfere with the needle proximal end 1426 are depicted in FIGS. 15A to 15D and 16 to 16A. FIG. 15A depicts a U-shaped retaining member/detent 1428 and a bushing/funnel 1430. After coupling the U-shaped retaining member/detent 1428 the bushing/funnel 1430, the bushing/funnel 1430 is screwed into the stopper member 1414. FIGS. 16 and 16A depict the stage in the manufacturing process identified at 1318 and also shown in FIG. 14F. As shown in FIG. 16A, the needle proximal end 1426 has an enlarged portion that interferes with the U-shaped retaining member/detent 1428. This interference increases the amount of force necessary to move the needle proximal end 1426 past the distal stopper member 1414. The increased amount of force allows a vacuum to be present in the distal chamber 1418 of the injection system/syringe body 1410 without prematurely moving the needle proximal end 1426 past the distal stopper member 1414 during storage of the multiple chamber safe injection system. The bushing funnel 1430 guides the needle proximal end 1426 to the U-shaped retaining member/detent 1428 during assembly.

Figure 14G:
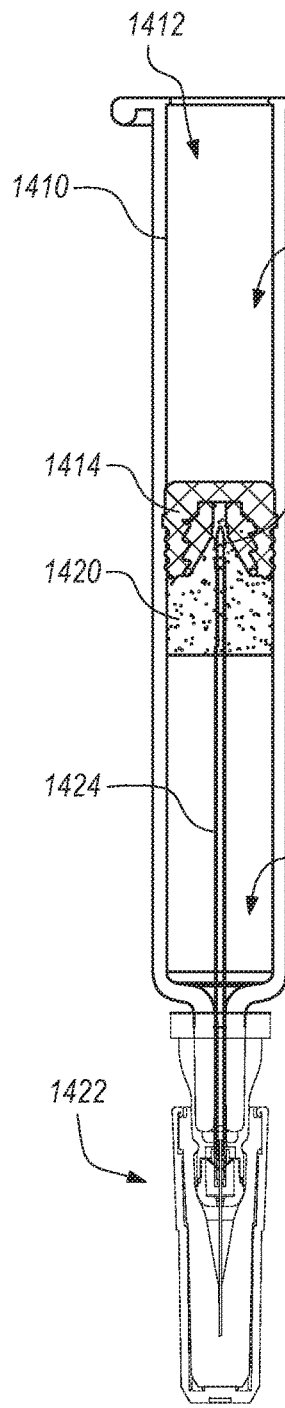

At 1320, the injection system/syringe body 1410 is turned back to the first (downward) configuration as shown in FIG. 14G. The injection system/syringe body 1410 may be repositioned in the rack after being turned back to the first configuration. Injection system/syringe body 1410 may be turned and/or repositioned by a user (e.g., using a tool) or by a mechanical device (e.g., robot).

Figure 14H:
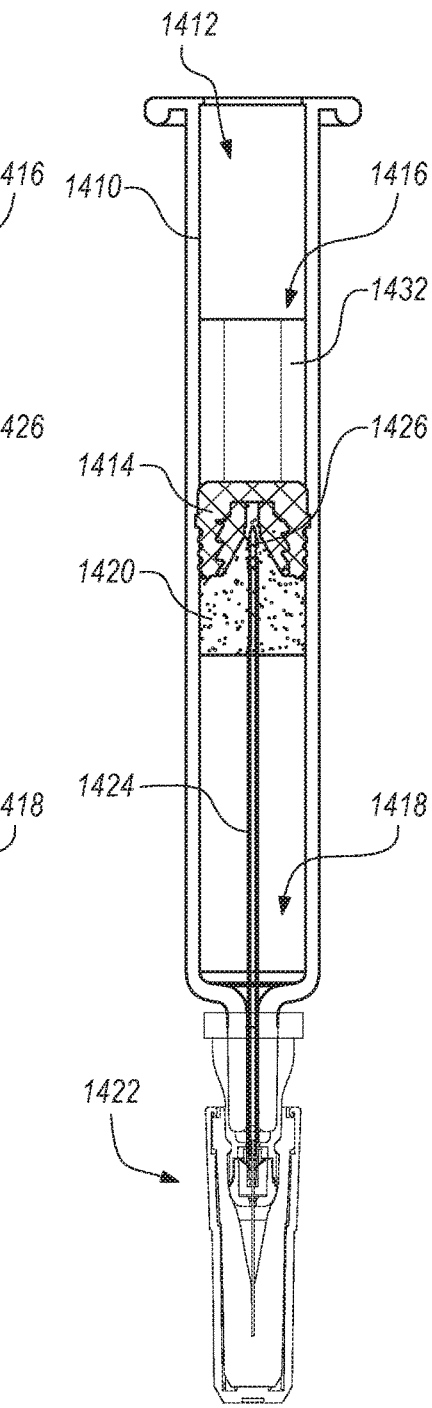

At 1322, a second substance 1432 is introduced into the proximal chamber 1416 through the open proximal end of the injection system/syringe body 1410 as shown in FIG. 14H. The second substance 1432 may be introduced directly through the opening at the proximal end of the injection system/syringe body 1410. The second substance 1432 may be a liquid or another fluid.

Figure 14I:
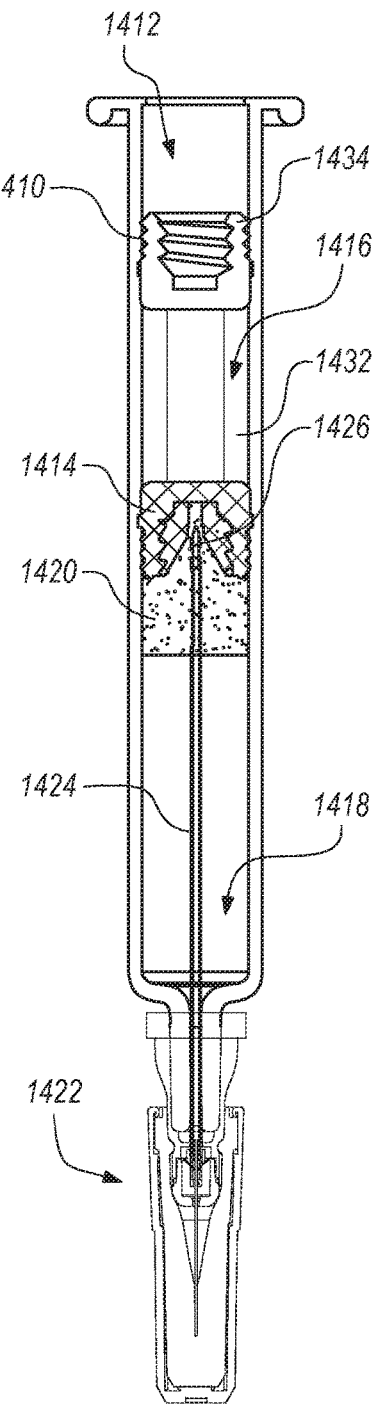

At 1324, a proximal stopper member 1434 is disposed in the interior 1412 of the injection system/syringe body 1410 as shown in FIG. 14I. The proximal stopper member 1434 may be inserted by a user (e.g., using a tool) or by a mechanical device (e.g., robot). The proximal stopper member 1434 closes the proximal chambers 1416 defined by the injection system/syringe body 1410 and the distal stopper member 1414. The proximal stopper member 1434 may be positioned over an open proximal end of the injection system/syringe body 1410 to facilitate insertion of the proximal stopper member 1434 into the body interior 1412.

A pressure differential on opposite sides of the proximal stopper member 1434 may be used to draw the proximal stopper member into the body interior 1412. For instance, a vacuum maybe formed on the distal side of the proximal stopper member 1434. In some embodiments, a small tube is disposed adjacent the proximal stopper member 1434 to release pressure that builds up as the proximal stopper member 1434 is inserted into the body interior 1412. The small tube is removed after assembly.

Figure 14J:
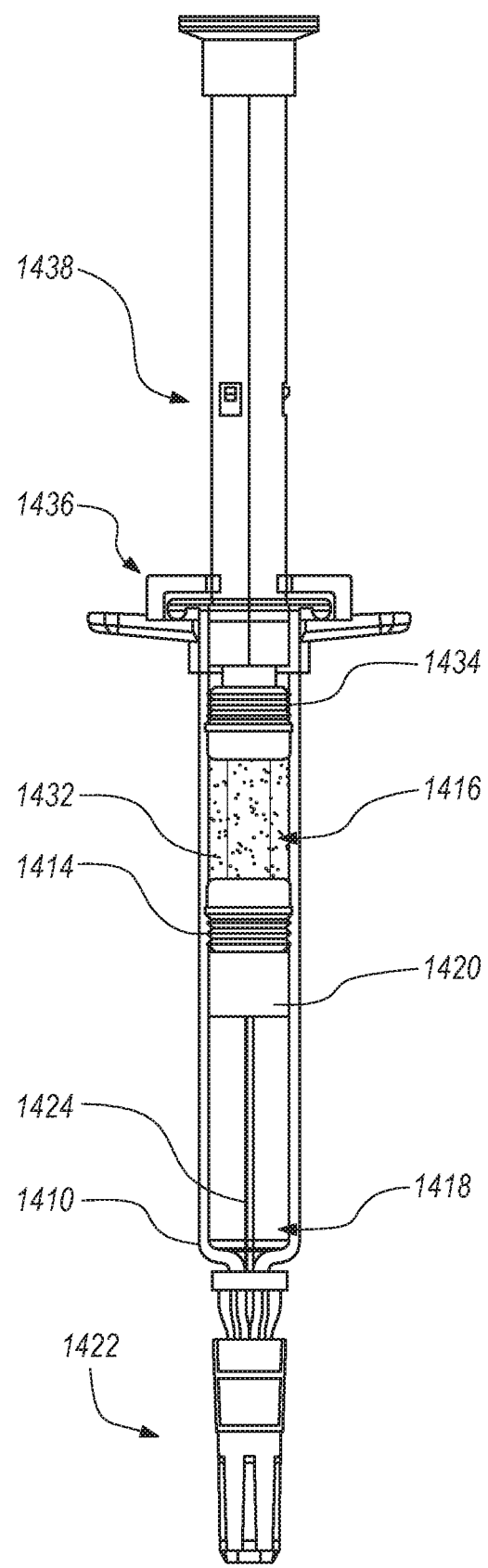

In an optional step shown in FIG. 14J, a finger flange 1336 and a plunger member 1438 are coupled to the injection system/syringe body 1410. The finger flange 1436 may be coupled to the injection system/syringe body 1410 such that it is prevented from moving along a longitudinal axis of the body 1410 (e.g., by snapping over a glass flange at the proximal end of the body 1410). The plunger member 1438 may be coupled to the injection system/syringe body 1410 such that it is movable along a longitudinal axis of the body 1410. A distal end of the plunger member 1438 is also coupled to the proximal stopper member 1434 (e.g., using a threaded screw), such that movement of the plunger member 1438 relative to the injection system/syringe body 1410 moves the proximal stopper member 1434. The finger flange 1436 and a plunger member 1438 may be coupled to the injection system/syringe body 1410 by a user (e.g., using a tool) or by a mechanical device (e.g., robot).

Further details regarding the injection system/syringe body 1410, the proximal and distal stopper members 1414, 1434, the needle hub assembly 1422, the finger flange 1436, and the plunger member 1438 are described in U.S. Utility patent application Ser. No. 15/801,259, which was previously incorporated by reference herein. The method 1300 of manufacturing/assembling a multiple chamber safe injection system depicted in FIG. 13 may take place, fully or in part, in a vacuum (e.g., vacuum chamber or vacuum room). The injection system/syringe body 1410, the proximal and distal stopper members 1414, 1434, the needle hub assembly 1422, the finger flange 1436, and the plunger member 1438 may be pre-sterilized before assembly.

While a single multiple chamber safe injection system is manufactured/assembled in the method 1300 depicted in FIGS. 13 and 14A to 14J, the same method 1300 may be used to manufacture/assemble a plurality of multiple chamber safe injection systems either in parallel or in series. While the method 1300 depicted in FIGS. 13 and 14A to 14J involves a dual chamber system with two stopper members 1414, 1434, in some embodiments, a third stopper member may be added to the multiple chamber safe injection system to define a third chamber using steps similar to those in 1322 and 1324 described above. In some embodiments, more than three stopper members and chambers may be formed in a multiple chamber safe injection system.

Injection System/Syringe Fill Distal Chamber from Back

Figure 17:
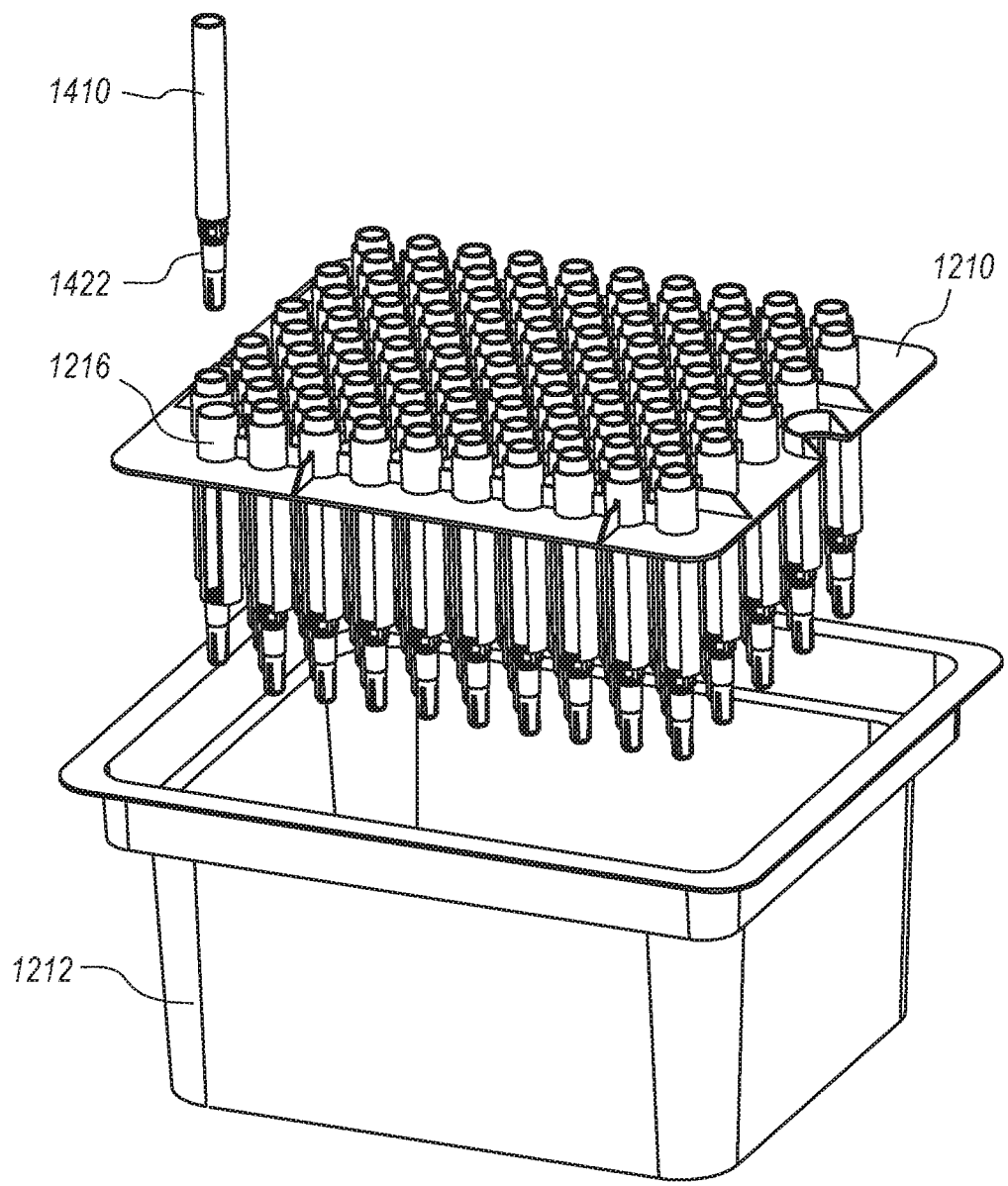
FIG. 17 depicts a rack containing a plurality of injection system/syringe bodies and stored in a container according to some embodiments.

FIG. 17 depicts a rack 1210 containing a plurality of injection system/syringe bodies 1410 coupled to a plurality of needle hub assemblies 1422 and stored in a container 1212. The rack 1210 and the container 1212 are made from materials that are sterilizable. The container 1212 is closable with a seal 1214 (see FIG. 12B) to maintain the sterility of the rack 1210 and injection system/syringe bodies 1410 and needle hub assemblies 1422 contained therein. The rack 1210 is removed from the container 1212 and one injection system/syringe body 1410 coupled to a needle hub assembly 1422 is removed from the rack 1210. The rack 1210 has a plurality of features (e.g., sleeves and/or flanges) 1216 to hold the injection system/syringe bodies 1410 and needle hub assemblies 1422 with the distal end of the injection system/syringe body 1410 is pointed in a generally downward direction (see FIG. 19A).

Figure 18:
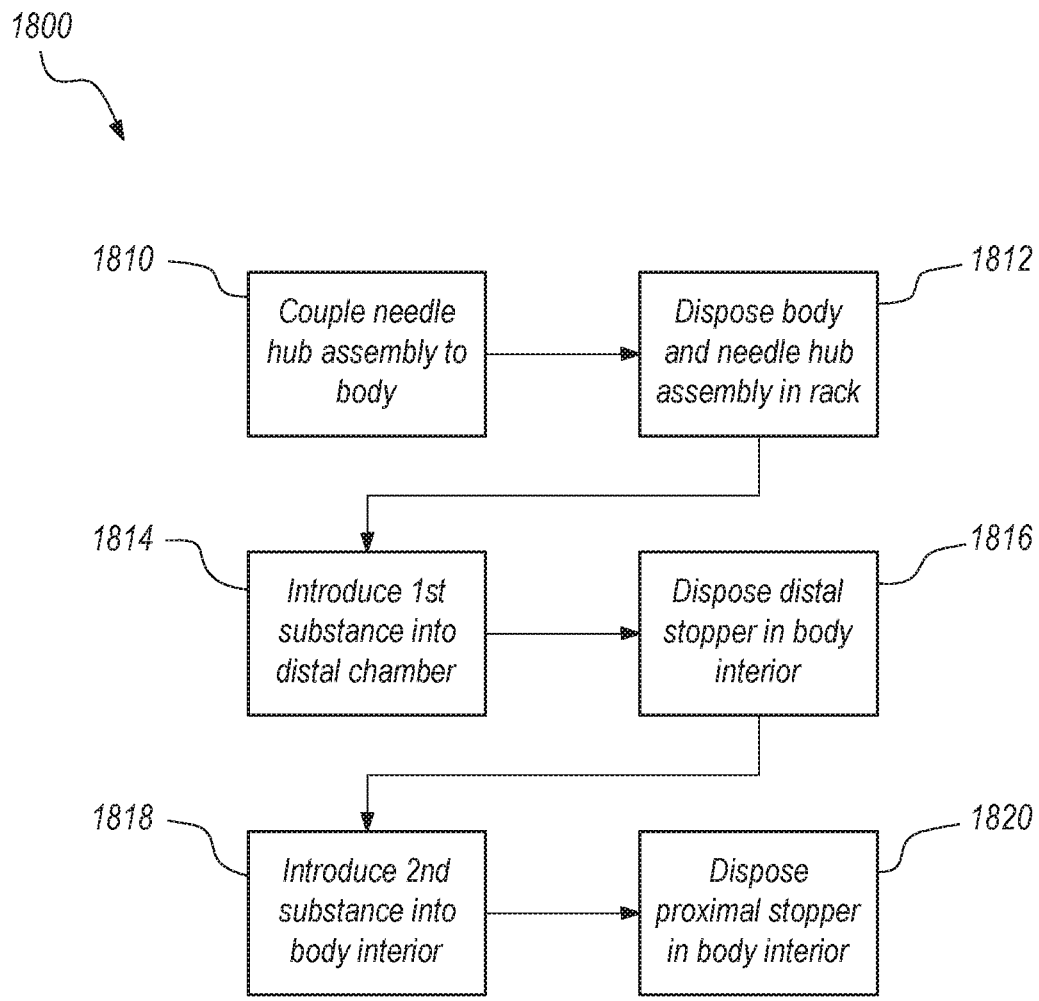
FIG. 18 is a flow chart illustrating a method for manufacturing/assembling a multiple chamber safe injection system according to some embodiments.

FIG. 18 depicts a method 1800 for manufacturing/assembling a multiple chamber safe injection system according to some embodiments. Corresponding partially assembled components are depicted in FIGS. 19A to 19H. The injection system/syringe body 1410, the proximal and distal stopper members 1414, 1434, the needle hub assembly 1422, the finger flange 1436, and the plunger member 1438 may be the same system components depicted in FIGS. 14A to 16A and described above.

Figure 19A:
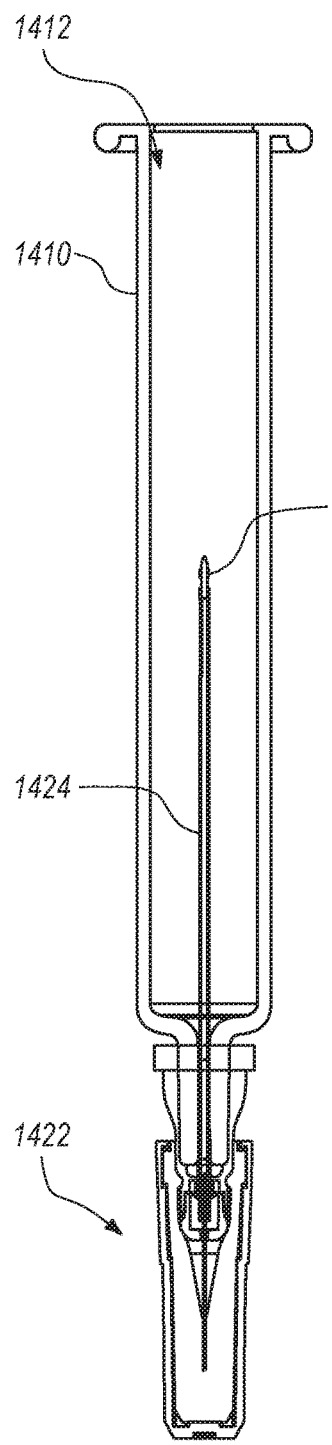

At 1810, a needle hub assembly 1422 is coupled to the distal end of the injection system/syringe body 1410 as shown in FIG. 19A. The needle hub assembly 1422 includes a needle 1424 having a needle proximal end 1426. The needle hub assembly 1422 is coupled to the distal end of the injection system/syringe body 1410 by a user (e.g., using a tool) or by a mechanical device (e.g., robot). In some alternative embodiments, the injection system/syringe body 1410 may be supplied with the needle hub assembly 1422 coupled thereto. In some embodiments, the coupled injection system/syringe body 1410 and needle hub assembly 1422 may be pre-sterilized. In other embodiments, pre-sterilized components may be supplied and assembled at the time of filling.

At 1812, the injection system/syringe body 1410 coupled to the needle hub assembly 1422 is disposed in a rack with the injection system/syringe body 1410 pointed downward as shown in FIGS. 17 and 19A. The injection system/syringe body 1410 may be disposed in the rack by a user (e.g., using a tool) or by a mechanical device (e.g., robot). Alternatively, the injection system/syringe body 1410 may be closed with a luer cap as disclosed in FIGS. 33-40 and described below. In this case the dual chamber system would be provided without a pre-attached needle. The transfer tube component may be pre-inserted into the syringe body or installed at the time of placing the luer cap. The user may attach a needle at the time of use by using a luer slip or luer lock connection method.

Figure 19B:
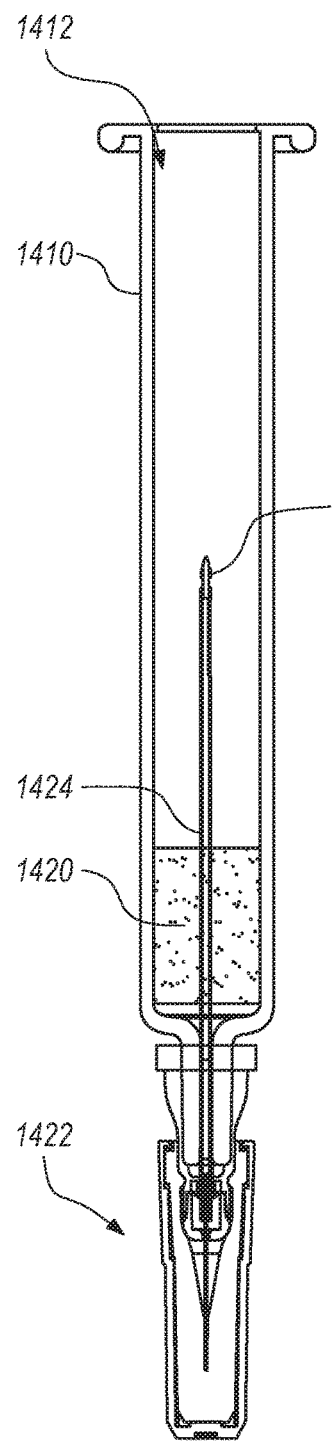

At 1814, a first substance 1420 is introduced into the distal chamber 1418 through the open proximal end of the injection system/syringe body 1410 as shown in FIG. 19B.

Figure 19C:
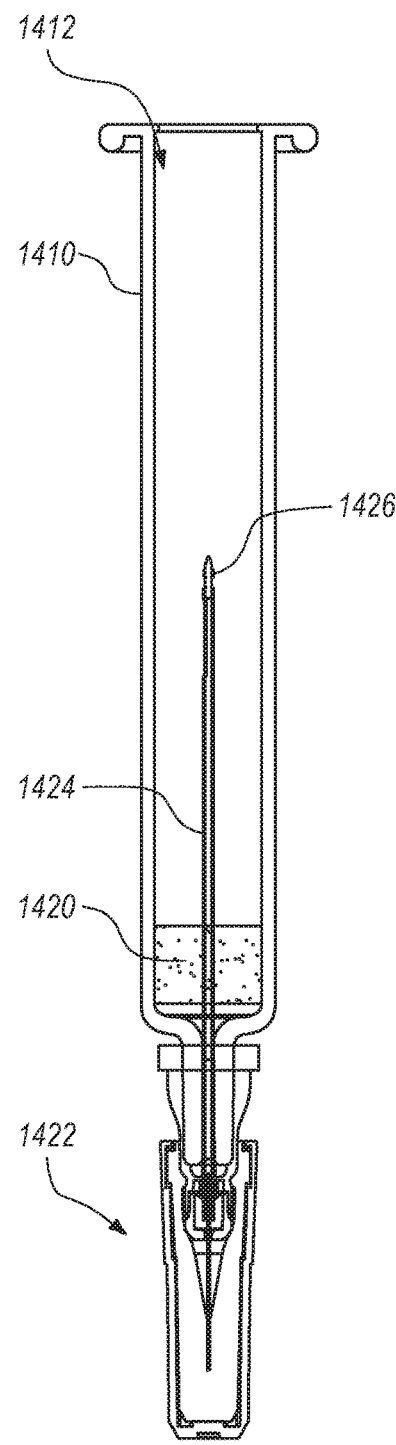

The first substance 1420 may be introduced directly through the opening at the proximal end of the injection system/syringe body 1410. The first substance 1420 may be a liquid, solid (e.g., compressed powder), and/or a powder. In some embodiments where the first substance 1420 is a liquid, the first substance 1420 may be lyophilized in an optional step to form a powder as shown in FIG. 19C.

At 1816, a distal stopper member 1414 is disposed in an interior 1412 of the injection system/syringe body 1410 as shown in FIGS. 19D and 19E. The distal stopper member 1414 may be inserted by a user (e.g., using a tool) or by a mechanical device (e.g., robot). The distal stopper member 1414 and the injection system/syringe body 1410 define proximal and distal chambers 1416, 1418 in the body interior 1412. The distal stopper member 1414 may be positioned over an open proximal end of the injection system/syringe body 1410 to facilitate insertion of the distal stopper member 1414 into the body interior 1412 as shown in FIG. 19D.

The needle proximal end 1426 interferes with the distal stopper member 1414 to temporarily prevent distal movement of the distal stopper member 1414 relative to the injection system/syringe body 1410. Components of the distal stopper member 1414 that interfere with the needle proximal end 1426 are depicted in FIGS. 15A to 15D and 16 to 16A, and described above.

At 1818, a second substance 1432 is introduced into the proximal chamber 1416 through the open proximal end of the injection system/syringe body 1410 as shown in FIG. 19F. The second substance 1432 may be introduced directly through the opening at the proximal end of the injection system/syringe body 1410. The second substance 1432 may be a liquid or another fluid.

Figure 19G:
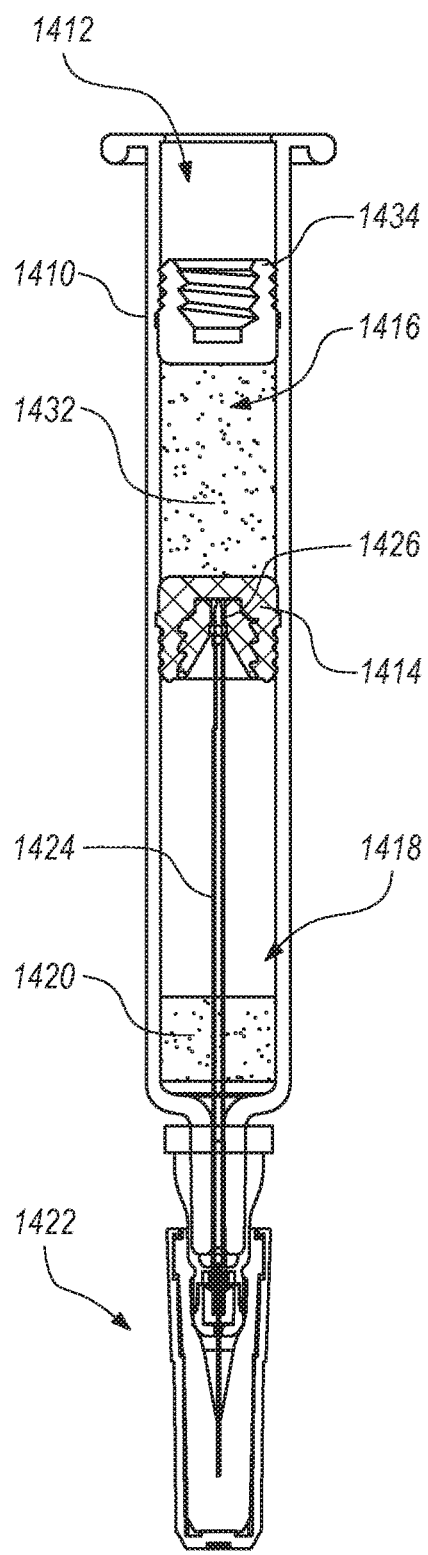

At 1820, a proximal stopper member 1434 is disposed in the interior 1412 of the injection system/syringe body 1410 as shown in FIG. 19G. The proximal stopper member 1434 may be inserted by a user (e.g., using a tool) or by a mechanical device (e.g., robot). The proximal stopper member 1434 closes the proximal chambers 1416 defined by the injection system/syringe body 1410 and the distal stopper member 1414. The proximal stopper member 1434 may be positioned over an open proximal end of the injection system/syringe body 1410 to facilitate insertion of the proximal stopper member 1434 into the body interior 1412. The proximal stopper member 1438 may be inserted using a pressure differential or a small tube as described above.

Figure 19H:
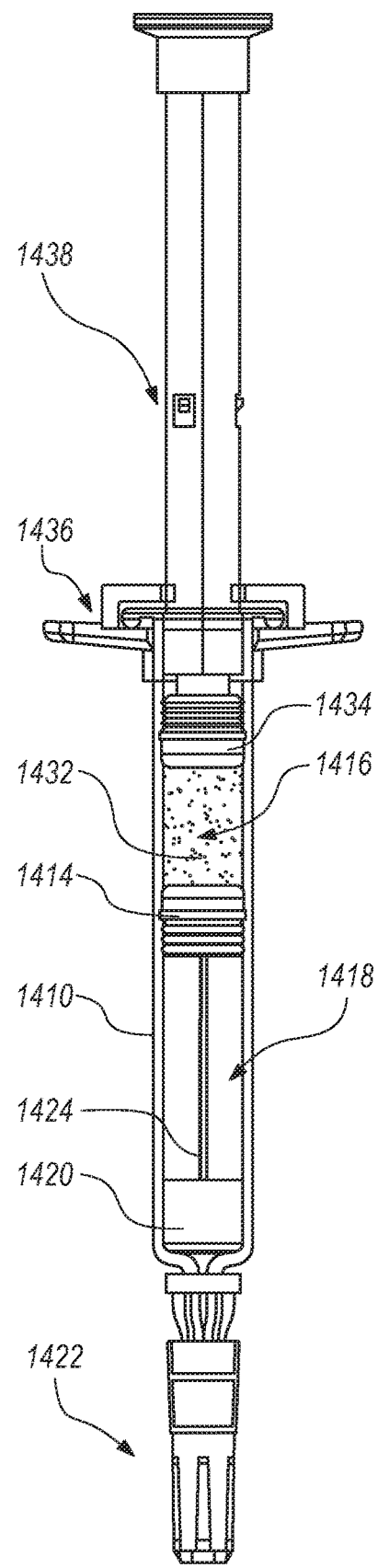

In an optional step shown in FIG. 19H, a finger flange 1436 and a plunger member 1438 are coupled to the injection system/syringe body 1410. The finger flange 1436 may be coupled to the injection system/syringe body 1410 such that it is prevented from moving along a longitudinal axis of the body 1410 (e.g., by snapping over a glass flange at the proximal end of the body 1410). The plunger member 1438 may be coupled to the injection system/syringe body 1410 such that it is movable along a longitudinal axis of the body 1410. A distal end of the plunger member 1438 is also coupled to the proximal stopper member 1434 (e.g., using a threaded screw), such that movement of the plunger member 1438 relative to the injection system/syringe body 1410 moves the proximal stopper member 1434. The finger flange 1436 and a plunger member 1438 may be coupled to the injection system/syringe body 1410 by a user (e.g., using a tool) or by a mechanical device (e.g., robot).

While a single multiple chamber safe injection system is manufactured/assembled in the method 1800 depicted in FIGS. 18 and 19A to 19H, the same method 1800 may be used to manufacture/assemble a plurality of multiple chamber safe injection systems either in parallel or in series. While the method 1800 depicted in FIGS. 18 and 19A to 19H involves a dual chamber system with two stopper members 1414, 1434, in some embodiments, a third stopper member may be added to the multiple chamber safe injection system to define a third chamber using steps similar to those in 1818 and 1820 described above. In some embodiments, more than three stopper members and chambers may be formed in a multiple chamber safe injection system.

Cartridge Fill Distal Chamber from Front

Figure 20A:
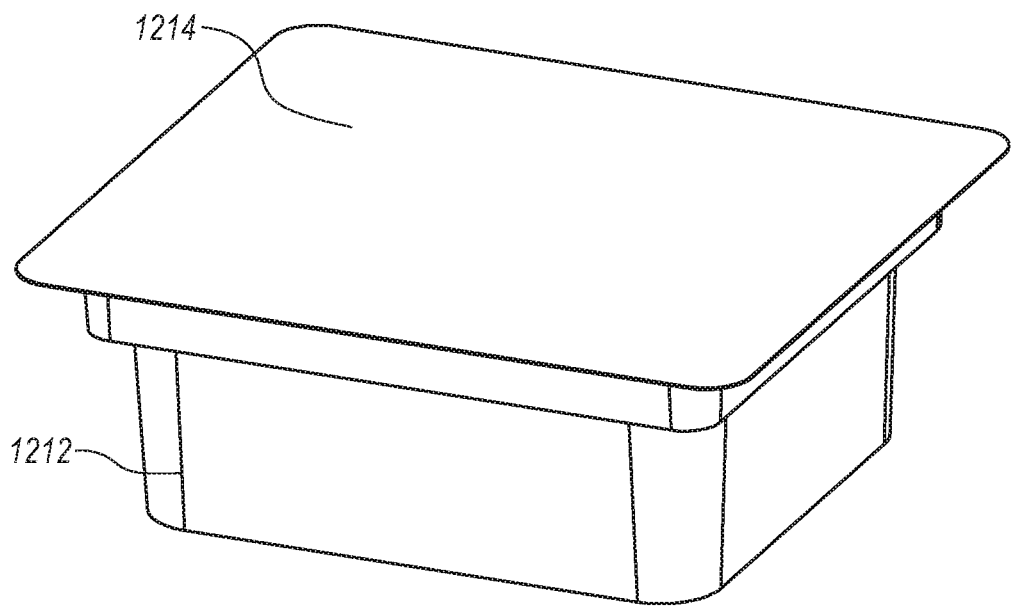
FIGS. 20A to 20D depict a rack containing a plurality of cartridge bodies and stored in a container according to some embodiments.
Figure 20B:
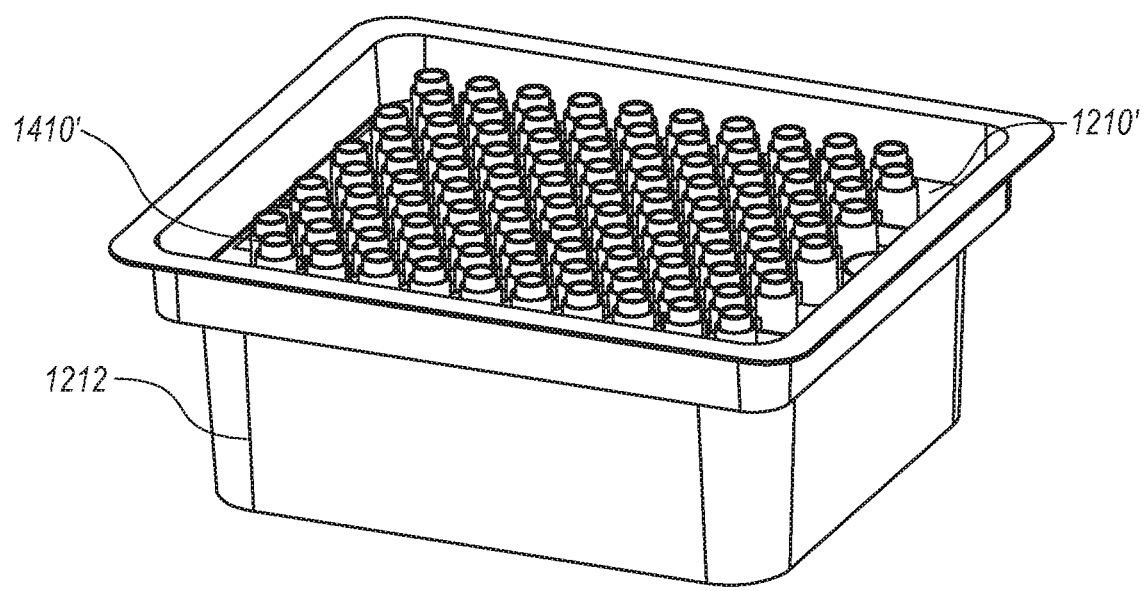

FIGS. 20A and 20B depict a rack 1210' containing a plurality of cartridges 1410' and stored in a container 1212. The rack 1210' and the container 1212 are made from materials that are sterilizable. The container 1212 is closable with a seal 1214 (FIG. 20A) to maintain the sterility of the rack 1210' and cartridges 1410' contained therein.

Figure 20C:
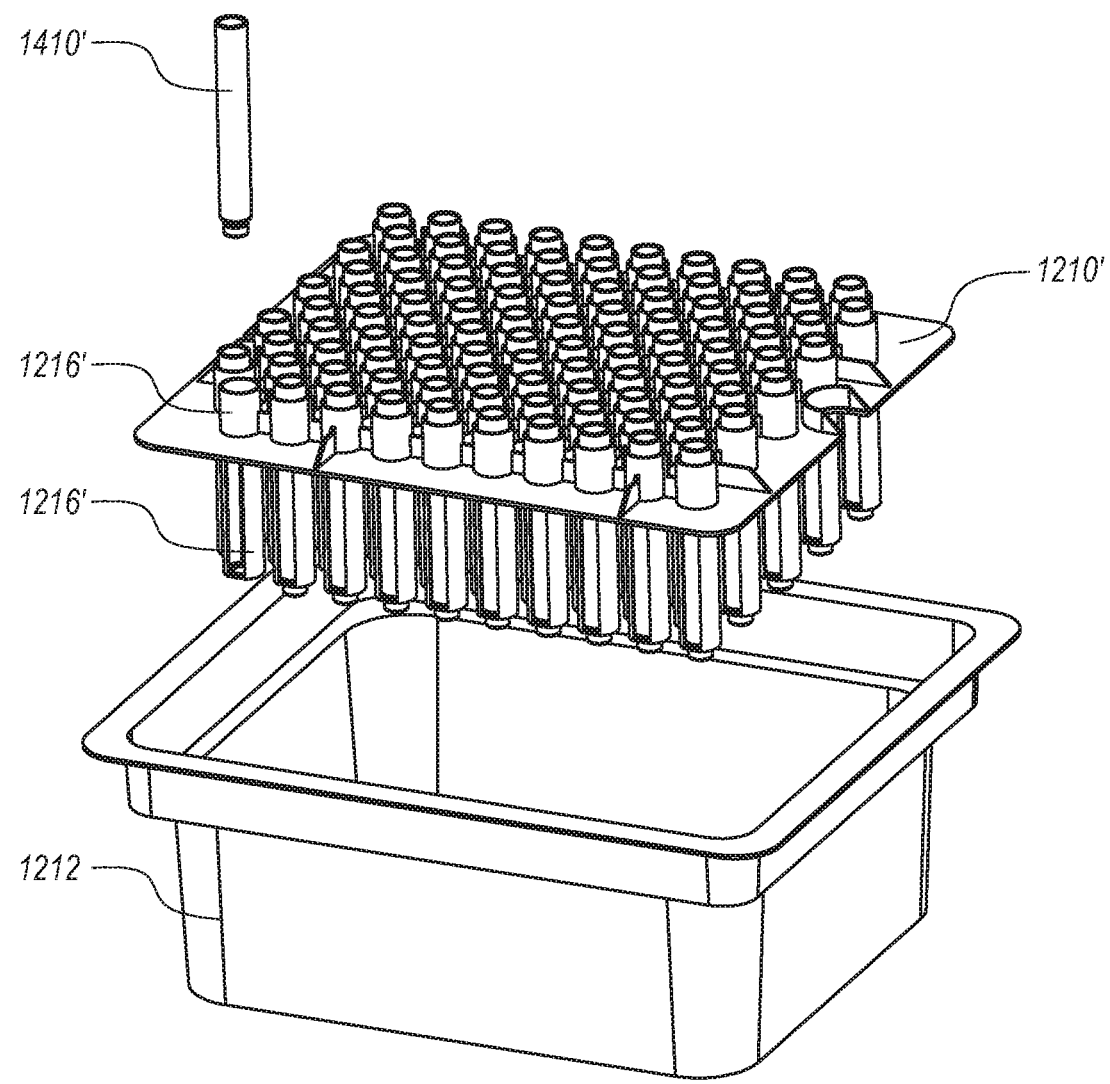
Figure 20D:
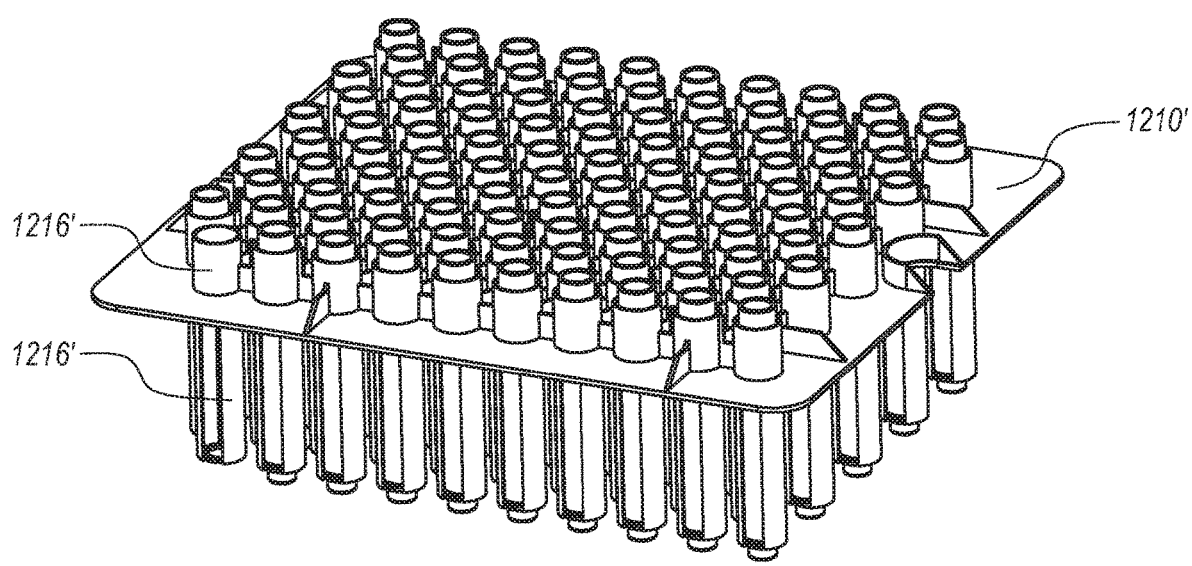

FIG. 20C depicts the rack 1210' removed from the container 1212 and one cartridge 1410' removed from the rack 1210'. The rack 1210' has a plurality of features (e.g., sleeves and/or flanges) 1216' to hold the cartridges 1410' in a first configuration in which the distal end of the cartridge 1410' is pointed in a generally downward direction (see FIG. 22A). In some embodiments, the features 1216' are also configured to hold the cartridges 1410' in a second configuration in which the proximal end of the cartridge 1410' is pointed in a generally downward direction (see FIG. 22C).

Figure 21:
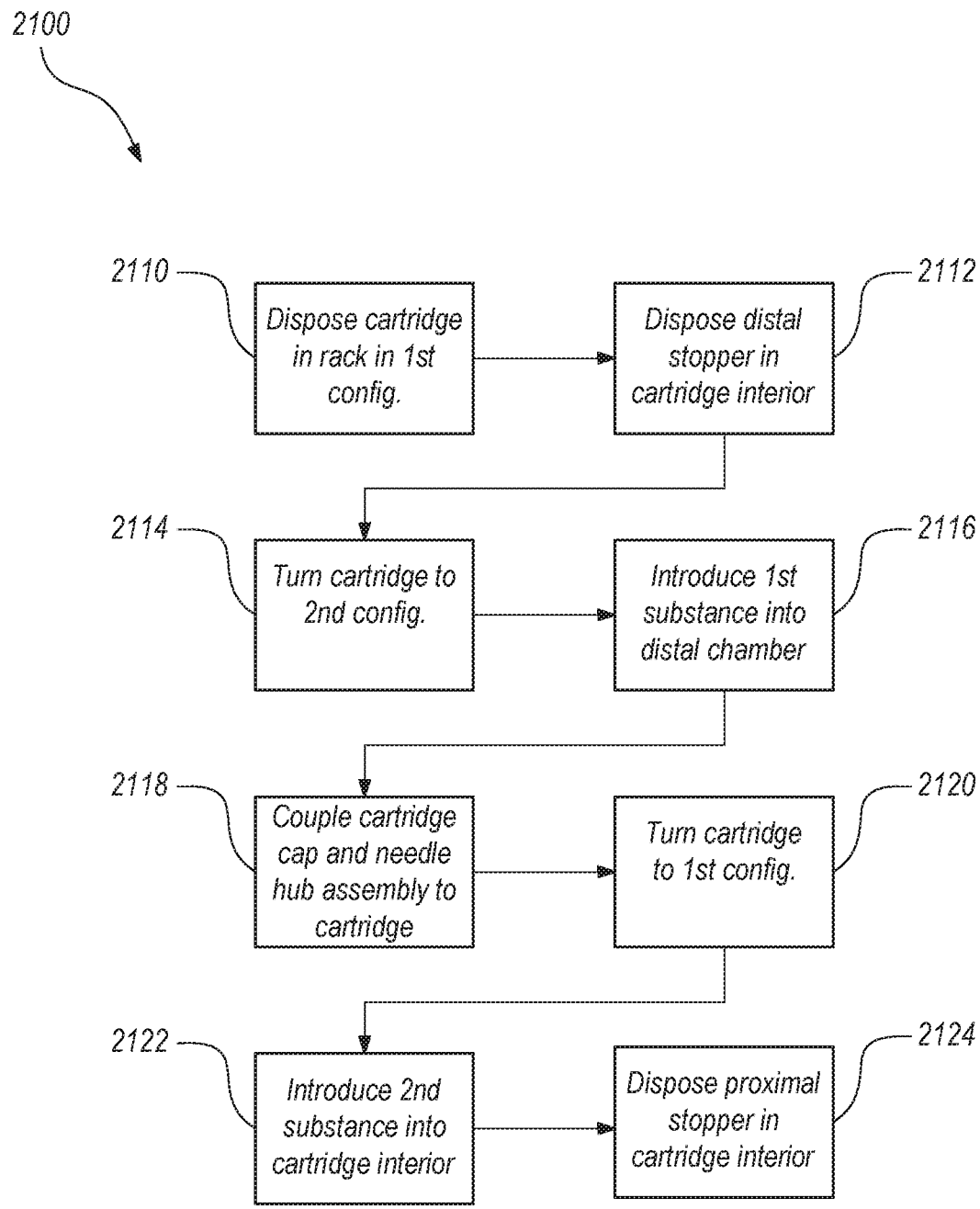
FIG. 21 is a flow chart illustrating a method for manufacturing/assembling a multiple chamber safe injection system according to some embodiments.

FIG. 21 depicts a method 2100 for manufacturing/assembling a multiple chamber safe injection system according to some embodiments. Corresponding partially assembled components are depicted in FIGS. 22A to 22J.

Figure 22A:
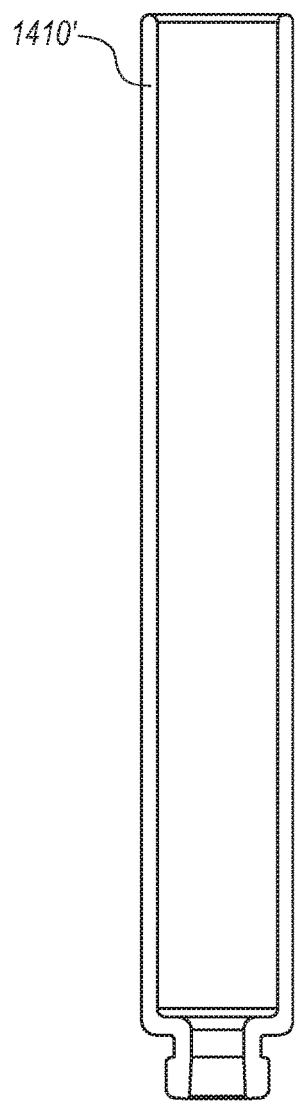
FIGS. 22A to 22J illustrate various steps in a method for manufacturing/assembling a multiple chamber safe injection system according to some embodiments.

At 2110, a cartridge 1410' is disposed in a rack in a first (downward) configuration as shown in FIG. 22A. The cartridge 1410' may be disposed in the rack by a user (e.g., using a tool) or by a mechanical device (e.g., robot).

Figure 22B:
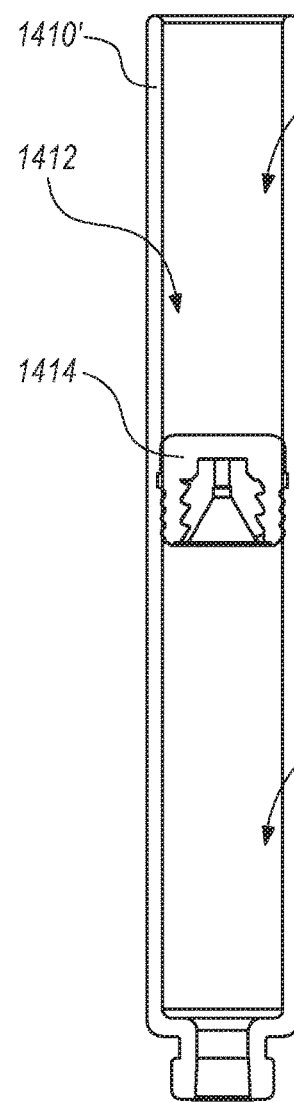

At 2112, a distal stopper member 1414 is disposed in an interior 1412 of the cartridge 1410' as shown in FIG. 22B. The distal stopper member 1414 may be inserted by a user (e.g., using a tool) or by a mechanical device (e.g., robot). The distal stopper member 1414 and the cartridge 1410' define proximal and distal chambers 1416, 1418 in the body interior 1412. The distal stopper member 1414 may be positioned over an open proximal end of the cartridge 1410' to facilitate insertion of the distal stopper member 1414 into the body interior 1412.

Figure 22C:
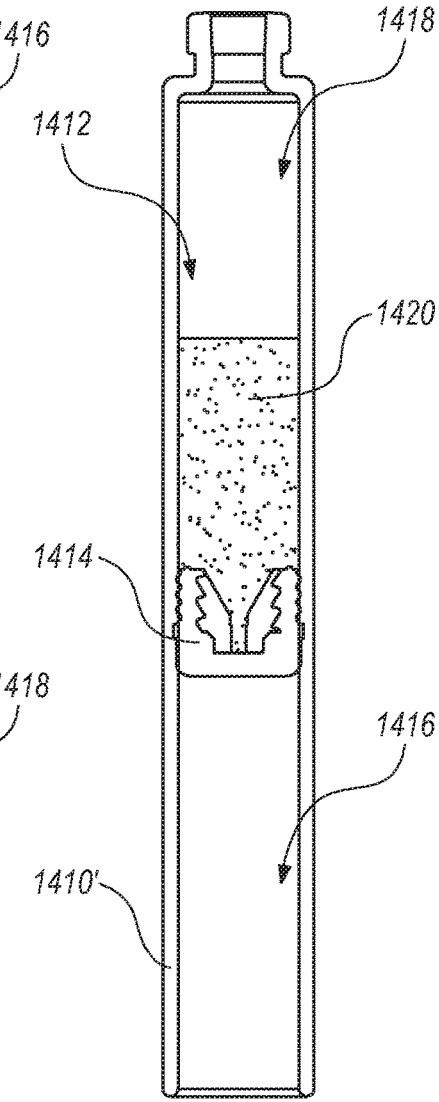

At 2114, the cartridge 1410' is turned to a second (upward) configuration as shown in FIG. 22C. The cartridge 1410' may be repositioned in the rack after being turned to the second configuration. Cartridge 1410' may be turned and/or repositioned by a user (e.g., using a tool) or by a mechanical device (e.g., robot).

At 2116, a first substance 1420 is introduced into the distal chamber 1418 through the open distal end of the cartridge 1410' as shown in FIG. 22C. The first substance 1420 may be introduced directly through the opening at the distal end of the cartridge 1410'. In some embodiments, a tube may be inserted through the opening at the distal end of the cartridge 1410', and the first substance 1420 may be introduced through the tube. The first substance 1420 may be a liquid, a solid (e.g., compressed powder), and/or a powder. In some embodiments where the first substance 1420 is a liquid, the first substance 1420 may be lyophilized in an optional step to form a powder as shown in FIG. 22D.

Figures 22D, 22E, 22F:
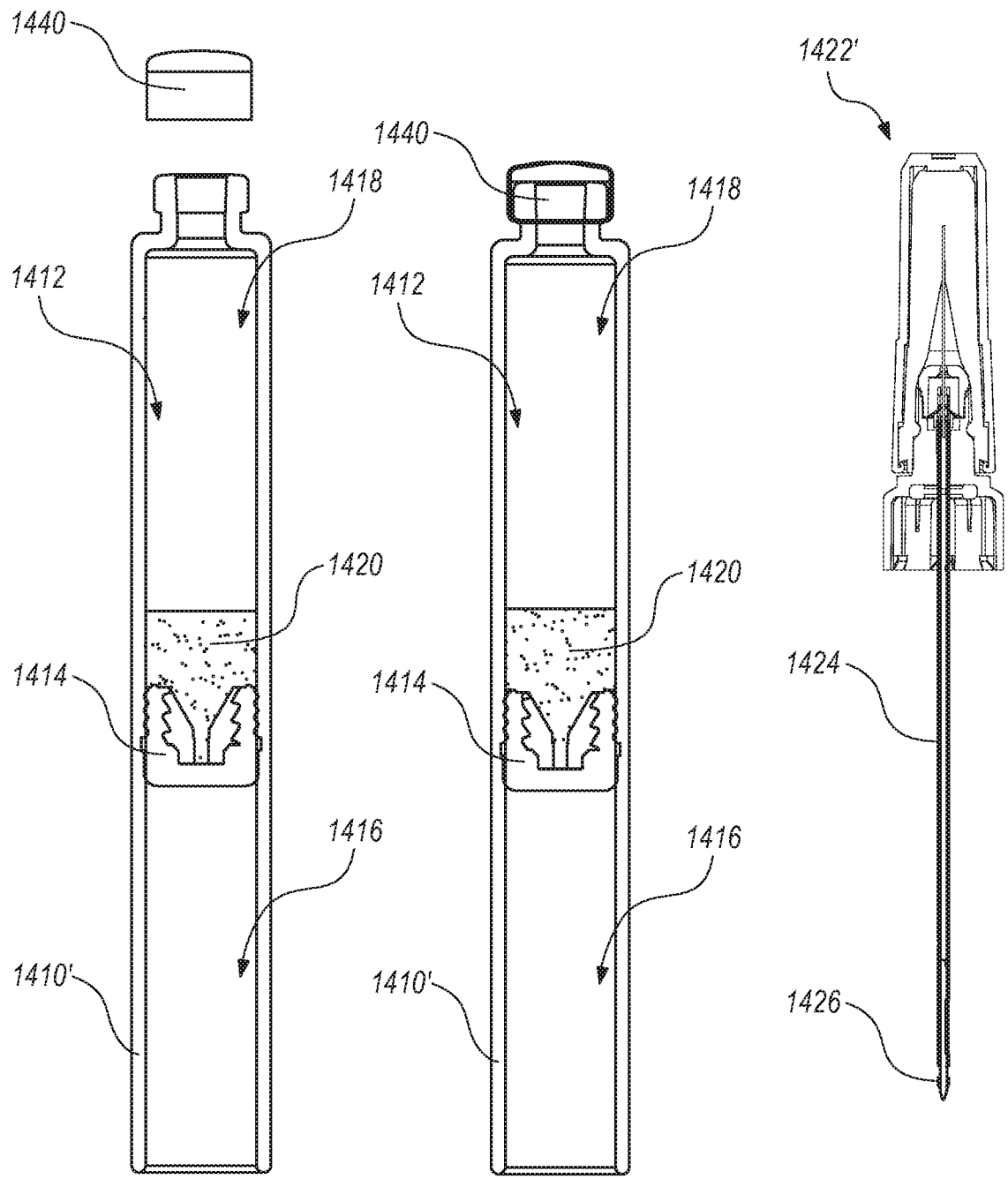

At 2118, a cartridge cap 1440 and a needle hub assembly 1422' are coupled to the distal end of the cartridge 1410' as shown in FIG. 22E. First, the cartridge cap 1440 may be coupled to the distal end of the cartridge 1410' by a user (e.g., using a tool) or by a mechanical device (e.g., robot).

Figure 23A:
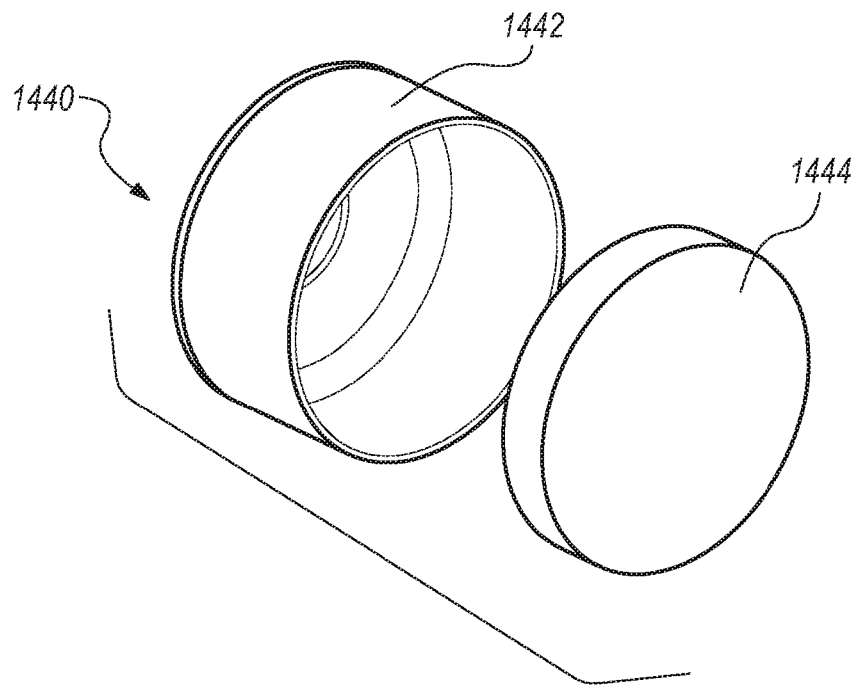
FIGS. 23A and 23B depict various aspects of a cartridge cap for use with a multiple chamber safe injection system according to some embodiments.
Figure 23B:
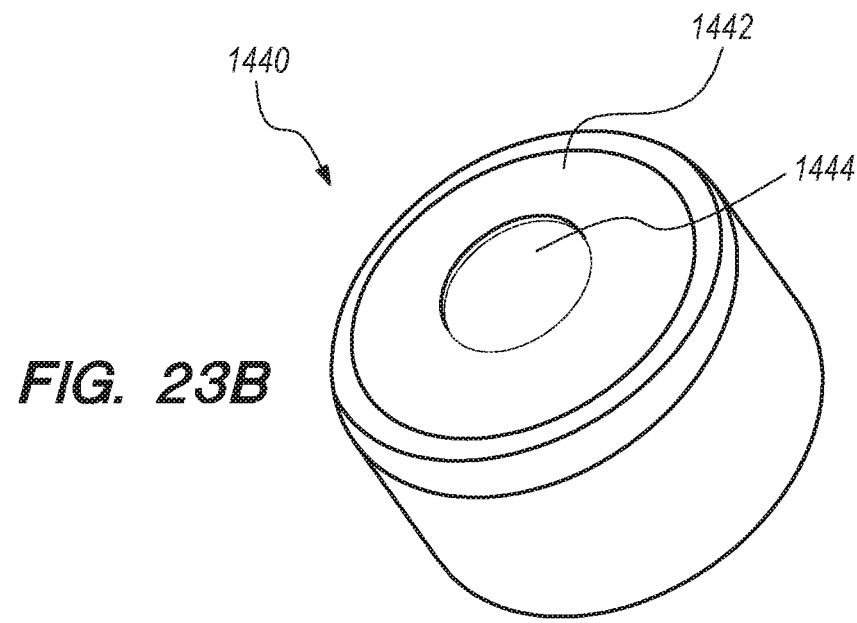

Exemplary cartridge caps 1440 are shown in FIGS. 23A and 23B. The cartridge caps 1440 include a crimp seal 1442 with an opening therein and a septum 1444. The crimp seal 1442 may be made from aluminum and the septum 1444 may be made from rubber. The cartridge cap 1440 may be coupled to the distal end of the cartridge 1410' by crimping the crimp seal 1442 around and enlarge portion of the cartridge 1410' at a distal end thereof.

Figure 22G:
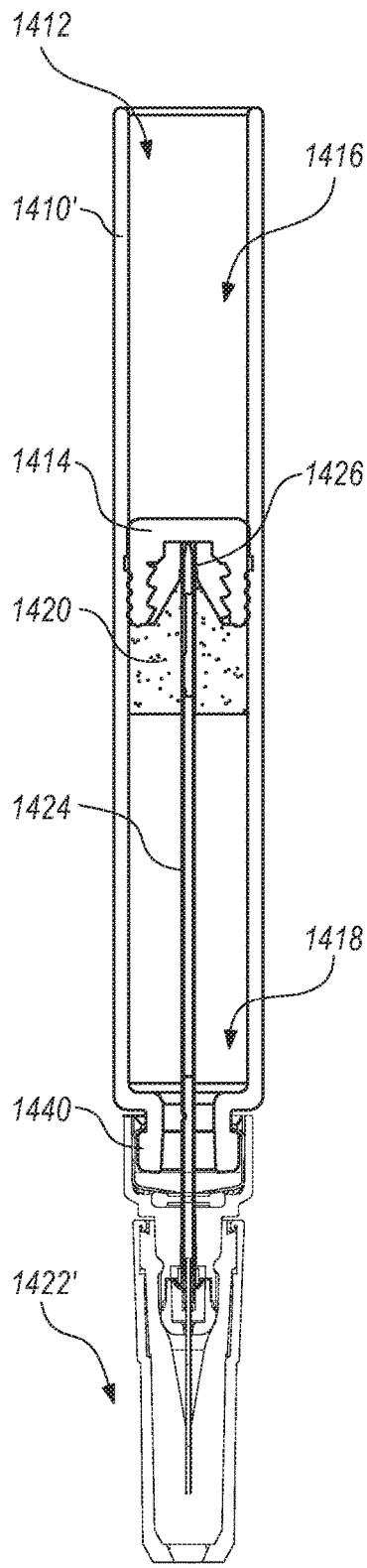

Next, the needle hub assembly 1422' is coupled to the distal end of the cartridge 1410' on top of the cartridge cap 1440 as shown in FIG. 22G. As shown in FIG. 22F, the needle hub assembly 1422' includes a needle 1424 having a needle proximal end 1426. The needle proximal end 1426 interferes with the distal stopper member 1414 to temporarily prevent distal movement of the distal stopper member 1414 relative to the cartridge 1410'. The needle hub assembly 1422' is coupled to the distal end of the cartridge 1410' by a user (e.g., using a tool) or by a mechanical device (e.g., robot). Components of the distal stopper member 1414 that interfere with the needle proximal end 1426 are depicted in FIGS. 15A to 15D and 16 to 16A, and described above.

In some alternative embodiments, the cartridge 1410' may be supplied with a needle hub assembly 1422' or luer cap coupled thereto. In some embodiments, the coupled the cartridge 1410', needle hub assembly 1422', and/or luer cap may be pre-sterilized. In other embodiments, pre-sterilized components may be supplied and assembled at the time of filling.

Figure 24A:
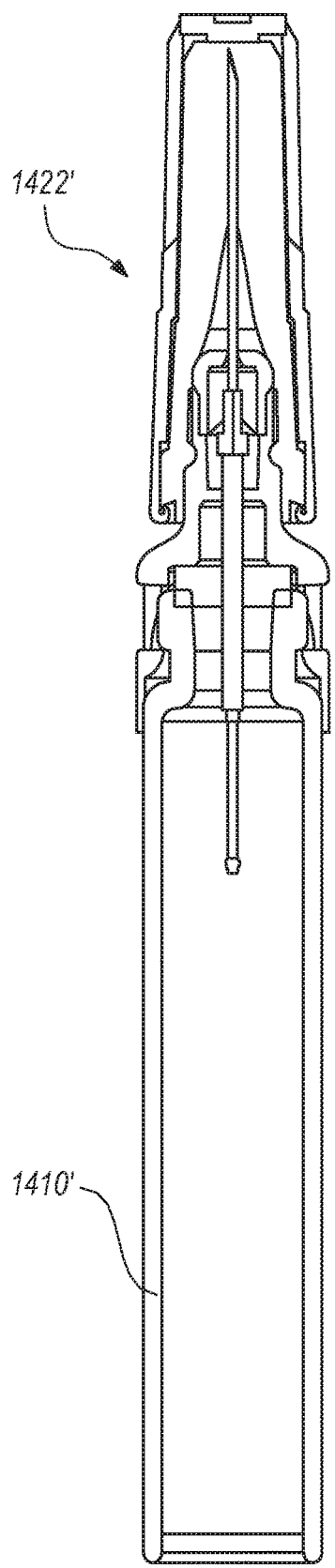
FIGS. 24A and 24B depict cartridge bodies for use with multiple chamber safe injection systems according to some embodiments.
Figure 24B:
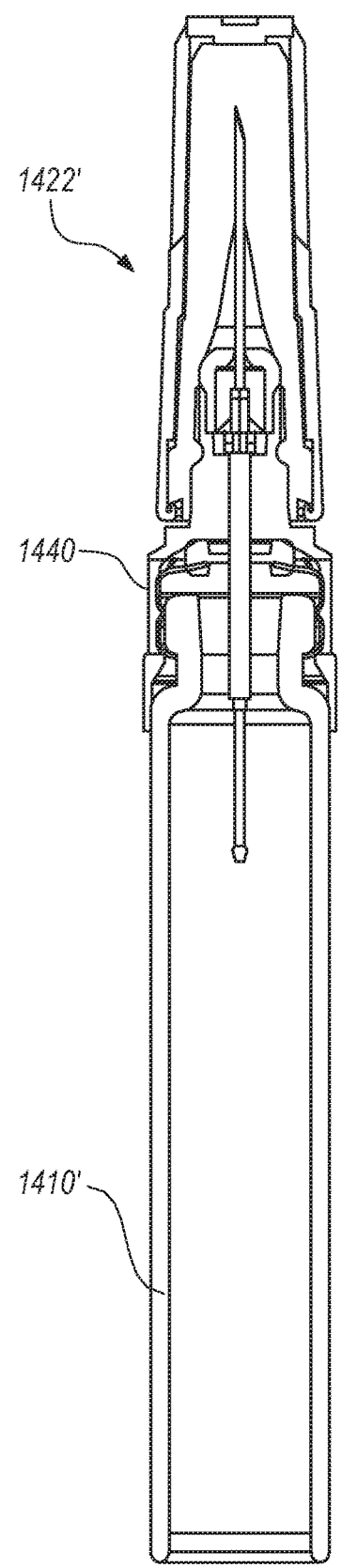

While a cartridge cap 1440 is included in the embodiment depicted in FIG. 22E, the cartridge cap 1440 is optional and the needle hub assembly 1422' is directly coupled to the distal end of the cartridge 1410' in some embodiments (compare FIGS. 24A (no cap) and 24B (with cap)).

At 2120, the cartridge 1410' is turned back to the first (downward) configuration as shown in FIG. 22G. The cartridge 1410' may be repositioned in the rack after being turned back to the first configuration. Cartridge 1410' may be turned and/or repositioned by a user (e.g., using a tool) or by a mechanical device (e.g., robot).

Figure 22H:
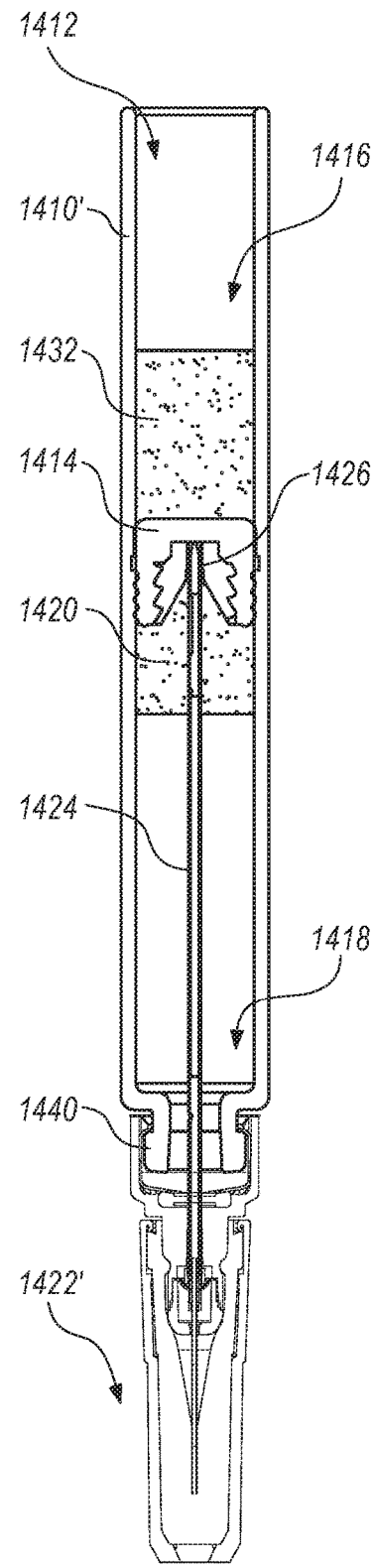

At 2122, a second substance 1432 is introduced into the proximal chamber 1416 through the open proximal end of the cartridge 1410' as shown in FIG. 22H. The second substance 1432 may be introduced directly through the opening at the proximal end of the cartridge 1410'. The second substance 1432 may be a liquid or another fluid.

Figure 22I:
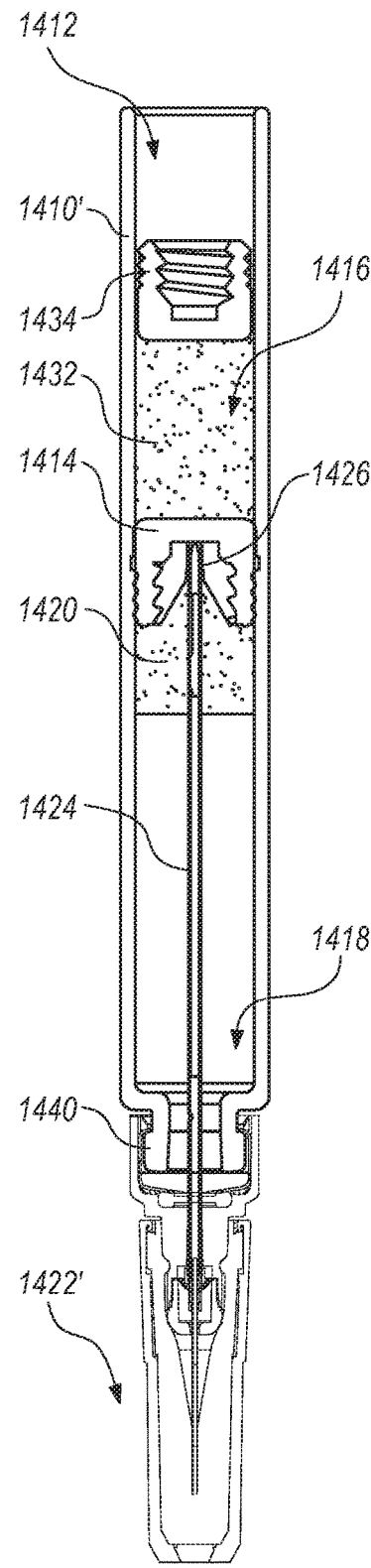

At 2124, a proximal stopper member 1434 is disposed in the interior 1412 of the cartridge 1410' as shown in FIG. 22I. The proximal stopper member 1434 may be inserted by a user (e.g., using a tool) or by a mechanical device (e.g., robot). The proximal stopper member 1434 closes the proximal chambers 1416 defined by the cartridge 1410' and the distal stopper member 1414. The proximal stopper member 1434 may be positioned over an open proximal end of the cartridge 1410' to facilitate insertion of the proximal stopper member 1434 into the body interior 1412. The proximal stopper member 1438 may be inserted using a pressure differential or a small tube as described above.

Figure 22J:
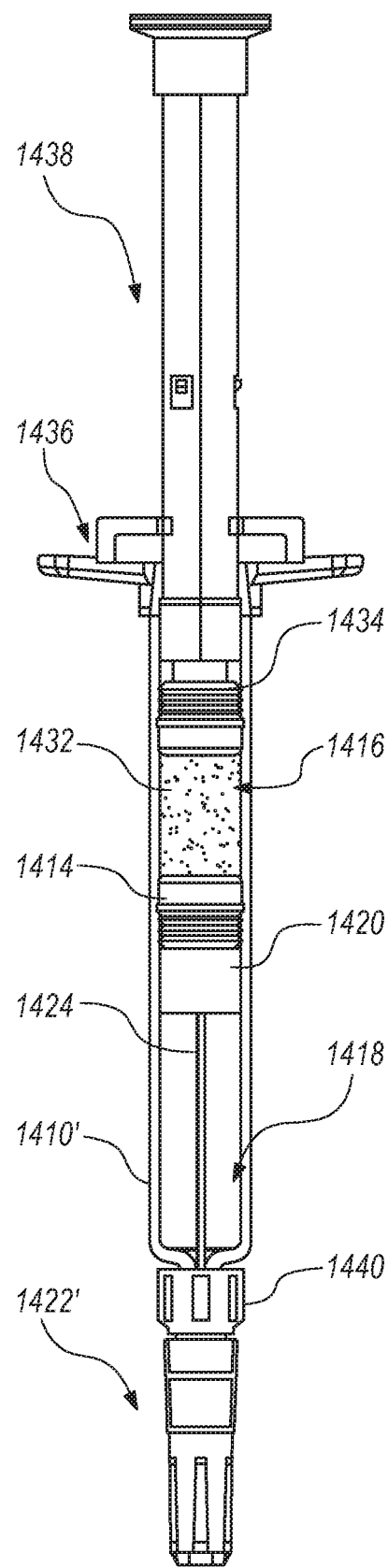

In an optional step shown in FIG. 22J, a finger flange 1436 and a plunger member 1438 are coupled to the cartridge 1410'. The finger flange 1436 may be coupled to the cartridge 1410' such that it is prevented from moving along a longitudinal axis of the body 1410 (e.g., using an adhesive). The plunger member 1438 may be coupled to the cartridge 1410' such that it is movable along a longitudinal axis of the body 1410. A distal end of the plunger member 1438 is also coupled to the proximal stopper member 1434 (e.g., using a threaded screw), such that movement of the plunger member 1438 relative to the cartridge 1410' moves the proximal stopper member 1434. The finger flange 1436 and a plunger member 1438 may be coupled to the cartridge 1410' by a user (e.g., using a tool) or by a mechanical device (e.g., robot).

Further details regarding the cartridge 1410', the proximal and distal stopper members 1414, 1434, the needle hub assembly 1422', the finger flange 1436, and the plunger member 1438 are described in U.S. Utility patent application Ser. No. 15/801,259, which was previously incorporated by reference herein. The method 2100 of manufacturing/assembling a multiple chamber safe injection system depicted in FIG. 21 may take place, fully or partially, in a vacuum (e.g., vacuum chamber or vacuum room). The cartridge 1410', the proximal and distal stopper members 1414, 1434, the needle hub assembly 1422', the finger flange 1436, and the plunger member 1438 may be pre-sterilized before assembly.

While a single multiple chamber safe injection system is manufactured/assembled in the method 2100 depicted in FIGS. 21 and 22A to 22J, the same method 2100 may be used to manufacture/assemble a plurality of multiple chamber safe injection systems either in parallel or in series. While the method 2100 depicted in FIGS. 21 and 22A to 22J involves a dual chamber system with two stopper members 1414, 1434, in some embodiments, a third stopper member may be added to the multiple chamber safe injection system to define a third chamber using steps similar to those in 2122 and 2124 described above. In some embodiments, more than three stopper members and chambers may be formed in a multiple chamber safe injection system.

Cartridge Fill Distal Chamber from Back, Pierce then Fill

Figure 25:
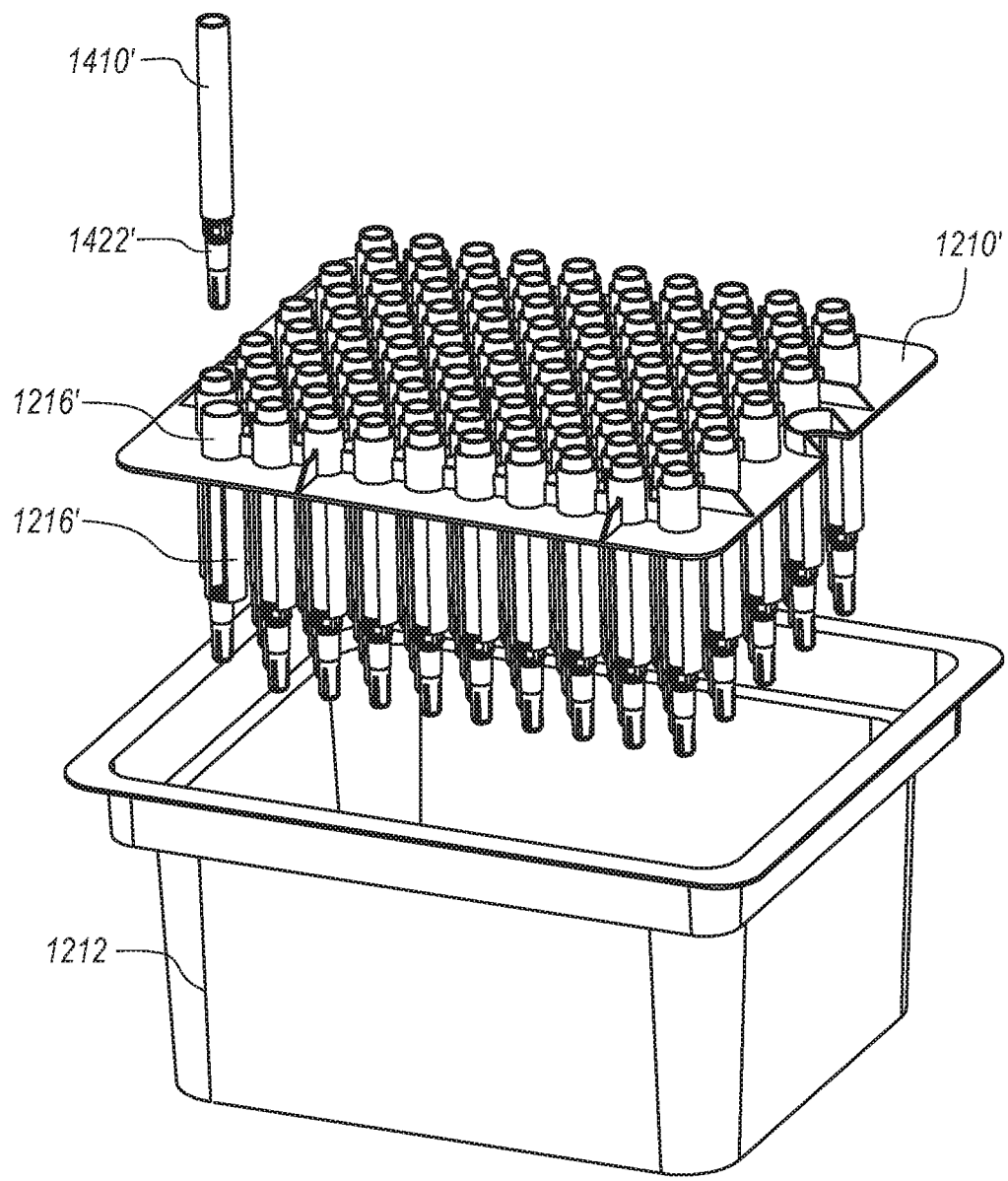
FIG. 25 depicts a rack containing a plurality of cartridge bodies and stored in a container according to some embodiments.

FIG. 25 depicts a rack 1210' containing a plurality of cartridges 1410' and coupled to a plurality of needle hub assemblies 1422' and stored in a container 1212. The rack 1210' and the container 1212 are made from materials that are sterilizable. The container 1212 is closable with a seal 1214 (see FIG. 12B) to maintain the sterility of the rack 1210' and cartridges 1410' and needle hub assemblies 1422' contained therein. The rack 1210' is removed from the container 1212 and one cartridge 1410' coupled to a needle hub assembly 1422' is removed from the rack 1210'. The rack 1210' has a plurality of features (e.g., sleeves and/or flanges) 1216' to hold the cartridges 1410' and needle hub assemblies 1422' with the distal end of the cartridge 1410' is pointed in a generally downward direction (see FIG. 27A).

Figure 26:
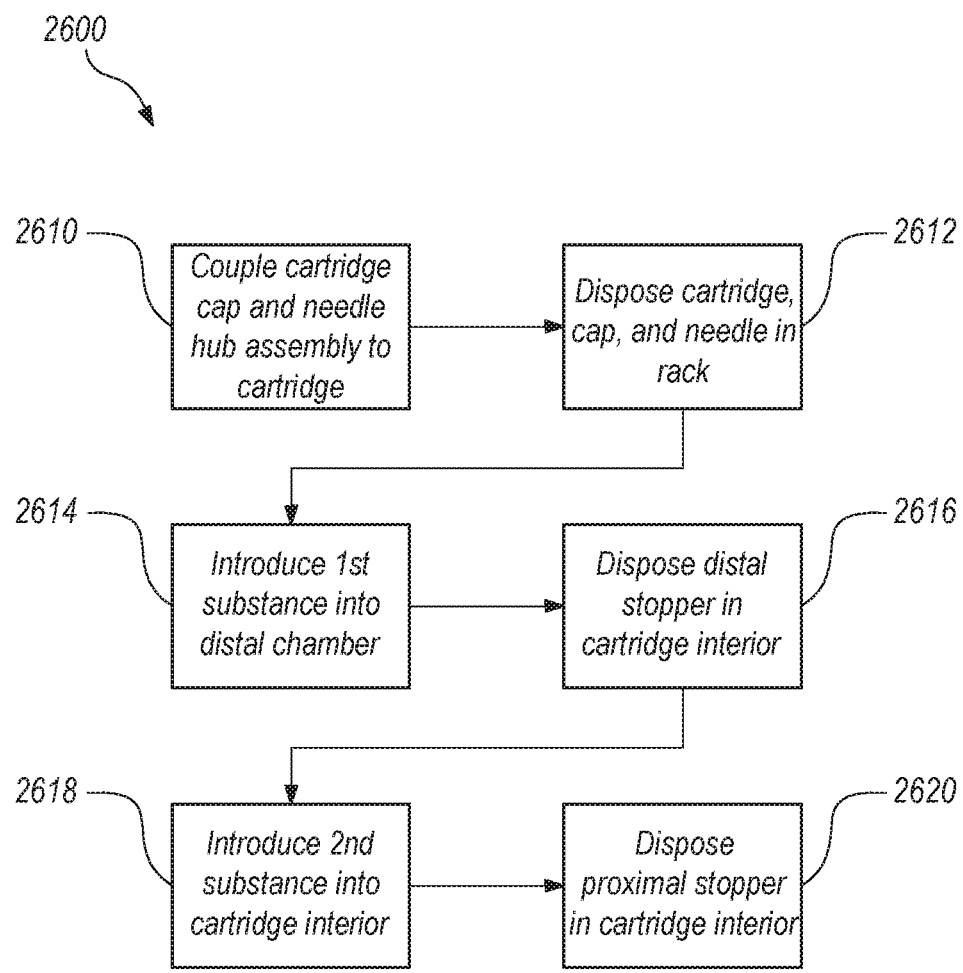
FIG. 26 is a flow chart illustrating a method for manufacturing/assembling a multiple chamber safe injection system according to some embodiments.

FIG. 26 depicts a method 2600 for manufacturing/assembling a multiple chamber safe injection system according to some embodiments. Corresponding partially assembled components are depicted in FIGS. 27A to 27G. The cartridge 1410', the proximal and distal stopper members 1414, 1434, the needle hub assembly 1422', cartridge cap 1440, the finger flange 1436, and the plunger member 1438 may be the same system components depicted in FIGS. 22A to 24B and described above.

At 2610, a cartridge cap 1440 and a needle hub assembly 1422' are coupled to the distal end of the cartridge 1410' as shown in FIG. 27A. First, the cartridge cap 1440 may be coupled to the distal end of the cartridge 1410' by a user (e.g., using a tool) or by a mechanical device (e.g., robot). Exemplary cartridge caps 1440 are shown in FIGS. 23A and 23B, and described above. The cartridge cap 1440 may be coupled to the distal end of the cartridge 1410' by crimping the crimp seal 1442 around and enlarged portion of the cartridge 1410' at a distal end thereof. This step may be performed at the time of filling or may be performed previous to filling and provided pre-sterilized to the filling machine.

Next, the needle hub assembly 1422' is coupled to the distal end of the cartridge 1410' on top of the cartridge cap 1440 as shown in FIG. 27A. As shown in FIG. 22F, the needle hub assembly 1422' includes a needle 1424 having a needle proximal end 1426. While a cartridge cap 1440 is included in the embodiment depicted in FIG. 27A, the cartridge cap 1440 is optional and the needle hub assembly 1422' is directly coupled to the distal end of the cartridge 1410' in some embodiments (compare FIGS. 24A (no cap) and 24B (with cap)). The coupling of the needle hub assembly 1422' to the cartridge 1410' may be performed at the time of filling or the coupling may be performed previous to filling and a pre-sterilized coupled system is provided to the filling machine.

At 2612, the cartridge 1410' coupled to the needle hub assembly 1422' is disposed in a rack with the cartridge 1410' pointed downward as shown in FIGS. 25 and 27A. The cartridge 1410' may be disposed in the rack by a user (e.g., using a tool) or by a mechanical device (e.g., robot).

At 2614, a first substance 1420 is introduced into the distal chamber 1418 through the open proximal end of the cartridge 1410' as shown in FIG. 27B. The first substance 1420 may be introduced directly through the opening at the proximal end of the cartridge 1410'. The first substance 1420 may be a liquid, a solid (e.g., compressed powder), and/or a powder. In some embodiments where the first substance 1420 is a liquid, the first substance 1420 may be lyophilized in an optional step to form a powder as shown in FIG. 27C.

Figures 27D, 27E, 27F:
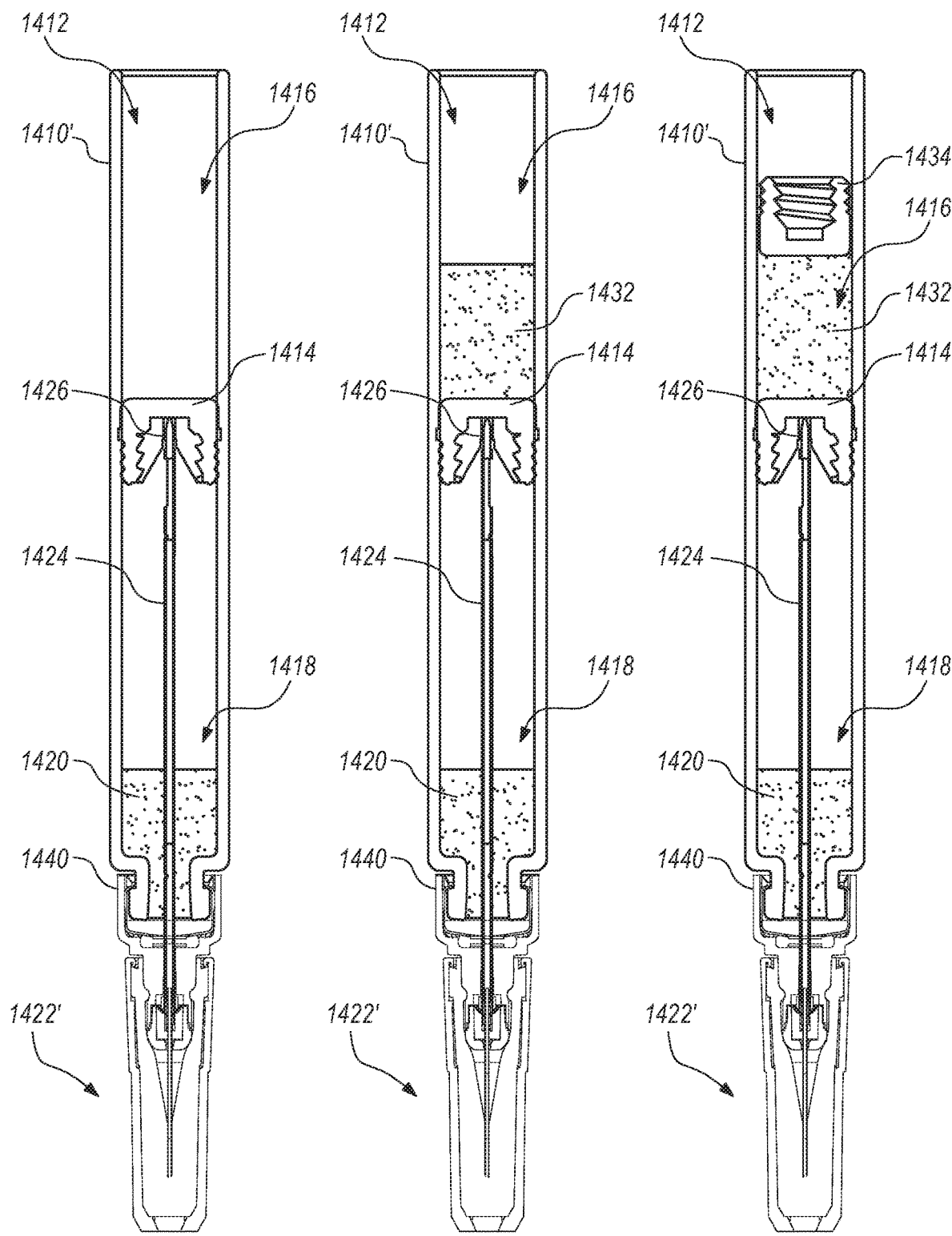

At 2616, a distal stopper member 1414 is disposed in an interior 1412 of the cartridge 1410' as shown in FIGS. 27C and 27D. The distal stopper member 1414 may be inserted by a user (e.g., using a tool) or by a mechanical device (e.g., robot). The distal stopper member 1414 and the cartridge 1410' define proximal and distal chambers 1416, 1418 in the body interior 1412. The distal stopper member 1414 may be positioned over an open proximal end of the cartridge 1410' to facilitate insertion of the distal stopper member 1414 into the body interior 1412 as shown in FIG. 27C.

The needle proximal end 1426 interferes with the distal stopper member 1414 to temporarily prevent distal movement of the distal stopper member 1414 relative to the cartridge 1410'. Components of the distal stopper member 1414 that interfere with the needle proximal end 1426 are depicted in FIGS. 15A to 15D and 16 to 16A, and described above.

At 2618, a second substance 1432 is introduced into the proximal chamber 1416 through the open proximal end of the cartridge 1410' as shown in FIG. 27E. The second substance 1432 may be introduced directly through the opening at the proximal end of the cartridge 1410'. The second substance 1432 may be a liquid or another fluid.

At 2620, a proximal stopper member 1434 is disposed in the interior 1412 of the cartridge 1410' as shown in FIG. 27F. The proximal stopper member 1434 may be inserted by a user (e.g., using a tool) or by a mechanical device (e.g., robot). The proximal stopper member 1434 closes the proximal chambers 1416 defined by the cartridge 1410' and the distal stopper member 1414. The proximal stopper member 1434 may be positioned over an open proximal end of the cartridge 1410' to facilitate insertion of the proximal stopper member 1434 into the body interior 1412. The proximal stopper member 1438 may be inserted using a pressure differential or a small tube as described above.

Figure 27G:
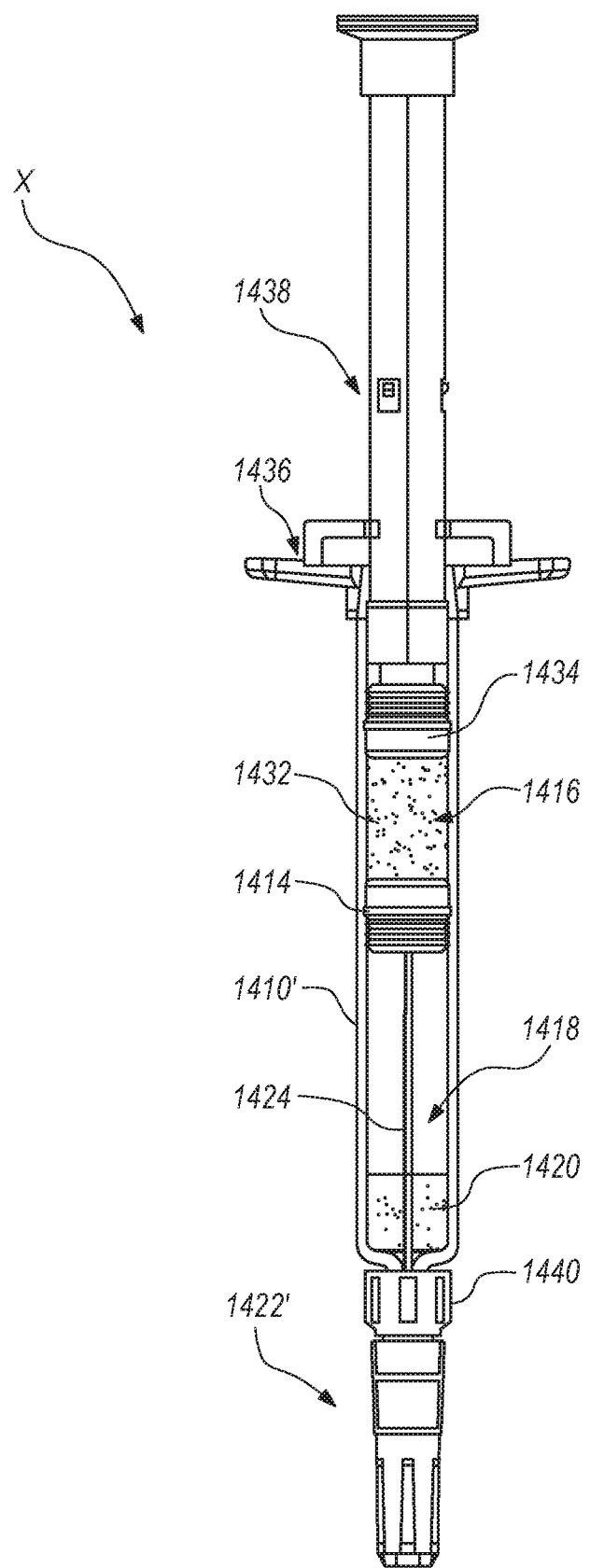

In an optional step shown in FIG. 27G, a finger flange 1436 and a plunger member 1438 are coupled to the cartridge 1410'. The finger flange 1436 may be coupled to the cartridge 1410' such that it is prevented from moving along a longitudinal axis of the body 1410 (e.g., by snapping over a glass flange at the proximal end of the body 1410). The plunger member 1438 may be coupled to the cartridge 1410' such that it is movable along a longitudinal axis of the body 1410. A distal end of the plunger member 1438 is also coupled to the proximal stopper member 1434 (e.g., using a threaded screw), such that movement of the plunger member 1438 relative to the cartridge 1410' moves the proximal stopper member 1434. The finger flange 1436 and a plunger member 1438 may be coupled to the cartridge 1410' by a user (e.g., using a tool) or by a mechanical device (e.g., robot).

While a single multiple chamber safe injection system is manufactured/assembled in the method 2600 depicted in FIGS. 26 and 27A to 27G, the same method 2600 may be used to manufacture/assemble a plurality of multiple chamber safe injection systems either in parallel or in series. While the method 2600 depicted in FIGS. 26 and 27A to 27G involves a dual chamber system with two stopper members 1414, 1434, in some embodiments, a third stopper member may be added to the multiple chamber safe injection system to define a third chamber using steps similar to those in 2618 and 2620 described above. In some embodiments, more than three stopper members and chambers may be formed in a multiple chamber safe injection system.

Cartridge Fill Distal Chamber from Back, Fill then Pierce

Figure 28:
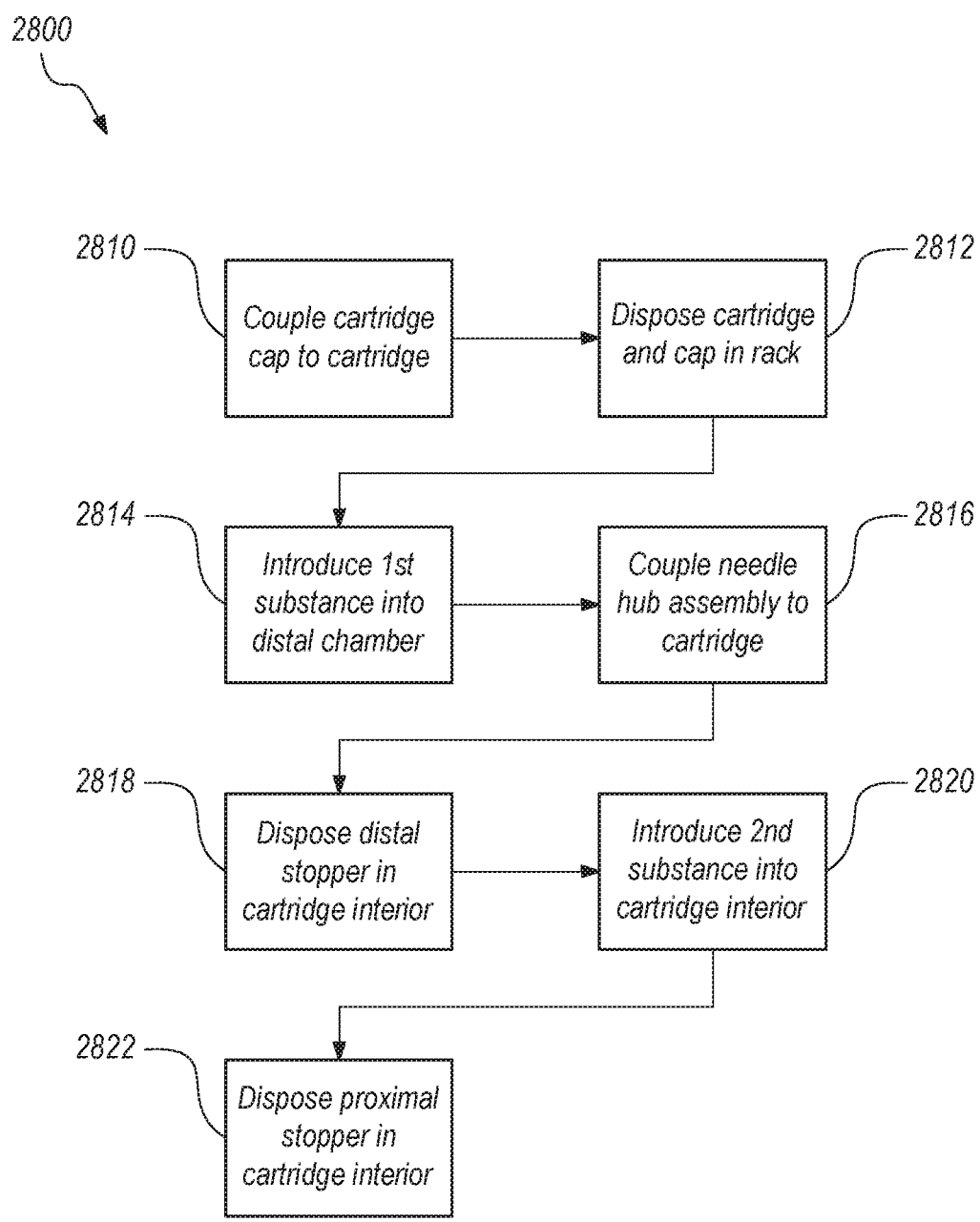
FIG. 28 is a flow chart illustrating a method for manufacturing/assembling a multiple chamber safe injection system according to some embodiments.

FIG. 28 depicts a method 2800 for manufacturing/assembling a multiple chamber safe injection system according to some embodiments. Corresponding partially assembled components are depicted in FIGS. 29A to 29G. The cartridge 1410', the proximal and distal stopper members 1414, 1434, the needle hub assembly 1422', cartridge cap 1440, the finger flange 1436, and the plunger member 1438 may be the same system components depicted in FIGS. 22A to 24B and described above.

Figure 29A:
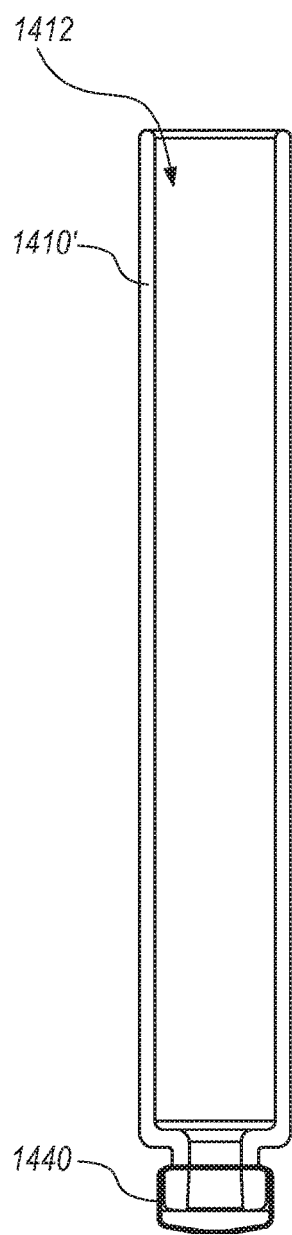
FIGS. 29A to 29H illustrate various steps in a method for manufacturing/assembling a multiple chamber safe injection system according to some embodiments.

At 2810, a cartridge cap 1440 is coupled to the distal end of the cartridge 1410' as shown in FIG. 29A. The cartridge cap 1440 may be coupled to the distal end of the cartridge 1410' by a user (e.g., using a tool) or by a mechanical device (e.g., robot). Exemplary cartridge caps 1440 are shown in FIGS. 23A and 23B, and described above. The cartridge cap 1440 may be coupled to the distal end of the cartridge 1410' by crimping the crimp seal 1442 around and enlarge portion of the cartridge 1410' at a distal end thereof. In some alternative embodiments, the cartridge 1410' may be supplied with the cartridge cap 1440 coupled and both components pre-sterilized.

At 2812, the cartridge 1410' coupled to the cartridge cap 1440 is disposed in a rack with the cartridge 1410' pointed downward as shown in FIGS. 20C and 29A. The cartridge 1410' may be disposed in the rack by a user (e.g., using a tool) or by a mechanical device (e.g., robot).

Figure 29B:
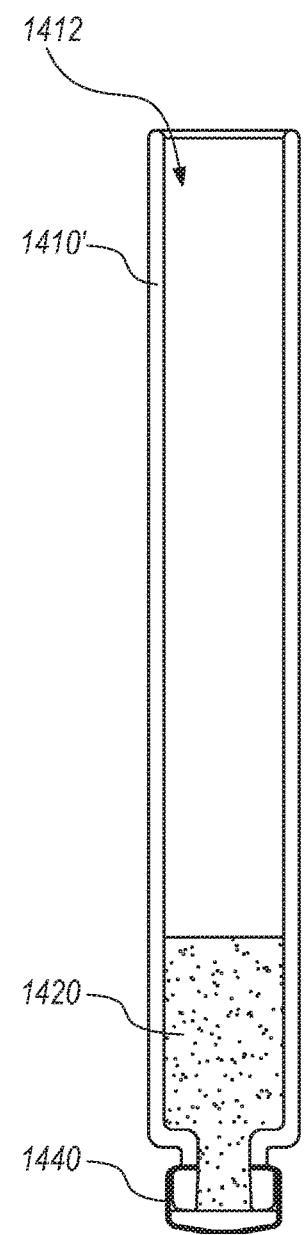
Figure 29C:
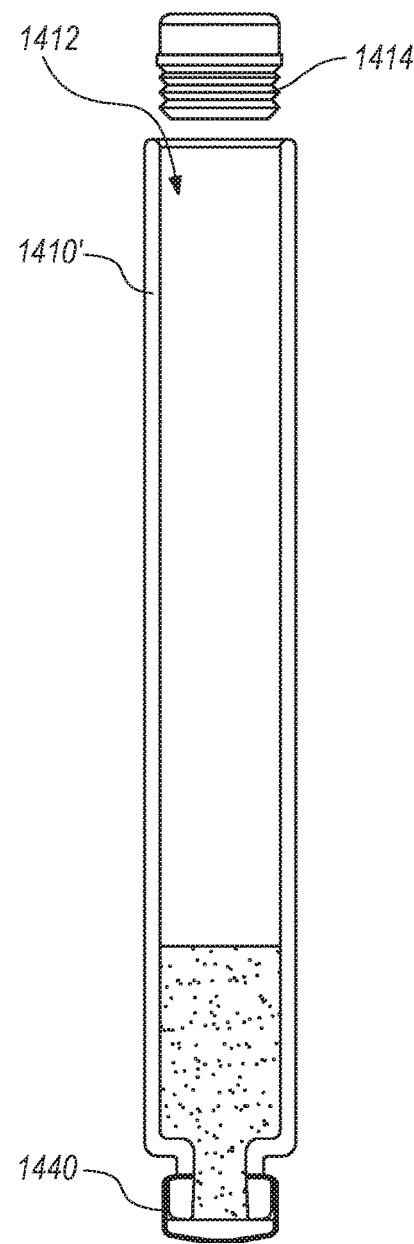
Figure 29D:
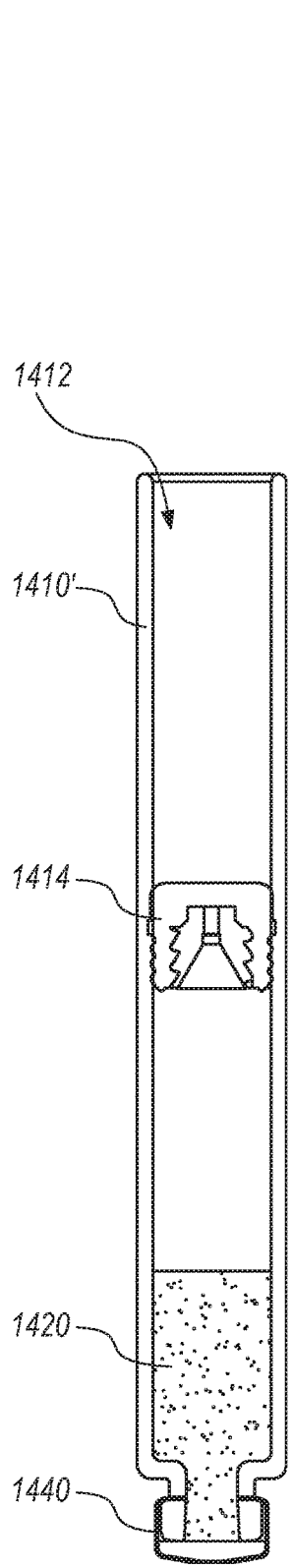

At 2814, a first substance 1420 is introduced into the distal chamber 1418 through the open proximal end of the cartridge 1410' as shown in FIG. 29B. The first substance 1420 may be introduced directly through the opening at the proximal end of the cartridge 1410'. The first substance 1420 may be a liquid, solid (e.g., compressed powder), and/or a powder. In some embodiments where the first substance 1420 is a liquid, the first substance 1420 may be lyophilized in an optional step to form a powder as shown in FIG. 29C.

Figure 29E:
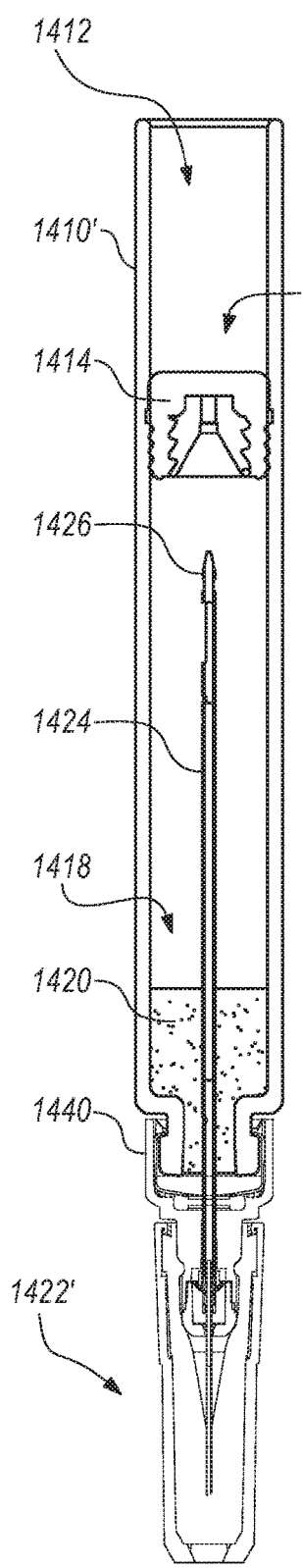

At 2816, a needle hub assembly 1422' is coupled to the distal end of the cartridge 1410' on top of the cartridge cap 1440 as shown in FIG. 29E. As shown in FIG. 22F, the needle hub assembly 1422' includes a needle 1424 having a needle proximal end 1426. During insertion of the needle hub assembly 1422' into the cartridge interior 1412, the needle 1424 and a needle proximal end 1426 pierce the cartridge cap 1440. The septum 1444 in the cartridge cap 1440 depicted in FIGS. 23A and 23B is configured to be pierced by the needle proximal end 1426. In some alternative embodiments, the cartridge 1410' may be supplied with the needle hub assembly 1422' coupled and both components pre-sterilized.

Figure 29F:
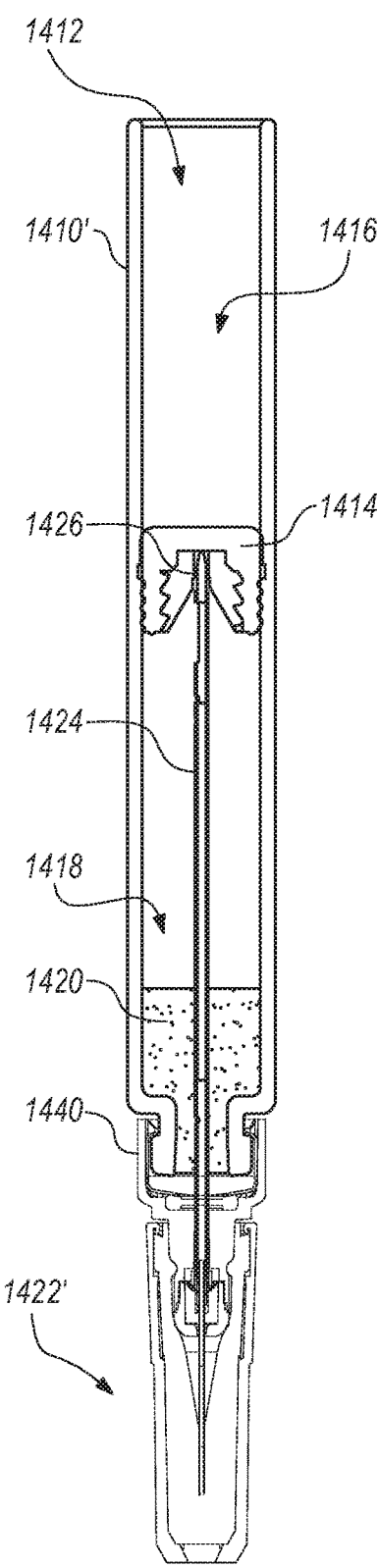

At 2818, a distal stopper member 1414 is disposed in an interior 1412 of the cartridge 1410' as shown in FIGS. 29E and 29F. The distal stopper member 1414 may be inserted by a user (e.g., using a tool) or by a mechanical device (e.g., robot). The distal stopper member 1414 and the cartridge 1410' define proximal and distal chambers 1416, 1418 in the body interior 1412. The distal stopper member 1414 may be positioned over an open proximal end of the cartridge 1410' to facilitate insertion of the distal stopper member 1414 into the body interior 1412. The distal stopper member 1414 may be inserted using a pressure differential or a small tube as described above.

The needle proximal end 1426 interferes with the distal stopper member 1414 to temporarily prevent distal movement of the distal stopper member 1414 relative to the cartridge 1410'. Components of the distal stopper member 1414 that interfere with the needle proximal end 1426 are depicted in FIGS. 15A to 15D and 16 to 16A, and described above.

Figure 29G:
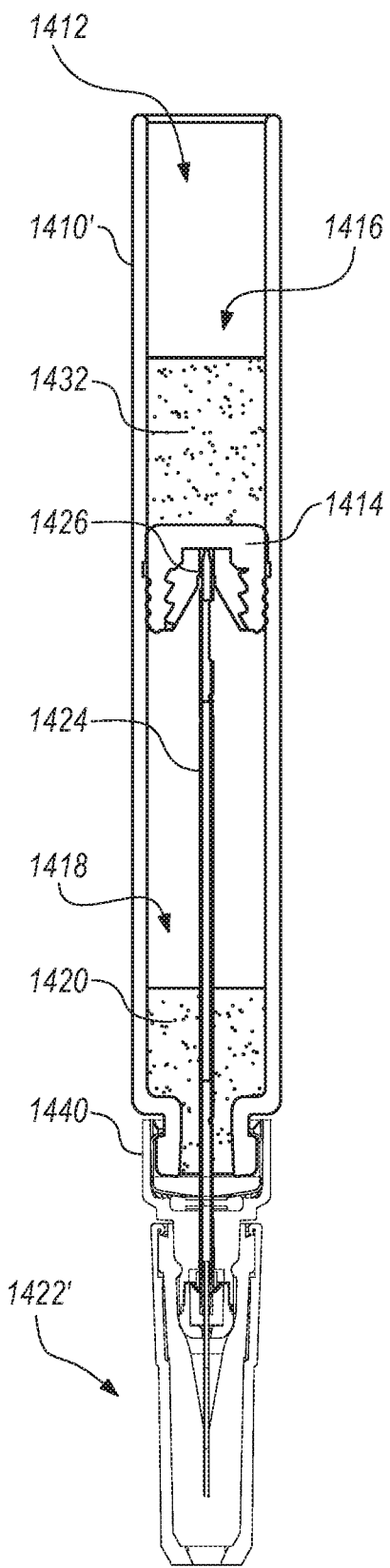

At 2820, a second substance 1432 is introduced into the proximal chamber 1416 through the open proximal end of the cartridge 1410' as shown in FIG. 29G. The second substance 1432 may be introduced directly through the opening at the proximal end of the cartridge 1410'. The second substance 1432 may be a liquid or another fluid.

Figure 29H:
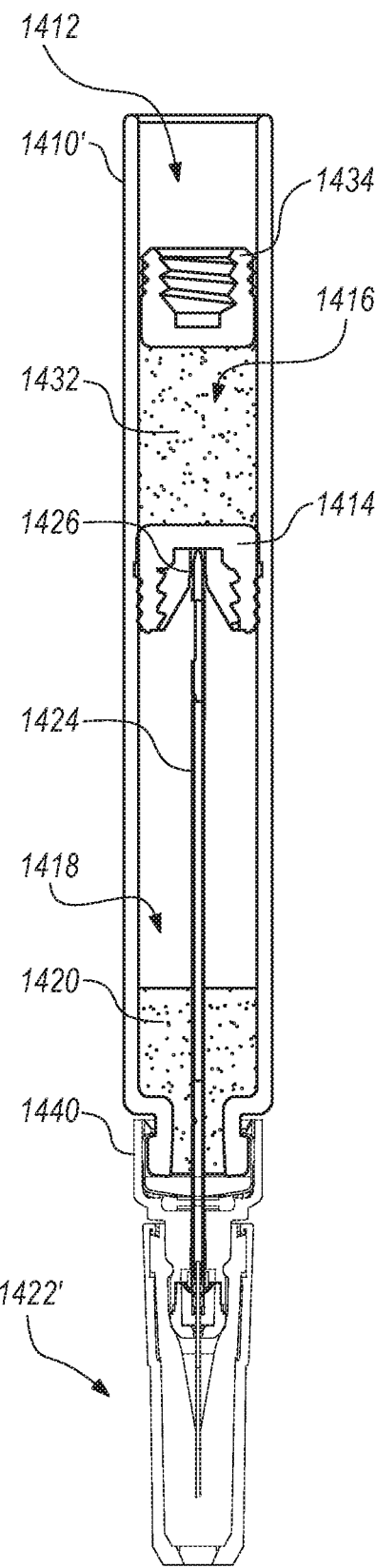

At 2822, a proximal stopper member 1434 is disposed in the interior 1412 of the cartridge 1410' as shown in FIG. 29H. The proximal stopper member 1434 may be inserted by a user (e.g., using a tool) or by a mechanical device (e.g., robot). The proximal stopper member 1434 closes the proximal chambers 1416 defined by the cartridge 1410' and the distal stopper member 1414. The proximal stopper member 1434 may be positioned over an open proximal end of the cartridge 1410' to facilitate insertion of the proximal stopper member 1434 into the body interior 1412. The proximal stopper member 1438 may be inserted using a pressure differential or a small tube as described above.

In an optional step (not shown), a finger flange and a plunger member are coupled to the cartridge 1410'. The finger flange may be coupled to the cartridge 1410' such that it is prevented from moving along a longitudinal axis of the body 1410 (e.g., by snapping over a glass flange at the proximal end of the body 1410). The plunger member may be coupled to the cartridge 1410' such that it is movable along a longitudinal axis of the body 1410. A distal end of the plunger member is also coupled to the proximal stopper member 1434 (e.g., using a threaded screw), such that movement of the plunger member relative to the cartridge 1410' moves the proximal stopper member 1434. The finger flange and a plunger member may be coupled to the cartridge 1410' by a user (e.g., using a tool) or by a mechanical device (e.g., robot).

While a single multiple chamber safe injection system is manufactured/assembled in the method 2800 depicted in FIGS. 28 and 29A to 29G, the same method 2800 may be used to manufacture/assemble a plurality of multiple chamber safe injection systems either in parallel or in series. While the method 2800 depicted in FIGS. 28 and 29A to 29G involves a dual chamber system with two stopper members 1414, 1434, in some embodiments, a third stopper member may be added to the multiple chamber safe injection system to define a third chamber using steps similar to those in 2818 and 2820 described above. In some embodiments, more than three stopper members and chambers may be formed in a multiple chamber safe injection system.

Figure 30:
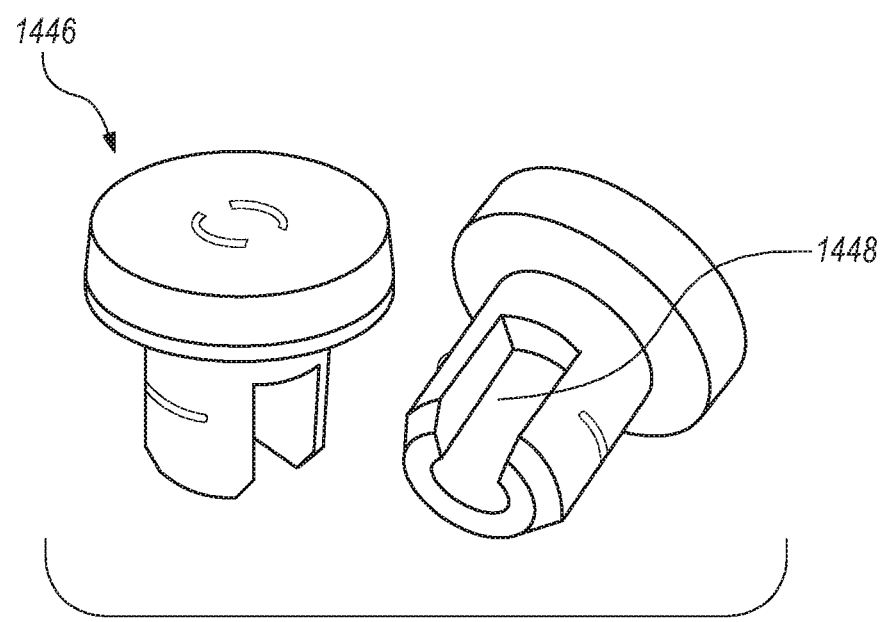
FIG. 30 depicts cartridge stoppers for use with multiple chamber safe injection systems according to some embodiments.

FIG. 30 depicts a cartridge stopper 1446 according to some embodiments. The cartridge stopper 1446 can be made from a soft polymer such that it is pierceable by the needle proximal end 1426. Further, the cartridge stopper 1446 includes a vent 1448 for lyophilization of liquids in the cartridge interior 1412.

Autoinjector System

Single Chamber

FIGS. 31A to 31H depict an auto injector system 3100 including a disposable injection system/syringe 3110 and a reusable drive system 3150 according to some embodiments. The autoinjector system 3100 allows use of injection system/syringes 3110 that are readily available in a clinical setting without having to add items to a supply chain. The autoinjector system 3100 also includes a safety function to minimize exposure of a sharp needle as described below. These and other advantages of the autoinjector system 3100 are explained below.

Figure 31A:
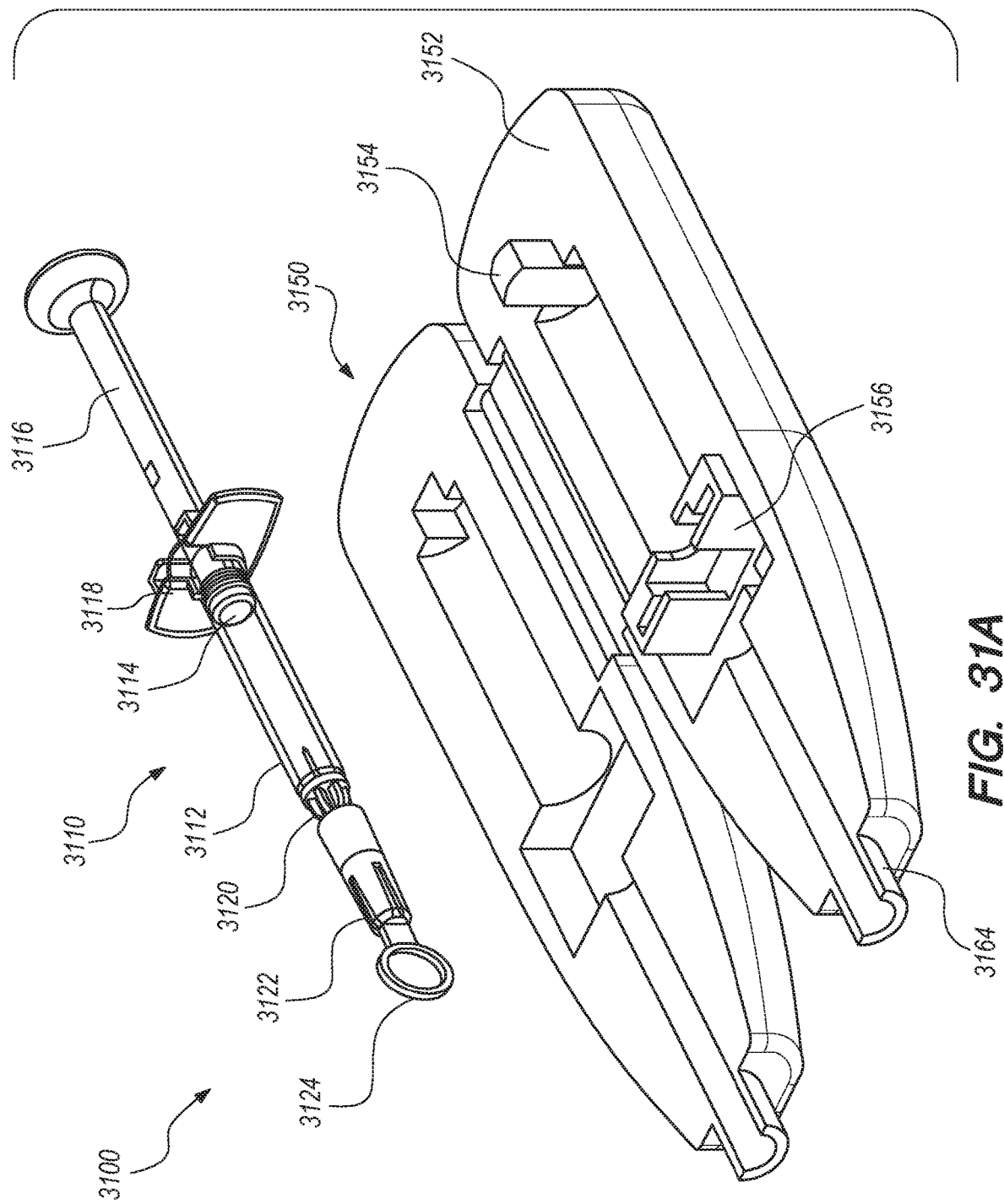

As shown in FIG. 31A, the disposable injection system/syringe 3110 includes an injection system/syringe body 3112, a stopper member 3114, a plunger member 3116, a finger flange 3118, a needle hub assembly 3120, a rigid needle shield 3122, and a pull ring 3124 to facilitate removal of the rigid needle shield 3122 from the needle hub assembly 3120. The injection system/syringe 3110 may be a safe injection system that retracts the sharp needle at least into the injection system/syringe body 3112 to minimize the risk of a needle stick. Examples of such safe injection systems are described in U.S. Utility patent application Ser. No. 14/696,342, which was previously incorporated by reference herein. The reusable drive system 3150 includes a drive system body 3152, a plunger actuator/pusher 3154, a flange holder/carriage 3156, and a collar 3164.

Figure 31B:
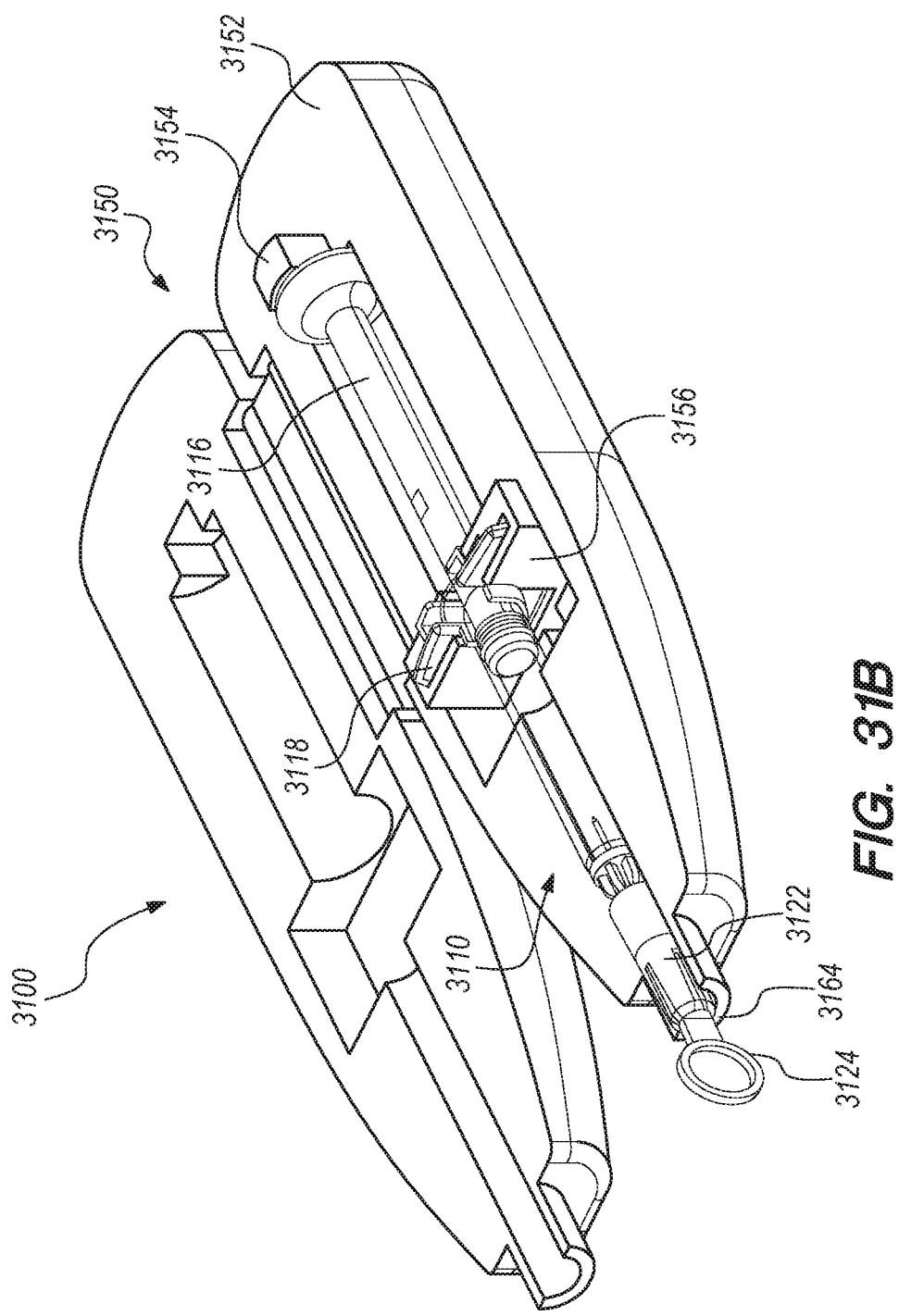

When the injection system/syringe 3110 is mounted in the drive system 3150, as shown in FIG. 31B, the plunger actuator/pusher 3154 is configured to move the plunger member 3116 distally relative to the injection system/syringe body 3112. The flange holder/carriage 3156 is configured to move the injection system 3110 distally and/or proximally relative to the drive system body 3152. The plunger actuator/pusher 3154 and the flange holder/carriage 3156 are in their respective full proximal positions in FIGS. 31A and 31B. In this position, the collar 3164 of the drive system 3150 prevents the sharp needle of the injection system/syringe 3110 from contacting a user's skin. In addition, in FIG. 31B, the rigid needle shield 3122 prevents the needle from contacting a user's skin.

Figure 31C:
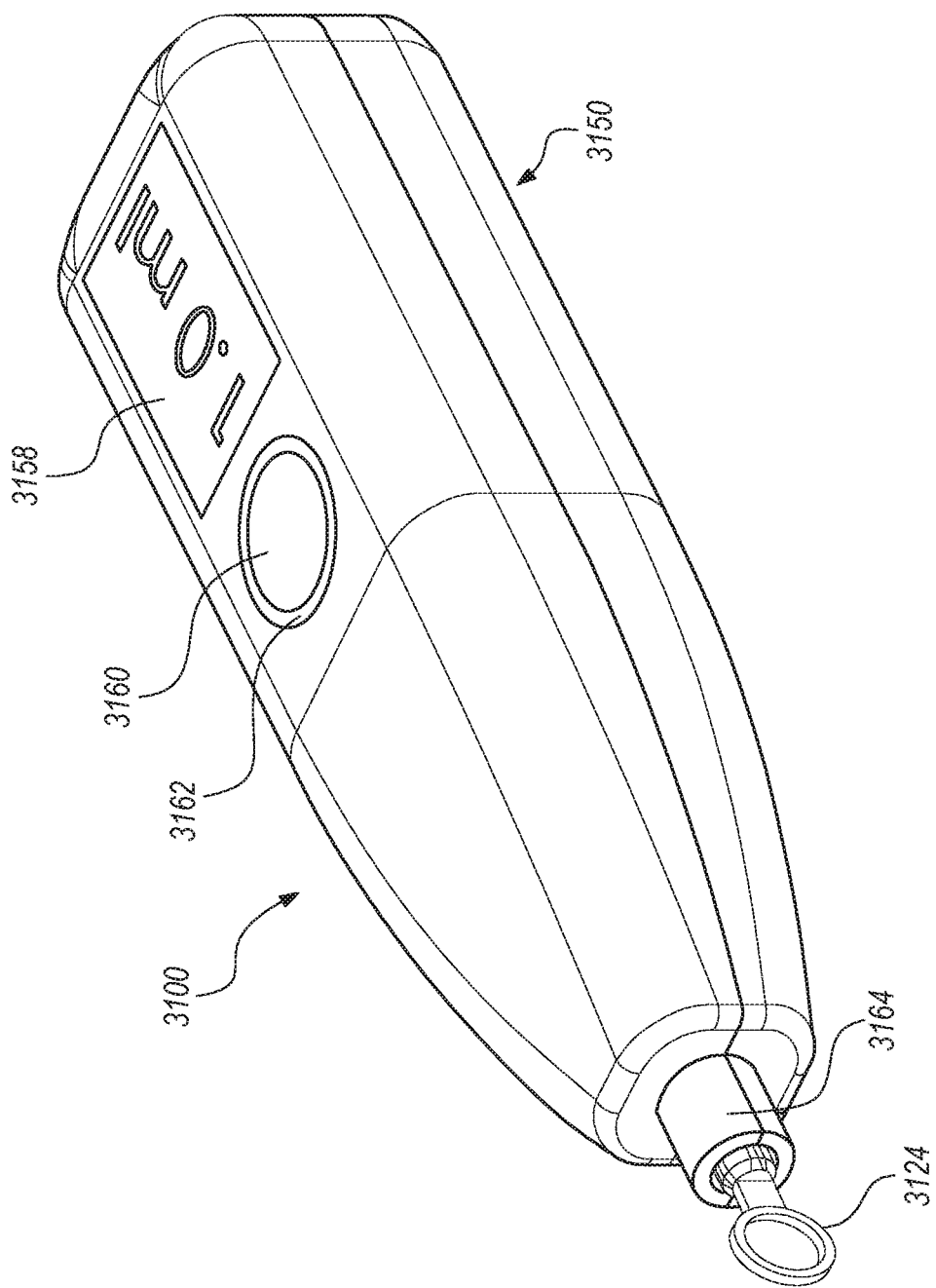

FIG. 31C shows the autoinjector system 3100 in a closed configuration (versus the open configuration in FIGS. 31A and 31B). In the close configuration, various user interface components of the drive system 3150 are visible. The drive system 3150 includes a display 3158, a button 3160, and the light ring 3162 around the button 3160. In the system configuration depicted in FIG. 31C, the display 3158 renders an indication of the size of the injection systems/syringe (e.g., 1.0 ml). The button 3160 allows a user to provide input to the autoinjector system 3100. The light ring 3162 can change colors to indicate various steps in the injection process. As shown in FIG. 31C, the pull ring 3124 is accessible at the distal end of the drive system 3150 because it extends distally beyond the collar 3164.

The top half of the drive system 3150 has been cut away from FIGS. 31D to 31G to visualize various components of the autoinjector system 3100 during injection with the drive system 3150 in a closed configuration.

Figure 31D:
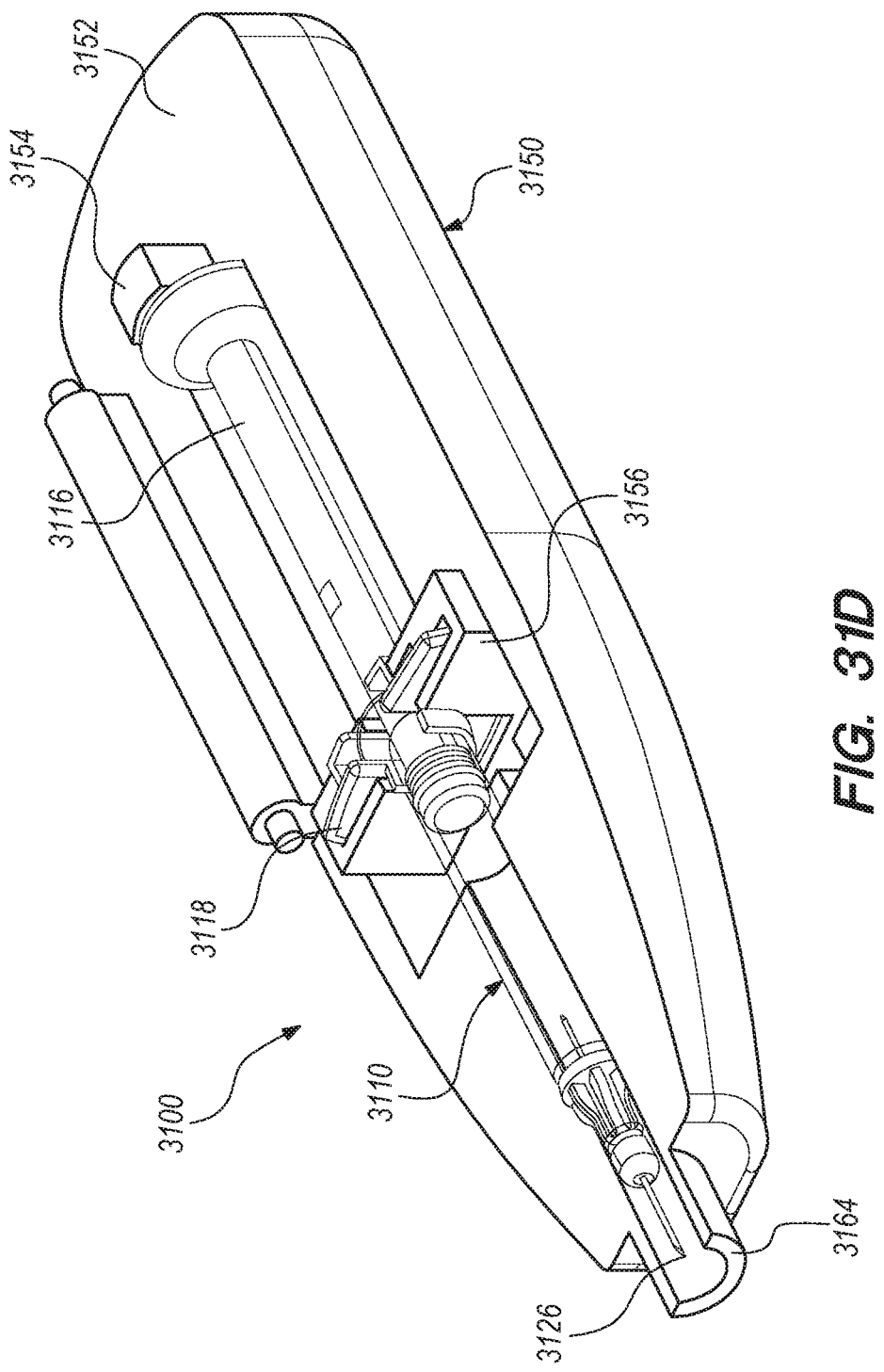

In FIG. 31D, the rigid needle shield 3122 has been removed from the needle hub assembly 3120. In some embodiments, the autoinjector system 3100 renders an instruction on the display 3158 for the user to pull on the pull ring 3124 to remove the rigid needle shield 3122 from the needle hub assembly 3120. In some embodiments, the autoinjector 3100 includes components that grasp the rigid needle shield 3122 (e.g., one or more arms) while the flange holder/carriage 3156 moves the injection system/syringe 3110 (e.g., from a distal position to a proximal position) to separate the rigid needle shield 3122 from the needle hub assembly 3120. In such embodiments, the user would only have to remove the separated rigid needle shield 3122 from the auto injection system 3100. The collar 3164 prevents exposure of the needle 3126 to a user.

Figure 31E:
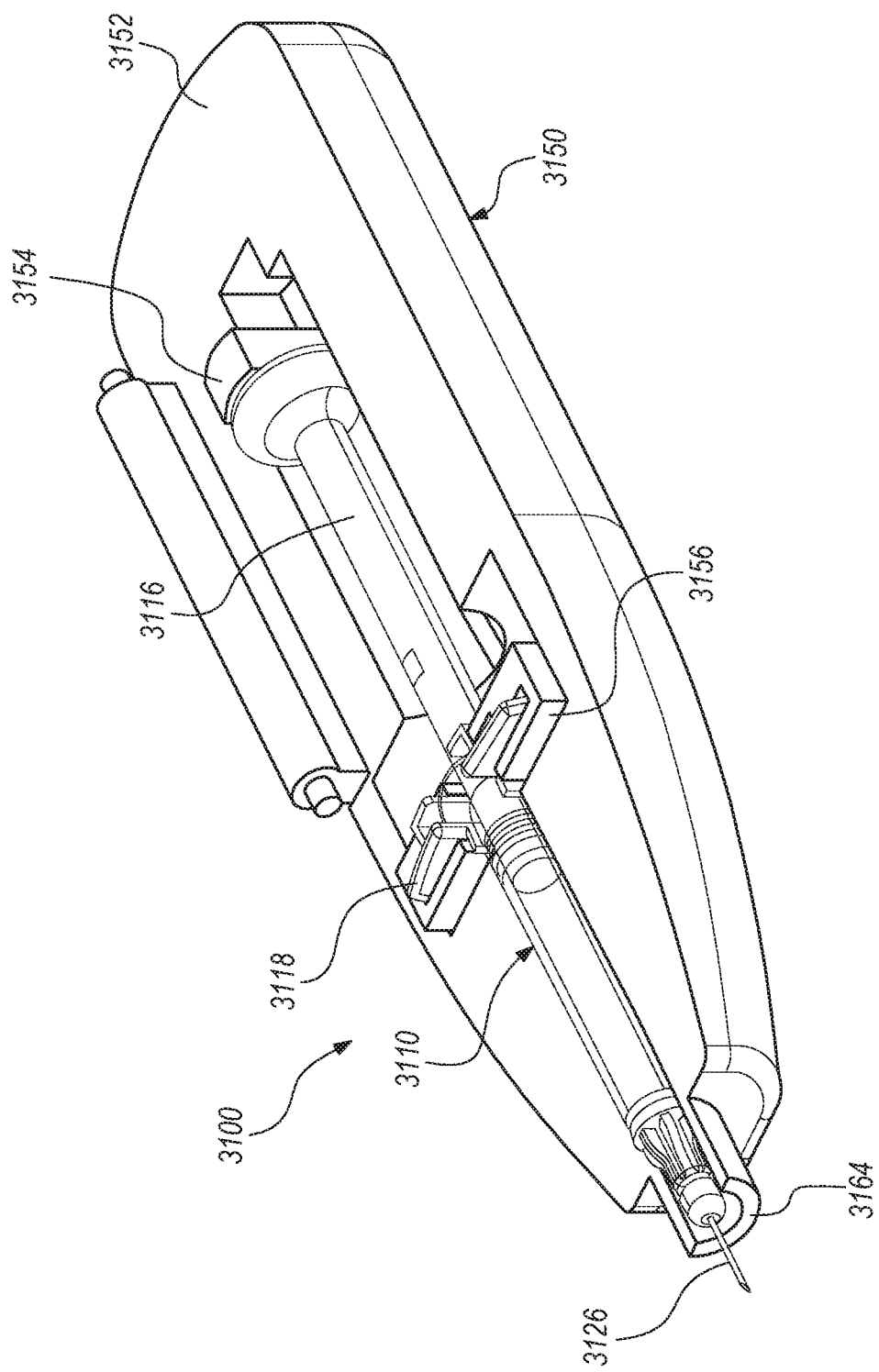

In FIG. 31E, the flange holder/carriage 3156 has moved the injection system/syringe 3110 distally. At the same time, the plunger actuator/pusher 3154 has moved the same distance distally to maintain contact with the thumb pad at the proximal end of the plunger member 3116. Moving the injection system/syringe 3110 distally extends the needle 3126 distally beyond the collar 3164, thereby exposing the needle 3126 for injection. Before the flange holder/carriage 3156 moves the injection system/syringe 3110 distally, the autoinjector system 3100 may render an instruction on the display 3158 for the user to press the autoinjector against an injection site. In such embodiments, moving the injection system/syringe 3110 distally may puncture the injection site.

In FIG. 31F, the plunger actuator/pusher 3154 has moved to its full distal position. This movement drives the plunger member 3116 and the stopper member 3114 attached thereto distally to eject a medicine from the injection systems/syringe 3110 through the needle 3126 and into the patient.

Figure 31G:
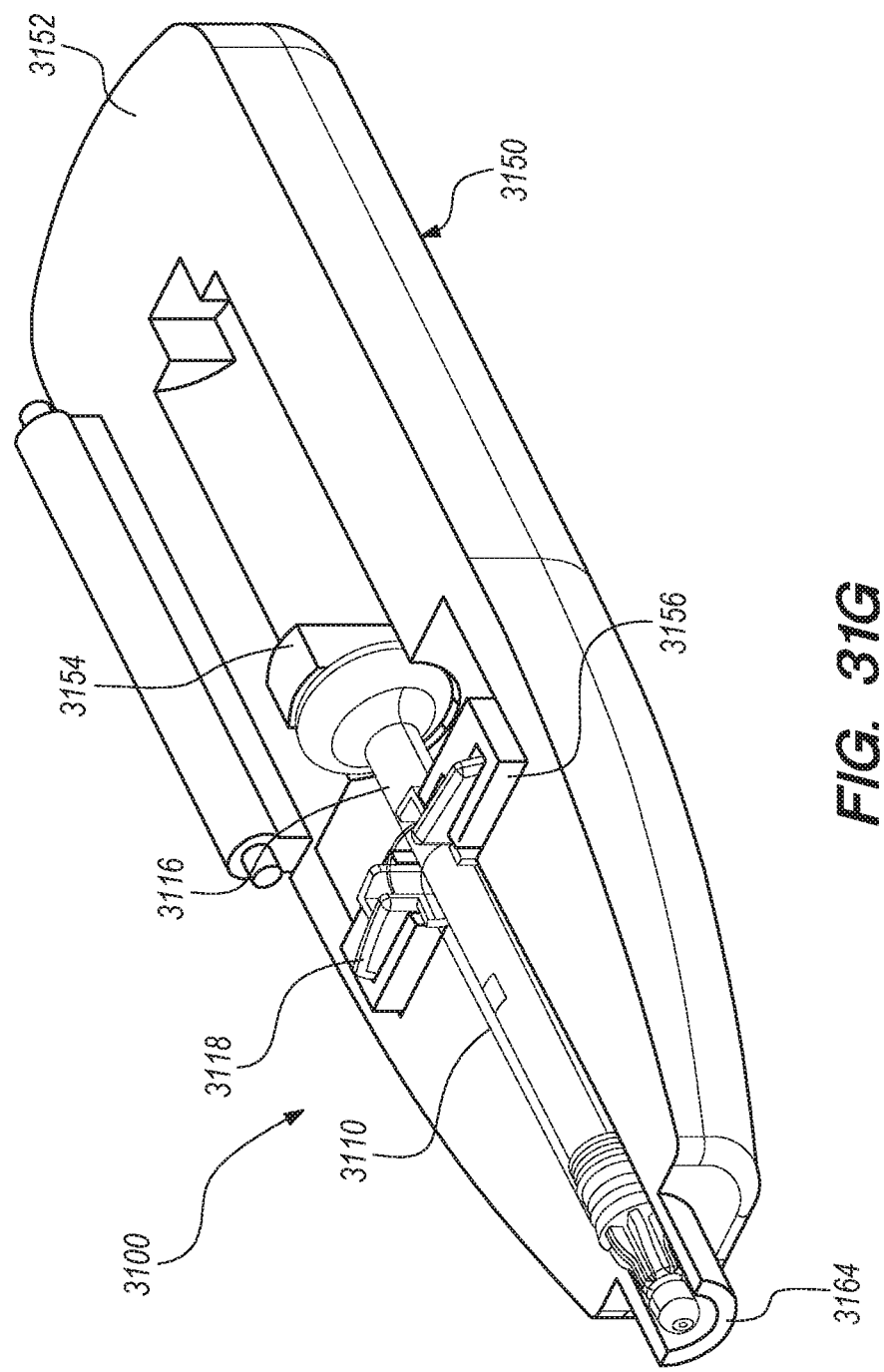
Figure 31H:
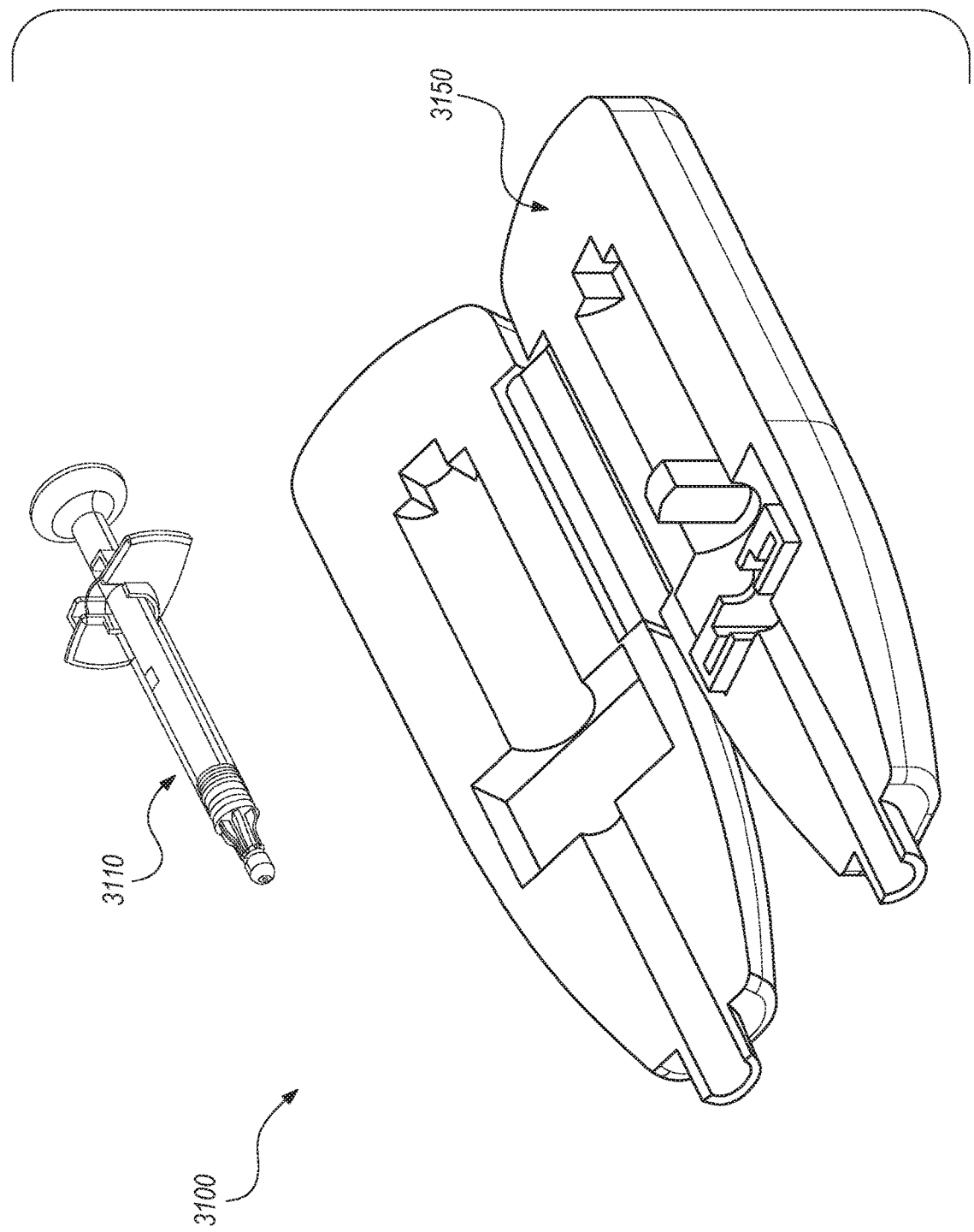

In FIG. 31G, movement of the plunger member 3116 and the stopper member 3114 to an end of injection position has caused the needle 3126 to be retracted into the injection systems/syringe body 3112 as described U.S. Utility patent application Ser. No. 14/696,342, which was previously Incorporated by reference herein. Retraction of the needle 3126 renders the injection systems/syringe 3110 safe for removal from the drive system 3150 as shown in FIG. 31H. After the used injection system/syringe 3110 has been removed, a new injection system/syringe 3110 can be loaded into the drive system 3150 to ready the auto injector system 3100 ready for another injection.

The drive system 3150 also includes a first motor to move the plunger actuator/pusher 3154, a second motor to move the flange holder/carriage 3156, a controller operatively coupled to the first and second motors, and one or more sensors operatively coupled to the controller. The sensors may include one or more of an accelerometer, a contact sensor, a position sensor, a gyroscope, a thermometer, and a skin contact sensor. In some embodiments, the sensor is a skin contact sensor, and the controller injects the medicine only when the skin contact sensor confirms contact between the autoinjector system 3100 and a patient.

Dual Chamber

FIGS. 32A to 32J depict an autoinjector system 3200 configured for use with a multiple chamber injection system 3210. The drive system 3250 depicted in FIGS. 32A to 32J is similar to the drive system 3150 depicted in FIGS. 31A to 31H. In fact, drive systems 3150, 3250 may be the same drive system with altered programming.

Figure 32A:
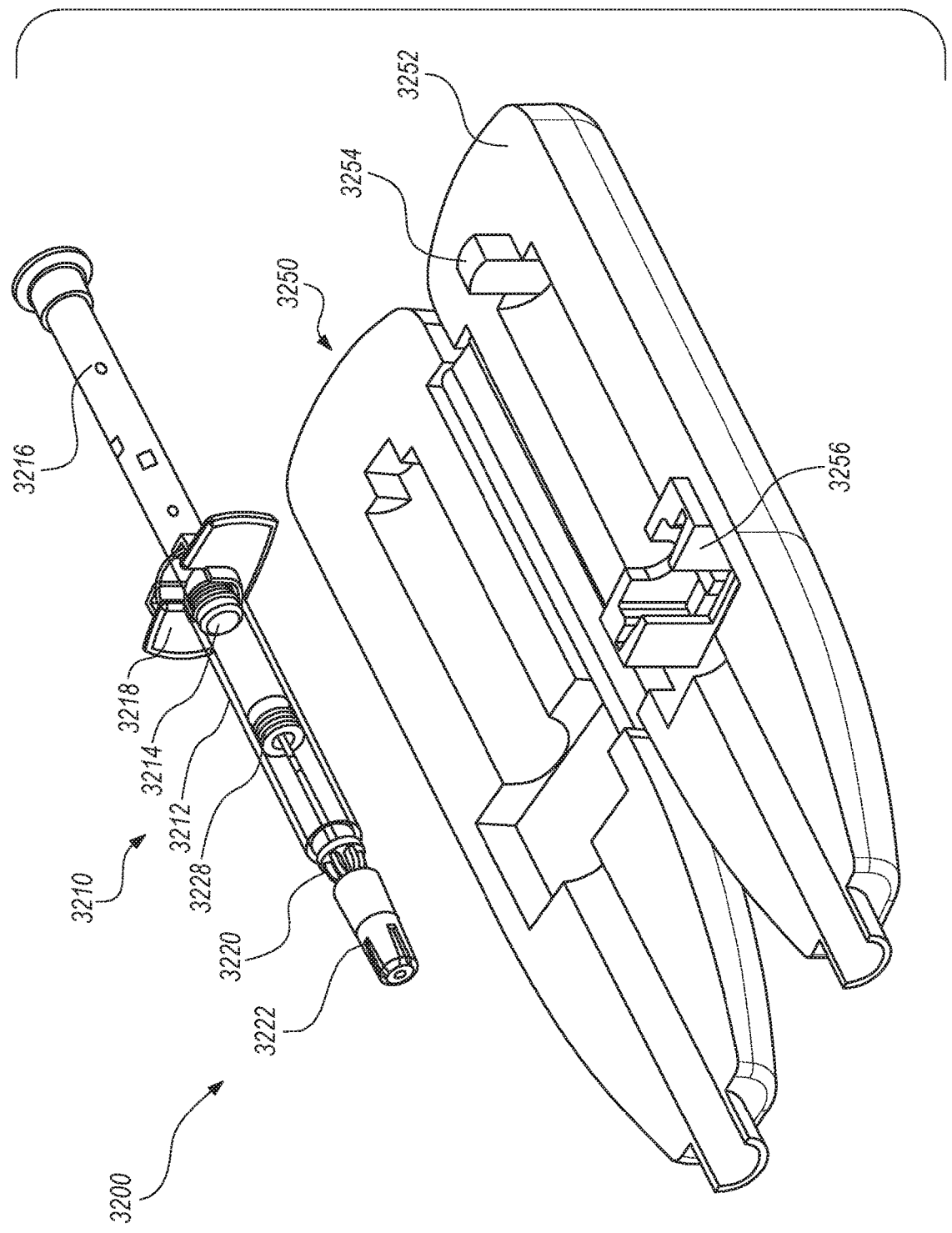
FIGS. 32A to 32J illustrate various steps in a method for mixing drug components and injecting the mixed drug using an autoinjector according to some embodiments.

As shown in FIG. 32A, the disposable injection system/syringe 3210 includes an injection system/syringe body 3212, first and second stopper members 3228, 3214, a plunger member 3216, a finger flange 3218, a needle hub assembly 3220, and a rigid needle shield 3222. The injection system/syringe 3210 may be a safe injection system that retracts the sharp needle at least into the injection system/syringe body 3212 to minimize the risk of a needle stick. Examples of such safe injection systems are described in U.S. Utility patent application Ser. No. 15/801,259, which was previously incorporated by reference herein. The reusable drive system 3250 includes a drive system body 3252, a plunger actuator/pusher 3254, a flange holder/carriage 3256, and a collar 3264.

Figure 32B:
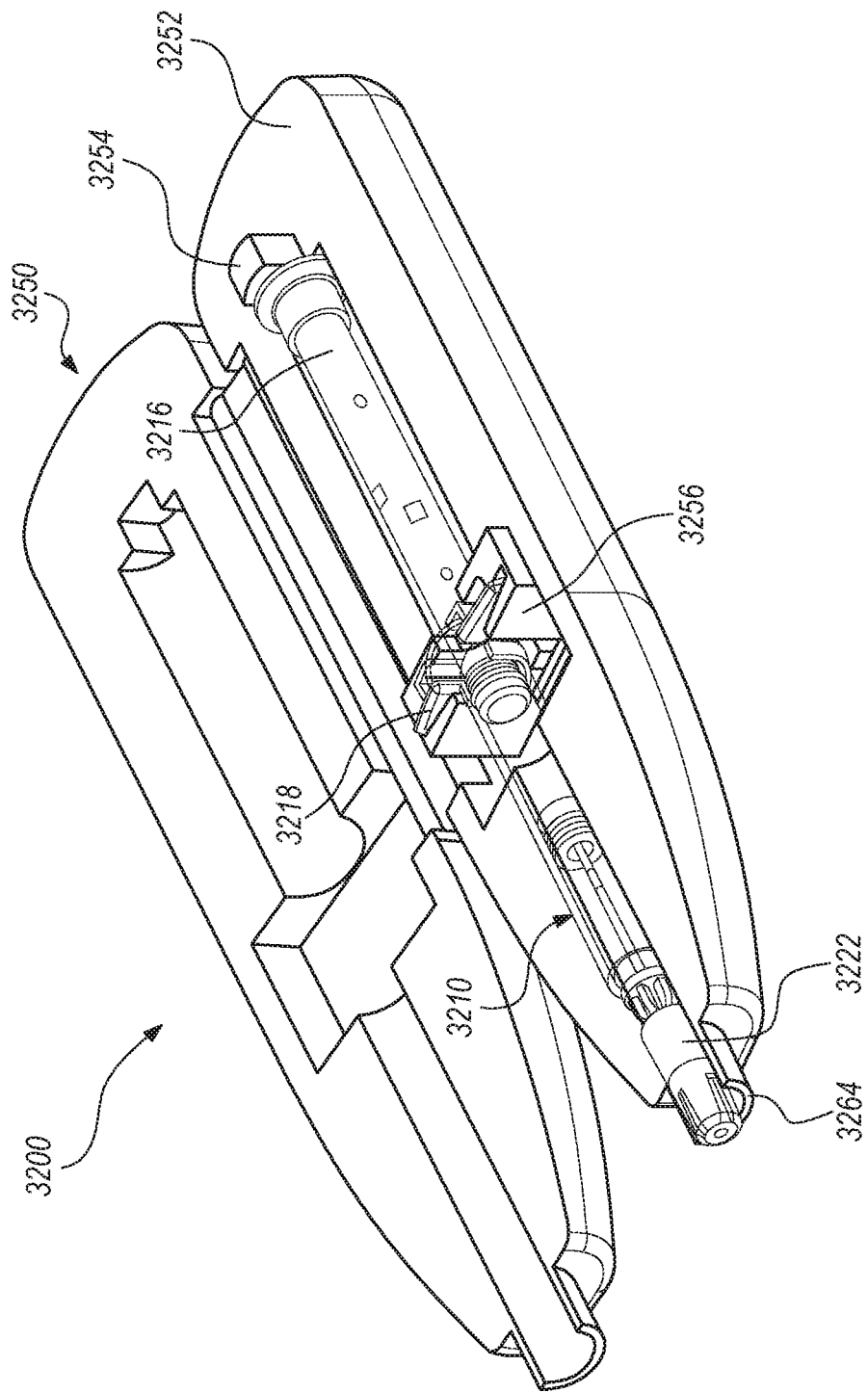

When the injection system/syringe 3210 is mounted in the drive system 3250, as shown in FIG. 32B, the plunger actuator/pusher 3254 is configured to move the plunger member 3216 distally relative to the injection system/syringe body 3212. The flange holder/carriage 3256 is configured to move the injection system 3210 distally and/or proximally relative to the drive system body 3252. The plunger actuator/pusher 3254 and the flange holder/carriage 3256 are in their respective full proximal positions in FIGS. 32A and 32B. In this position, the collar 3264 of the drive system 3250 prevents the sharp needle of the injection system/syringe 3210 from contacting a user's skin. In addition, in FIG. 32B, the rigid needle shield 3222 prevents the needle from contacting a user's skin.

Figure 32C:
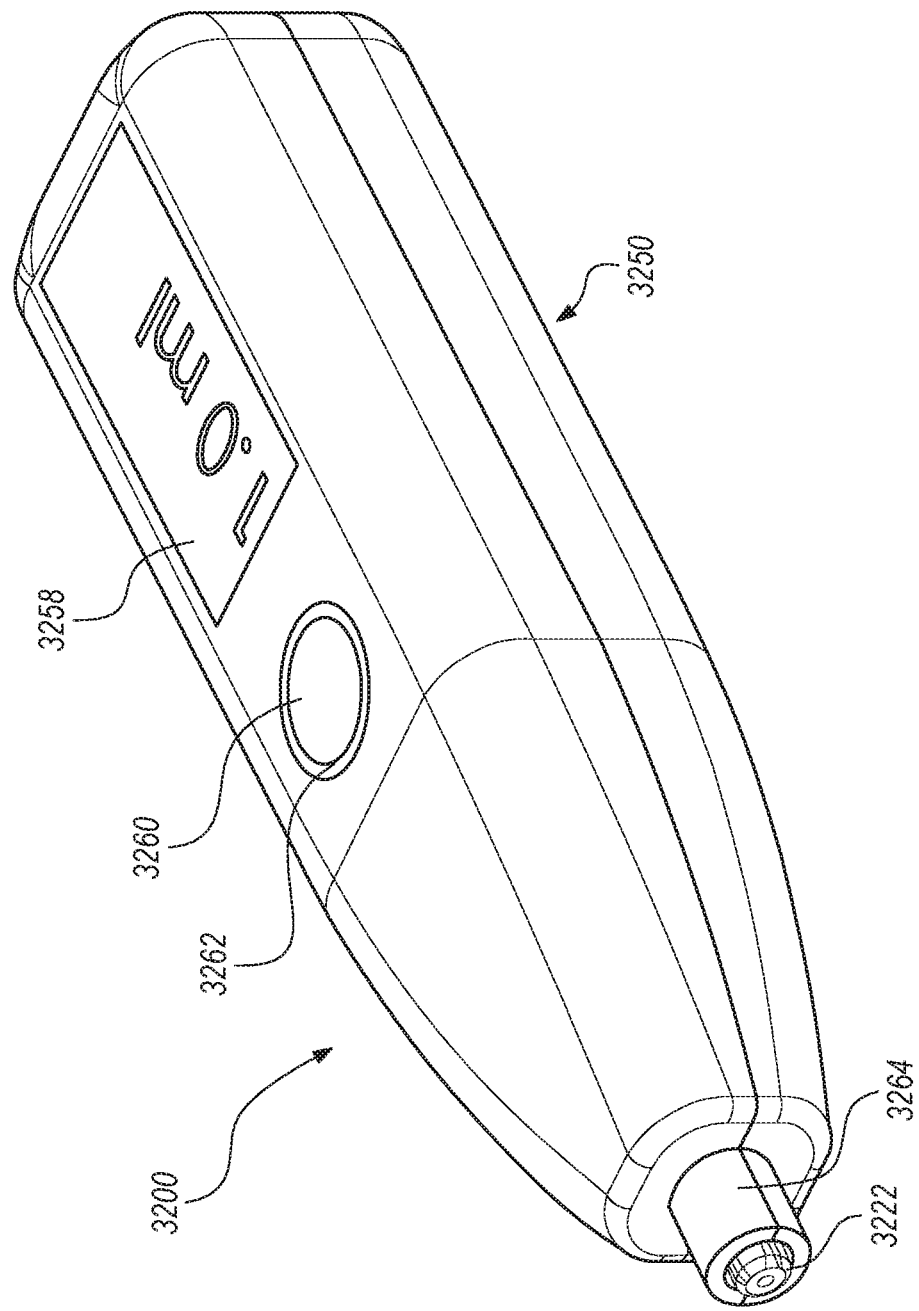

FIG. 32C shows the autoinjector system 3200 in a closed configuration (versus the open configuration in FIGS. 32A and 32B). In the close configuration, various user interface components of the drive system 3250 are visible. The drive system 3250 includes a display 3258, a button 3260, and the light ring 3262 around the button 3260. In the system configuration depicted in FIG. 32C, the display 3258 renders an indication of the size of the injection systems/syringe (e.g., 1.0 ml). The button 3260 allows a user to provide input to the autoinjector system 3200. The light ring 3262 can change colors to indicate various steps in the injection process. As shown in FIG. 32C, the rigid needle shield 3222 is not easily accessible at the distal end of the drive system 3250 because it barely extends distally beyond the collar 3264.

Figure 32D:
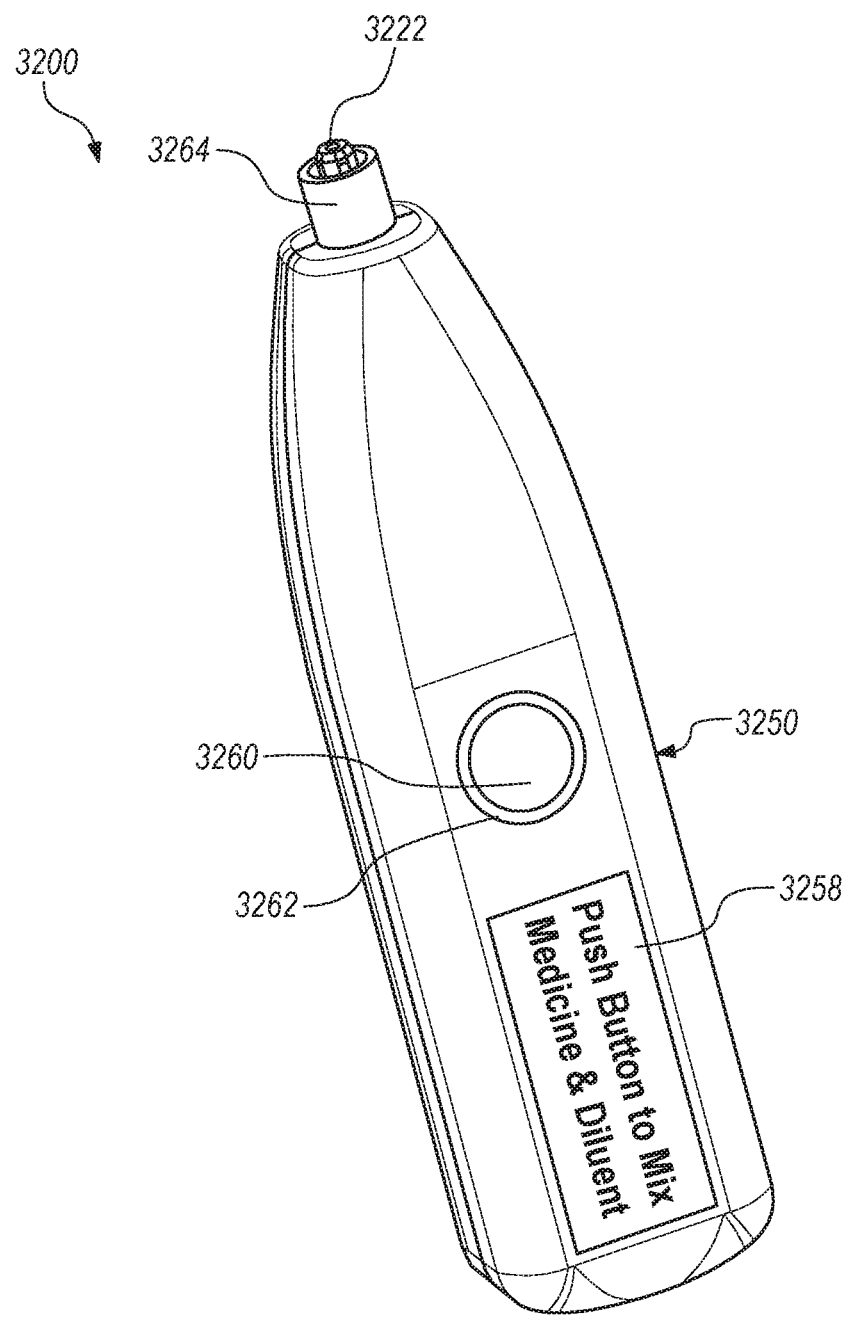
Figure 32E:
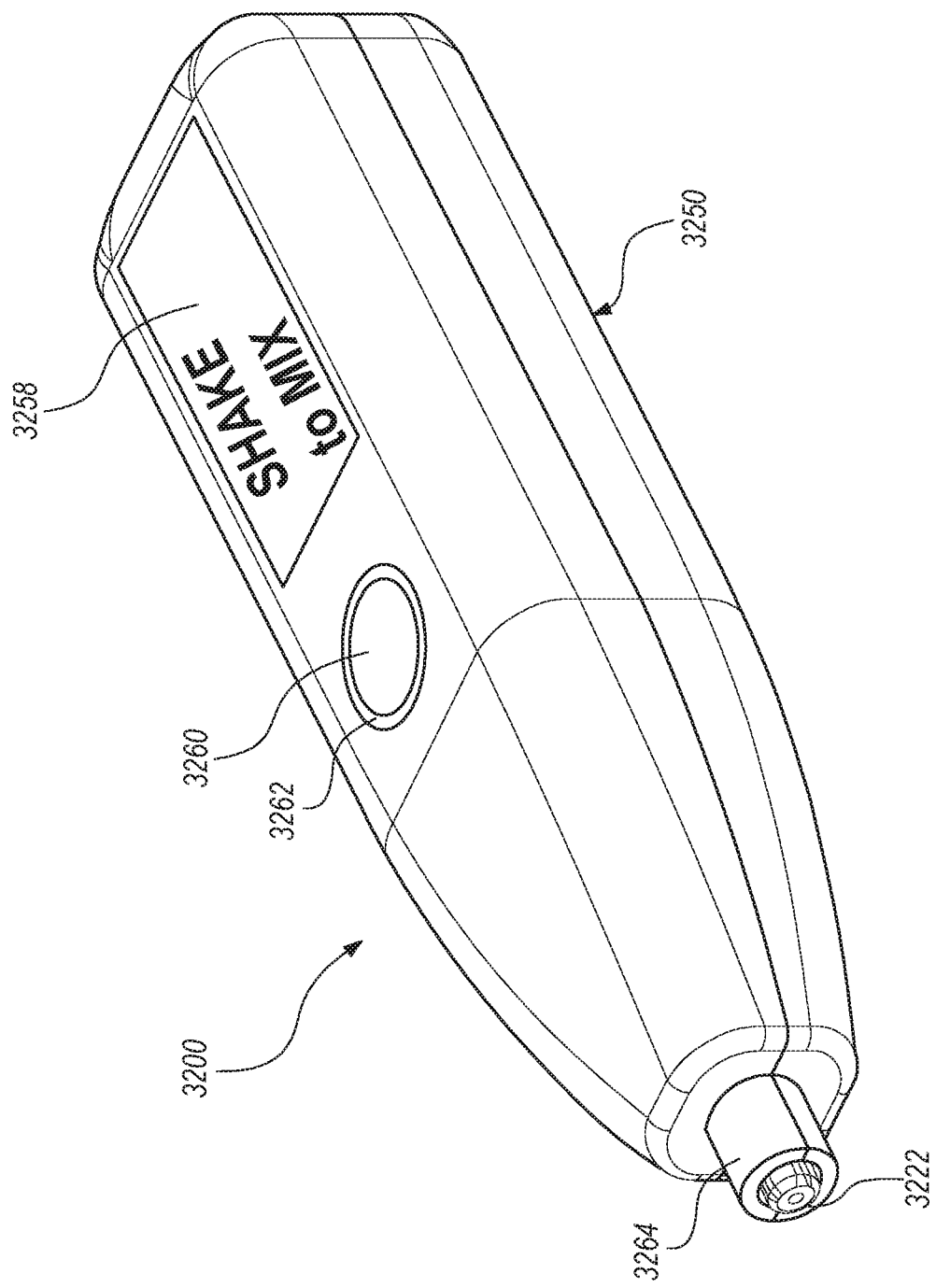

FIGS. 32D to 32J depict various steps in a method of mixing and injecting medicines using the autoinjector system 3200 according to some embodiments. In FIG. 32D, the display 3258 is rendering a message instructing a user to push the button 3262 mix a medicine with a diluent. This message can be accompanied by the light ring 3262 turning green to signal go. When the user presses the button 3262, the plunger actuator/pusher 3254 moves distally to transfer diluent from a proximal chamber to a distal chamber as shown in FIG. 7G to 7J. In FIG. 32E, the display 3250 is rendering a message instructing a user to shake the autoinjector system 3202 mix the medicine with the diluent.

Figure 32F:
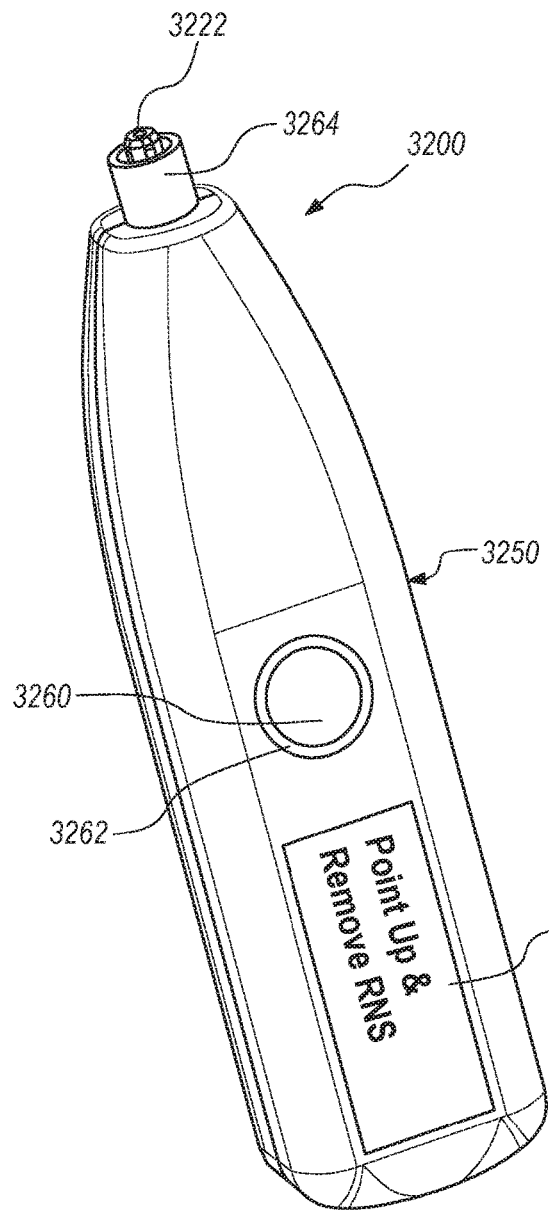
Figure 32G:
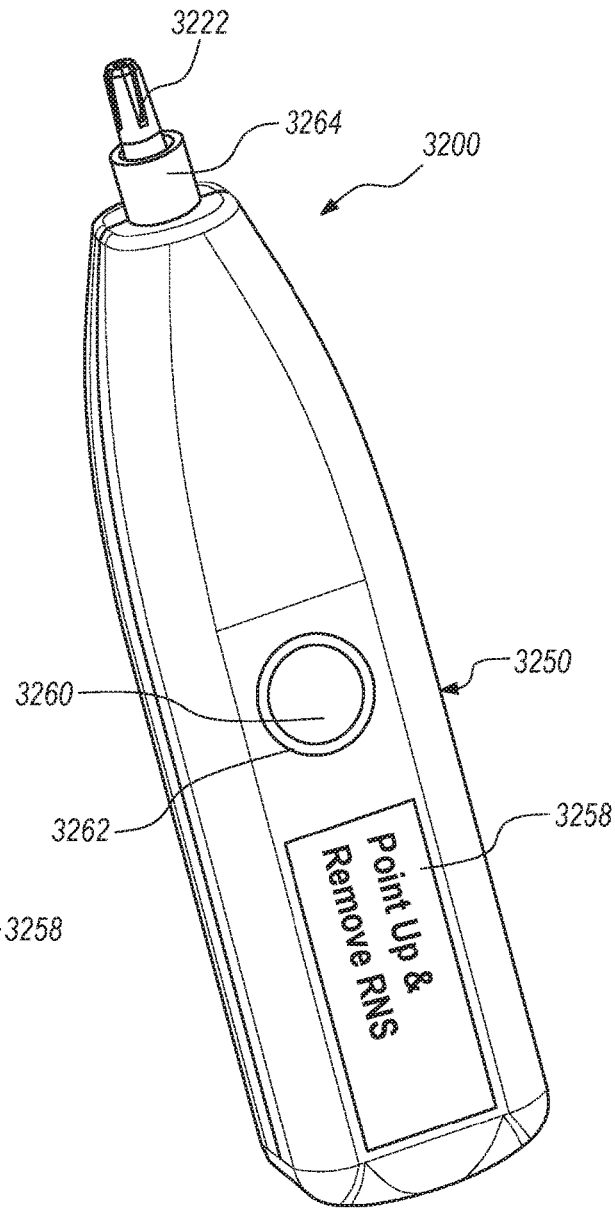

In FIG. 32F, the display 3250 is rendering a message instructing a user to point the autoinjector system 3200 upward and will move the rigid needle shield 3222. As shown in FIG. 32G, when a position sensor in the autoinjector system 3200 detects that the system 3200 is pointed upward, the flange holder/carriage 3256 moves the injection systems/syringe 3210 distally to extend the rigid needle shield 3222 for removal. Removing the rigid needle shield 3222 only when the system 3200 is pointed upward prevents accidental expulsion of medicine due to pressure buildup from fluid transfer and mixing.

Figures 32H, 32I:
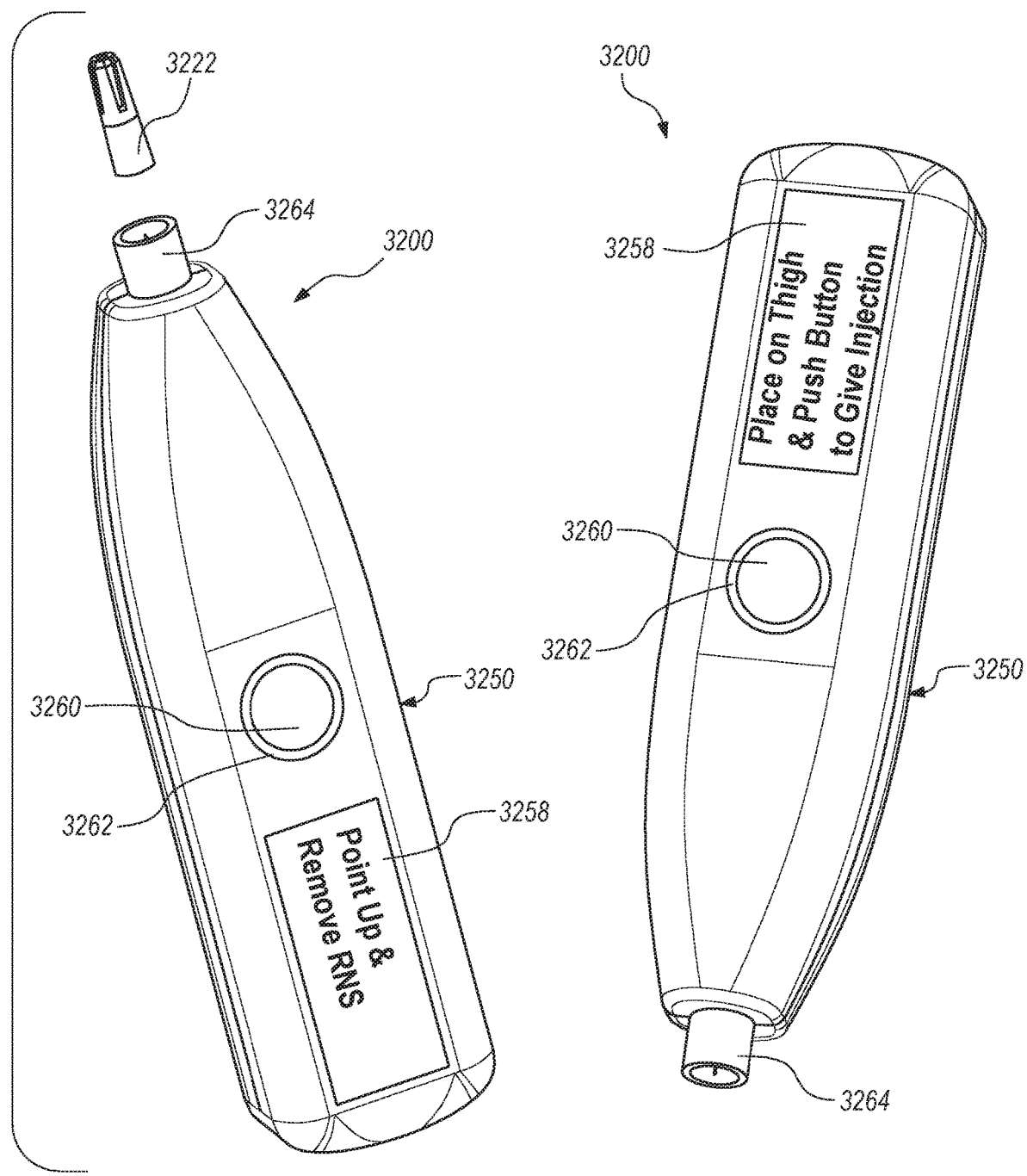
Figure 32J:
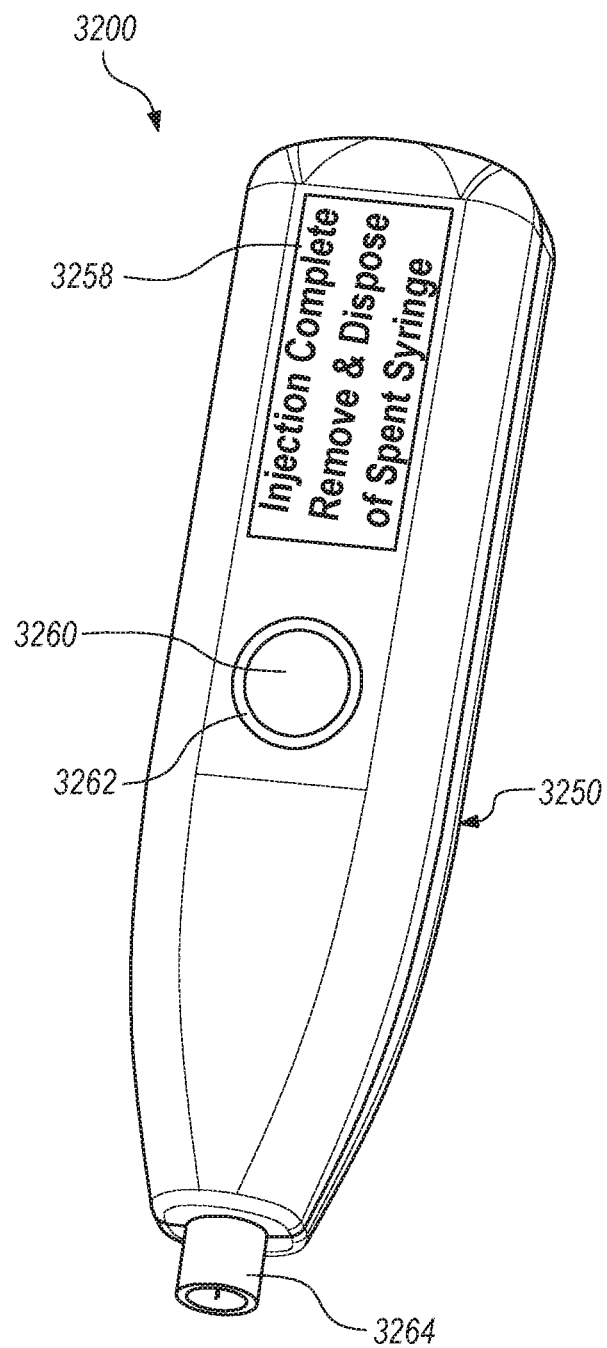

In some embodiments, the user is expected to pull on the rigid needle shield 3222 to remove it from the needle hub assembly 3220. In some embodiments, the autoinjector 3200 includes components that grasp the rigid needle shield 3222 (e.g., one or more arms) while the flange holder/carriage 3256 moves the injection system/syringe 3210 (e.g., from a distal position to a proximal position) to separate the rigid needle shield 3222 from the needle hub assembly 3220. In such embodiments, the user would only have to remove the separated rigid needle shield 3222 from the auto injection system 3200. The collar 3264 prevents exposure of the needle 3226 to a user as shown in FIG. 32H.

In FIG. 32F, the display 3250 is rendering a message instructing a user to place the autoinjector system 3200 on user's thigh and to press the button 3260 to give the injection. In some embodiments, a skin contact sensor prevents injection until contact between the autoinjector system 3200 and the user is detected. Detection of contact and readiness for injection can be indicated using the light ring 3262 (e.g., a green ring for go). When the user presses the button 3260 for injection, the flange holder/carriage 3256 moves the injection systems/syringe 3210 distally to insert the needle into the patient, and the plunger actuator/ pusher 3254 moves distally to complete the injection as shown in FIGS. 7K to 7P.

After the injection is completed, the display 3250 renders a message confirming the injection and instructing a user to remove and dispose of the spent syringe. A new injection system/syringe 3210 can be loaded into the drive system 3252 prepare the autoinjector system 3200 for another injection.

Multiple Chamber Safe Injection System with Luer Connector

FIGS. 33 to 40 depict a multiple chamber safe injection system 3300 with a luer connector 3310. As shown in FIGS. 33 and 34, the luer connector 3310 is a standard connector that facilitates use of the system 3300 with a wide variety of needles and tubing. The system 3300 includes a standard luer cap 3312 that seals the luer connector 3310 during mixing of the drug components before delivery/injection.

In some embodiments, the drug components include a drug solvent 3314 in a proximal chamber and a drug powder and/or solid (e.g., compressed powder) 3316 and a distal chamber. The drug solvent 3314 can be transferred from the proximal chamber to the distal chamber to mix with the drug powder and/or solid 3316 via a transfer pipe 3318 with various openings. The distal end of the transfer pipe 3318 is coupleable via the Luer connector 3310 with a wide variety of needles and tubing. The finger flange and a plunger member also include a ratcheting/anti-retraction system 3320 to limit motion of the plunger member during mixing to the distal direction.

FIG. 35 depicts a transfer pipe 3318 for use with the multiple chamber safe injection system 3300 according to some embodiments. The proximal end of the transfer pipe 3318 includes a piercing tip 3322 configured to pierce the distal stopper member to allow the drug diluent 3314 to transfer from the proximal chamber to the distal chamber to mix with the drug powder and/or solid 3316. The next feature distally along the transfer pipe 3318 is a liquid entrance slot 3324 configured to allow the drug diluent 3314 to enter from the proximal chamber. The next feature is a liquid exit opening 3326 configured to allow the drug diluent 3314 to exit to the distal chamber. The liquid entrance slot 3324 and the liquid exit opening 3326 are configured such that they span the distal stopper member to maximize liquid transfer. The next feature is a blocking rod 3328 to prevent the drug diluent 3314 from exiting out the distal end of the transfer pipe 3318. The next feature is a washer 3330 configured to provide a reactive force to allow the piercing tip 3322 to pierce the distal stopper member. The next feature is an exit slot 3332 configured to allow the mixed drug to enter the distal end of the transfer pipe 3318. The distal most feature is an expanded end opening 3334 configured to mate with a variety of needles and tubing via the luer connector 3310. The expanded end opening also provides friction with the luer passage to hold the transfer pipe 3318 in place during filling of the system 3300.

FIG. 36 depicts the fluid path 3336 during transfer of the drug diluent 3314 from the proximal chamber to the distal chamber. As described above, the fluid path 3336 goes through the liquid entrance slot 3324, travels along a proximal portion of the transfer pipe 3318, and exits the liquid exit opening 3326. Transfer of the drug diluent 3314 from the proximal chamber to the distal chamber increases the pressure in the distal chamber. The ratcheting/anti-retraction system 3320 prevents unwanted proximal movement of the plunger member resulting from the built-up pressure in the distal chamber. The teeth 3338 of the ratcheting/anti-retraction system 3320 are only present at a distal portion of the plunger member, which interacts with tabs 3340 in the finger flange during mixing. Even if the user releases pressure on the plunger member during transfer, the ratcheting system/anti-retraction 3320 holds the plunger member in place. An alternative ratcheting/anti-retraction system is described below.

FIG. 37 depicts the fluid path 3336 at the end of the transfer of the drug diluent 3314 from the proximal chamber to the distal chamber. The liquid entrance slot 3324 allows the drug diluent to continue to transfer even as the proximal and distal stoppers approach each other.

Figure 38:
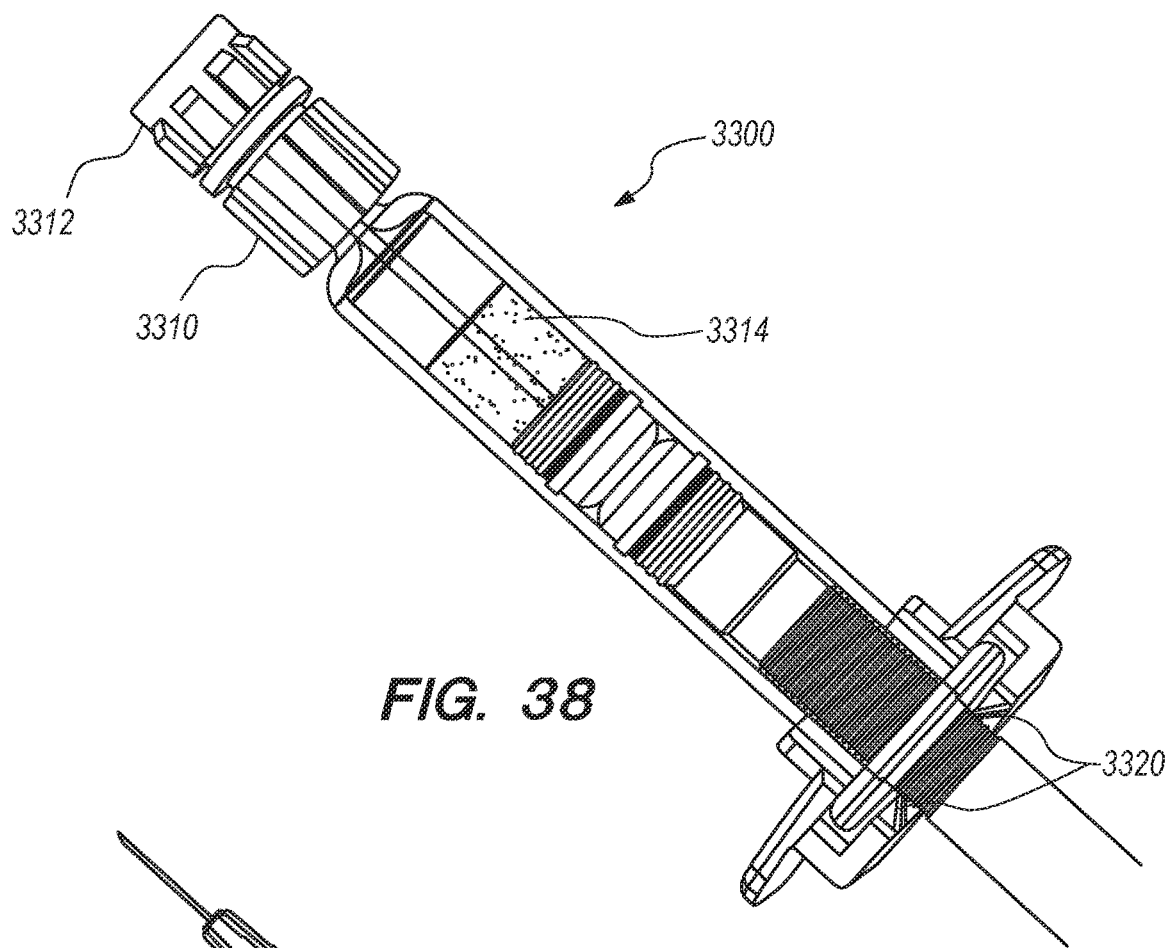

FIG. 38 depicts the multiple chamber safe injection system 3300 after the transfer of the drug diluent 3314 is complete. Pressurized air in the distal chamber is prevented from pushing the plunger member proximally by the ratcheting system 3320. The user can shake the system 3300 to mix the drug diluent 3314 with the drug powder and/or solid 3316 in the distal chamber.

Figure 39:
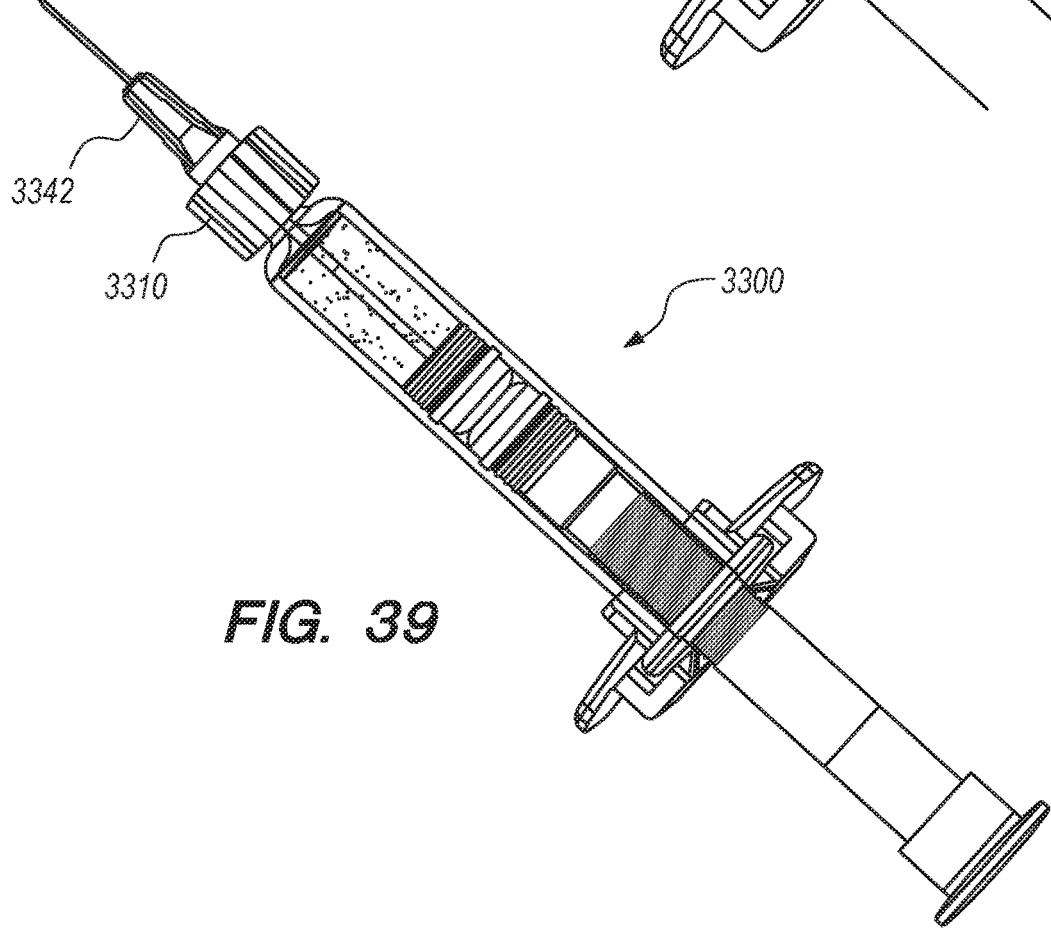

FIG. 39 depicts the multiple chamber safe injection system 3300 after the luer cap 3312 has been removed with the system 3300 in an upward position to avoid the pressure in the distal chamber interjecting any of the mixed drug therein. Instead pressurized air is purged from the distal chamber. A needle 3342 with a corresponding luer connector is coupled to the luer connector 3310 in the system 3300 to prepare the system 3300 for injection.

FIG. 40 depicts the multiple chamber safe injection system 3300 during injection. The fluid path 3344 during injection is along the outside of the distal end of the transfer pipe 3318 and through the needle 3342. During injection, the blocking rod 3328 prevents the mixed drug from traveling retrograde into the plunger member. The plunger member also includes an elastomeric seal to prevent backflow. Because the plunger member has moved relative to the finger flange such that the ratchet teeth at this gauge from the tabs, the plunger member can be moved in both a distal and a proximal direction during injection.

Vent Plug

FIGS. 41 to 47 depict a multiple chamber injection system 4100 with a vent plug 4154 according to some embodiments.

The vent plug 4154 is configured (e.g., sized and shaped) to allow air to escape the system 4100 while substantially retaining liquids. As shown in FIG. 41, the system 4100 includes a syringe body 4110 having a needle coupling member 4156 at a distal end thereof. The needle coupling member 4156 may be a female Luer connector. The system 4100 also includes a finger flange 4136 coupled to a proximal end of the syringe body 4110 and a plunger member 4138 inserted through the finger flange 4136 and into an interior of the syringe body 4110.

Figure 41A:
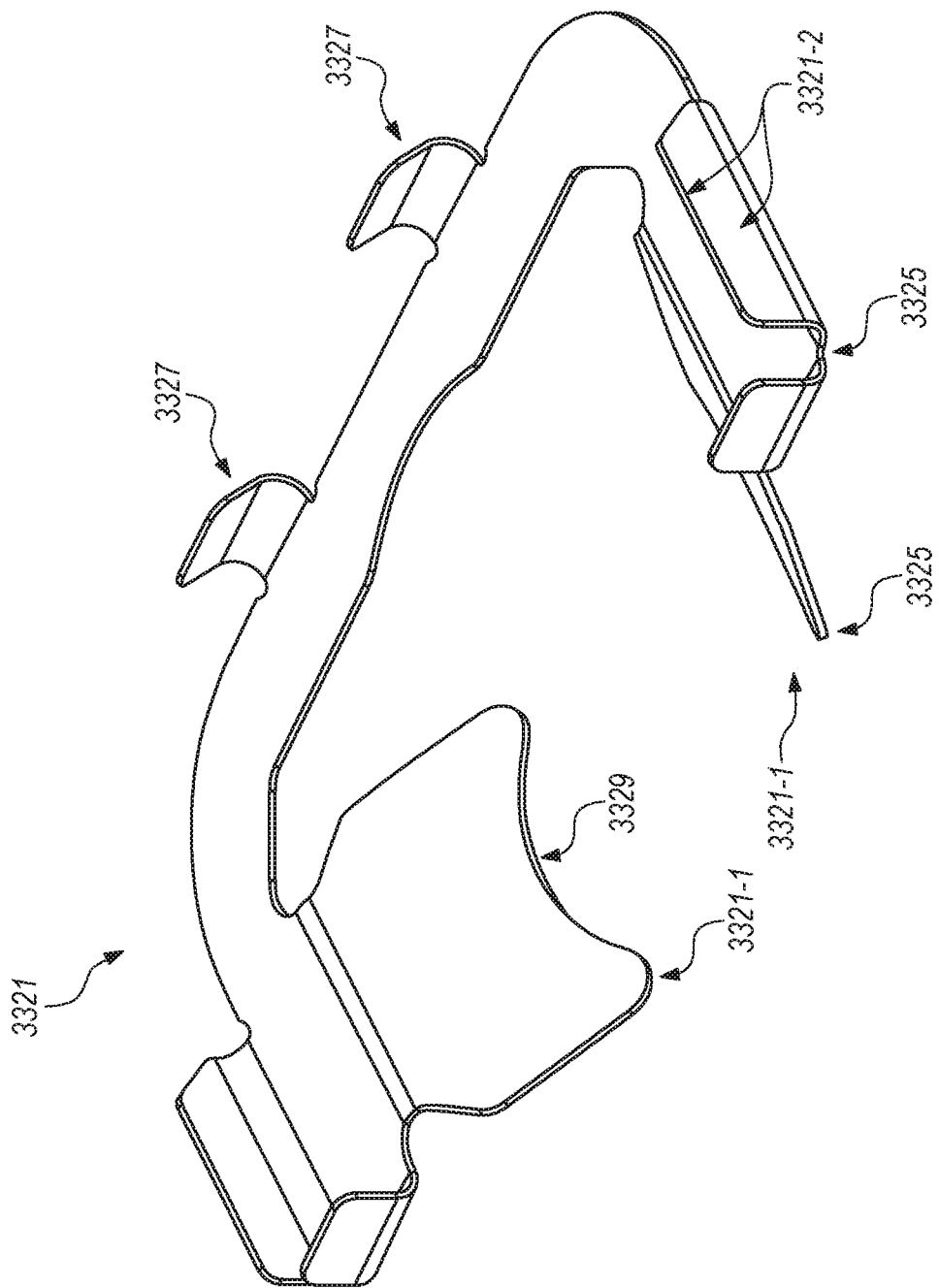
FIGS. 41A and 49 to 56 depict anti-retraction mechanisms according to some embodiments.

Also disposed in the interior of the syringe body 4110 are proximal and distal stopper members 4134, 4114. The proximal and distal stopper members 4134, 4114 and the syringe body 4110 define a proximal chamber 4116. The distal stopper member 4114 and the syringe body 4110 define a distal chamber 4118. In the embodiment depicted in FIG. 41, the distal chamber 4118 contains a gas 4152 (e.g., air) and the proximal chamber 4116 contains a liquid 4132. The system 4100 also includes a mix tube 4124 configured to pierce the distal stopper member 4114 to fluidly couple the proximal and distal chambers 4116, 4118. FIG. 41A depicts an anti-retraction mechanism 3321 (described below) for use with the multiple chamber injection system 4100 according to some embodiments.

The system 4100 further includes a cap 4150 (e.g., Luer cap) coupled to the needle coupling member 4156 for storage of the system 4100 components before use (e.g., injection). Moreover, the system 4100 includes a vent plug 4154 disposed at least partially in the needle coupling member 4156 and around a distal end of the mix tube 4124. The vent plug 4154 is configured (sized and shaped) to allow air to escape the system 4100 while substantially retaining liquids.

Figure 42:
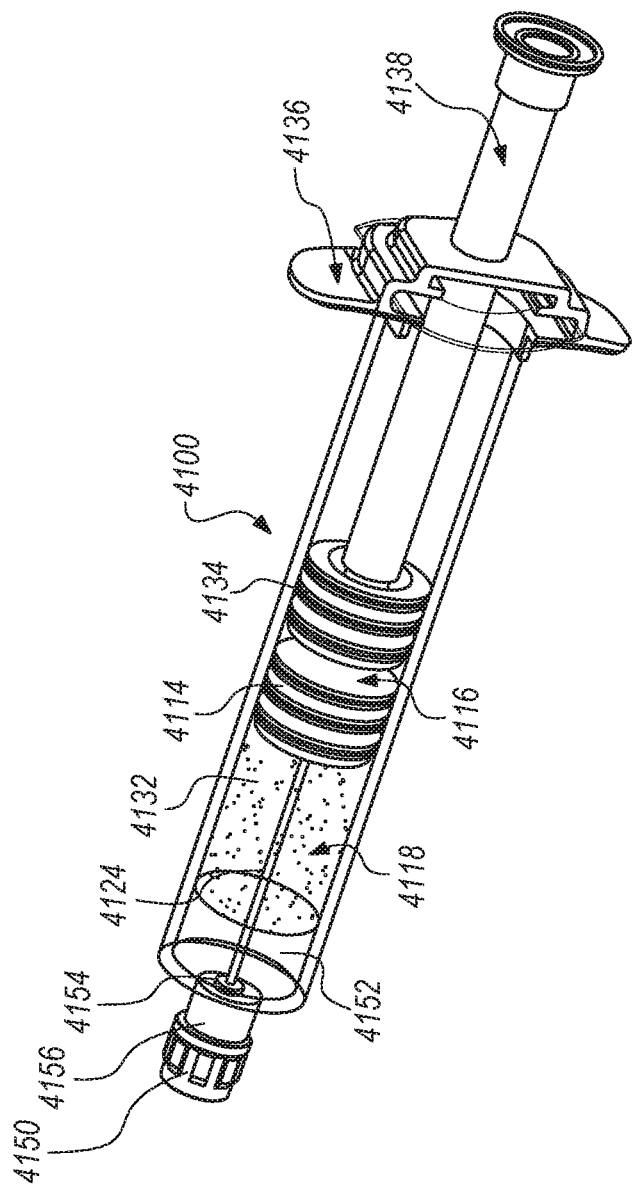
Figure 43:
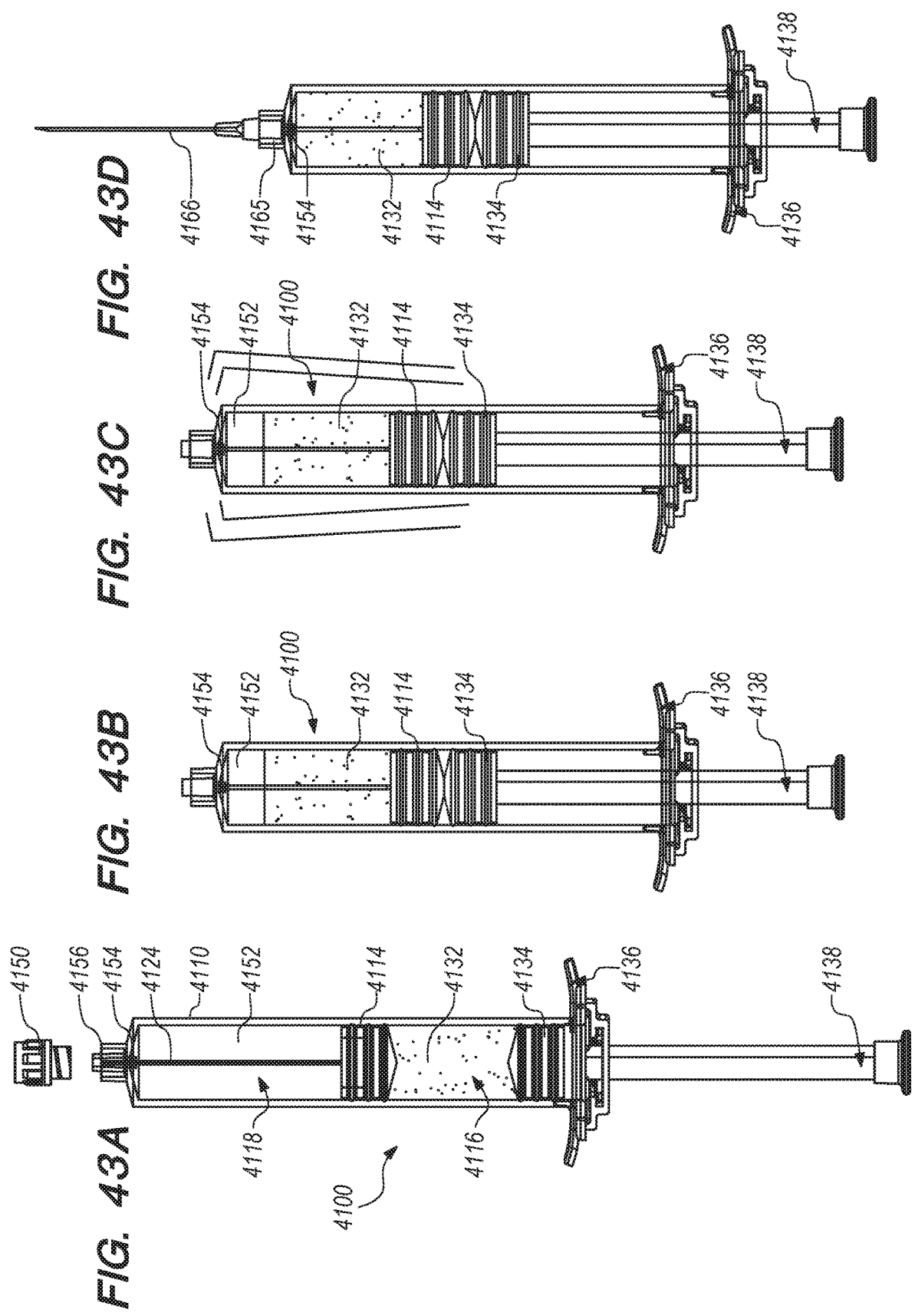

FIG. 42 depicts the system 4100 depicted in FIG. 41 after the plunger member 4138 and the proximal stopper member 4134 coupled thereto have been inserted distally into the interior of the syringe body 4110 according to some embodiments. Before the proximal end of the mix tube 4124 pierces completely through the distal stopper member 4114 (as shown in FIG. 41), the incompressibility of the liquid 4132 in the proximal chamber 4116 transmits distally directed force from the plunger member 4138 and the proximal stopper member 4134 to the distal stopper member 4114 moving the distal stopper member 4114 distally. Distal movement of the distal stopper member 4114 causes the proximal end of the mix tube 4124 to pierce completely through the distal stopper member 4114 and fluidly couple the proximal and distal chambers 4116, 4118. Fluidly coupling the proximal and distal chambers 4116, 4118 allows the liquid 4132 to be driven from the proximal chamber 4116 to the distal chamber 4118 by a distally directed force from the plunger member 4138 and the proximal stopper member 4134 as shown in FIG. 42.

Also shown in FIG. 42, the proximal chamber 4116 has collapsed almost completely, and almost all of the liquid 4132 has been driven from the proximal chamber 4116 to the distal chamber 4118. The volume of the liquid 4132 driven into the distal chamber 4118 compresses the gas 4152 in the distal chamber 4118 increasing the pressure in the distal chamber 4118. If this increased pressure is not vented from the distal chamber 4118, it may unintentionally eject some of the liquid 4132 from the distal chamber 4118, both wasting the liquid 4132 and reducing the accuracy and precision of the system 4100. Before the cap 4150 is removed from the system 4100, the increased pressure in the distal chamber 4118 may also be exerted back through the mix tube 4124, thereby moving some of the liquid 4132 back into the proximal chamber 4116 and reducing the accuracy and precision of the system 4100. The back pressure may also move the proximal stopper member 4134 and the plunger member 4138 proximally. Some multiple chamber injection systems include latches on the plunger member to prevent proximal movement of the plunger member.

FIGS. 43A-43D depicts a method of mixing a two part injectable substance (e.g., medication) for injection according to some embodiments. The multiple chamber injection system 4100 depicted in FIGS. 43A-43D is similar to the multiple chamber injection system 4100 depicted in FIGS. 41 and 42 and described above. One difference is that the system 4100 depicted in FIGS. 43A-43D includes a dry component (e.g., lyophilized powder and/or solid, e.g., compressed powder) (not shown) in the distal chamber 4118 to be solubilized by the liquid 4132 to for the two part injectable substance. In FIG. 43A, the cap 4150 is removed from the needle coupling member 4156. In FIG. 43B, a distally directed force from the plunger member 4138 and the proximal stopper member 4134 causes distal movement of the distal stopper member 4114, which in turn causes the proximal end of the mix tube 4124 to pierce completely through the distal stopper member 4114 and drives the liquid 4132 from the proximal chamber 4116 to the distal chamber 4118. In FIG. 43C, the system 4100 is shaken to mix the liquid 4132 in the distal chamber 4118 with the dry component (not shown) therein. In FIG. 43D, a needle 4166 is attached via a needle coupling member 4156 (e.g., male Luer connector) to prepare the system 4100 for injection. Without a venting/liquid restricting component, during the mixing in FIG. 43C, the increased pressure in the distal chamber 4118 may eject some of the liquid 4132 (and the solubilized dry component), reducing the accuracy and precision of the system 4100.

Figure 44:
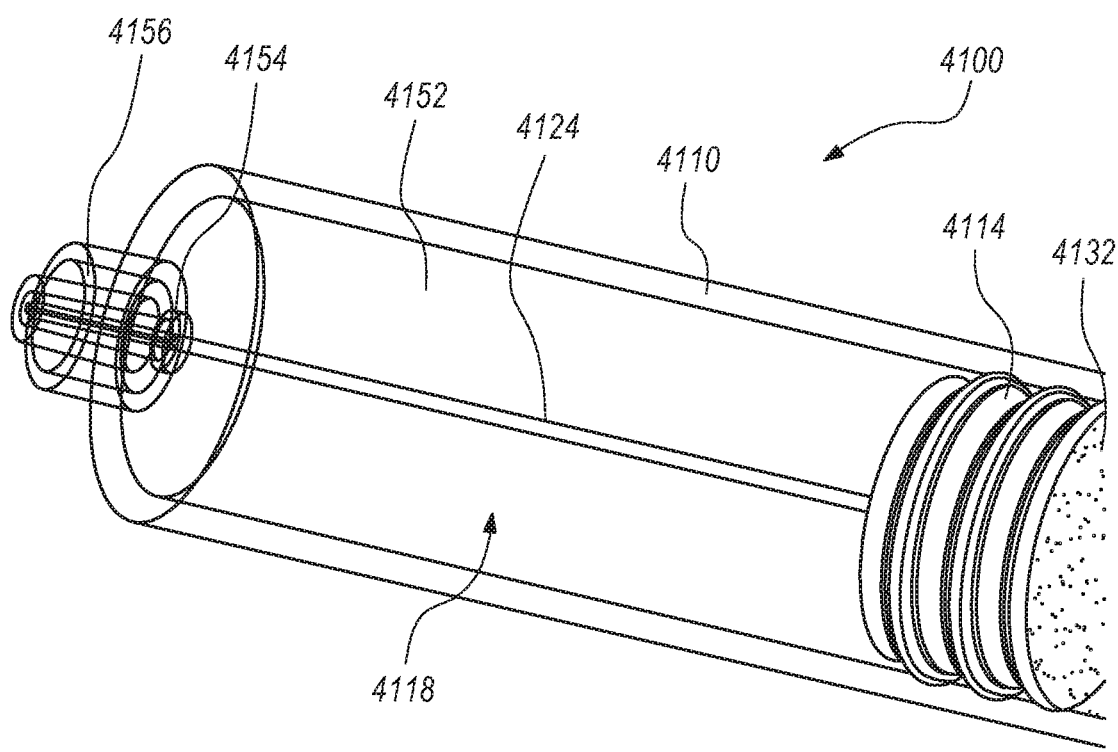
Figure 45:
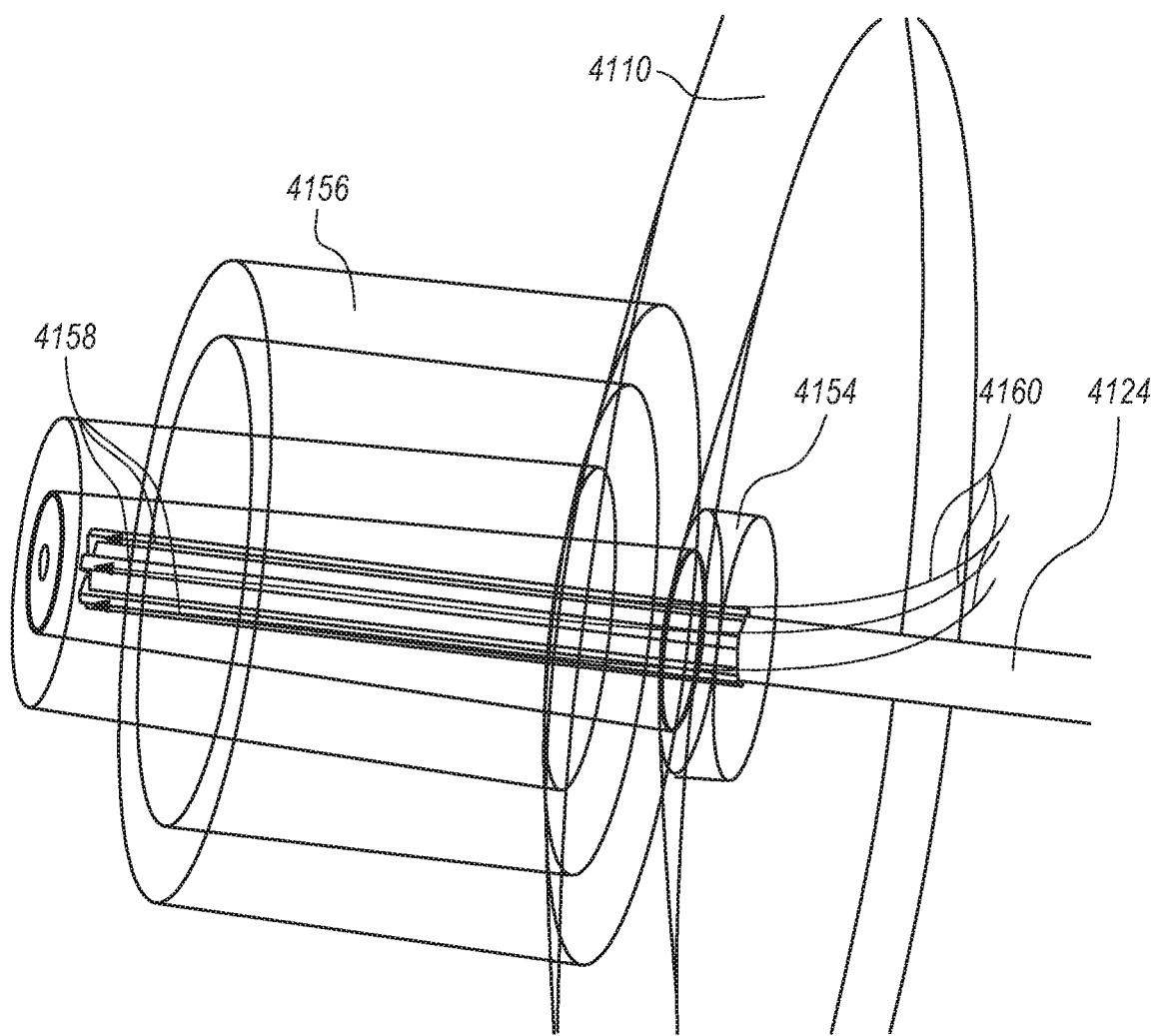

FIG. 44 is a detailed view of the distal end of the syringe body 4110, including a vent plug 4154 which is disposed at least partially in the needle coupling member 4156 and around a distal end of the mix tube 4124 according to some embodiments. FIG. 45 is an even more detailed view of the distal end of the syringe body 4110, including the vent plug 4154 according to some embodiments. FIG. 45 shows that the vent plug includes a plurality of channels 4158, which are configured (e.g., sized and shaped) to allow gases (e.g., air) to escape 4160 the interior of the syringe body 4110 (e.g., distal chamber 4118 see FIG. 44), while preventing liquids from escaping the interior of the syringe body 4110.

Figure 46:
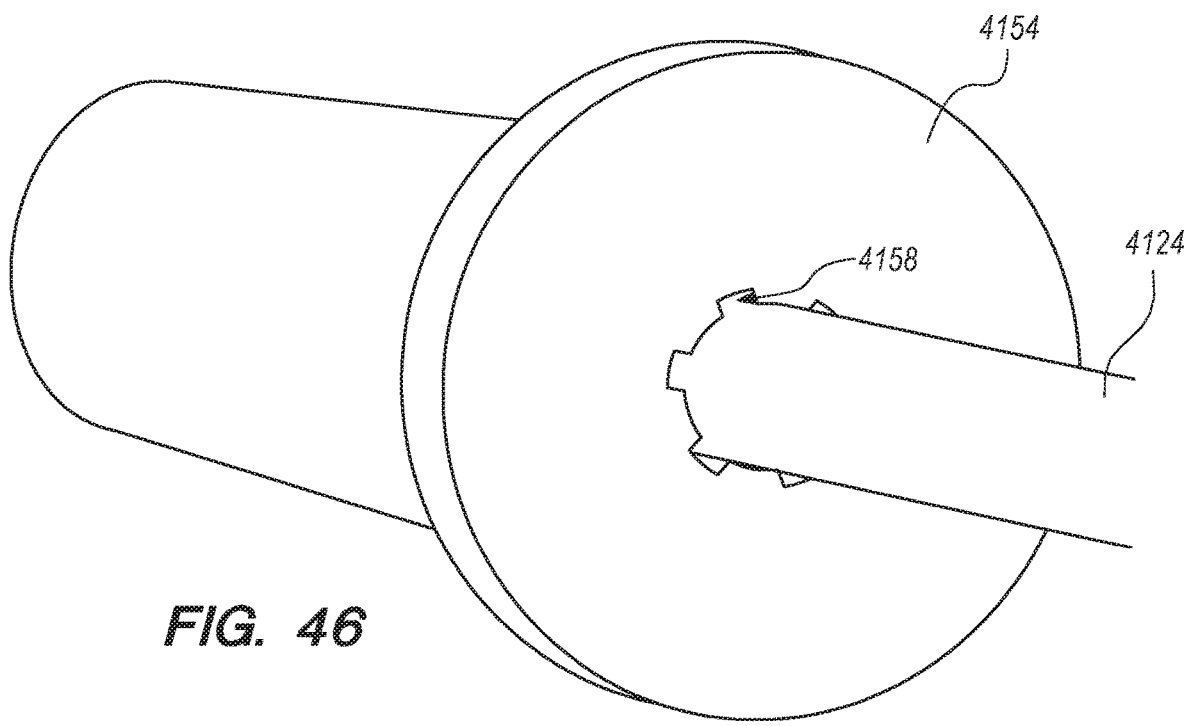
Figure 47:
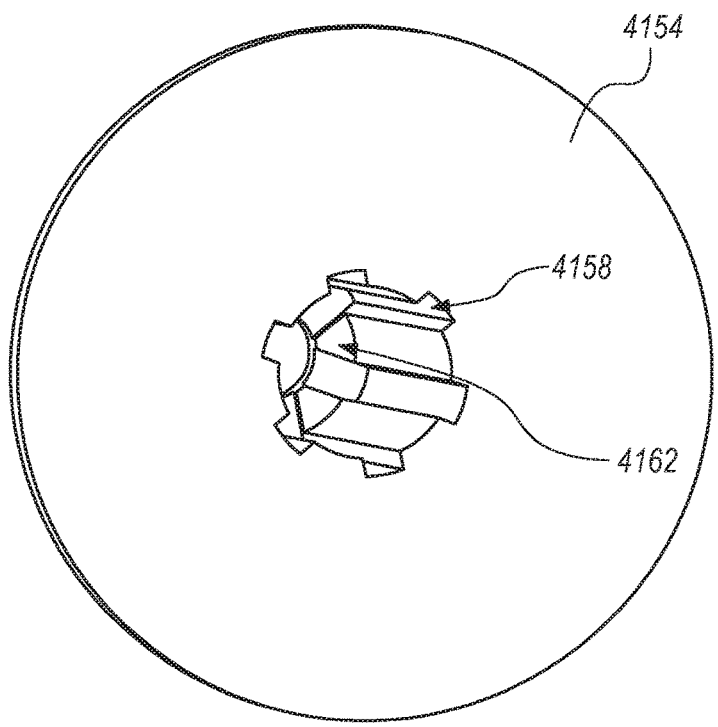

FIG. 46 is a detailed view of a vent plug 4154 for use in a multiple chamber injection system 4100 according to some embodiments. Many components of the system 4100 are omitted for clarity. The vent plug 4154 is disposed around a mix tube 4124 and includes a plurality of channels 4158. FIG. 47 is a detailed view of a vent plug 4154 for use in a multiple chamber injection system 4100 according to some embodiments. FIG. 47 depicts the center opening 4162 of the vent plug 4154 through which a mix tube 4124 may be inserted. FIG. 47 also depicts a plurality of channels 4158 that may be molded into an interior surface of the vent plug 4154. The plurality of channels 4158 are configured (e.g., sized and shaped) to allow gases to escape/vent from the interior of the syringe body 4110 while preventing liquids from escaping the interior of the syringe body 4110. Venting gases and releasing pressure from the interior of the syringe body 4110 minimizes unintended ejection of liquid from the interior of the syringe body 4110 and increases accuracy and precision of the system 4100. Venting gases and releasing pressure from the interior of the syringe body 4110 also minimizes unintended proximal movement of the plunger member 4138 from back pressure, thereby eliminating the need for latches on the plunger member 4138 to prevent proximal movement thereof.

Figure 48:
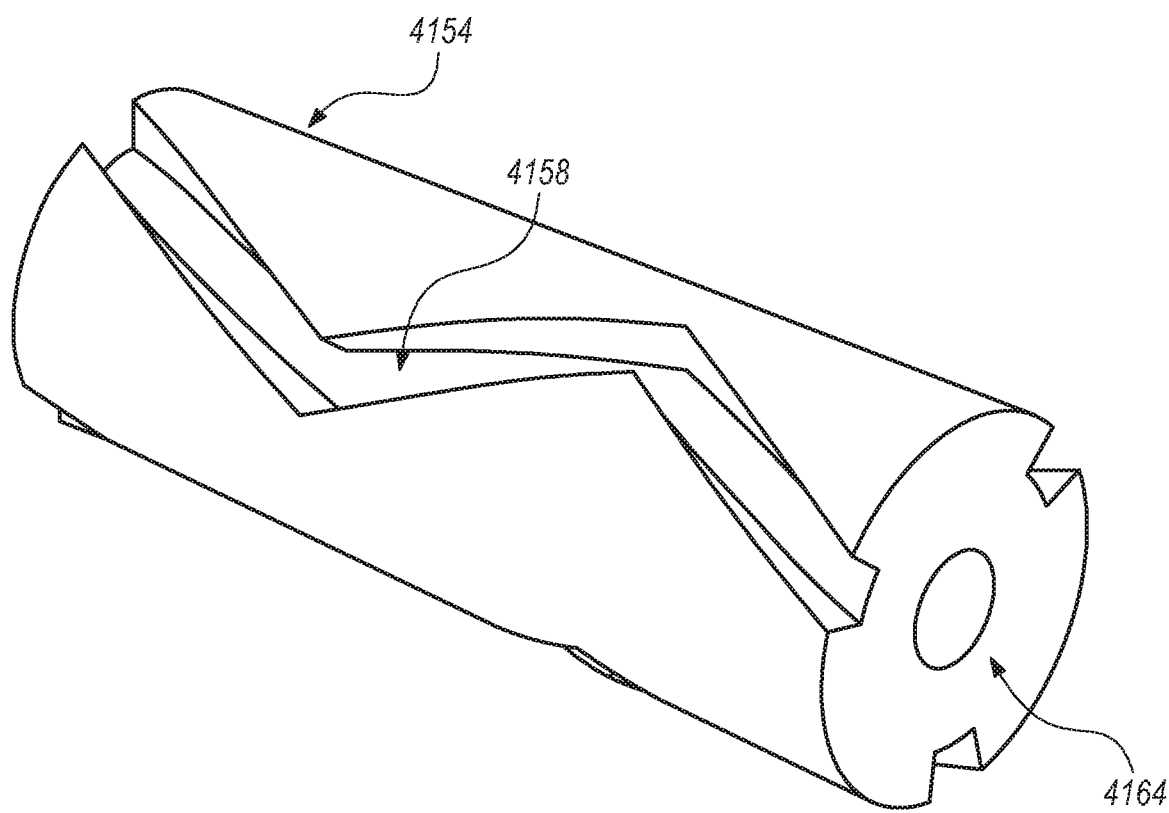
FIG. 48 depicts a vent plug according to some embodiments.

FIG. 48 depicts an alternative embodiment of the vent plug 4154 where the vent channels 4158 are present in an exterior surface of the vent plug 4154. The vent plug 4154 is configured to be installed into the distal needle interface 4156 (see FIG. 45), where the vent channels 4158 are in contact with the interior surface of the distal needle interface 4156, maintaining the open vent channel 4158 to an exterior of the syringe body 4110. The vent channels 4184 may be linear or may be non-linear with bends and turns along the longitudinal axis of the vent plug 4154 (as shown in FIG. 48). FIG. 48 illustrates vent channels 4184 that are non-linear, creating a tortuous path for fluid flow along the longitudinal axis of the vent plug 4154. As fluid is forced through the vent channels 4158, bends or corners in the vent channels 4158 provide impediments/resistance to fluid flow. These impediments are configured to take advantage of fluid frictional effects such that more viscous fluids (e.g., liquids) require higher pressure to flow through the vent channels 4158. For example, gases (e.g., air) will flow through these vent channels 4158 at a predetermined pressure generated in the syringe body 4110. Liquids (e.g., water or liquid drugs) require a higher pressure to flow through the vent channels 4158. This pressure differential requirement for fluid flow provides a restriction to prevent water or liquid drug from being unintentionally expelled from the end of the syringe body 4110 during mixing (see FIG. 43C) when the syringe cap 4150 is removed. The pressure for fluid flow may also be generated by shaking the syringe during mixing, such as g-forces from shaking applied over the surface of the liquid. The vent channels 4158 are configured such that high g-forces resulting from shaking the syringe during mixing do not apply a large enough force on the liquid to expel the liquid during shaking. The vent channels 4158 may be constructed to provide orifices for fluid flow, capillary channels, and/or high fluid friction surfaces to tailor the flow restriction for different fluids. This embodiment also depicts a central opening 4164 of the vent plug 4154 through which a mix tube 4124 may be inserted. The central opening 4164 may be disposed entirely through the vent plug or may be a blind hole with a bottom for locating the distal end of the mix tube 4124.

Alternative Ratcheting/Anti-Retraction System

Figure 49:
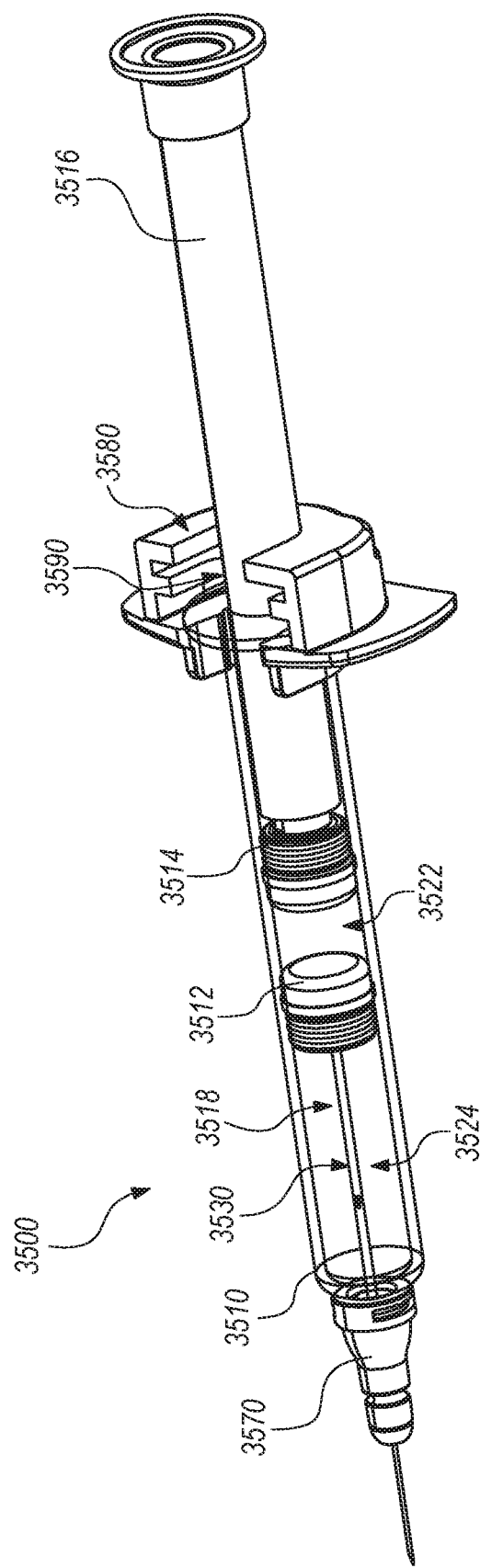

An alternative embodiment of the ratcheting/anti-retraction system is illustrated in FIGS. 41, 41A and 49-56. As shown in FIGS. 41 and 49, this ratcheting/anti-retraction system is configured for use with a plunger member 4138, 3516 having a smooth exterior. An anti-retraction feature 3321, 4090 (see FIGS. 41A and 42) includes at least one brake tab 3321-1, 4092. The brake tab 3321-1, 4092 may be constructed from sheet metal, or a polymer material. Sheet metal brake tab 3321-1, 4092 may be configured to have sharp edges on the plunger member engaging surfaces 3329 which enable the brake tab 3321-1, 4092 to deform the exterior surface of the plunger member 4138, 3516. The anti-retraction feature 3321, 4090 and intercoupled brake tabs 3321-1, 4092 may be configured to elastically deform upon insertion of the plunger member 4138, 3516 through the anti-retraction feature 3321, 4090, deflecting the brake tabs 3321-1, 4092. The elasticity of the brake tabs 3321-1, 4092 provides a biasing force which ensures there is contact between the plunger member engaging surfaces 3329 and the exterior of the plunger member 4138, 3516.

The anti-retraction feature 3321, 4090 is inserted into a transverse slot 3323, 3584 in the finger flange 4136, 3580 with the brake tabs 3321-1, 4092 bent distally 3325. Pre-bending the brake tabs 3321-1, 4092 allows the brake tabs 3321-1, 4092 to flex distally upon insertion of the plunger member 4138, 3516 into the finger flange 4136, 3580, while preventing movement of the plunger member 4138, 3516 in a proximal direction. The amount of pre-bend may be between approximately 10 degrees and approximately 80 degrees, preferably 45 degrees per brake tab 3321-1, 4092. Alternatively, the brake tab 3321-1, 4092 may be flat when inserted into the transverse slot 3323, 3584, and may be bent upon insertion of the plunger member 4138, 3516 into the finger flange 4136, 3580. Bearing surfaces/fit tabs 3321-2, 3596, 4096 on the anti-retraction feature 3321, 4090 are configured to engage the interior surfaces of the finger flange 4136, 3580 defining the transverse slot 3323, 3584 to react the forces applied to the brake tab 3321-1, 4092 from insertion of the plunger member 4138, 3516. The anti-retraction feature 3321, 4090 may have retention barbs/tabs 3327, 3594, 4094 to hold the anti-retraction feature 3321, 4090 in the transverse slot 3323, 3584 in the finger flange 4136, 3580. While the ratcheting systems herein are depicted and described for use with a dual chamber syringe the ratcheting systems may be used with any syringe or cartridge injection system where it is desired to prevent movement of the plunger member in the proximal direction.

FIGS. 49 to 56 depict the addition of a one-way ratchet to the dual chamber injection systems described herein (and in the other patent applications incorporated by reference herein). The one-way ratchet enables the plunger member to be moved distally with minimal drag force and prevents the plunger member from moving proximally by the engagement of ratchet teeth onto the outer surface of the plunger member. During the mixing phase of the multi-component injectable preparation air pressure accumulates in the distal chamber as the liquid is transferred. This pressure builds and produces a proximally directed reaction force on the user's thumb. The addition of a toothless ratchet counteracts this reaction force, preventing the plunger member from moving proximally. With the toothless ratchet engaged, the user does not need to continually apply a distally directed force to maintain plunger member position. The ratchet may be toothless, where the plunger member is smooth on the outside surface and the ratchet arms are configured to dig into the plunger member. In this case the position of the plunger member is maintained in infinitely small increments. Alternatively, the ratchet may engage with annular grooves in or threads on the outside surface of the plunger member, providing an incremental position stop. The annular grooves may provide a tactile and/or audible click or feedback to the user that the ratchet is engaged.

FIG. 49 depicts a dual chamber injection system 3500 with a finger flange 3580 having an anti-retraction feature 3590 according to some embodiments. The anti-retraction feature 3590 prevents proximal movement of the plunger member 3516 relative to the syringe body 3510, while allowing distal movement. In addition to the syringe body 3510, the plunger member 3516, the finger flange 3580, and the anti-retraction feature 3590, the dual chamber injection system 3500 also includes proximal and distal stopper members 3512, 3514, and a needle hub assembly 3570. The injection system 3500 depicted in FIG. 49 may also include a needle assembly 3530 which has a proximal and distal end. The proximal end is configured to have fluid passages (not shown, but see FIG. 35 (3324), FIG. 9C (885), and/or FIG. 7E (270)) for transferring fluid from the proximal chamber 3522 to the distal chamber 3524 when the plunger member 3516 is moved distally. The plunger member 3516 is inserted into an interior 3518 of the syringe body 3510 via a proximal opening in the syringe body. The proximal and distal stopper members 3512, 3514 together with the syringe body 3510 define a proximal drug chamber 3522. The distal stopper member 3514 and the syringe body 3510 define a distal drug chamber 3524. The plunger member 3516 may be manually manipulated to insert the proximal stopper member 3512 relative to the syringe body 3510. If a non-compressible fluid is disposed in the proximal drug chamber 3522, inserting the proximal stopper member 3512 also inserts the distal stopper member 3514 relative to the syringe body 3510.

Figure 50:
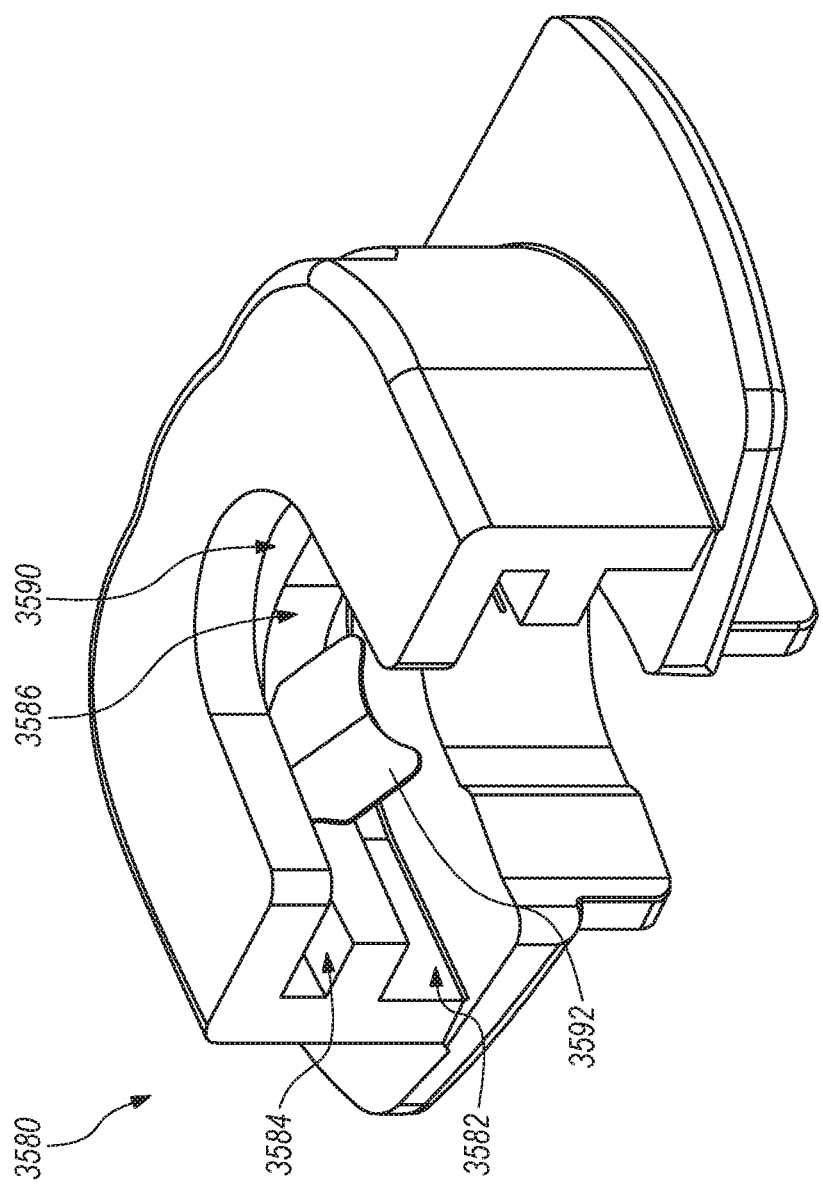
Figure 53:
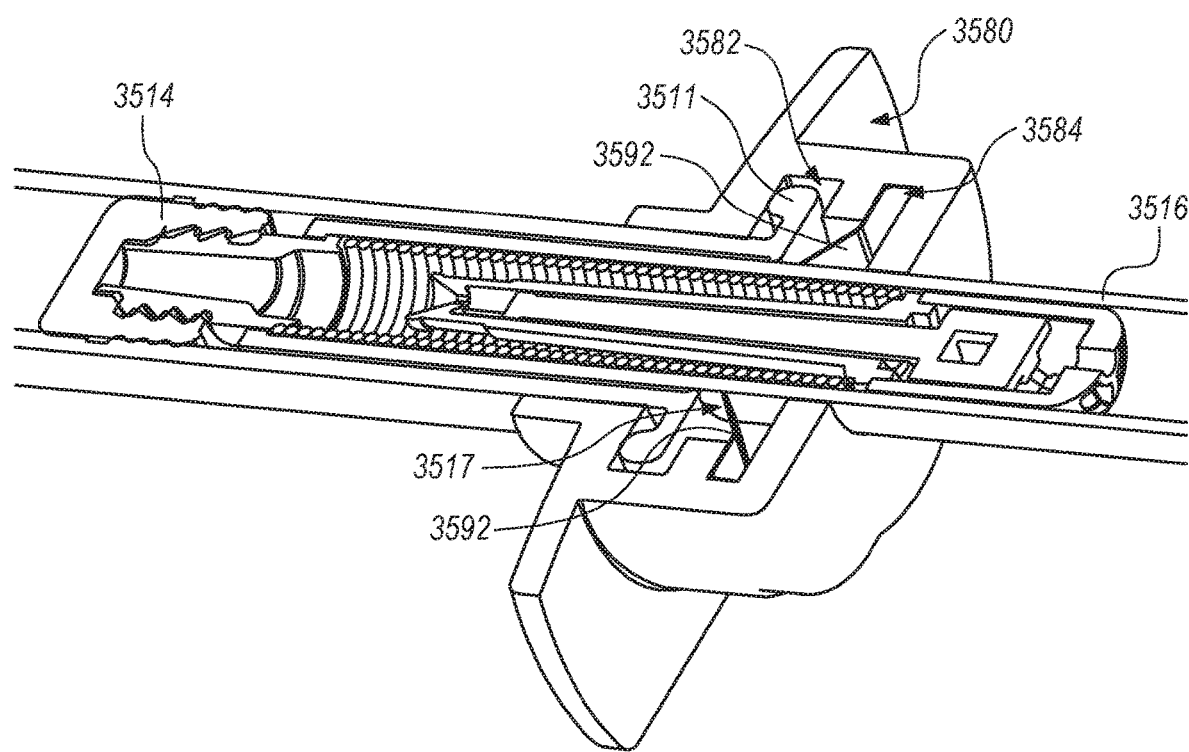

FIGS. 50 to 53 depict the finger flange 3580, which is configured to be mounted onto a small flange 3511 formed at the proximal end of the syringe body 3510 (see FIG. 53). As shown in FIG. 50, the finger flange 3580 defines a first recess 3582 configured to receive the small flange 3511 to couple the finger flange 3580 to the syringe body 3510. The finger flange 3580 also defines a second recess 3584 configured to receive the anti-retraction mechanism 3590. The anti-retraction mechanism 3590 includes a pair of brake tabs 3592 configured to provide an opposing force with proximal movement of the plunger member 3516 relative to the anti-retraction mechanism 3590, while allowing distal movement. The opposing force may include a frictional force as the brake tabs 3592 contact an outer surface 3517 of the plunger member 3516 and a reaction force as the brake tabs 3592 dig into an outer surface 3517 of the plunger member 3516. The acute angle of the brake tabs 3592 creates the reaction force parallel to the plunger member 3516, exerted by a sharp curved edge of each of the brake tabs 3592 contacting the surface 3517 of the plunger member 3516. This reaction force along with the frictional force prevents the plunger member 3516 from moving in the proximal direction. The finger flange 3580 further defines a "C" shaped opening 3586 configured to receive the plunger member 3516 (see FIG. 50). Due to the "C" shaped opening 3586, the finger flange 3580 can be slid onto the small flange 3511 from the side of the small flange 3511 after the plunger member 3516 is inserted during assembly. The "C" shaped finger flange 3580 and anti-retraction mechanism 3590 depicted in FIGS. 49 to 53 can be slid/snapped on to the small flange 3511 of the syringe body 3510 after the plunger member 3516 is inserted. Syringe bodies 3510 with plunger members 3516 screwed into proximal stopper members 3514 are able to pack more tightly into shipping trays for transportation. The finger flange 3580 with is the anti-retraction mechanism 3590 is snapped after shipping, and snaps around both the syringe body 3510 and the plunger member 3516.

Figure 51:
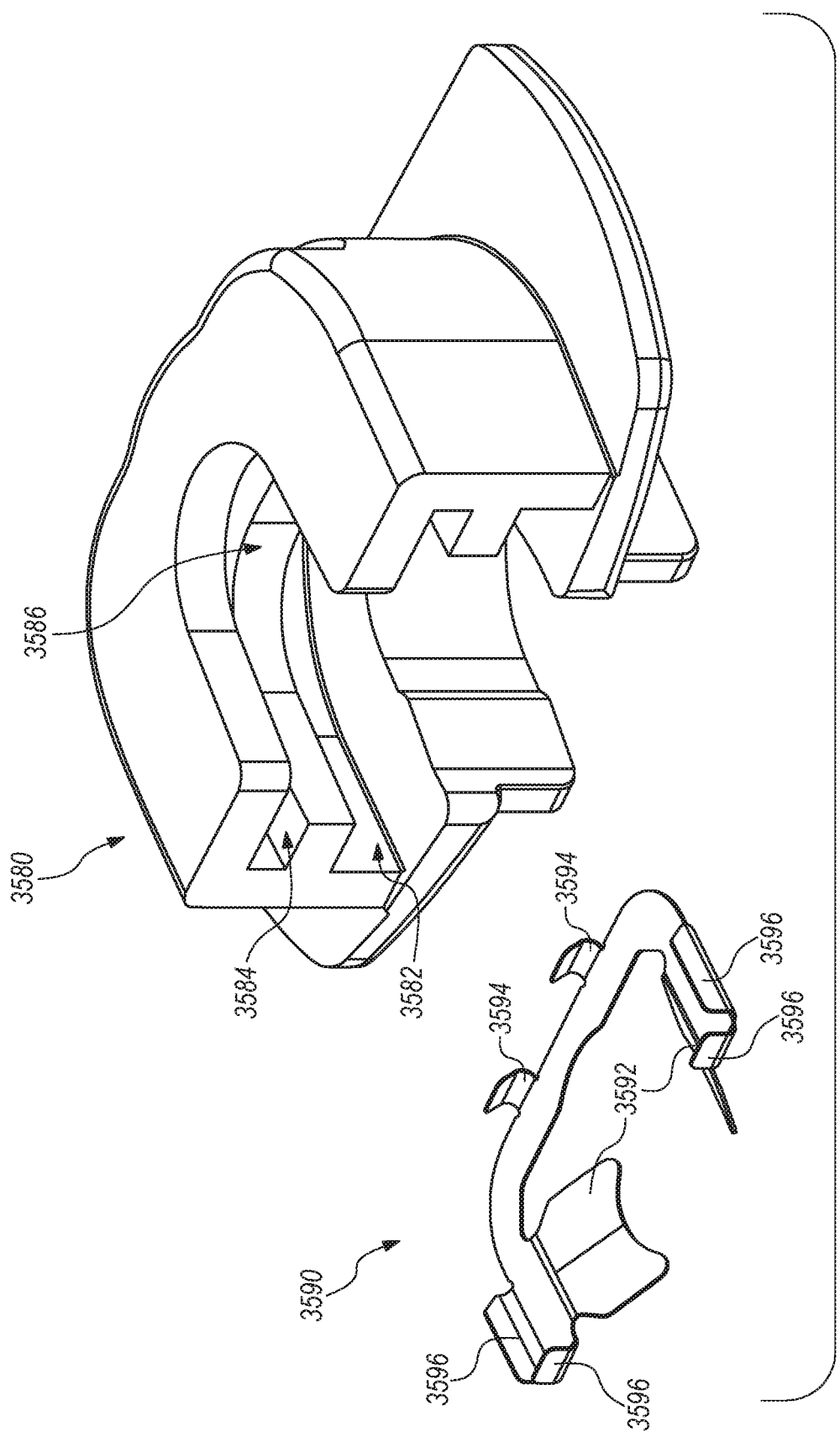
Figure 52:
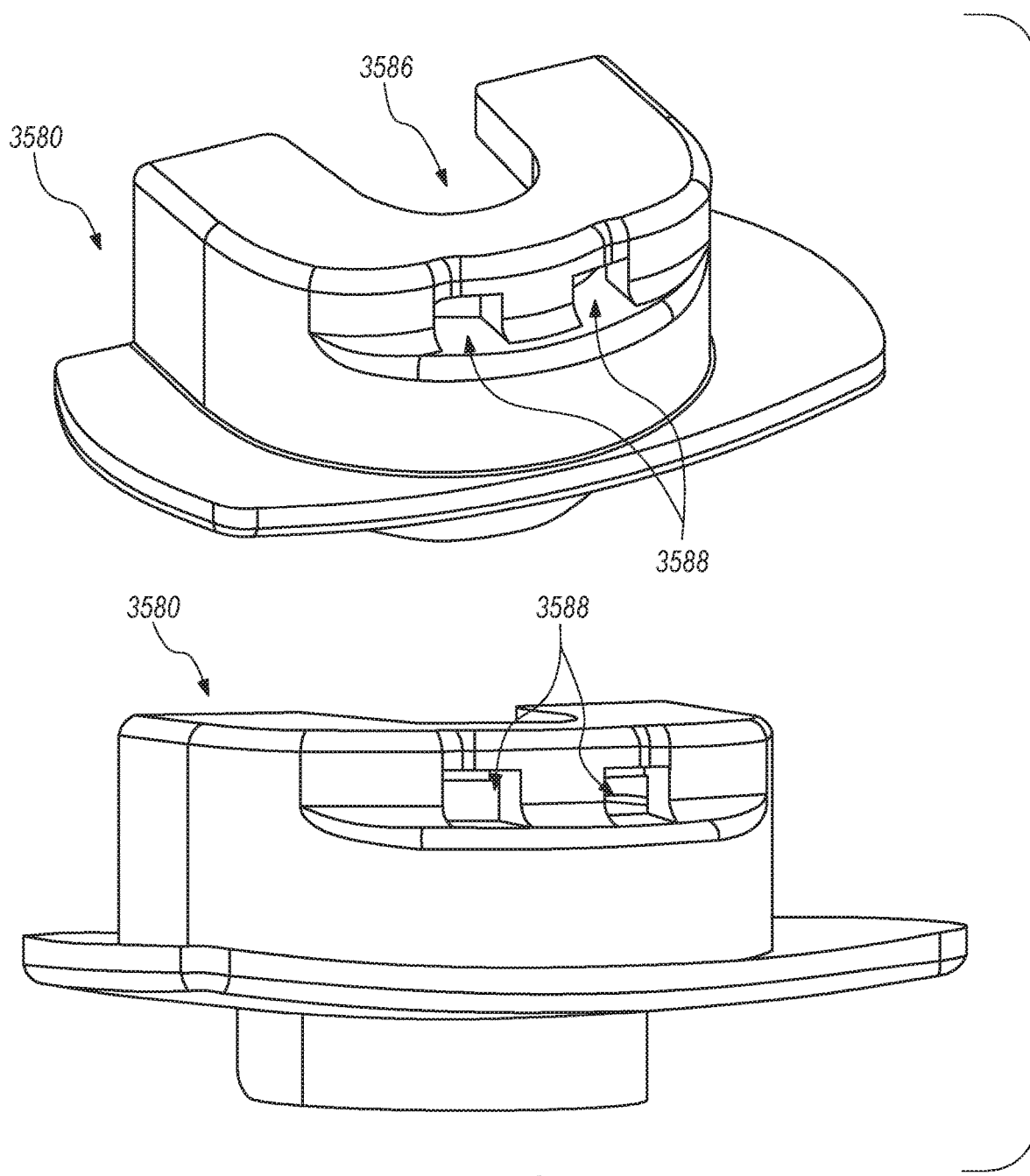

As shown in FIG. 51, the anti-retraction mechanism 3590 is a generally "C" shaped clip. In some embodiments, the anti-retraction mechanism 3590 is cut or stamped from a sheet of metal and then certain portions thereof are bent to the final shape. The anti-retraction mechanism 3590 includes a pair of brake tabs 3592 configured to provide an opposing frictional force with proximal movement of the plunger member 3516 as described above. The brake tabs 3592 are the elastically deformable and self-energizing. The brake tabs 3592 extend at an acute angle in a distal direction relative to the plane of the anti-retraction mechanism 3590 (i.e., the brake tabs 3592 are bent downwards). The angle and elasticity of the brake tabs 3592 allows the plunger member 3516 to slide past the break tabs 3592 in the in distal direction. When the plunger member 3516 is pulled in a proximal direction relative to the brake tabs 3592, the brake tabs 3592 make contact with and dig into an outer surface 3517 of the plunger member 3516 and prevent proximal plunger member 3516 movement relative to the break tabs 3592. Because the brake tabs 3592 are self-energizing, with attempted proximal movement, the brake tabs 3592 engages with the plunger member 3516 by increasing a frictional force applied to the plunger member 3516 and an amount of digging into the plunger member 3516 to prevent its proximal movement. In effect, the brake tabs 3592 form a pair of pawls to engage the plunger member 3516 and prevent proximal movement thereof. In some embodiments, the plunger member (not shown) may have annular grooves threads and/or formed thereon to increase the ratcheting effect of the brake tabs 3592. The anti-retraction mechanism 3590 and the brake tabs 3592 prevent removal of the plunger member 3516 from the dual chamber injection system 3500 after use.

The anti-retraction mechanism 3590 also includes a pair of retention tabs 3594 configured to hold the anti-retraction mechanism 3590 in the second recess 3584 of the finger flange 3580. The retention tabs 3594 are bent inward so that they are configured to grip the inside of the second recess 3584 in the finger flange 3580 with a frictional force and a reaction force to prevent removal of the anti-retraction mechanism 3590 from the second recess 3584. The retention tabs 3594 are also self-energizing to provide increasing frictional and reaction force as the anti-retraction mechanism 3590 is pulled from the second recess 3584. In the embodiment depicted in FIG. 52, the finger flange 3580 includes a pair of openings 3588 configured to receive the retention tabs 3594 from the anti-retraction mechanism 3590 to retain the anti-retraction mechanism 3590 in the second recess 3584 by interference instead of friction.

As shown in FIG. 51, the anti-retraction mechanism 3590 also includes four fit tabs 3596 configured to reduce a tolerance between the second recess 3584 and the anti-retraction mechanism 3590 thereby providing a tighter fit of the anti-retraction mechanism 3590 in the second recess 3584. The original tolerance is larger because, in some embodiments, the finger flange 3580 is molded from a polymer, and therefore has minimum size limitations for recesses that can be accurately and precisely formed therein. On the other hand, the anti-retraction mechanism 3590 is cut from a sheet of metal, and therefore has a thinner profile then the height of the second recess 3584. The fit tabs 3596 increase the thickness/height of the anti-retraction mechanism 3590, thereby providing a tighter fit in the second recess 3584. The fit tabs 3596 also provide rigidity to the anti-retraction mechanism 3590. Accordingly, when the plunger member 3516 is pulled proximally, the brake tabs 3592 (because of their elasticity and angle) exert an outward force on the anti-retraction mechanism 3590. This outward force is transferred through the anti-retraction mechanism 3590 and the fit tabs 3596 to push against the inside of the second recess 3584 of the finger flange 3500 due to the rigidity of the anti-retraction mechanism 3590. This outward force is the reactive force to the frictional and reaction forces applied to the plunger member 3516 to prevent its proximal movement.

Figure 54:
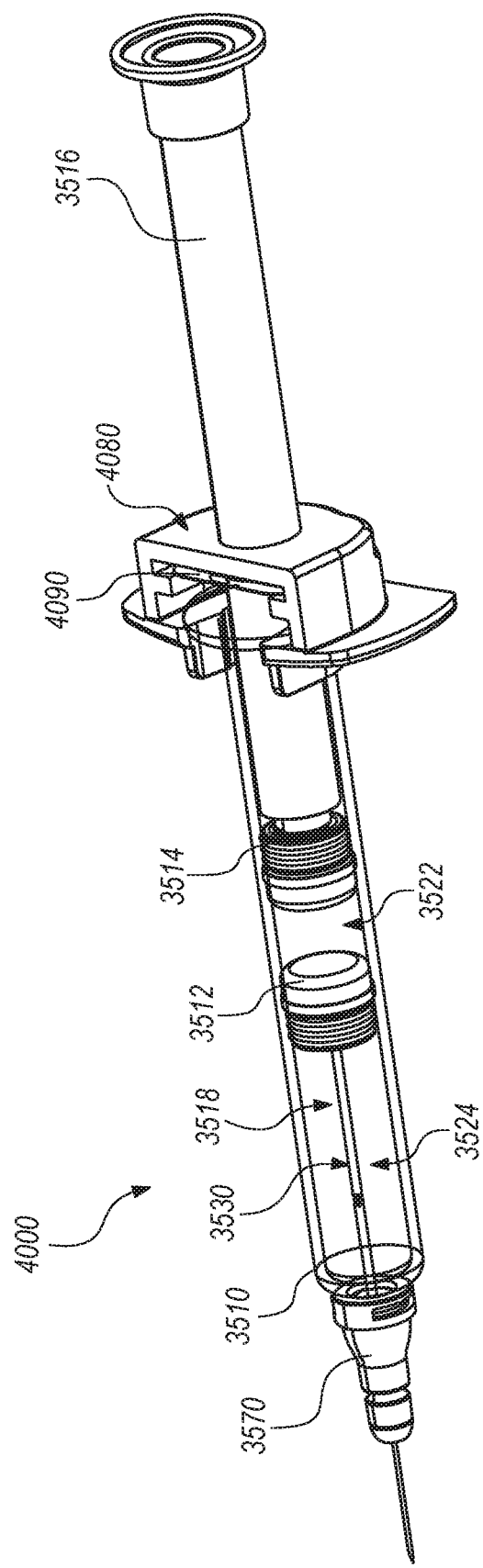
Figure 55:
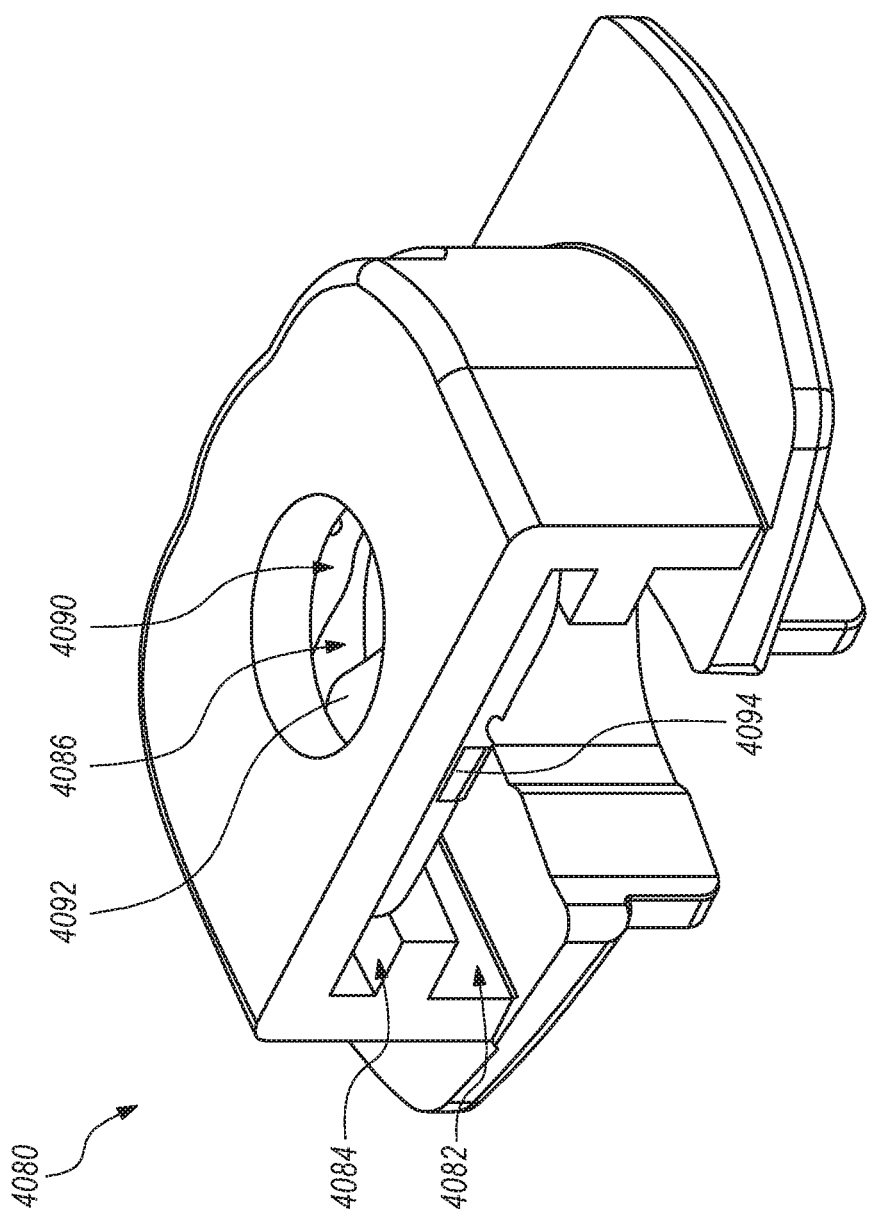
Figure 56:
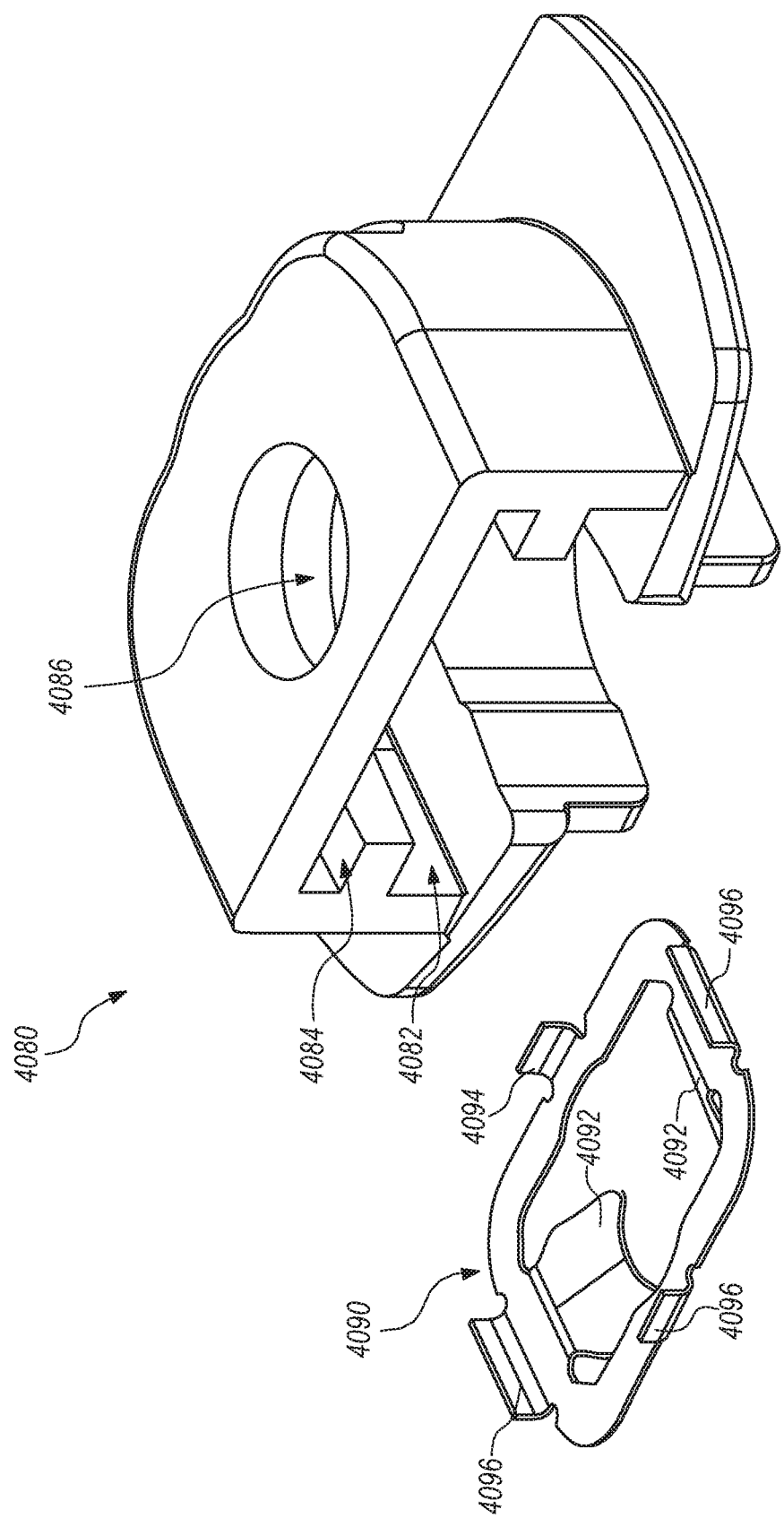

FIGS. 54 to 56 depict a dual chamber injection system 4000 with a finger flange 4080 having an anti-retraction feature 4090 according to some embodiments. The dual chamber injection system 4000 has many of the same components as the dual chamber injection system 3500 depicted in FIGS. 49 to 53 and described above. Those components have the same reference numerals as the corresponding components in the dual chamber injection system 3500. The difference between the dual chamber injection systems 3500, 4000 is in the finger flanges 3590, 4090. Unlike the finger flange 3590 depicted in FIGS. 50 and 51, which has a "C" shaped opening 3586 for receiving the plunger member 3516, the finger flange 4090 depicted in FIGS. 55 and 56 has an "O" shaped opening 4086 for receiving the plunger member 3516. The "O" shaped opening 4086 provides an additional mechanism for preventing removal of the plunger member 3516 from the dual chamber injection system 4000 after use.

As shown in FIG. 56, the anti-retraction mechanism 4090 in the finger flange 4080 has an "O" and/or rectangular shape. The anti-retraction mechanism 4090 can be cut from a sheet of metal. Due to the "O" and/or rectangular shape of the finger flange 4080, the finger flange 4080 is snapped onto the small flange 3511 from a proximal direction during assembly. Then the plunger member 3516 is inserted through an "O" shaped opening 4086 in the finger flange 4080. The "O" shaped opening 4086 in the finger flange 4080 also aligns the plunger member 3516 in the syringe body 3510.

The brake tabs 4092 in the anti-retraction mechanism 4090 depicted in FIG. 56 are identical to the brake tabs 3592 in the anti-retraction mechanism 3590 depicted in FIG. 51, which are described above. The retention tab 4094 in the anti-retraction mechanism 4090 depicted in FIG. 56 are similar to the retention tabs 3594 in the anti-retraction mechanism 3590 depicted in FIG. 51, which are described above. The difference is that there is a single retention tab 4094 in anti-retraction mechanism 4090, while there is a pair of retention tabs 3594 in anti-retraction mechanism 3590. The fit tabs 4096 in the anti-retraction mechanism 4090 depicted in FIG. 56 are similar to the fit tabs 3596 in the anti-retraction mechanism 3590 depicted in FIG. 51, which are described above. The difference is that there are three fit tabs 4096 in anti-retraction mechanism 4090, while there are four fit tabs 3594 in anti-retraction mechanism 3590.

The anti-retraction mechanism 4090 depicted in FIGS. 54 to 56 is symmetrical, simplifying high volume assembly whether manual or automated. In embodiments where the plunger member (not shown) has annular grooves and/or threads, the anti-retraction mechanism 4090 may prevent removal of plunger member 3516 from the dual chamber injection system 4000. Further, the pair of long beams in the "O" shaped anti-retraction mechanism 4090 are deformable, allowing the anti-retraction mechanism 4092 bow outward, thereby transferring an outside reactive force to the interior walls of the second recess 4084 via the outside/long fit tabs 4096.

While the prefilled dual chamber safety injection systems depicted and described herein include syringes with staked needles, the injection configurations and detent dual chamber configurations described herein can be used with cartridges an auto injector, and injection systems with Luer connectors, transfer pipes, and no needles such as those described in U.S. Utility patent application Ser. Nos. 15/801,281 and 15/801,259, which were previously incorporated by reference herein.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A method for preparing a pre-filled multi-chamber injection system, the method comprising:
    introducing a first medicine component into a distal end of a body interior of an injection system body, wherein the injection system body defines an open proximal end, the body interior, and an open distal end;
    disposing a distal stopper member in the body interior through the open proximal end of the injection system body, the distal stopper member and the injection system body defining proximal and distal chambers in the body interior, wherein the first medicine component is disposed in the distal chamber;
    introducing a second medicine component into the body interior;
    disposing a proximal stopper member in the body interior through the open proximal end of the injection system body, such that the proximal stopper member defines a proximal end of the proximal chamber, wherein the second medicine component is disposed in the proximal chamber;
    inserting an elongate member at least partially into the body interior, the elongate member having a plurality of flow channels for fluidly coupling the proximal and distal chambers and a proximal end configured to penetrate the distal stopper member with distal movement of the distal stopper member relative to the injection system body; and
    coupling a plunger member to the proximal stopper member,
    the distal stopper member comprising a funnel therein, the method further comprising the funnel guiding the elongate member proximal end to a center of the distal stopper member, and
    wherein the funnel comprises a U-shaped retaining member/detent.

2. The method of claim 1, wherein introducing the first medicine component into the distal end of the body interior comprises introducing a liquid into the distal end of the body interior and lyophilizing the liquid.

3. The method of claim 1, wherein introducing the first medicine component into the distal end of the body interior comprises introducing a powder or solid into the distal end of the body interior.

4. The method of claim 1, further comprising disposing the injection system body in a rack in a first configuration before disposing the distal stopper member in the body interior,
    wherein, when the injection system body is in the first configuration, the distal end of the injection system body is pointed in a downward direction.

5. The method of claim 4, further comprising turning the injection system body in the rack to a second configuration before introducing the first medicine component into the distal chamber through the open distal end
    wherein, when the injection system body is in the second configuration, the proximal end of the injection system body is pointed in a downward direction.

6. The method of claim 5, further comprising returning the injection system body in the rack to the first configuration before introducing the second medicine component into the body interior and disposing the proximal stopper member in the body interior.

7. The method of claim 6, wherein the rack comprises a feature to hold the injection system body in the first and second configurations in the rack.

8. The method of claim 1, the elongate member proximal end comprising a 3D arrowhead shape, the method further comprising the 3D arrowhead interfering with the U-shaped retaining member/detent to temporarily prevent distal movement of the distal stopper member.

9. The method of claim 1, further comprising lyophilizing the first medicine component in the distal chamber before coupling the elongate member to the distal end of the injection system body.

10. The method of claim 1, further comprising utilizing a pressure differential on proximal and distal sides of the proximal stopper member to insert the proximal stopper member into the body interior through the open proximal end of the injection system body.

11. The method of claim 10, further comprising maintaining a vacuum in the proximal chamber during insertion of the proximal stopper member into the body interior through the open proximal end of the injection system body.

12. The method of claim 10, further comprising disposing the proximal stopper member above the open proximal end of the injection system body before inserting the proximal stopper member into the body interior.

13. The method of claim 1, further comprising disposing a tube adjacent the proximal stopper member such that the proximal chamber is fluidly coupled to an atmosphere during insertion of the proximal stopper member into the body interior through the open proximal end of the injection system body.

14. The method of claim 1, further comprising maintaining a vacuum in the distal chamber during the method.

15. The method of claim 1, further comprising performing one or more steps of the method in a vacuum.

16. The method of claim 1, further comprising coupling a flange to the injection system body such that the flange is prevented from moving along a longitudinal axis and the plunger member is moveable on the longitudinal axis relative to the flange.

17. The method of claim 16, further comprising coupling the plunger member to the proximal stopper member to facilitate movement of the proximal stopper member along the longitudinal axis.

18. The method of claim 1, wherein the injection system body, the elongate member, and the proximal and distal stopper members are pre-sterilized.

19. The method of claim 1, further comprising preparing a plurality of pre-filled multi-chamber injection systems.

20. The method of claim 1, further comprising introducing a third medicine component into the body interior through the open proximal end; and disposing a second proximal stopper member in the body interior through the open proximal end of the injection system body, such that the second proximal stopper member defines a proximal end of a second proximal chamber, wherein the third medicine component is disposed in the second proximal chamber.

\* \* \* \* \*